(12) United States Patent
Barlow et al.

(10) Patent No.: US 11,534,567 B2
(45) Date of Patent: Dec. 27, 2022

(54) ORO-NASAL PATIENT INTERFACE

(71) Applicant: ResMed Pty Ltd, Bella Vista (AU)

(72) Inventors: Adam Francis Barlow, Sydney (AU);
Rupert Christian Scheiner, Sydney (AU); Lachlan Richard Goldspink, Sydney (AU); Lemmy Nga, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

(21) Appl. No.: 17/576,008

(22) Filed: Jan. 14, 2022

(65) Prior Publication Data

US 2022/0134040 A1    May 5, 2022

Related U.S. Application Data

(63) Continuation of application No. 14/889,034, filed as application No. PCT/AU2014/050036 on May 14, 2014.

(Continued)

(51) Int. Cl.
*A61M 16/06* (2006.01)
*A61M 16/08* (2006.01)
*A61M 16/20* (2006.01)

(52) U.S. Cl.
CPC ........ *A61M 16/0622* (2014.02); *A61M 16/06* (2013.01); *A61M 16/0611* (2014.02);
(Continued)

(58) Field of Classification Search
CPC .............. A61M 16/06; A61M 16/0622; A61M 16/0611; A61M 16/0683; A61M 16/0816;
(Continued)

(56) References Cited

U.S. PATENT DOCUMENTS 2,415,846 A   10/1944 Randall
5,233,978 A    8/1993 Callaway
(Continued)

FOREIGN PATENT DOCUMENTS

CN      1628869 A   6/2005
CN     201064608    5/2008
(Continued)

OTHER PUBLICATIONS

Extended European Search Report dated Jun. 25, 2019 issued in European Application No. 19155652.1 (29 pages).
(Continued)

*Primary Examiner* — Colin W Stuart
*Assistant Examiner* — Douglas Y Sul
(74) *Attorney, Agent, or Firm* — Nixon & Vanderhye P.C.

(57) ABSTRACT

A patient interface to provide breathable gas to a patient, comprising: a plenum chamber assembly, comprising: a nasal plenum chamber at least partly defining an upper gas chamber; an oral plenum chamber at least partly defining a lower gas chamber; and a decoupling structure at least partly connecting the nasal plenum chamber and the oral plenum chamber and at least party defining a flow path; a top plate including at least one connection feature configured to releasably retain a first portion of a positioning and stabilising structure; and a faceplate configured to releasably retain a second portion of a positioning and stabilising structure.

30 Claims, 147 Drawing Sheets

Related U.S. Application Data

(60) Provisional application No. 61/954,201, filed on Mar. 17, 2014, provisional application No. 61/823,353, filed on May 14, 2013.

(52) U.S. Cl.
CPC .... *A61M 16/0683* (2013.01); *A61M 16/0816* (2013.01); *A61M 16/0825* (2014.02); *A61M 16/208* (2013.01); *A61M 2205/42* (2013.01); *A61M 2205/581* (2013.01); *A61M 2210/0618* (2013.01); *A61M 2210/0625* (2013.01)

(58) Field of Classification Search
CPC .......... A61M 16/0825; A61M 16/0666; A61M 2210/0618; A61M 2210/0625
See application file for complete search history.

(56) References Cited

U.S. PATENT DOCUMENTS

| | | | |
|---|---|---|---|
| 5,474,060 | A | 12/1995 | Evans |
| 5,540,223 | A | 7/1996 | Starr et al. |
| 5,560,354 | A | 10/1996 | Berthon-Jones et al. |
| 5,758,642 | A | 6/1998 | Choi |
| 6,019,101 | A | 2/2000 | Cotner et al. |
| 6,857,428 | B2 | 2/2005 | Thornton |
| 6,886,564 | B2 | 5/2005 | Sullivan et al. |
| 7,152,602 | B2 | 12/2006 | Bateman et al. |
| 7,243,650 | B2 | 7/2007 | Thornton |
| 7,448,386 | B2 | 11/2008 | Ho et al. |
| 7,793,987 | B1 | 9/2010 | Busch et al. |
| 7,909,035 | B2 | 3/2011 | Thornton |
| 7,942,148 | B2 | 5/2011 | Davidson et al. |
| 8,028,699 | B2 | 10/2011 | Ho et al. |
| 8,136,525 | B2 | 3/2012 | Lubke et al. |
| 8,347,886 | B2 | 1/2013 | Ho et al. |
| 11,065,413 | B2* | 7/2021 | Barlow ............. A61M 16/0622 |
| 2003/0196655 | A1 | 10/2003 | Ging et al. |
| 2004/0112384 | A1* | 6/2004 | Lithgow ........... A61M 16/0633 128/207.11 |
| 2005/0155604 | A1 | 7/2005 | Ging |
| 2006/0096598 | A1 | 5/2006 | Ho |
| 2006/0174892 | A1 | 8/2006 | Leksutin |
| 2006/0283461 | A1* | 12/2006 | Lubke ............... A61M 16/0825 128/201.19 |
| 2007/0006879 | A1 | 1/2007 | Thornton |
| 2007/0028919 | A1 | 2/2007 | Ho et al. |
| 2007/0125385 | A1* | 6/2007 | Ho .................... A61M 16/0683 128/206.26 |
| 2007/0186930 | A1 | 8/2007 | Davidson |
| 2009/0032026 | A1 | 2/2009 | Price et al. |
| 2009/0145429 | A1 | 6/2009 | Ging et al. |
| 2009/0159084 | A1 | 6/2009 | Sher et al. |
| 2010/0000534 | A1 | 1/2010 | Kooij |
| 2010/0229866 | A1 | 9/2010 | Sullivan |
| 2010/0282265 | A1 | 11/2010 | Melidis et al. |
| 2010/0319700 | A1 | 12/2010 | Ng et al. |
| 2011/0056497 | A1 | 3/2011 | Scheiner |
| 2011/0308526 | A1 | 12/2011 | Ho et al. |
| 2012/0067349 | A1 | 3/2012 | Barlow et al. |
| 2012/0080035 | A1 | 4/2012 | Guney et al. |
| 2012/0234326 | A1 | 9/2012 | Mazzone et al. |
| 2013/0008449 | A1 | 1/2013 | Busch et al. |
| 2014/0299134 | A1 | 10/2014 | Matula |
| 2015/0328423 | A1* | 11/2015 | Siew ................. A61M 16/0666 128/205.25 |
| 2016/0022944 | A1 | 1/2016 | Chodkowski et al. |
| 2016/0082214 | A1 | 3/2016 | Barlow et al. |

FOREIGN PATENT DOCUMENTS

| | | | |
|---|---|---|---|
| CN | 101378810 | A | 3/2009 |
| CN | 101687085 | A | 3/2010 |
| CN | 102014999 | A | 4/2011 |
| CN | 202505937 | | 10/2012 |
| CN | 202637661 | | 1/2013 |
| CN | 103052421 | A | 4/2013 |
| DE | 40 04 157 | | 4/1991 |
| EP | 0 264 772 | | 4/1988 |
| EP | 0 634 186 | | 8/2000 |
| GB | 2 385 533 | | 8/2003 |
| JP | 2007-222527 | A | 9/2007 |
| JP | 2008-532659 | | 8/2008 |
| JP | 2011-512967 | | 4/2011 |
| JP | 2012-528608 | | 11/2012 |
| WO | WO 98/04310 | | 2/1998 |
| WO | WO 98/34665 | | 8/1998 |
| WO | WO 00/78381 | | 12/2000 |
| WO | 01/97892 | A1 | 12/2001 |
| WO | WO 03/090827 | | 11/2003 |
| WO | WO 2004/073778 | | 9/2004 |
| WO | WO 2005/063328 | | 7/2005 |
| WO | WO 2006/074513 | | 7/2006 |
| WO | WO 2006/130903 | | 12/2006 |
| WO | WO 2008/070929 | A1 | 6/2008 |
| WO | 2009/026627 | A1 | 3/2009 |
| WO | WO 2009/052560 | | 4/2009 |
| WO | 2009/108995 | A1 | 9/2009 |
| WO | 2010/067235 | A1 | 6/2010 |
| WO | WO 2010/067235 | | 6/2010 |
| WO | WO 2010/135785 | | 12/2010 |
| WO | WO 2010/139014 | | 12/2010 |
| WO | WO 2010/0139014 | A1 | 12/2010 |
| WO | 2011/005955 | A2 | 1/2011 |
| WO | 2011/022751 | A1 | 3/2011 |
| WO | WO-2011022751 | A * | 3/2011 ............. A61M 16/06 |
| WO | 2011/060479 | A1 | 5/2011 |
| WO | WO 2012/040791 | | 4/2012 |
| WO | WO 2012/040792 | | 4/2012 |
| WO | WO-2012040791 | A * | 4/2012 ........ A61M 16/0057 |
| WO | WO-2012040792 | A1 * | 4/2012 ........ A61M 16/0057 |
| WO | WO 2012/171072 | | 12/2012 |
| WO | WO 2013/020167 | | 2/2013 |
| WO | WO 2013/066195 | | 5/2013 |
| WO | WO 2013/142909 | | 10/2013 |
| WO | 2014/015382 | A1 | 1/2014 |
| WO | 2014/077708 | | 5/2014 |
| WO | 2014/110626 | | 7/2014 |
| WO | 2014/141029 | | 9/2014 |
| WO | 2015/009172 | | 1/2015 |

OTHER PUBLICATIONS

Office Action dated Sep. 9, 2019 issued in Japanese Application No. 2018-187334 with English translation (10 pages).
European Search Report issued in related European Application No. 14797982.7 dated Sep. 22, 2016 (12 pages).
Second Office Action issued in related Chinese Application No. 201480028435.5, with English translation, dated Oct. 9, 2017, 12 pages.
First Office Action issued in related Taiwanese Application No. 103116909 with English translation, dated Mar. 16, 2018, 10 pages.
Patent Examination Report No. 1 issued in related Australian Application No. 2014268127 dated Feb. 5, 2016 (3 pages).
First Examination Report issued in related New Zealand Application No. 631020 dated Dec. 18, 2015, 2 pages.
First Office Action issued in related Japanese Application No. 2016-513178 dated Apr. 9, 2018, with English translation, 7 pages.
International Search Report for PCT/AU2014/050036 dated Sep. 2, 2014, 10 pages.
Written Opinion of the ISA for PCT/AU2014/050036 dated Sep. 2, 2014, 16 pages.
International Preliminary Report on Patentability for PCT/AU2014/050036 dated May 1, 2015, 132 pages.
First Office Action issued in related Chinese Application No. 201480028435.5, along with English Translation, dated Mar. 31, 2017 (14 pages).
Extended European Search Report dated Apr. 15, 2021 issued in European Application 20195150.6 (22 pages).

(56) References Cited

OTHER PUBLICATIONS

Office Action dated May 6, 2020 issued in Chinese Application No. 201810310617.1 with English translation (16 pages).

* cited by examiner

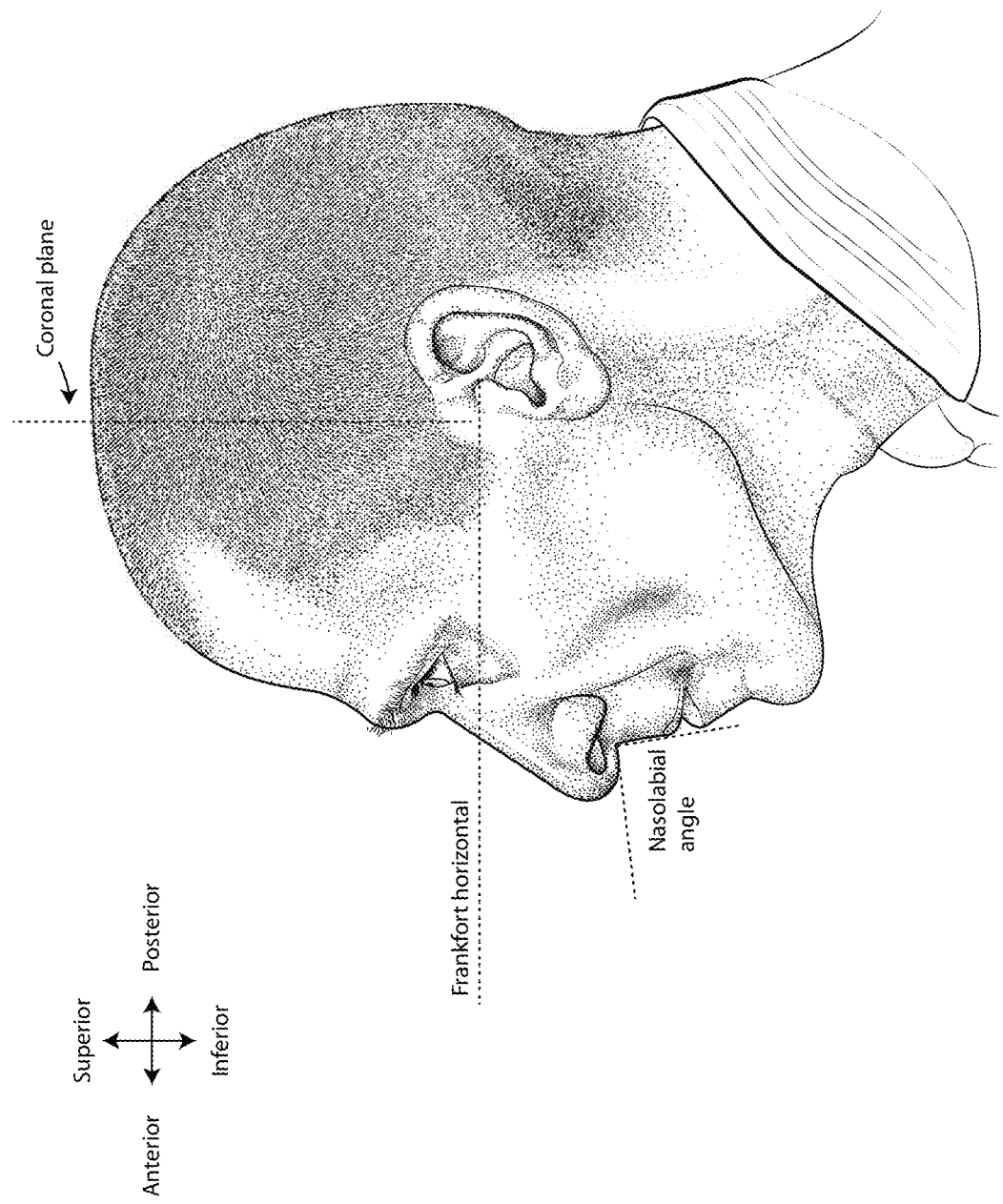

Copyright 2012 ResMed Limited

Copyright 2012 ResMed Limited

Copyright 2012 ResMed Limited

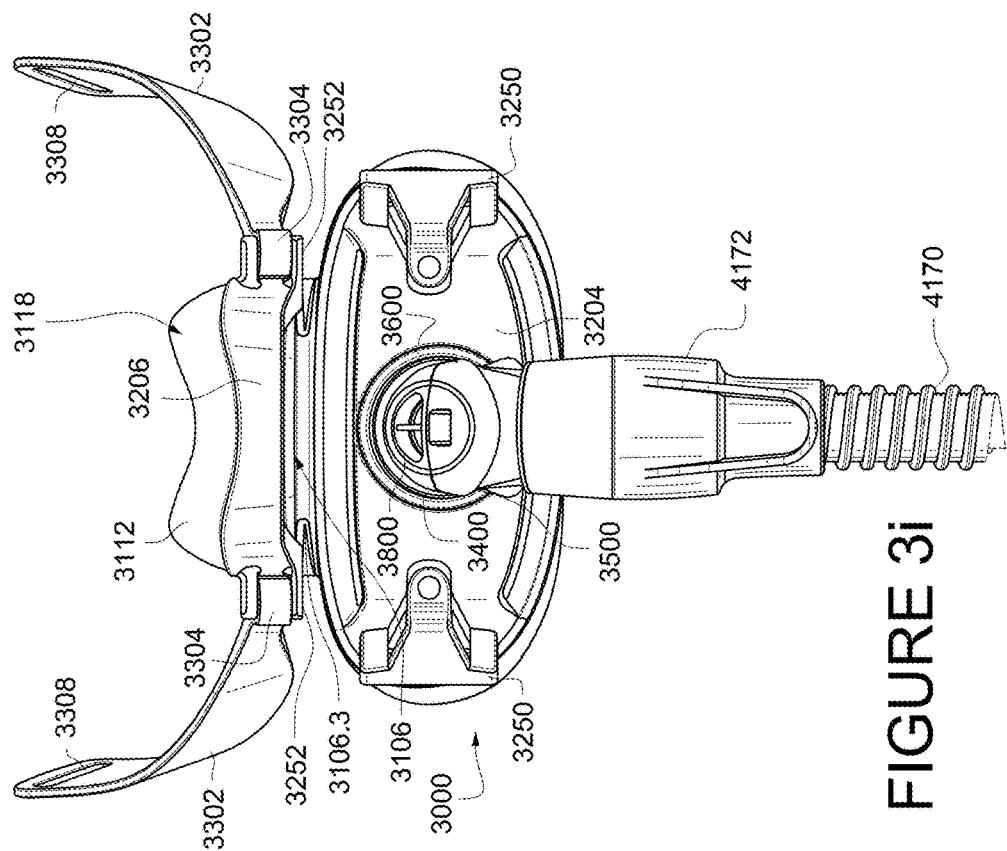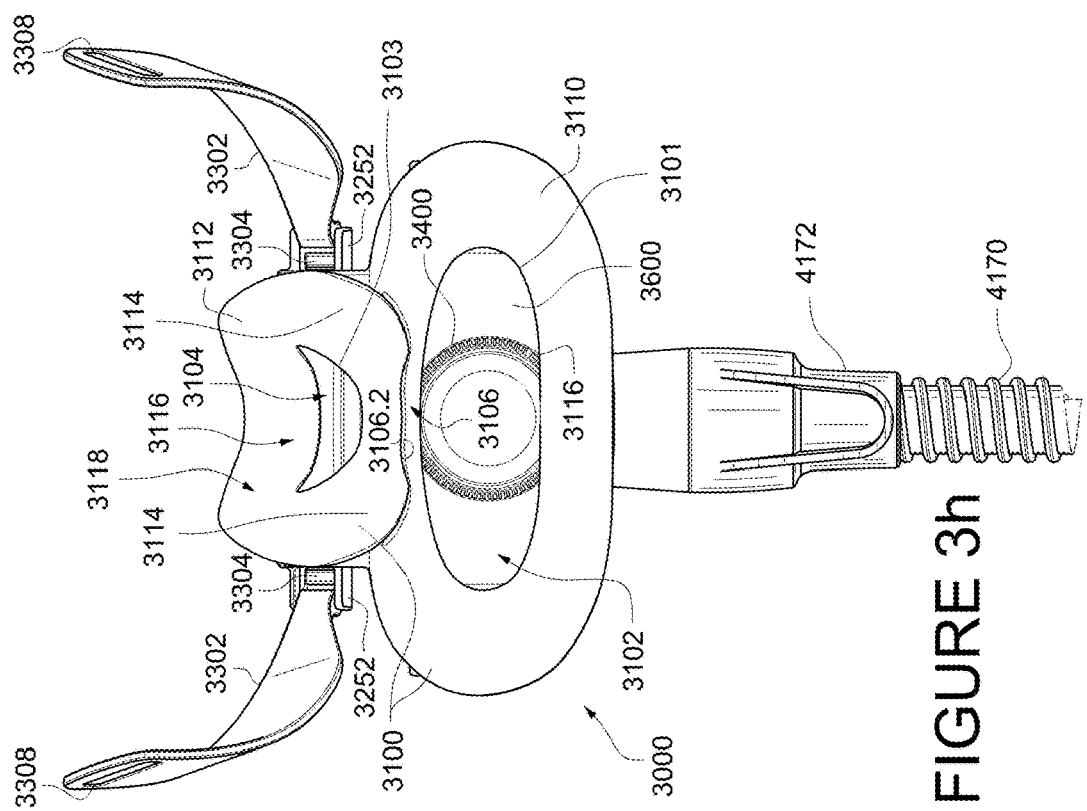

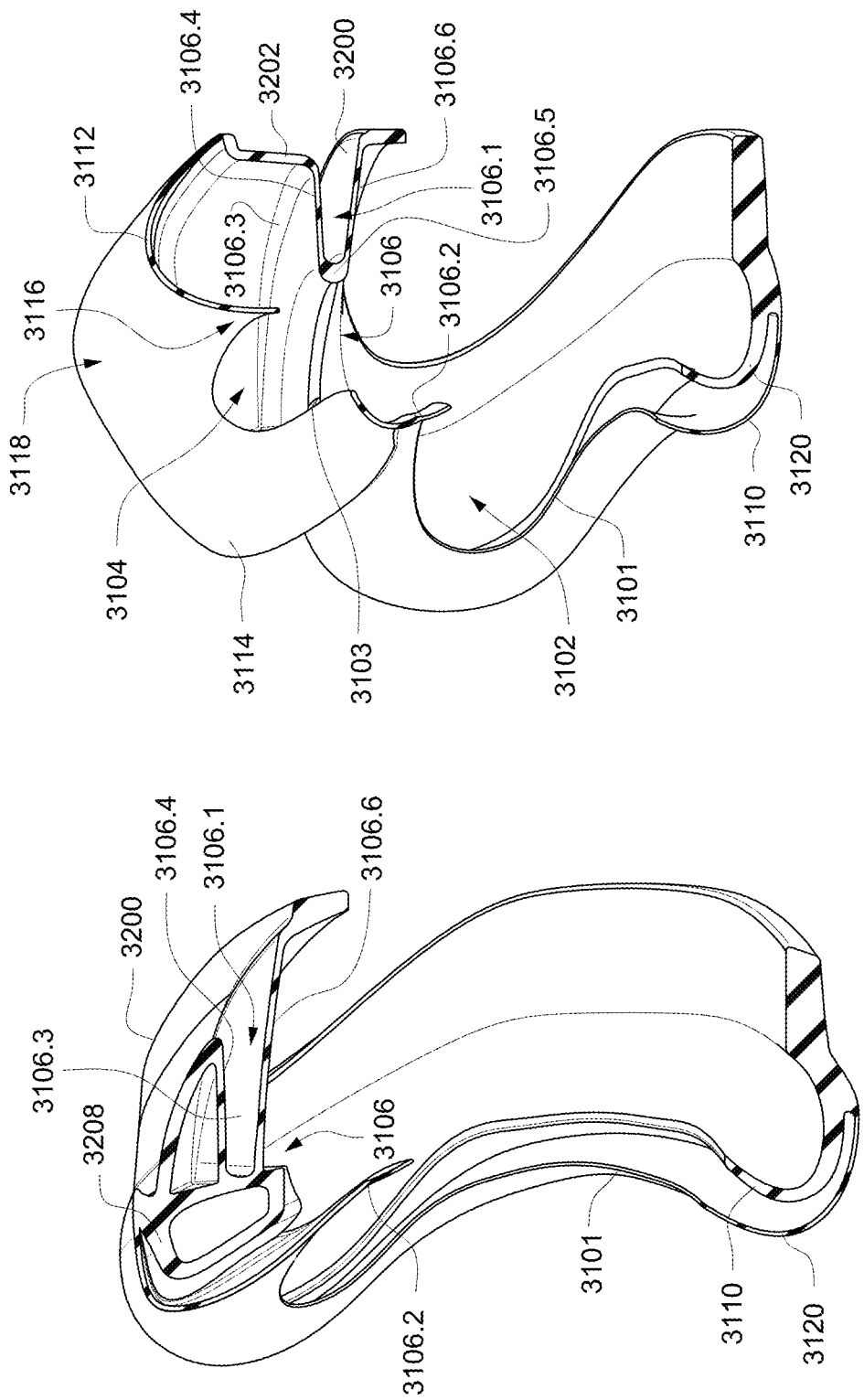

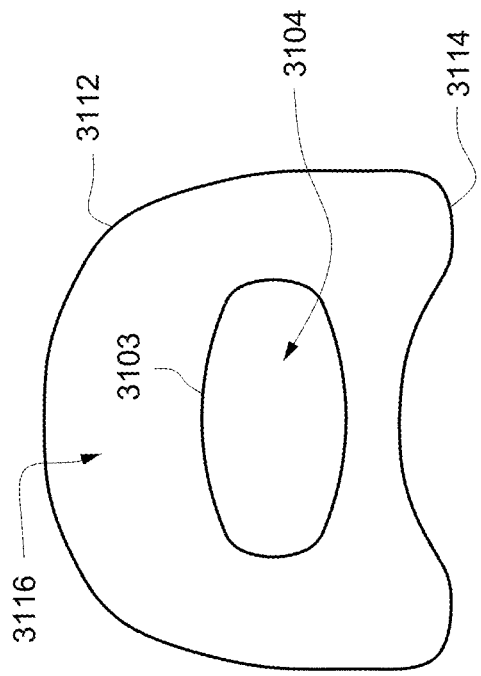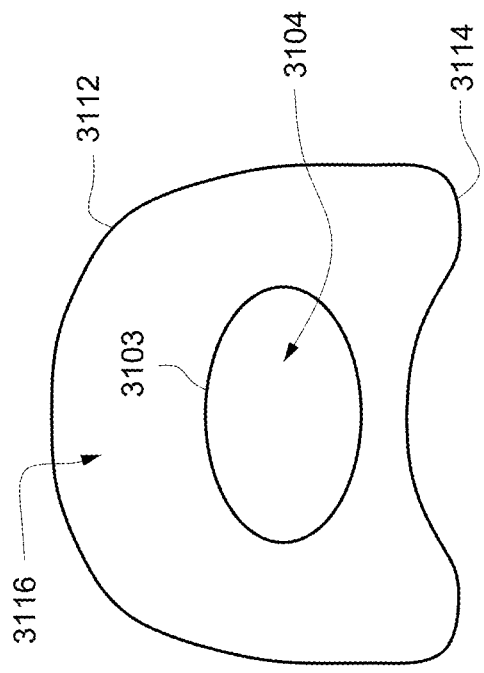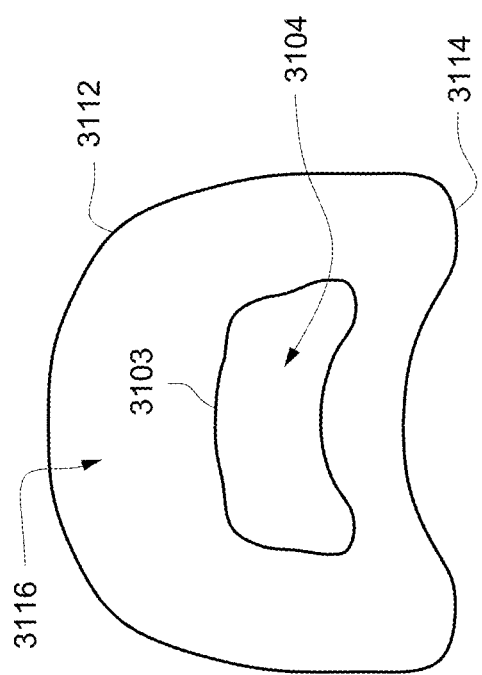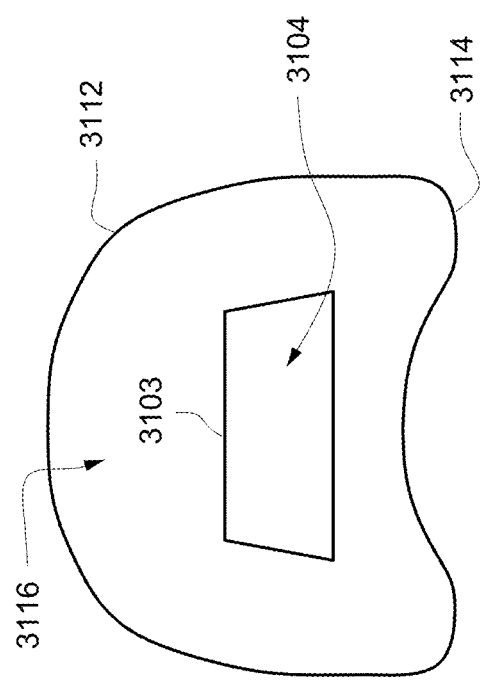

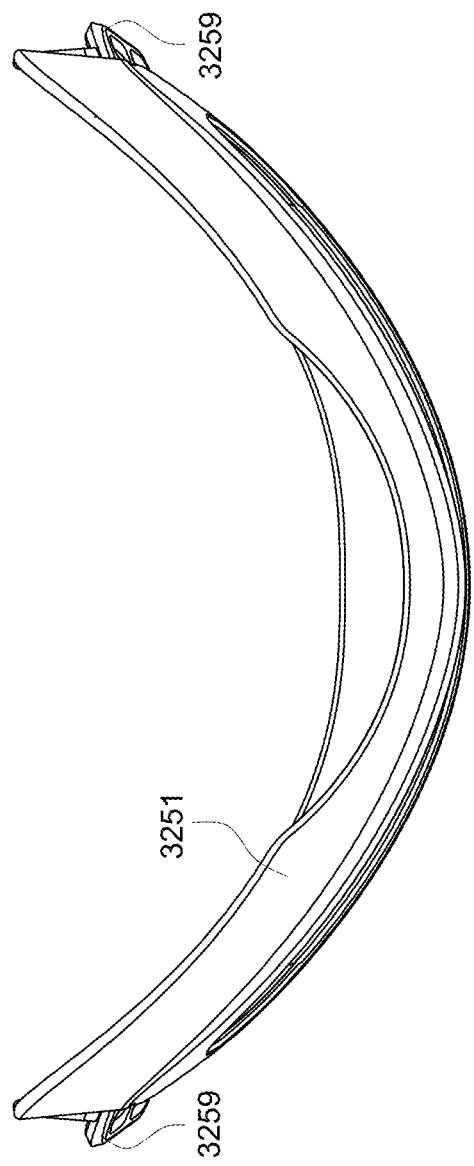

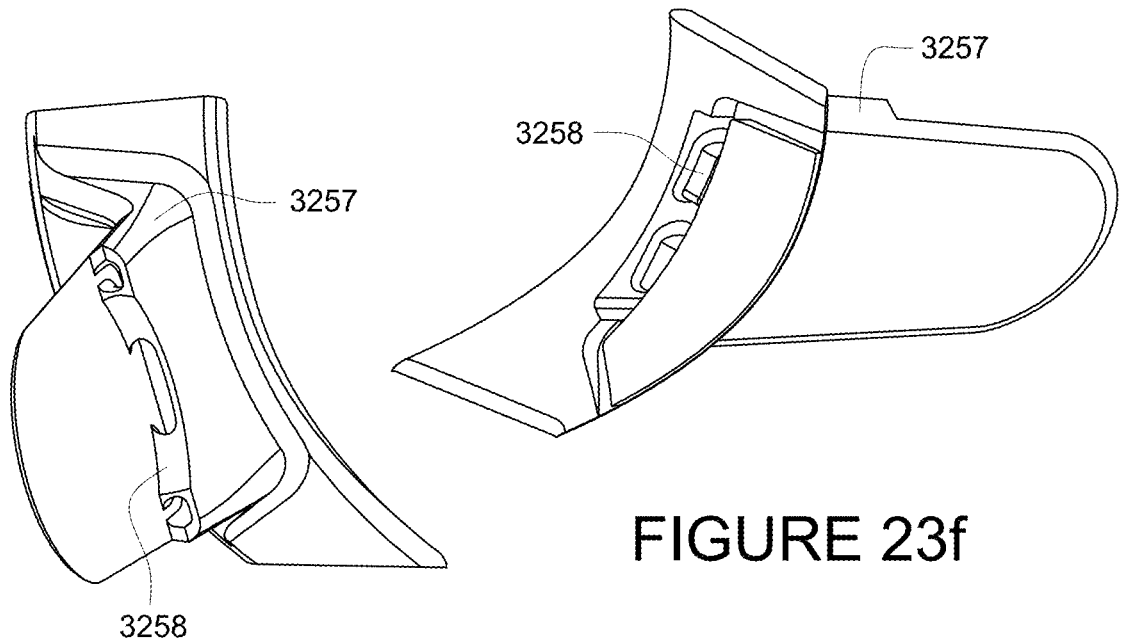
FIGURE 23e
FIGURE 23f
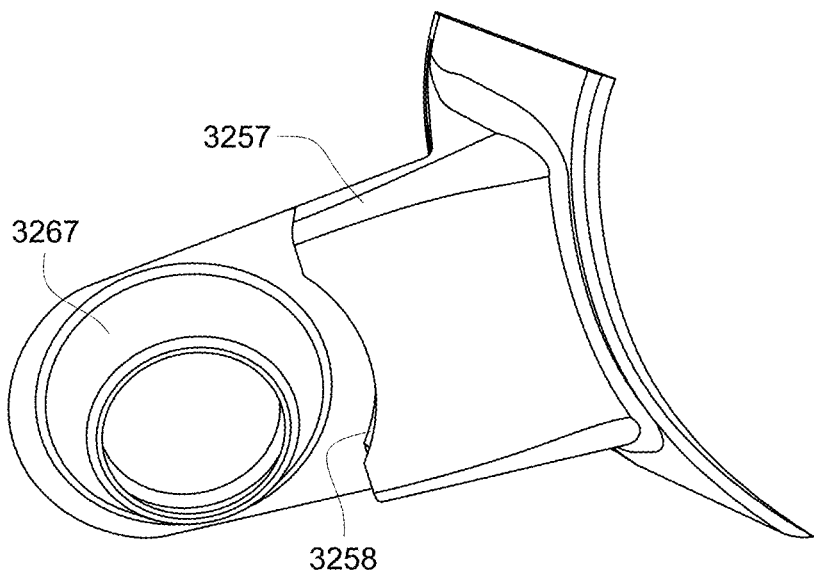
FIGURE 23g

ORO-NASAL PATIENT INTERFACE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1 CROSS-REFERENCE TO RELATED APPLICATIONS

This application is a continuation of U.S. application Ser. No. 14/889,034, filed Nov. 4, 2015, now pending, which is the U.S. national phase of International Application No. PCT/AU2014/050036 filed May 14, 2014 which designated the U.S. and claims the benefit of U.S. Provisional Application No. 61/823,353, filed May 14, 2013, and U.S. Provisional Application No. 61/954,201, filed Mar. 17, 2014, the entire contents of each of which are hereby incorporated by reference.

2 BACKGROUND OF THE TECHNOLOGY

2.1 Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

2.2 Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

Traditional oro-nasal masks include full face masks or ResMed LIBERTY full-face mask. Due to their size and bulk, they may less comfortable and more intrusive than other masks due to physiological reasons including claustrophobia or clithrophobia. Oro-nasal masks are typically bulky and heavy and can interfere with patient comfort and prevent wearing of eyeglasses.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may consist of an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808. Table of Noise of Prior Masks (ISO 17510-2:2007, 10 cmH$_2$O Pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(* one specimen only, measured using test method specified in ISO3744 in CPAP mode at 10 cm H$_2$O)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

An aspect of the present technology may be directed to a patient interface to provide breathable gas to a patient. The patient interface may comprise: a plenum chamber assembly, comprising: a nasal plenum chamber at least partly defining a first gas chamber, the nasal plenum chamber structured to contact the patient's nose below the bridge of the nose and around the lower periphery of the nose; an oral plenum chamber at least partly defining a second gas chamber, the oral plenum chamber structured to seal around the patient's mouth; and a decoupling structure at least partly connecting the nasal plenum chamber and the oral plenum chamber and at least partly defining a flow path between the nasal plenum chamber and the oral plenum chamber, the decoupling structure configured to decouple relative movement between the nasal plenum chamber and the oral plenum chamber; a top plate operatively connected to the plenum chamber assembly at the nasal plenum chamber, including at least one connection feature configured to releasably retain a first portion of a positioning and stabilising structure; and a faceplate operatively connected to the plenum chamber assembly at the oral plenum chamber, and configured to releasably retain a second portion of the positioning and stabilising structure, wherein the top plate and faceplate are more rigid than the plenum chamber assembly.

In examples, (a) said flow path may pneumatically connect the first gas chamber and the second gas chamber, (b) said top plate and said faceplate may be releasably attachable to the plenum chamber assembly, (c) said positioning and stabilising structure may comprise a rigidiser arm assembly having a pair of rigidiser arms, the rigidiser arm assembly may be connected to the top plate, (d) each of the pair of rigidiser arms may be permitted to flex in a plane parallel to the patient's transverse plane, and each of the pair of rigidiser arms may be structured to resist flexing in a plane perpendicular to the patient's transverse plane, resist twisting, and/or resist stretching, (e) each of the rigidiser arms may have an ellipsoidal profile to conform with the curvature of a patient's cheek, (f) said nasal plenum chamber may comprise a nasal flange defining a nasal opening, and said nasal flange may be configured to form a seal with at least the nose of the patient, (g) said nasal flange may include a recessed portion to receive the tip of the nose of the patient, (h) said oral plenum chamber may comprise an oral flange defining an oral opening, and said oral flange may be configured to form a seal with at least the mouth of the patient, (i) said oral flange may be formed around the entire perimeter of the oral plenum chamber, or around two opposing sides of the perimeter of the oral plenum chamber, or the majority of the perimeter of the oral plenum chamber, (j) said oral plenum chamber may comprise a pair of oral undercushion portions each disposed on a respective side of said oral plenum chamber to support said oral flange, (k) said oral plenum chamber may comprise an oral undercushion portion disposed circumferentially about said oral plenum chamber and extending radially from each end of the decoupling structure to support said oral flange, (j) said decoupling structure may connect the nasal flange and the oral flange, (k) the decoupling structure may comprise an upper surface, a lower surface, and a connecting surface, the connecting surface having a greater stiffness than the upper surface and the lower surface, (l) said decoupling structure may be stiffer at a portion opposite the face of the patient than at a portion adjacent to the face of the patient, (m) said decoupling structure may have a stiffness that increases radially from a portion adjacent to the face of the patient to a portion opposite the face of the patient, (n) a nose-contacting portion of said nasal flange may be stiffer at a portion that does not contact the nose of the patient than at a portion of said nasal flange that does not contact the nose of the patient, (o) said nasal flange may increase in stiffness outwardly from said nasal opening, (p) said nasal flange may have a varied stiffness around said nasal opening at predetermined positions, (q) a lower portion of said nasal flange proximal to said decoupling structure may be concave to seal against the upper lip of the patient, (r) said nasal flange may comprise a pair of protruding ends extending symmetrically about the nasal opening, each protruding end configured to seal against a corresponding alae of the nose of the patient, (s) said nasal plenum chamber may comprise a pair of nasal undercushion sections, each of the pair of nasal undercushion sections supporting one of the pair of protruding ends, (t) each said nasal undercushion section may be disposed on an upper portion of said oral plenum chamber, (u) the patient interface may comprise headgear to releasably secure said patient interface to the patient, said headgear including a pair of upper straps configured to connect to the nasal plenum chamber and a pair of lower straps configured to connect to the oral plenum chamber, (v) the top plate may be permanently connected to the nasal plenum chamber, (w) the top plate may be removably attachable to a soft connection region of the nasal plenum chamber, (x) the top plate may be removably attachable to a hard connection region of the nasal plenum chamber, and/or (y) the top plate and the rigidiser arms may comprise one piece and the rigidiser arms are flexible relative to the top plate in a plane parallel to the patient's transverse plane.

Another aspect of the present technology may be directed to a patient interface to provide breathable gas to a patient. The patient interface may comprise: a nasal cushion to at least partially define a nasal gas chamber; an oral cushion to at least partially define an oral gas chamber distinct from said nasal gas chamber; a decoupling structure disposed between said nasal cushion and said oral cushion; a top plate fixed to the nasal cushion and a pair of upper attachment features configured to releasably attach a pair of upper side straps of a positioning and stabilizing structure to the top plate; and a faceplate fixed to the oral cushion and a pair of lower attachment features configured to releasably attach a pair of lower side straps of the positioning and stabilizing structure.

In examples, (a) said decoupling structure may be adapted to form a pneumatic connection between said nasal gas chamber and said oral gas chamber, (b) the decoupling structure may comprise an upper surface, a lower surface, and a connecting surface, the connecting surface having a greater stiffness than the upper surface and the lower surface, (c) said decoupling structure may have a stiffness that is radially variable about its perimeter such that a portion distal to the face of the patient is stiffer than a portion proximal to the face of the patient, and the nasal cushion may be structured to move independently of the oral cushion, (d) a nose-contacting portion of the nasal cushion may be less stiff than a portion of the nasal cushion that does not contact the patient's nose, (e) said decoupling structure may be structured to support the nasal cushion against the nose of the patient, (f) said nasal cushion may be stiffer at a portion of said nasal cushion that does not contact the nose of the patient than at a nose-contacting portion, (g) said nasal cushion may comprise a concave portion to seal against the upper lip of the patient, (h) said nasal cushion may comprise a pair of protruding ends that are each configured to form a seal between respective alae and nasolabial sulci of the face of the patient, (i) said nasal cushion may comprise a pair of nasal undercushion portions each disposed under each respective protruding end to support each respective protruding end against the face of the patient, (j) said nasal cushion may comprise a wing on each side of the nasal cushion to seal against respective alae of the nose of the patient, (k) said oral cushion may comprise an oral undercushion portion extending radially about said oral cushion from either side end said of decoupling structure to support said oral cushion against the face of the patient, (l) said oral cushion may comprise a pair of oral undercushion portions each disposed on a respective side of said oral cushion to support said oral cushion against the face of the patient, (m) said nasal cushion may be shaped to include a recessed portion configured to receive the tip of the nose of the patient, (n) said nasal cushion may be configured to contact the inferior periphery of the nose of the patient below the bridge of the nose, (o) said nasal cushion, said oral cushion, and said decoupling structure may comprise one piece, (p) the top plate may be permanently connected to the nasal plenum chamber, (q) the top plate may be removably attachable to a soft connection region of the nasal plenum chamber, (r) the top plate may be removably attachable to a hard connection region of the nasal plenum chamber, (s) the top plate and a rigidiser arm assembly may comprise one piece and a pair of rigidiser arms of the rigidiser arm assembly are flexible relative to the top plate in a plane parallel to the patient's transverse plane, (t) the positioning and stabilising structure may comprise a rigidiser arm assembly releasably attachable to the top plate at the upper attachment features, (u) the patient interface may comprising a frame releasably attachable to the faceplate and the lower attachment features may be disposed on the frame, (v) each of the lower attachment features may comprise a mating portion having a mating portion magnet to releasably connect to corresponding clips of the positioning and stabilising structure and each of the corresponding clips may include a clip magnet oriented such that when each clip magnet is magnetically attracted to each mating portion magnet the mating portion is joined to the corresponding clip, (w) the patient interface may comprise a top plate buffer to dampen the connection between the top plate and the rigidiser arm assembly and a faceplate buffer to dampen the connection between the faceplate and the frame, and/or (x) the frame may be shaped to join around the periphery of the faceplate, the frame may comprise catches and the faceplate comprises cutouts, and engagement between the catches and the cutouts may join the frame to the faceplate.

Another aspect of the present technology may be directed to a patient interface to provide breathable gas to a patient. The patient interface may comprising: a plenum chamber assembly, comprising: a nasal plenum chamber at least partly defining an first gas chamber, the nasal plenum chamber is adapted to seal against the patient below the bridge of the nose and around the inferior periphery of the patient's nose; and an oral plenum chamber at least partly defining a second gas chamber operatively connected to the nasal plenum chamber; and a unitary plate member having an upper portion releasably attachable to the nasal plenum chamber and a lower portion releasably attachable to the oral plenum chamber; wherein the upper portion of the plate member includes at least one connection feature configured to releasably retain a first portion of a positioning and stabilising structure having a pair of rigidiser arms, and the lower portion of the plate member is configured to releasably retain a second portion of the positioning and stabilising structure.

In examples, (a) the plenum chamber assembly may comprise a decoupling structure at least partly connecting the nasal plenum chamber and the oral plenum chamber, the decoupling structure at least partly defining a flow path between the nasal plenum chamber and the oral plenum chamber, (b) each of the pair of rigidiser arms may be permitted to flex in a plane parallel to the patient's transverse plane, and each of the pair of rigidiser arms may be structured to resist flexing in a plane perpendicular to the patient's transverse plane, resist twisting, and/or resist stretching, (c) each said at least one connection feature may comprise a hinge to allow a corresponding one of the pair of rigidiser arms to rotate relative to the rigid top plate upper portion of the unitary plate member in a plane parallel to the patient's transverse plane, (d) the first portion of a positioning and stabilising structure may include a hook to pivotably connect with the connection feature of the upper portion of the unitary plate member, (e) said nasal plenum chamber may comprise a nasal flange defining a nasal opening, and said nasal flange may be configured to form a seal with at least the nose of the patient, (e) said nasal flange may include a recessed portion to receive the tip of the nose of the patient, (f) said oral plenum chamber may comprise an oral flange defining an oral opening, and said oral flange may be configured to form a seal with at least the mouth of the patient, (g) said oral flange may be formed around the entire perimeter of the oral plenum chamber, or around two opposing sides of the perimeter of the oral plenum chamber, or the majority of the perimeter of the oral plenum chamber, (h) said oral plenum chamber may comprise a pair of oral undercushion portions each disposed on a respective side of said oral plenum chamber to support said oral flange, (i) said oral plenum chamber may comprise an oral undercushion portion disposed circumferentially about said oral plenum chamber and extending radially from each end of the decoupling structure to support said oral flange, (j) said decoupling structure may connect the nasal flange and the oral flange, (k) said decoupling structure may be stiffer at a portion opposite the face of the patient than at a portion adjacent to the face of the patient, (l) said decoupling structure may have a stiffness that increases radially from a portion adjacent to the face of the patient to a portion opposite the face of the patient, (m) a nose-contacting portion of said nasal flange may be stiffer at a portion that does not contact the nose of the patient than at a portion of said nasal flange that does not contact the nose of the patient, (n) said nasal flange may increase in stiffness outwardly from said nasal opening, (o) said nasal flange may have a varied stiffness around said nasal opening at predetermined positions, (p) a lower portion of said nasal flange proximal to said decoupling structure may be concave to seal against the upper lip of the patient, (q) said nasal flange may comprise a pair of protruding ends extending symmetrically about the nasal opening, each protruding end configured to seal against a corresponding alae of the nose of the patient, (r) said nasal plenum chamber may comprise a pair of nasal undercushion sections each corresponding to each protruding end to support each protruding end, (s) each said nasal undercushion section may be disposed on an upper portion of said oral plenum chamber, and/or (t) each of said pair of rigidiser arms may have an ellipsoidal curvature between the first end and the second end.

Another aspect of the present technology may be directed to a cushion assembly for a patient interface for treatment of sleep disordered breathing of a patient, comprising: a nasal cushion joined to a nasal plenum chamber, the nasal cushion structured to seal around the lower periphery of the patient's nose; an oral cushion joined to an oral plenum chamber, the oral cushion structured to seal around the patient's mouth; a decoupling structure connecting the nasal cushion and the nasal plenum chamber to the oral cushion and the oral plenum chamber, the decoupling structure configured to allow the nasal cushion and the nasal plenum chamber to move relative to the oral cushion and the oral plenum chamber; a pair of side supports, each of the pair of side supports located on opposite sides of the nasal cushion and joining respective lateral sides of the nasal cushion to the oral cushion; a pair of undercushion support walls provided to support protruding ends positioned posteriorly on the nasal cushion; and a pair of pockets, each of the pair of pockets located on opposite sides of the nasal cushion, each of the pair of pockets including an upper surface defined by the nasal cushion and the nasal plenum chamber, each of the pair of pockets including a lower surface defined by the oral cushion and the oral plenum chamber, and each of the pair of pockets including side surfaces defined by the decoupling structure and respective ones of the pair of side supports, wherein an opening of each of the pair of pockets is positioned opposite the face of the patient when the patient interface is donned by the patient.

In examples, (a) each of the pair of side supports may include a notch to provide a pivot point for relative movement between the nasal cushion and the oral cushion, (b) the notch of each of the pair of side supports may be open in a direction opposite the face of the patient when the patient interface is donned by the patient, (c) the nasal cushion may comprise a pair of stiffened sections, each of the pair of stiffened sections may be located at opposite lateral sides of the nasal cushion, and the stiffened sections may be stiffer than the remainder of the nasal cushion, (d) the pair of stiffened sections may comprise a thickness greater than other portions of the nasal cushion, (e) the pair of stiffened sections may extend internally relative to the nasal cushion and the nasal plenum chamber such that an external surface of the nasal cushion is not raised, (f) the nasal cushion may comprises a nasal sling, the nasal sling being formed in-plane with the nasal cushion, and the nasal sling being structured to contact the patient's columella, (g) the nasal cushion and the nasal sling may define a pair of nare ports, each of the pair of nare ports structured to pneumatically communicate with a respective one of the patient's nares, and/or (h) the nasal sling may be structured to prevent the tip of the patient's nose from extending into a nasal gas chamber, the nasal gas chamber defined at least in part by the nasal cushion and the nasal plenum chamber.

Another aspect of the present technology is directed to a patient interface system to provide breathable gas to a patient. The patient interface may comprise: a cushion assembly, the cushion assembly may comprise: a nasal cushion to at least partially define a nasal gas chamber; an oral cushion to at least partially define an oral gas chamber distinct from said nasal gas chamber; and a decoupling structure disposed between said nasal cushion and said oral cushion; a positioning and stabilizing structure with a pair of lower side straps; and a pair of lower attachment features configured to releasably attach a corresponding one of the pair of lower side straps of the positioning and stabilizing structure to the cushion assembly, wherein each of the pair of lower attachment features comprises a thermoplastic elastomer and each of the pair of lower attachment features has a first magnet embedded therein.

In examples, (a) the patient interface system may comprise: a faceplate fixed to the oral cushion; and a frame releasably attachable to the faceplate, wherein the pair of lower attachment features are fixed to the frame, (b) the frame may comprise a material more rigid than thermoplastic elastomer, (c) the pair of lower attachment features may be molded onto the frame, (d) the positioning and stabilizing structure may comprise a pair of clips to attach a corresponding one of the pair of lower side straps to corresponding one of the pair of lower attachment features, (e) each of the pair of clips may comprise a second magnet to attach each of the pair of clips to a corresponding one of the pair of lower attachment features, (f) each of the pair of clips may comprise a notch and each of the pair of lower attachment features may comprise a protrusion, and the protrusion may engage with the notch when each of the pair of clips are engaged with a corresponding one of the pair of lower attachment features, (g) each of the pair of lower attachment features may comprise a flex point, each of the pair of the pair of lower attachment features structured to flex at said flex point, and/or (h) each of the pair of lower attachment features may include a region of reduced thickness at the flex point.

Another aspect of the present technology is directed to a patient interface to provide breathable gas to a patient. The patient interface may comprise: a nasal cushion to at least partially define a nasal gas chamber; an oral cushion to at least partially define an oral gas chamber distinct from said nasal gas chamber; a decoupling structure disposed between said nasal cushion and said oral cushion; a top plate fixed to the nasal cushion; and a rigidiser arm assembly releasably attachable to the top plate, wherein the rigidiser arm assembly and the top plate engage at at least three points of contact.

In examples, (a) the top plate may comprise a pair of upper attachment features and the rigidiser arm assembly may comprise a pair of connection features, each of the pair of connection features may be structured to engage with a corresponding one of the pair of upper attachment features, (b) the rigidiser arm assembly may comprise a rib to engage with the top plate when the rigidiser arm assembly is engaged with the top plate, (c) the patient interface may comprise a top plate buffer to dampen engagement between the rigidiser arm assembly and the top plate, the top plate buffer may be positioned on an anterior side of the top plate to contact a posterior side of the rigidiser arm assembly, (d) the top plate buffer and the nasal cushion may comprise one piece, the top plate buffer extending through the top plate from the nasal cushion, (e) the rigidiser arm assembly may comprise a pair of rigidiser arms, each of the pair of rigidiser arms may be structured to a receive an upper side strap of a positioning and stabilizing structure, and/or (f) each of the pair of rigidiser arms may comprise a pad to cushion the pair of rigidiser arms against the patient's face.

Another aspect of the present technology is directed to a patient interface to provide breathable gas to a patient. The patient interface may comprise: a nasal cushion to at least partially define a nasal gas chamber; an oral cushion to at least partially define an oral gas chamber distinct from said nasal gas chamber; and a decoupling structure disposed between said nasal cushion and said oral cushion, wherein the decoupling structure comprises an upper surface joining the decoupling structure to the nasal cushion, a lower surface joining the decoupling structure to the oral cushion, and a connecting surface joining the upper surface and the lower surface, wherein the upper surface and the lower surface are substantially equal in thickness, and wherein the connecting surface is thicker than the upper surface and the lower surface.

In examples, (a) the connecting surface may be about twice as thick as the upper surface and the lower surface, (b) the decoupling structure may be structured to be flexible such that the upper surface and the lower surface can be positioned at up to 50° relative to one another, and/or (c) the upper surface and the lower surface may be about 0.5 mm thick and the connecting surface is about 1.2 mm thick.

Another aspect of one form of the present technology is a patient interface that is moulded or otherwise constructed with a clearly defined perimeter shape which is intended to match that of an intended wearer. The patient interface system may have a reduced part count compared to currently available patient interface systems. The patient interface system may provide a visible mouth region of the patient if the faceplate is semi-transparent or transparent. The patient interface system is an oro-nasal mask meaning it covers the nasal airways and the mouth. It may not obstruct the patient's line of sight, and may be considered physiologically non-threatening and may increase patient selection of the system and adherence to therapy. The patient interface system may flex to adapt to changes in jaw movement and head position throughout the night. The patient interface system may provide a supply of pressurised air or breathable gas to a patient's nasal passages and may prevent or reduce mouth leak by providing an effective seal with both the patient's mouth and the patient's nasal passages.

Another aspect of one form of the present technology is a patient interface that may have a reduced skin contact area and less total points of contact with the face, when compared to most known full face masks. This may allow a far reduced headgear tension to be applied, significantly improving patient comfort. Patient comfort may be further enhanced since the patient is less likely to feel claustrophobic, particularly with the removal of any mass that is close to the eyes.

Another aspect of one form of the present technology is a patient interface that may be quick and easy to fit by all customer segments including patient, home medical equipment dealers and clinicians. It may simplify mask selection for clinicians and dealers due to its superior ease of use (fitting, sealing, size selection, sometimes remotely) and intuitiveness to assemble and fit allowing greater success in remote setups done in an unassisted environment without instruction. The patient interface may have one primary size fitting the majority of the general adult patient population, and no more than two additional sizes. It is envisaged that three sizes of the patient interface will fit at least 90% of the general adult population.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. A bed partner 1100 is also shown.

4.2 Therapy

4.2.1 Respiratory System

Figure 1A:
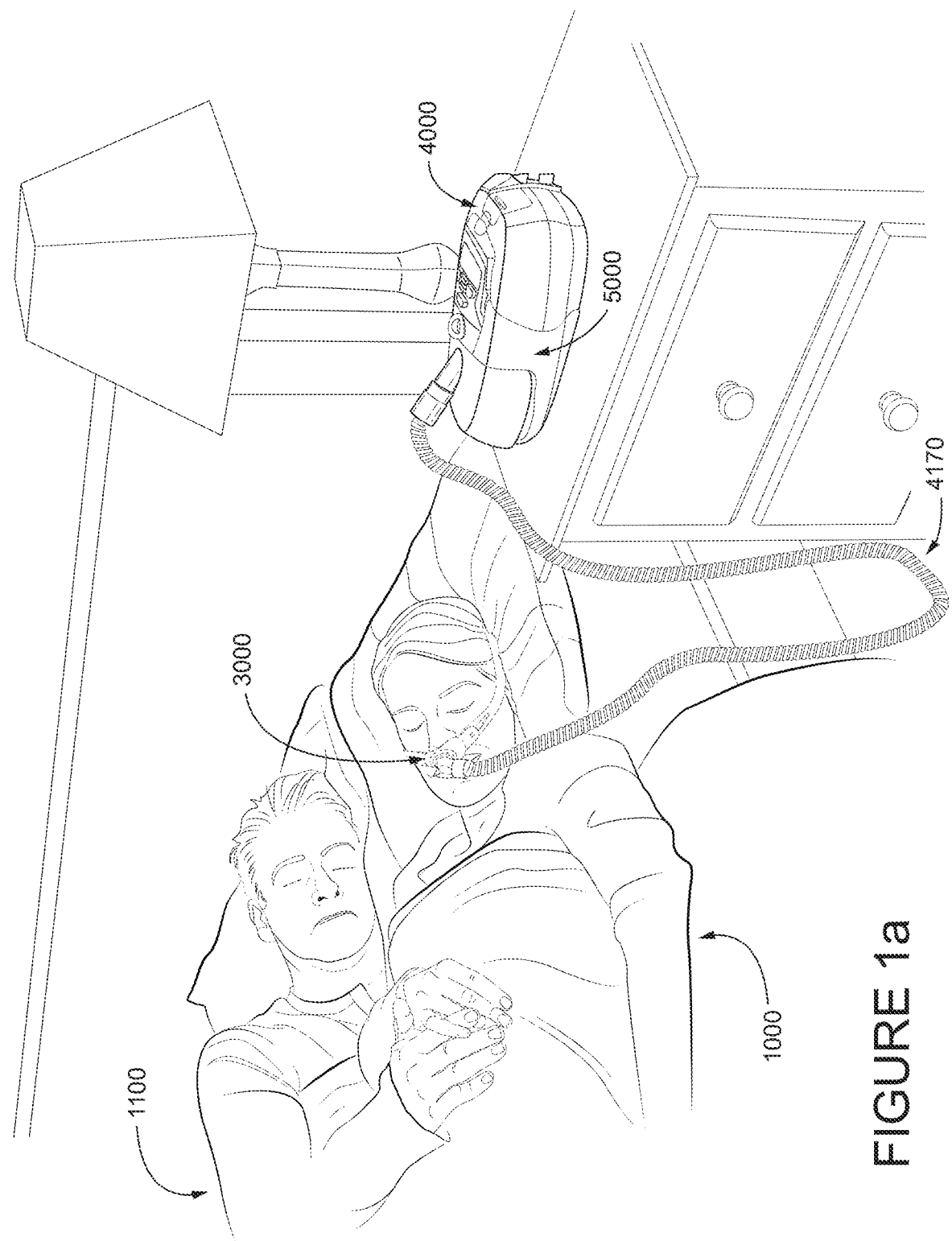
FIG. 1b shows a PAP device in use on a patient with a nasal mask.
FIG. 1c shows a PAP device in use on a patient with a full-face mask.
Figure 1B:
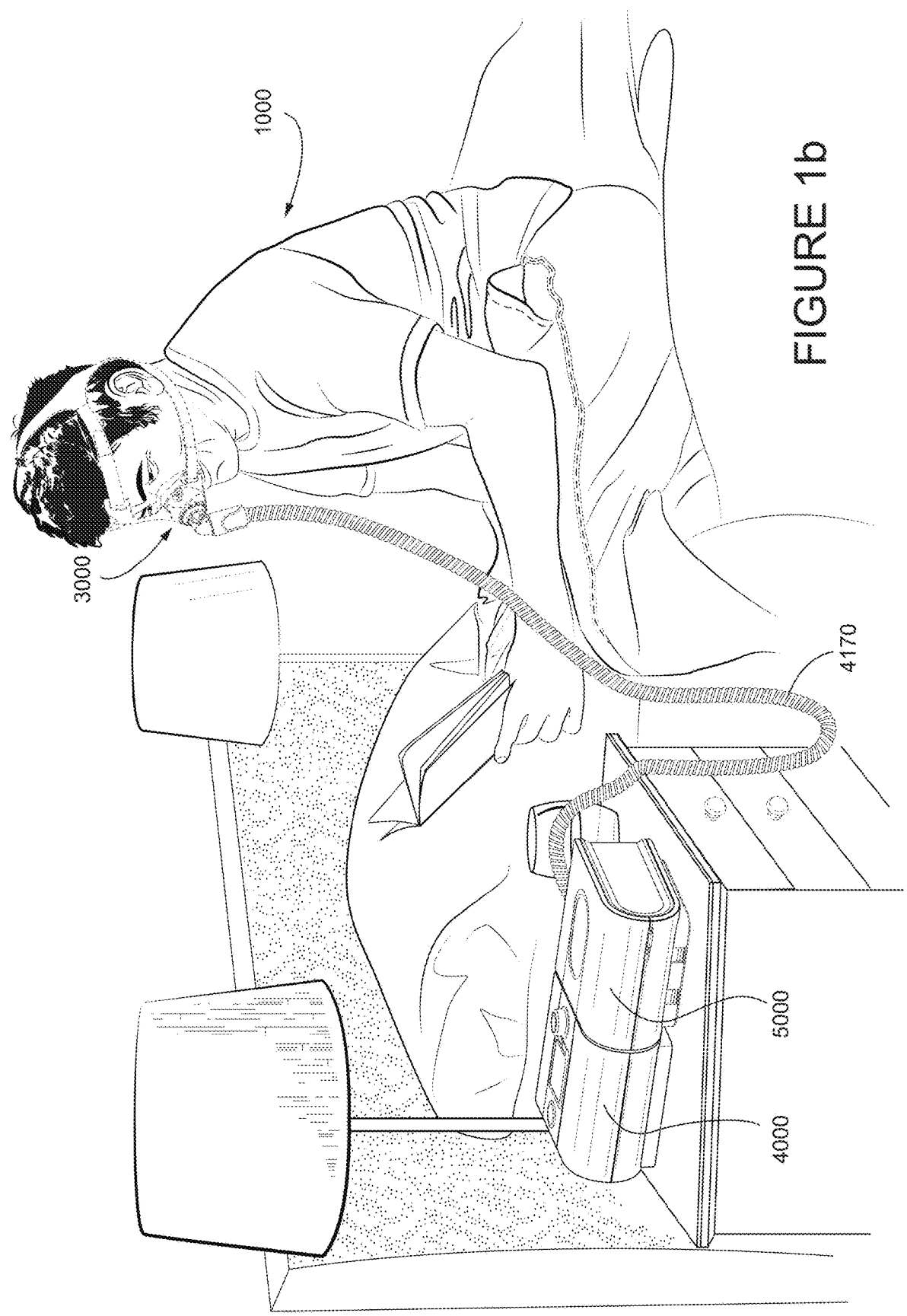
Figure 1C:
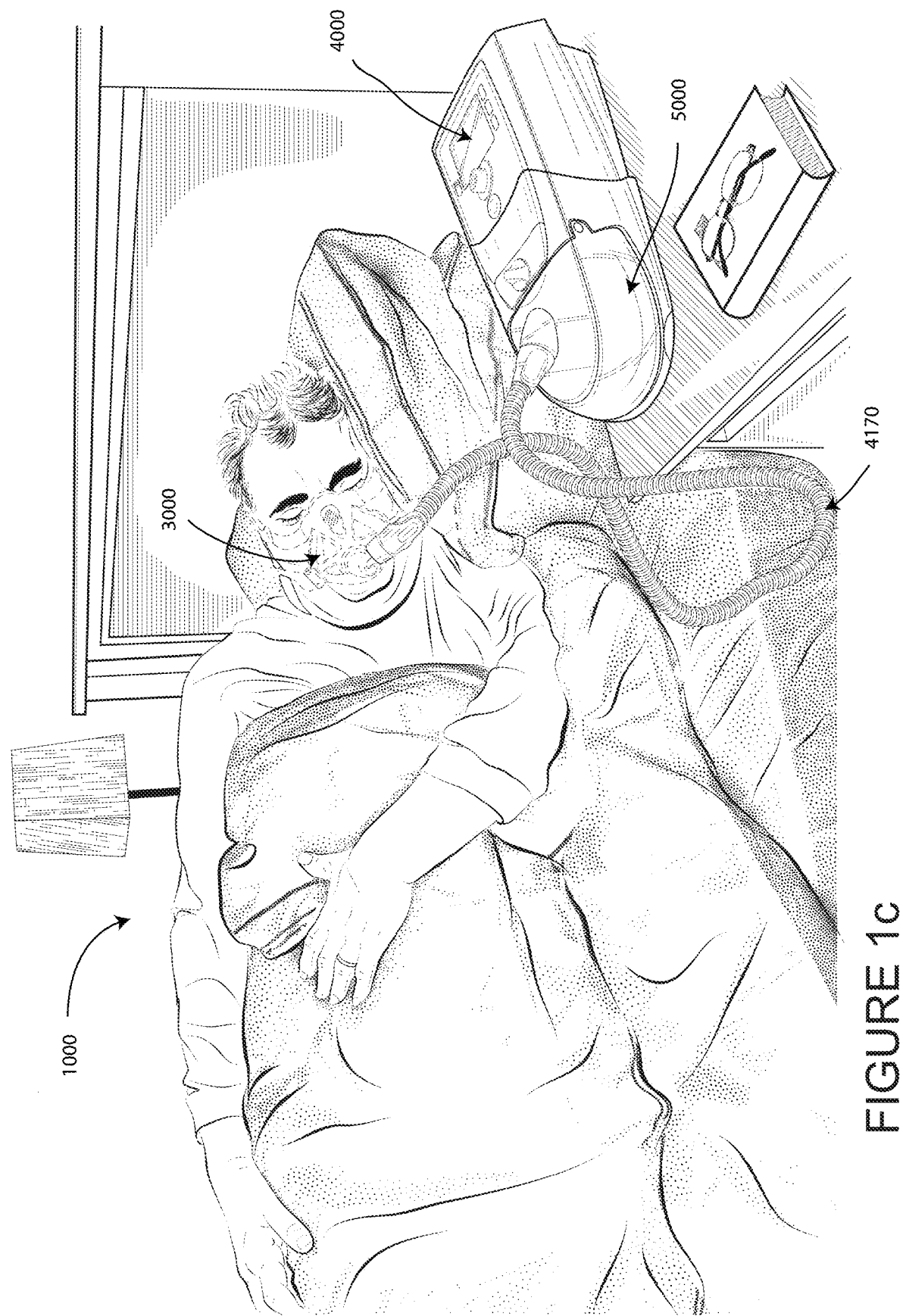
Figure 2A:
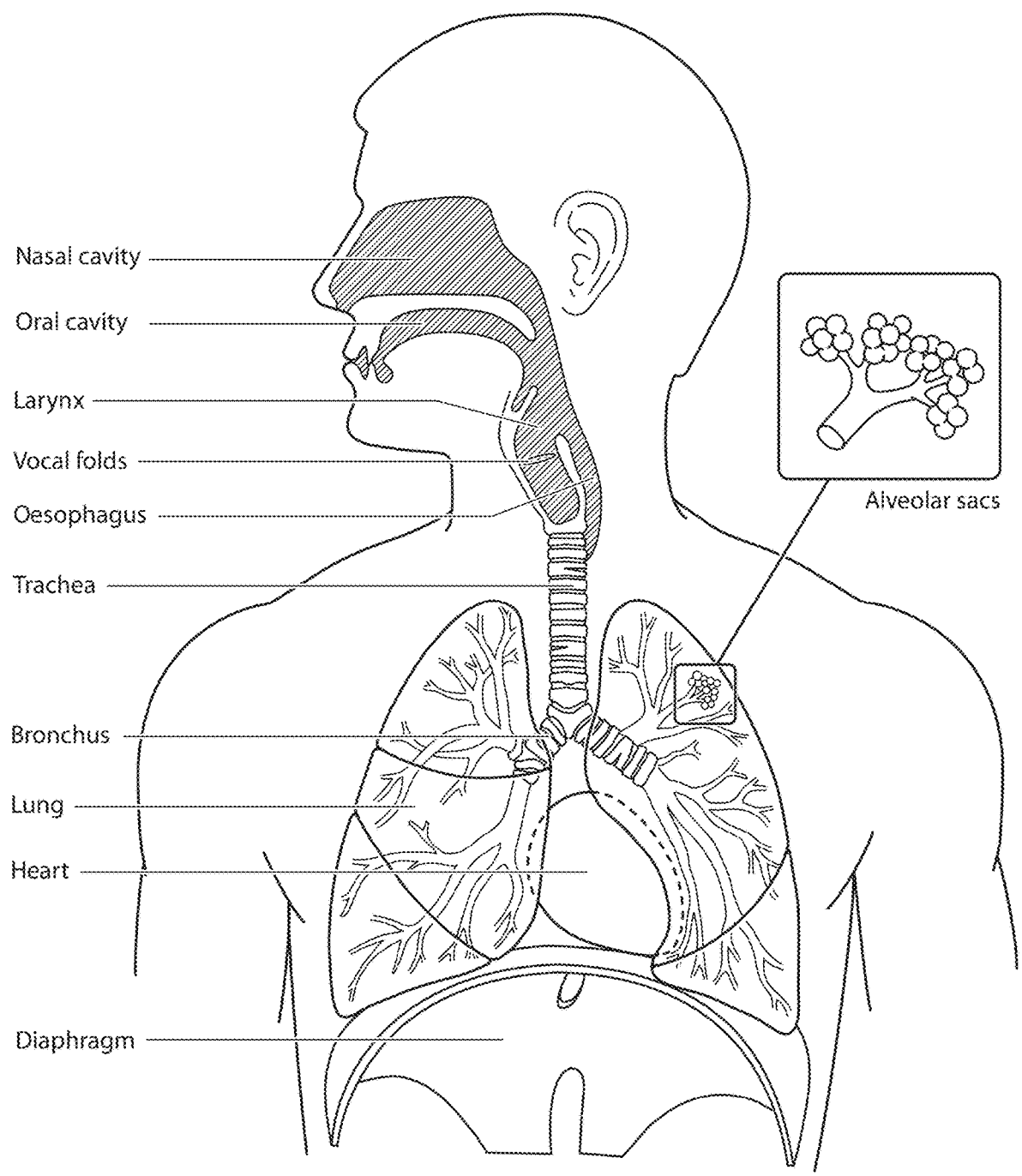

FIG. 2a shows an overview of a human respiratory system including the nasal and oral cavities, the larynx, vocal folds, oesophagus, trachea, bronchus, lung, alveolar sacs, heart and diaphragm.

Figure 2B:
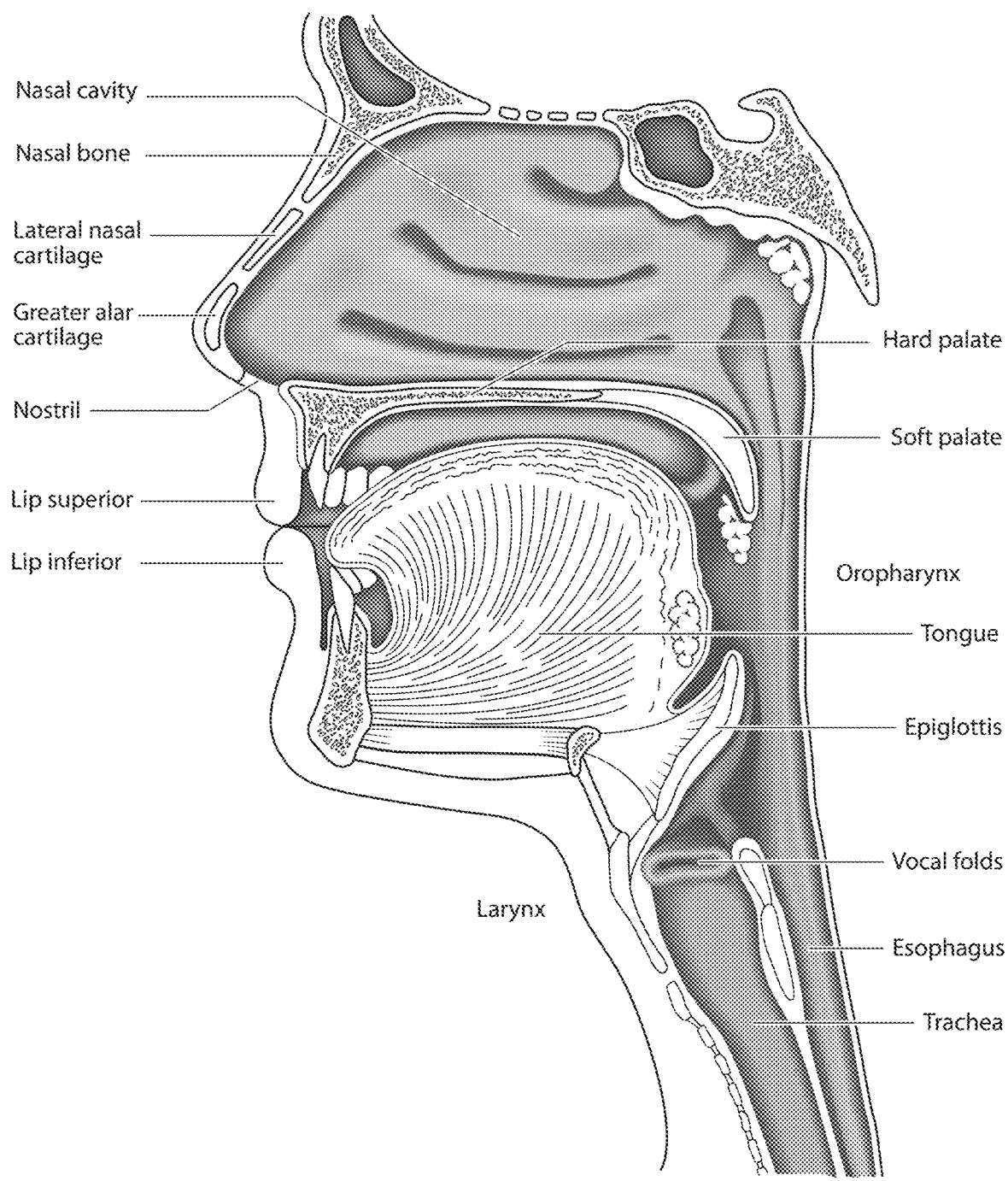

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.2.2 Facial Anatomy

Figure 2C:
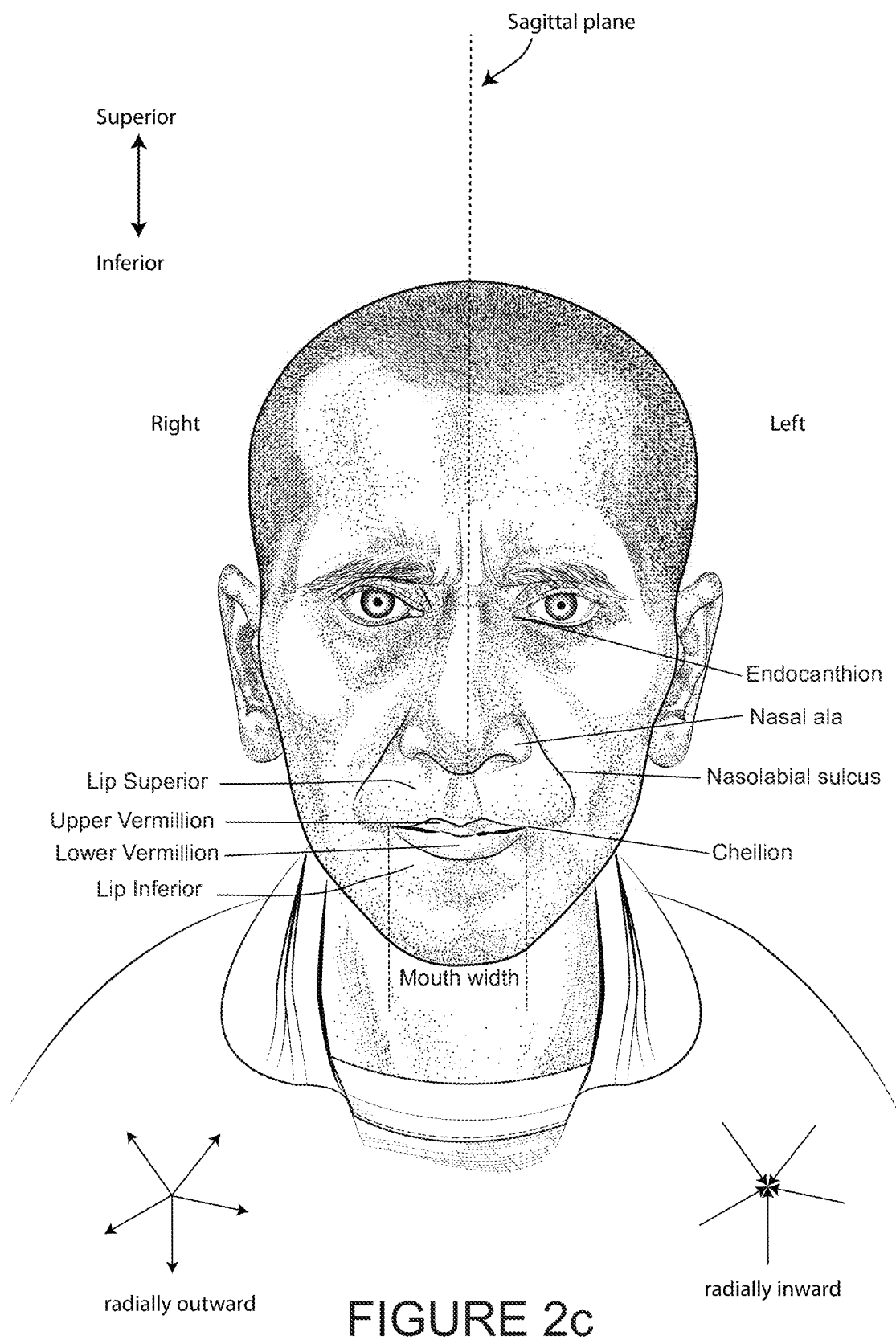

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
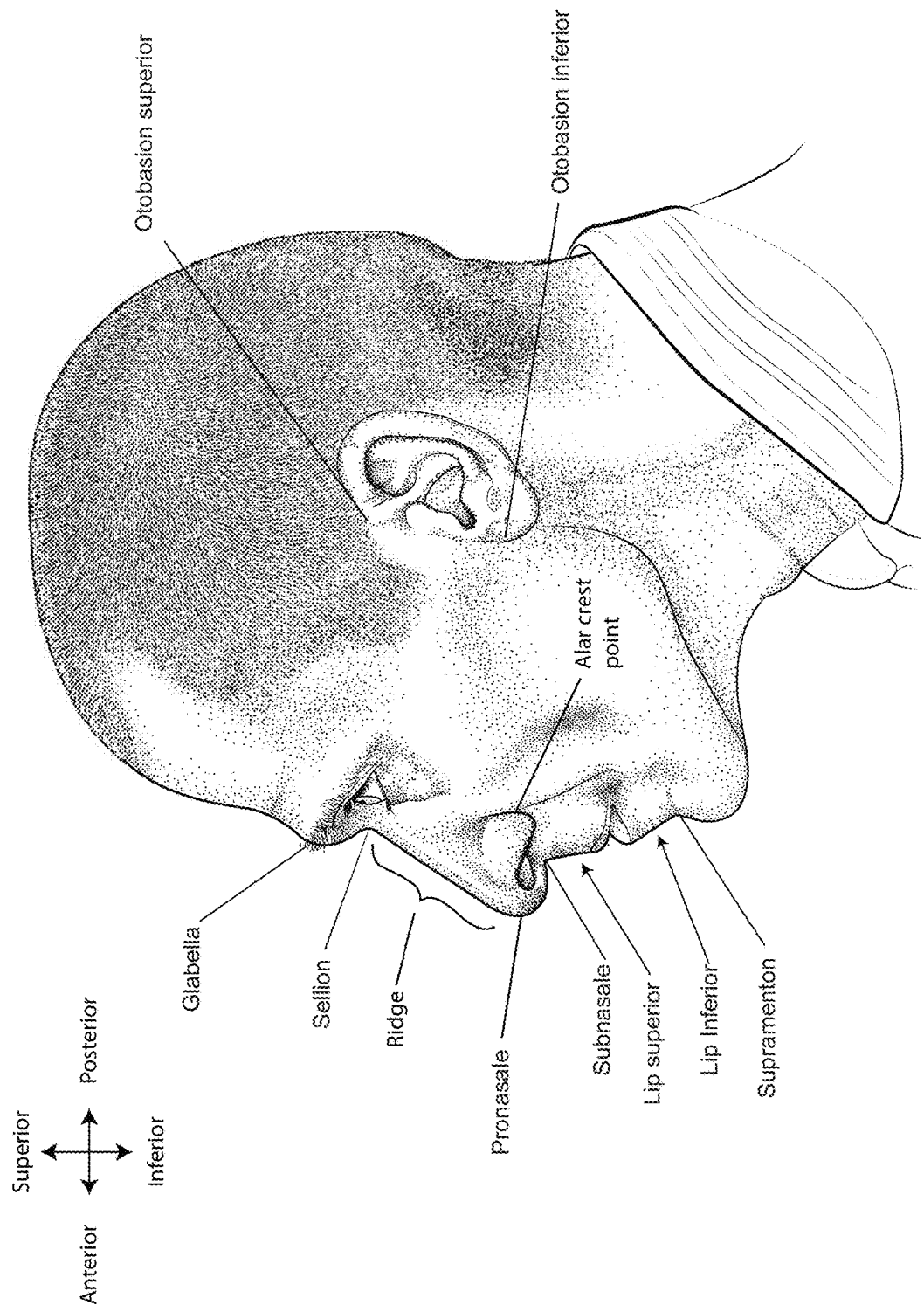

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

FIG. 2e is a further side view of a head. The approximate locations of the Frankfort horizontal and nasolabial angle are indicated.

Figure 2F:
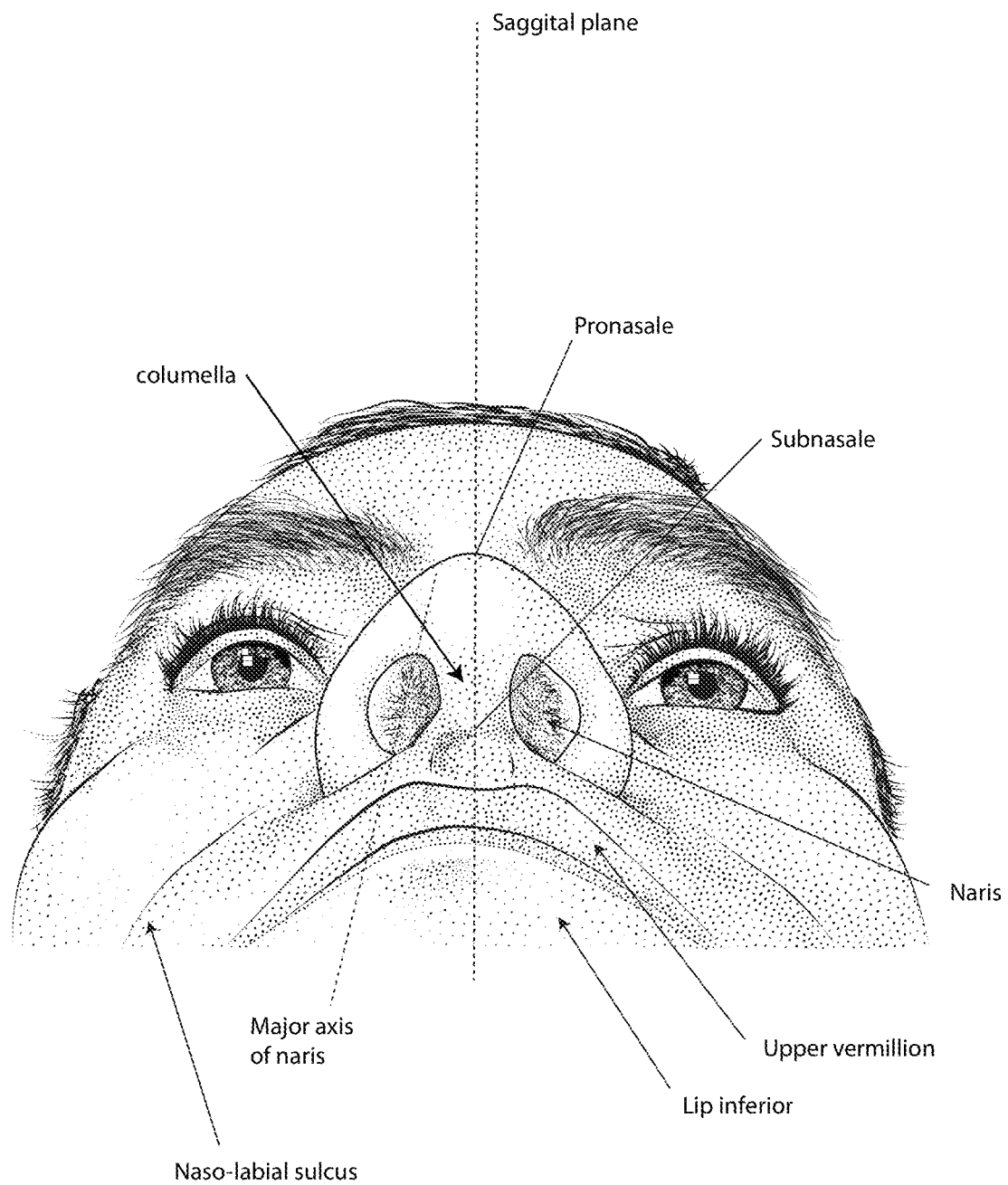

FIG. 2f shows a base view of a nose.

Figure 2I:
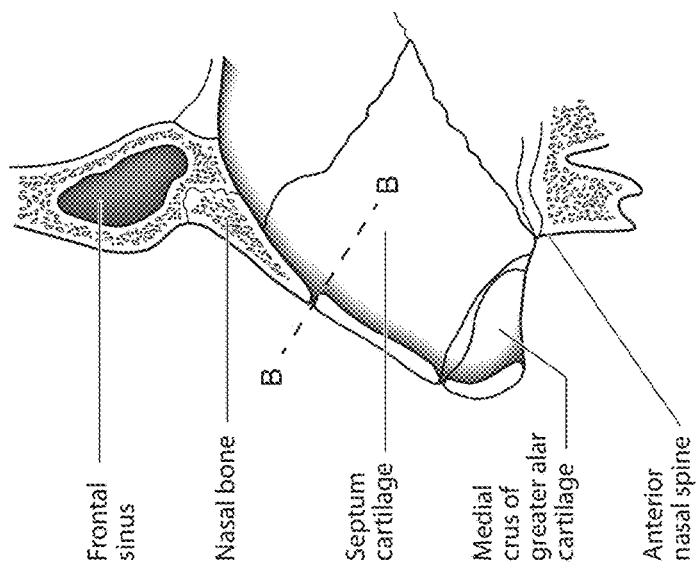
Figure 2H:
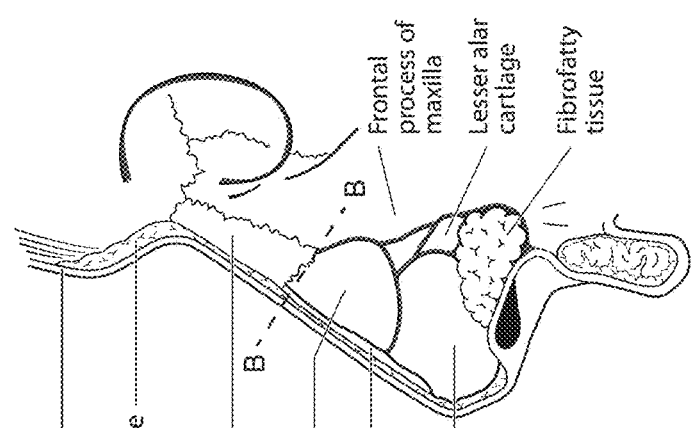
Figure 2G:
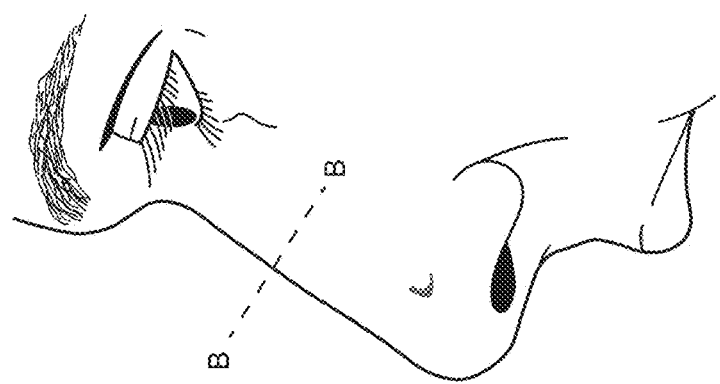

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
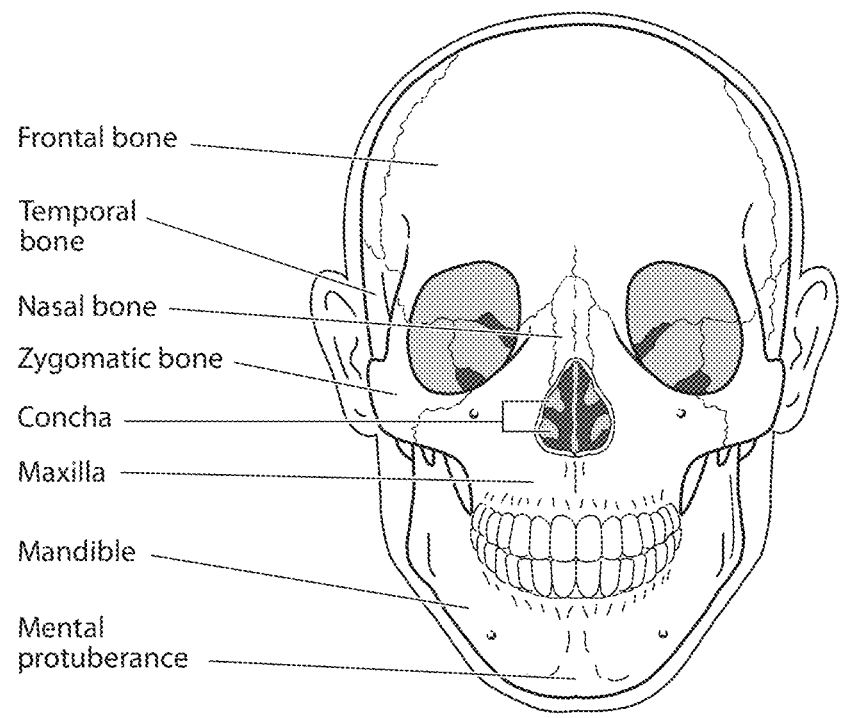

FIG. 2j shows a front view of the bones of a skull including the frontal, temporal, nasal and zygomatic bones. Nasal concha are indicated, as are the maxilla, mandible and mental protuberance.

Figure 2K:
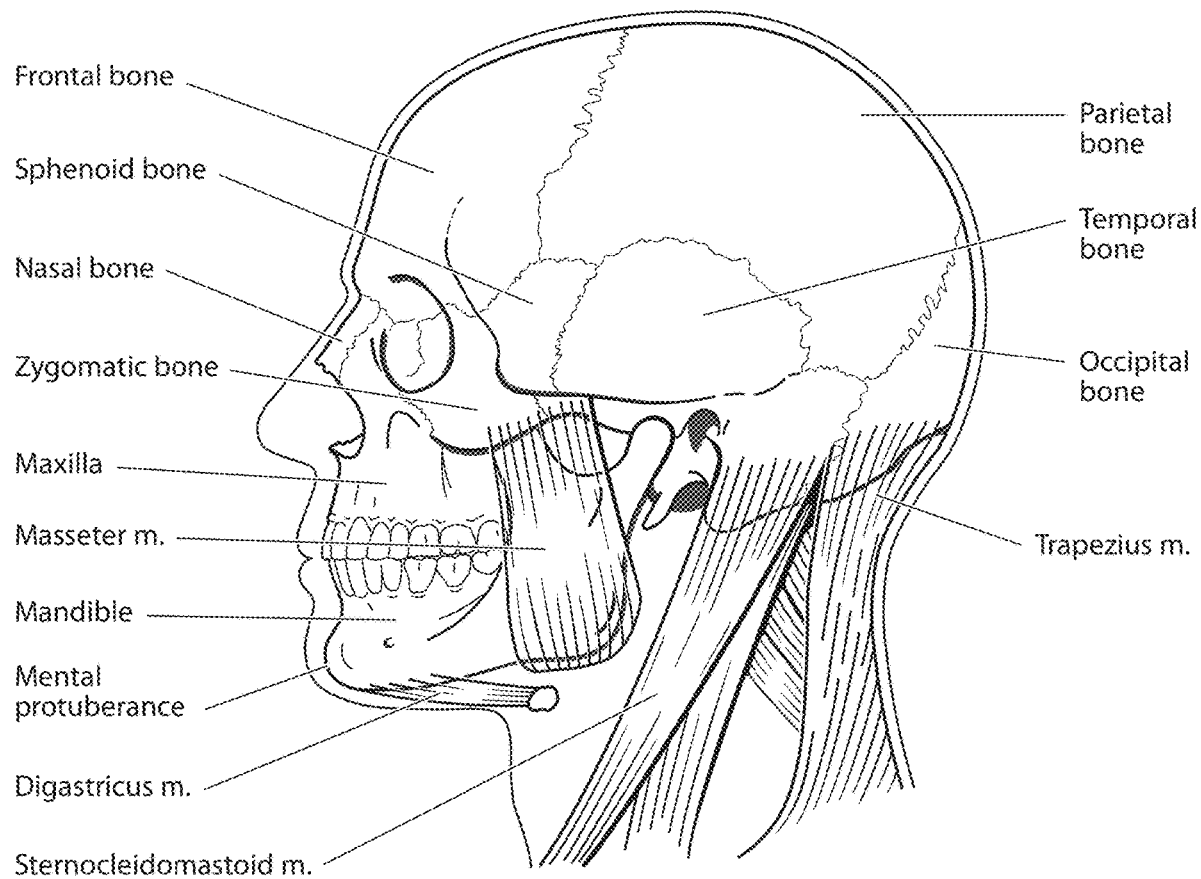
Figure 2I:
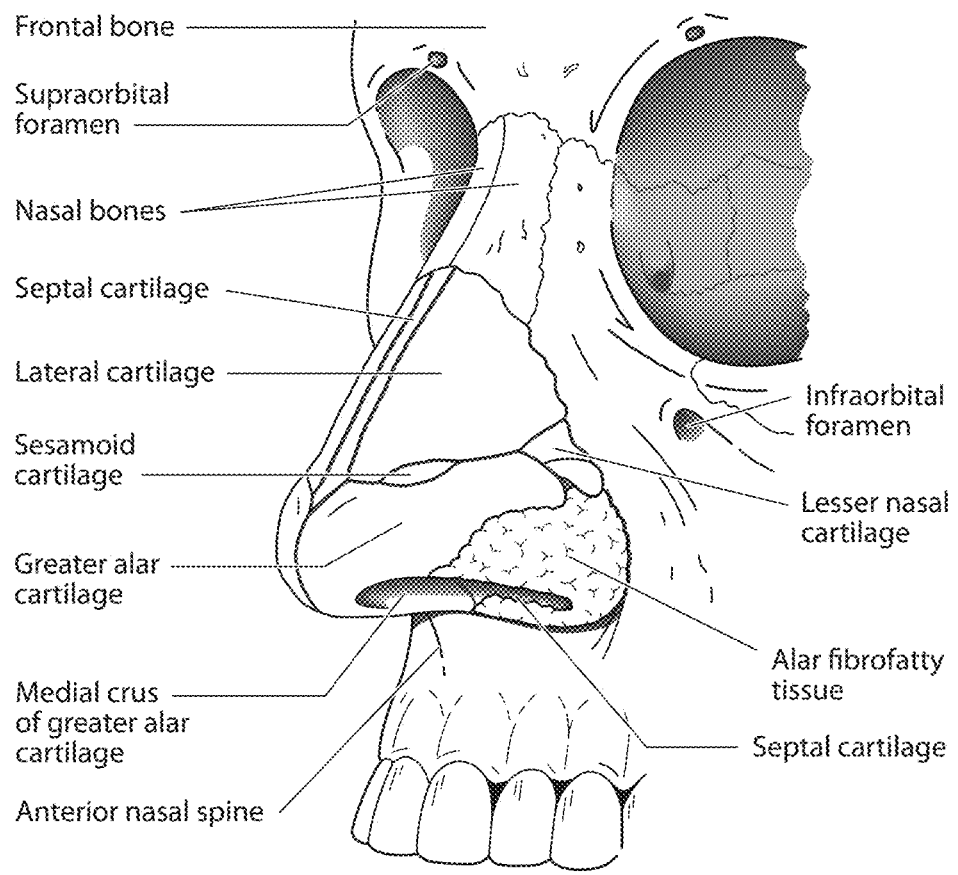

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows anterolateral view of the skull and tissue structures.

4.3 Patient Interface

Figure 3A:
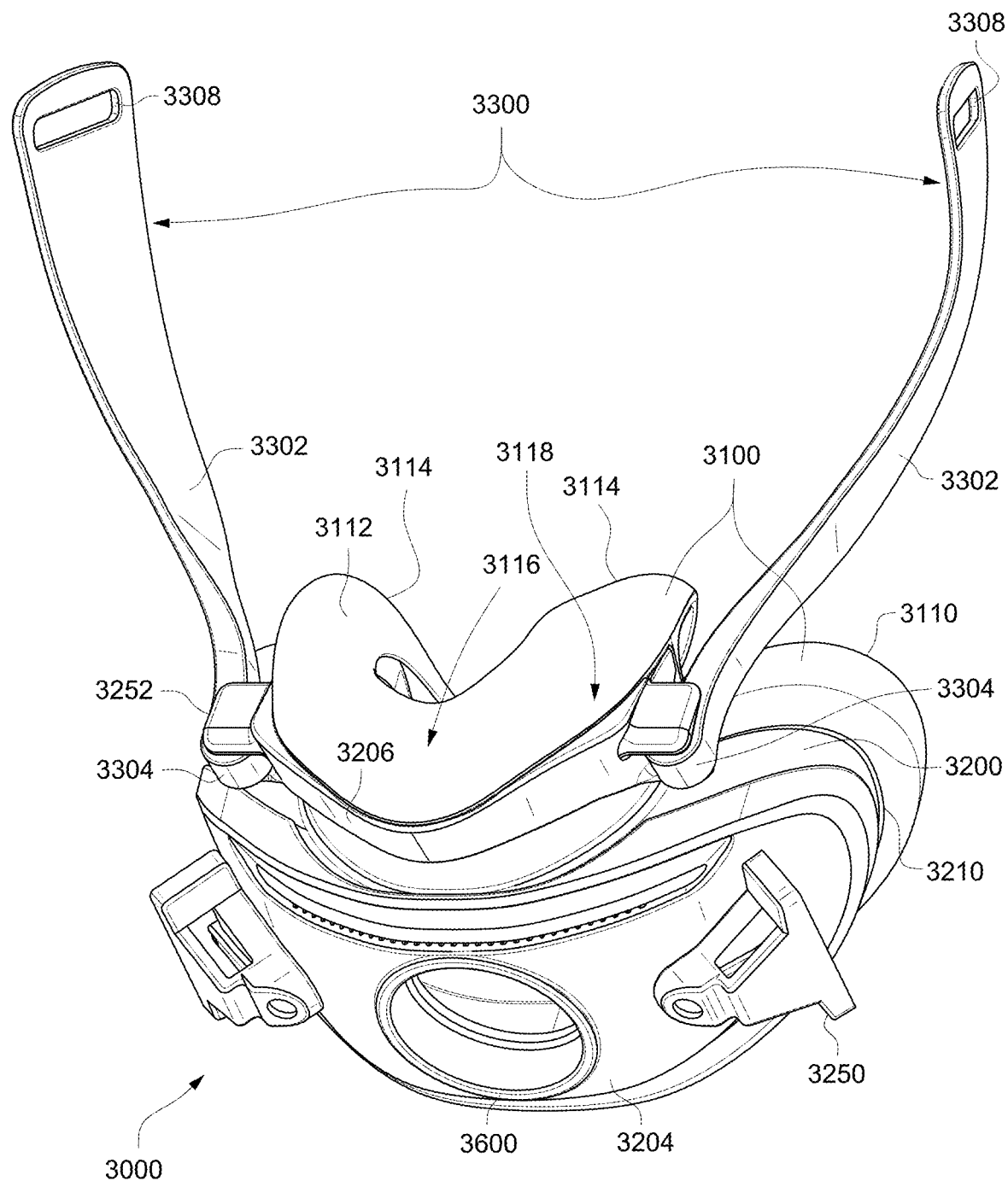

FIG. 3a shows a perspective view of a patient interface in accordance with an example of the present technology.

Figure 3B:
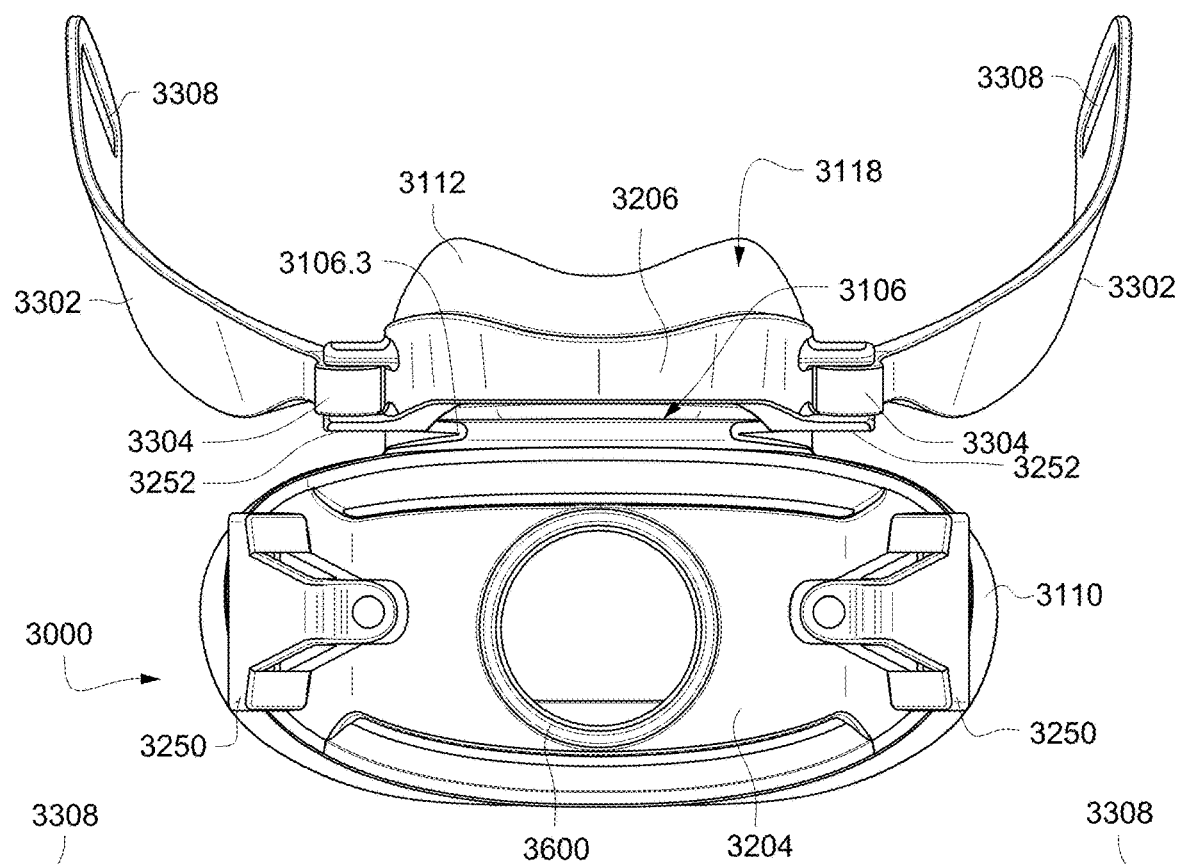

FIG. 3b shows a front view of a patient interface in accordance with an example of the present technology.

Figure 3C:
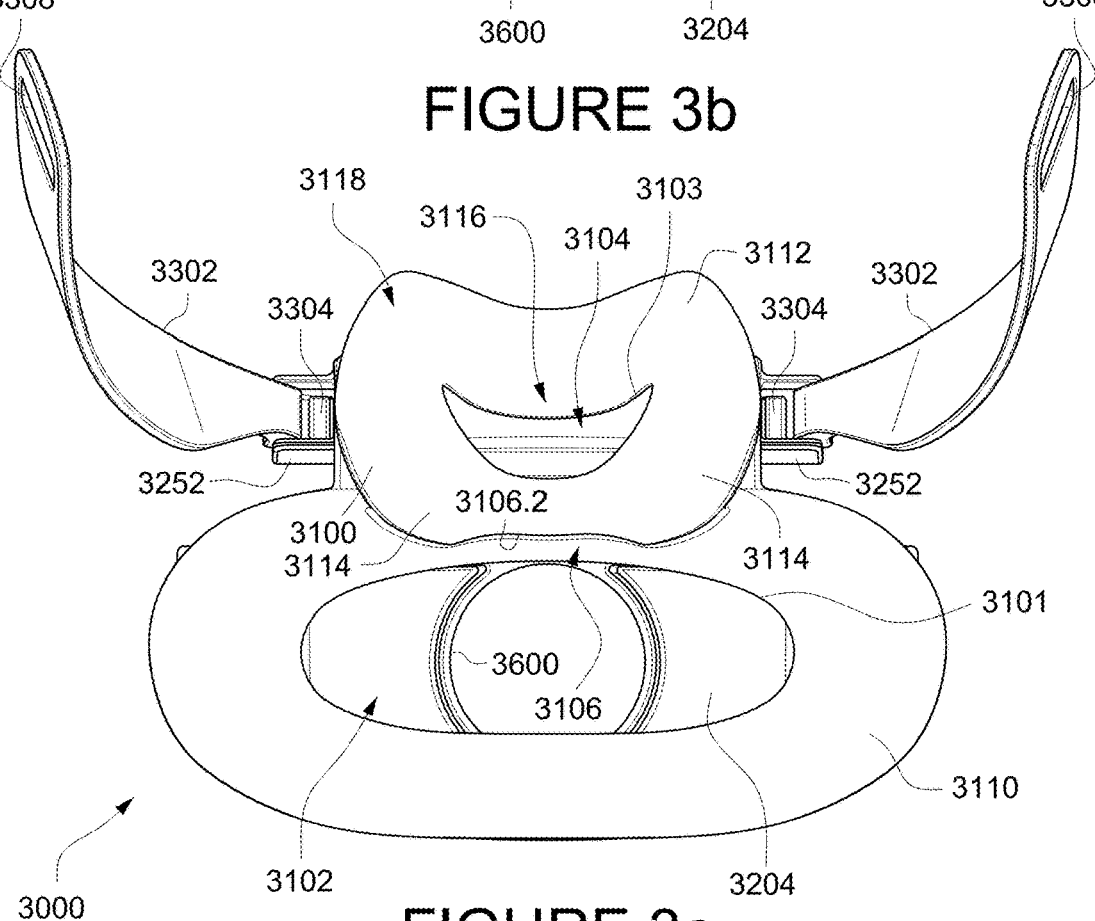

FIG. 3c shows a rear view of a patient interface in accordance with an example of the present technology.

Figure 3D:
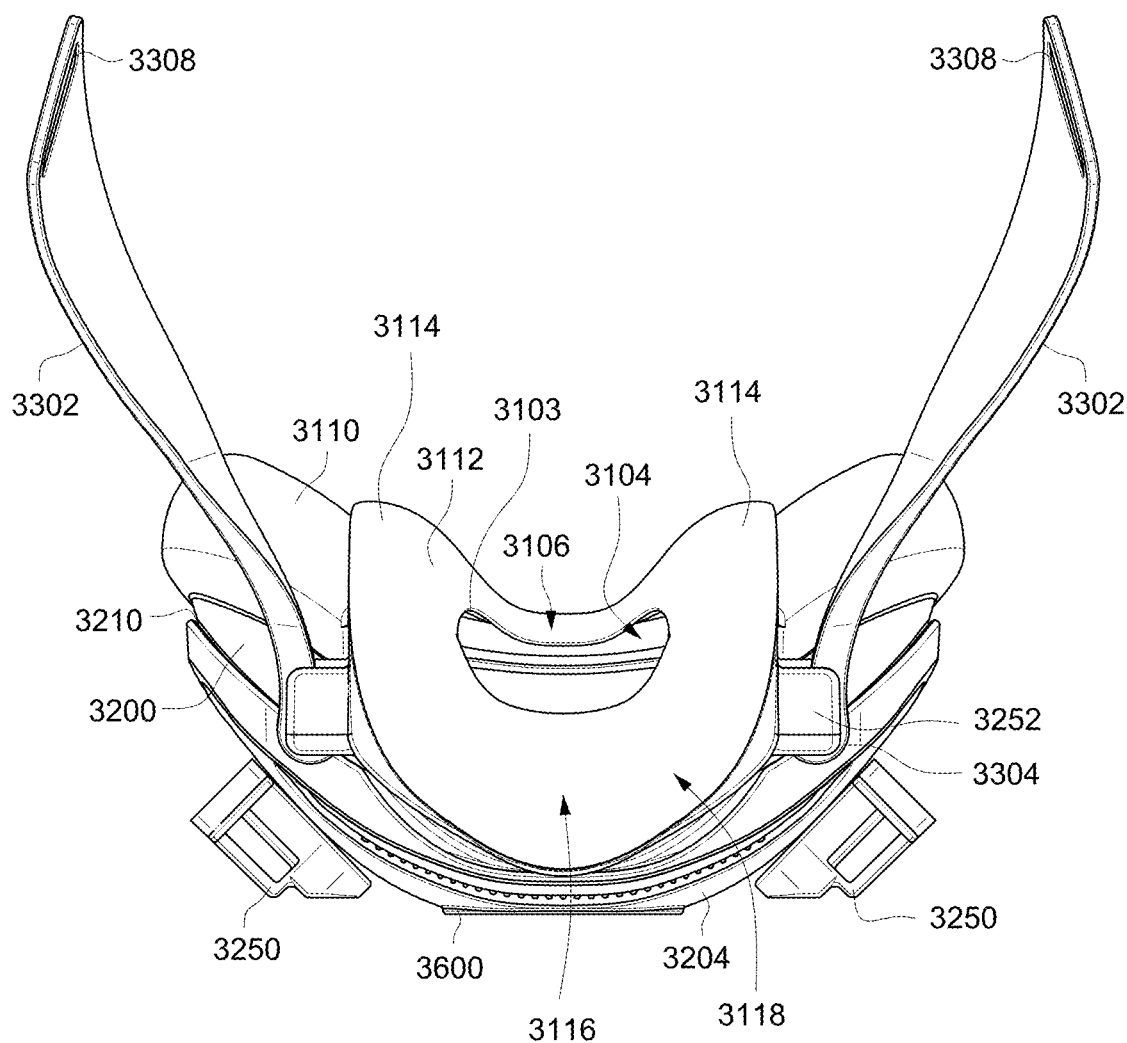

FIG. 3d shows a top view of a patient interface in accordance with an example of the present technology.

Figure 3E:
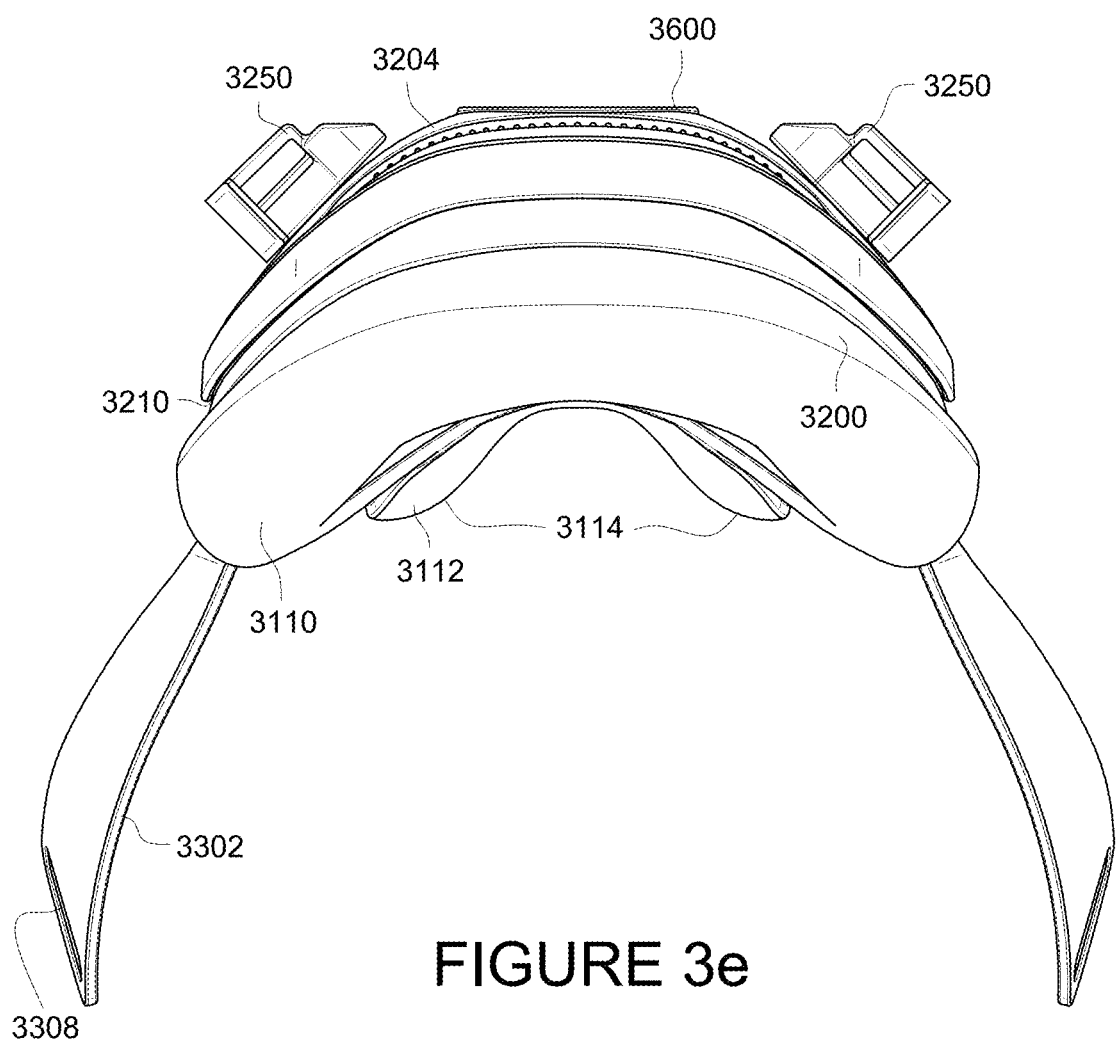

FIG. 3e shows a bottom view of a patient interface in accordance with an example of the present technology.

Figure 3F:
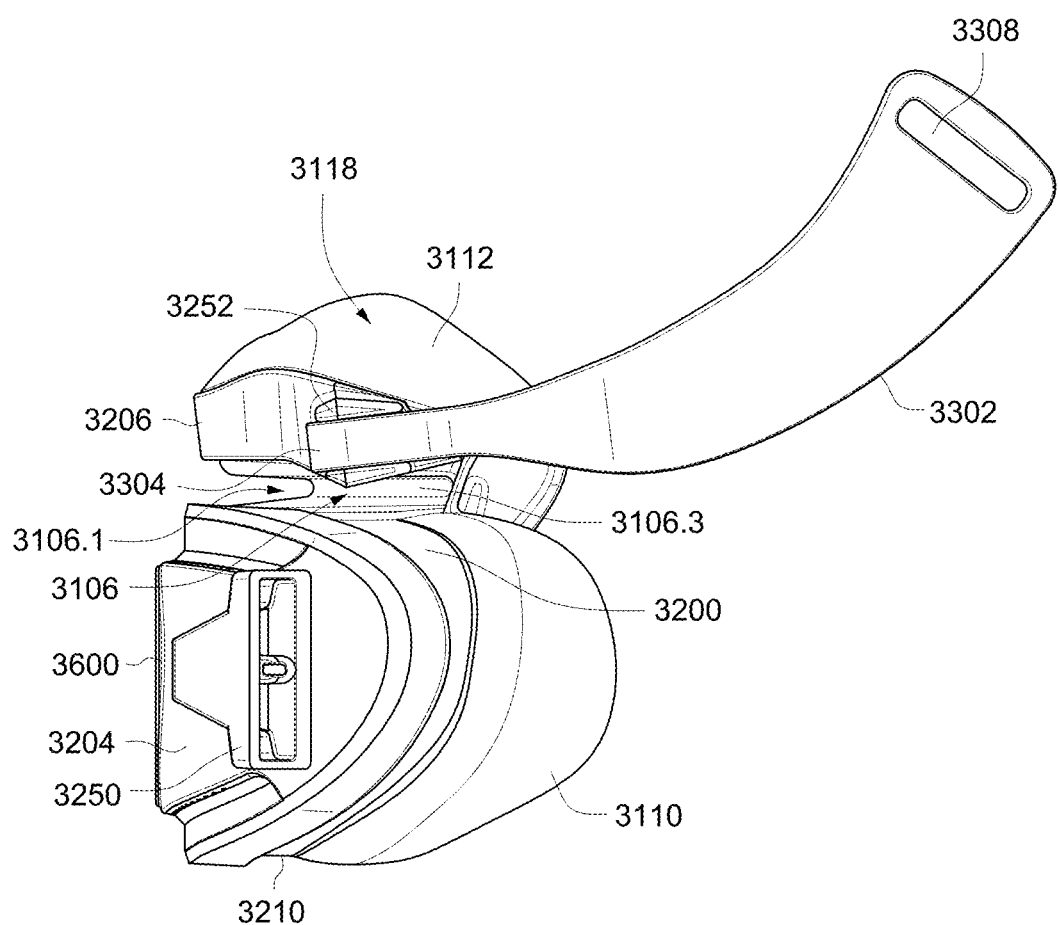

FIG. 3f shows a side view of a patient interface in accordance with an example of the present technology.

Figure 3G:
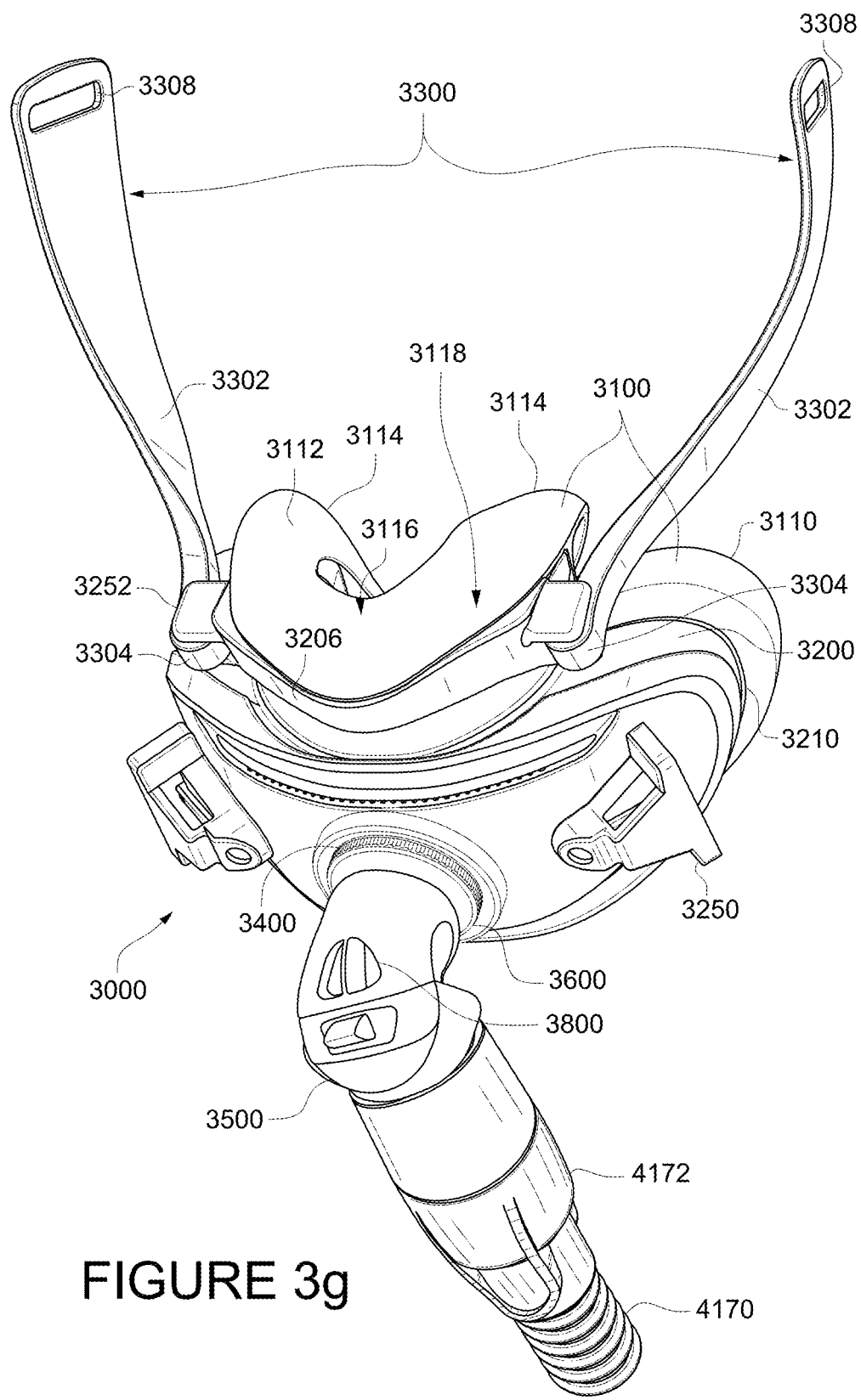

FIG. 3g shows a perspective view of a patient interface including a air circuit in accordance with an example of the present technology.

FIG. 3h shows a rear view of a patient interface including a air circuit in accordance with an example of the present technology.

Figure 3J:
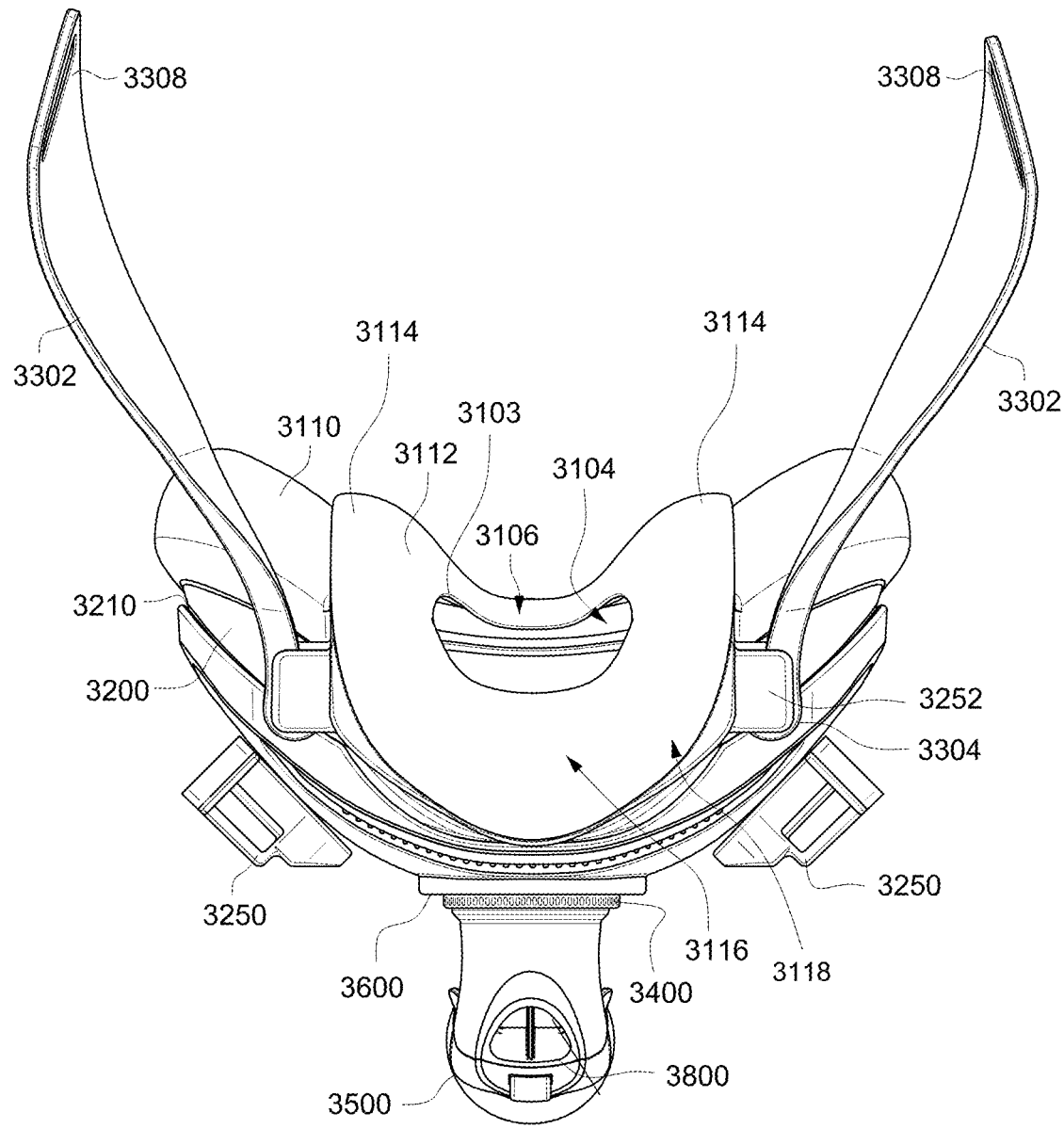
Figure 3K:
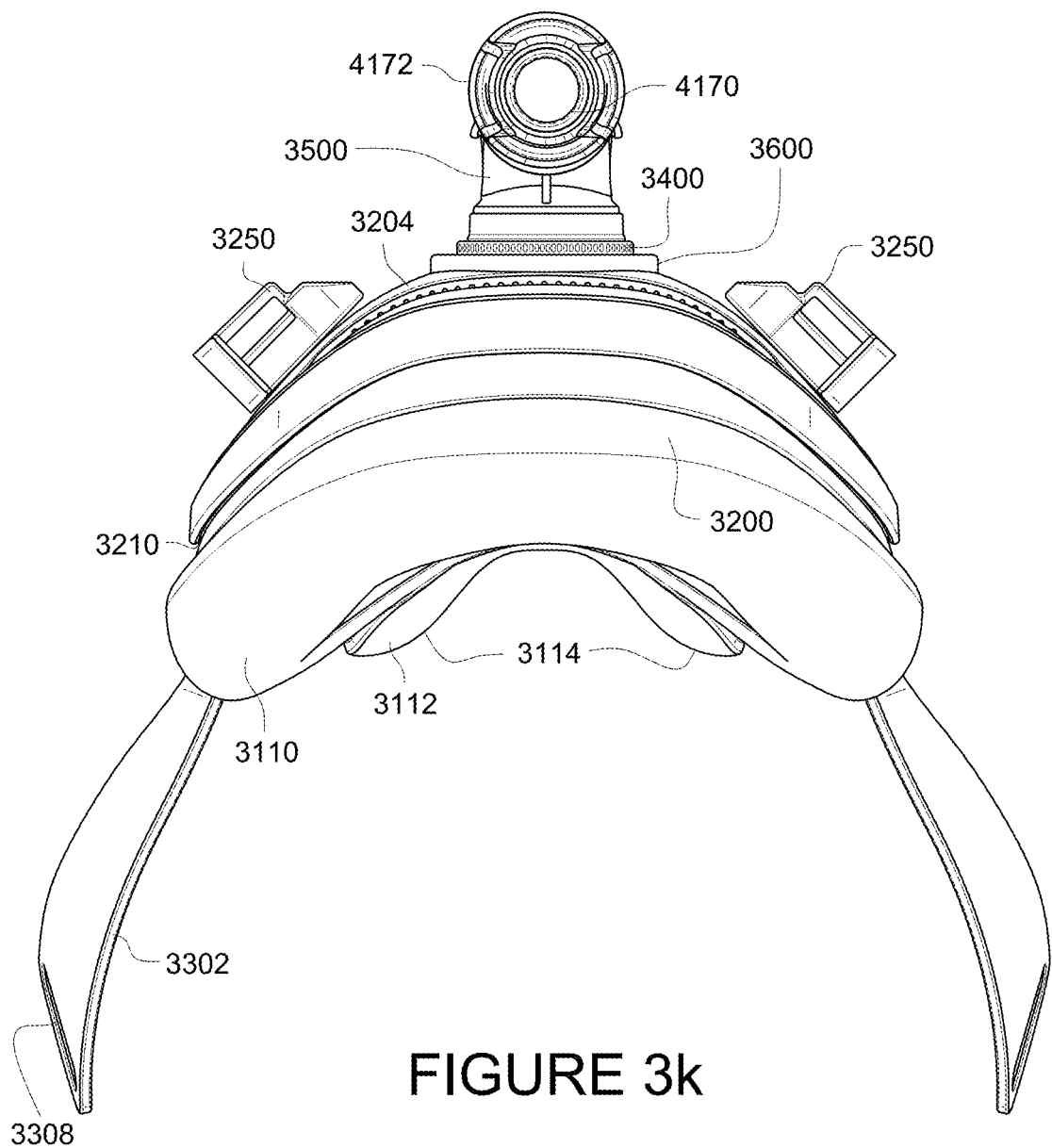
Figure 3I:
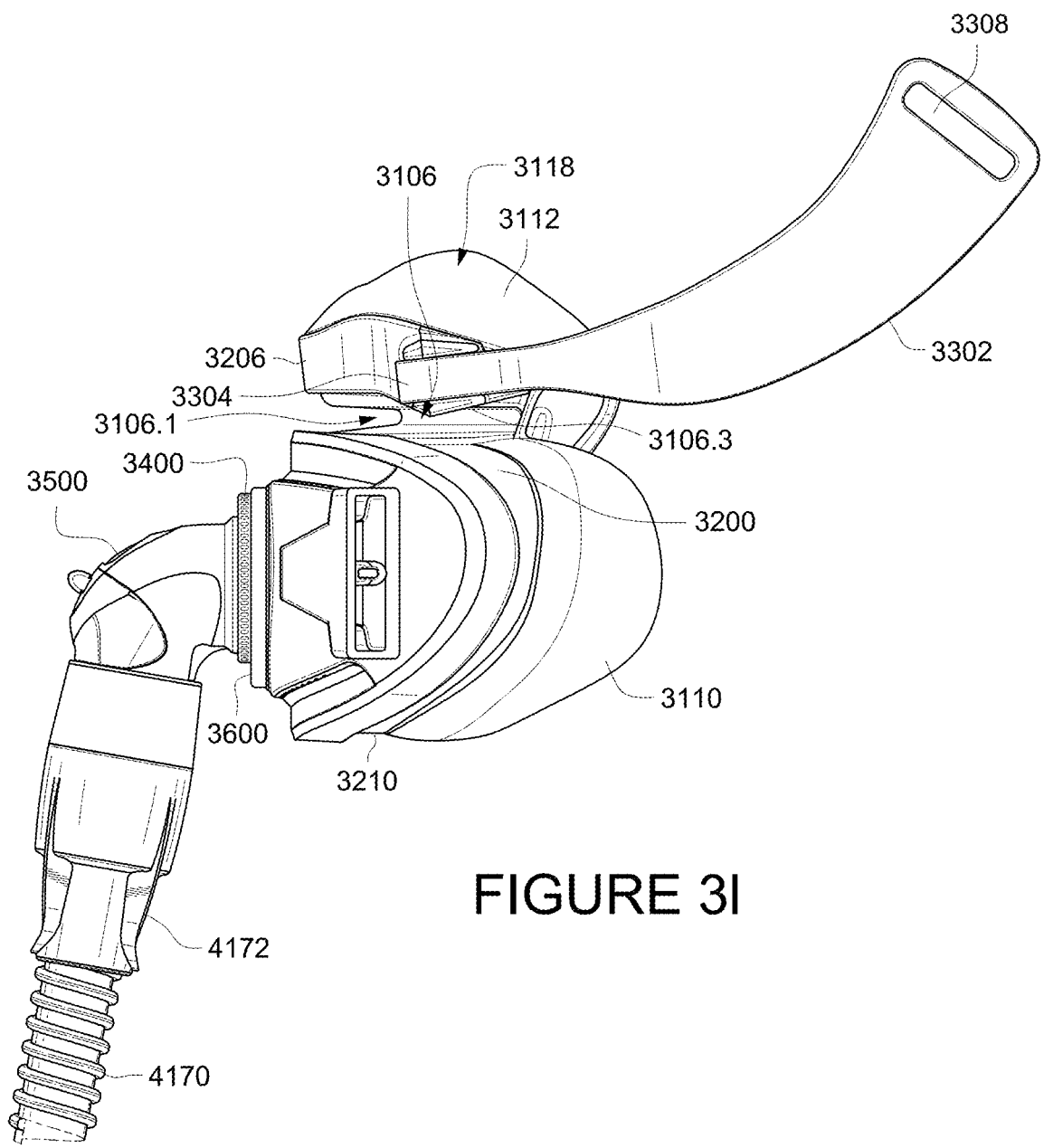

FIG. 3i shows a front view of a patient interface including a air circuit in accordance with an example of the present technology.

FIG. 3j shows a top view of a patient interface including a air circuit in accordance with an example of the present technology.

FIG. 3k shows a bottom view of a patient interface including a air circuit in accordance with an example of the present technology.

FIG. 3l shows a side view of a patient interface including a air circuit in accordance with an example of the present technology.

Figure 3M:
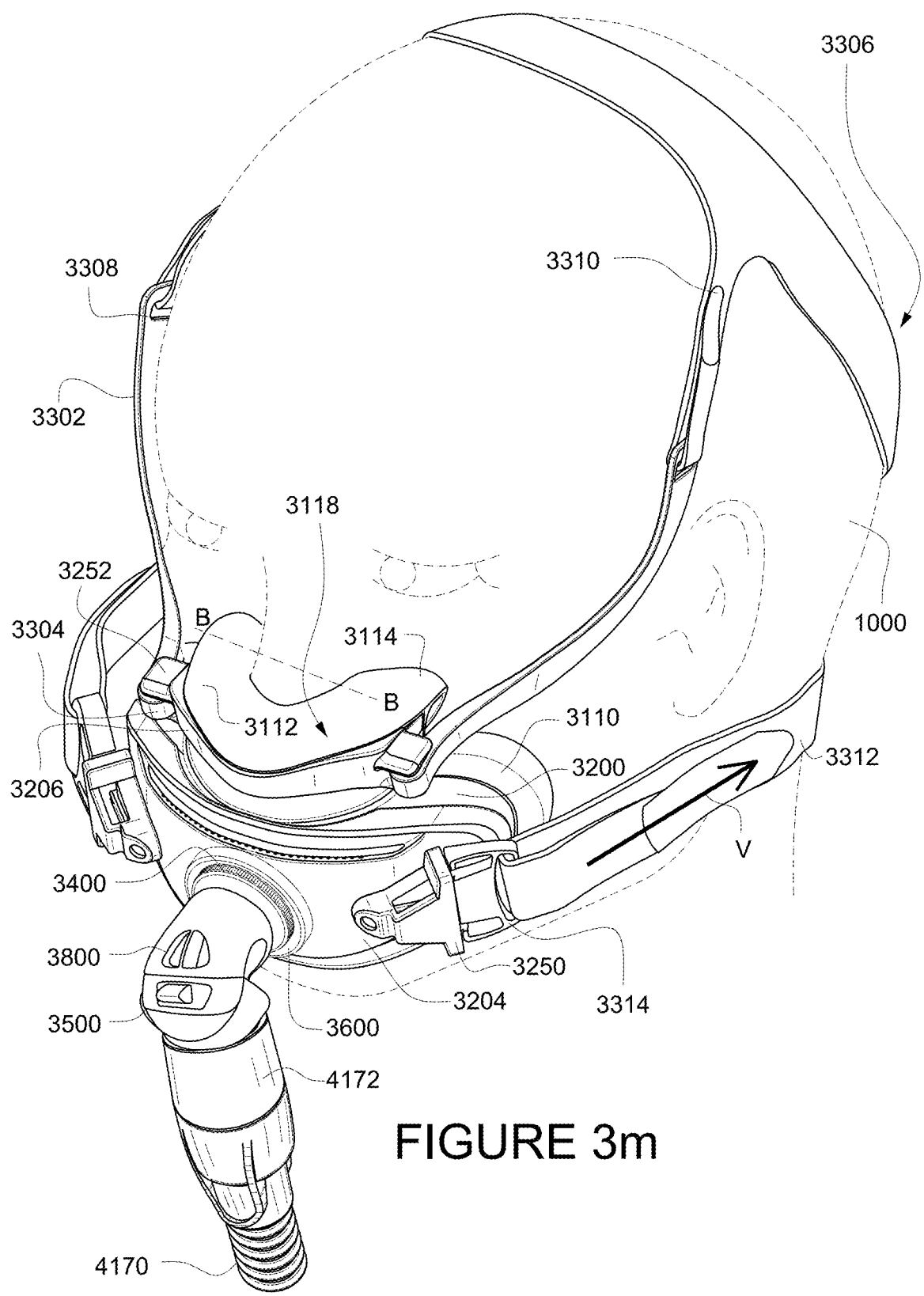

FIG. 3m shows a perspective view of a patient interface including a air circuit donned on a patient in accordance with an example of the present technology.

Figure 3N:
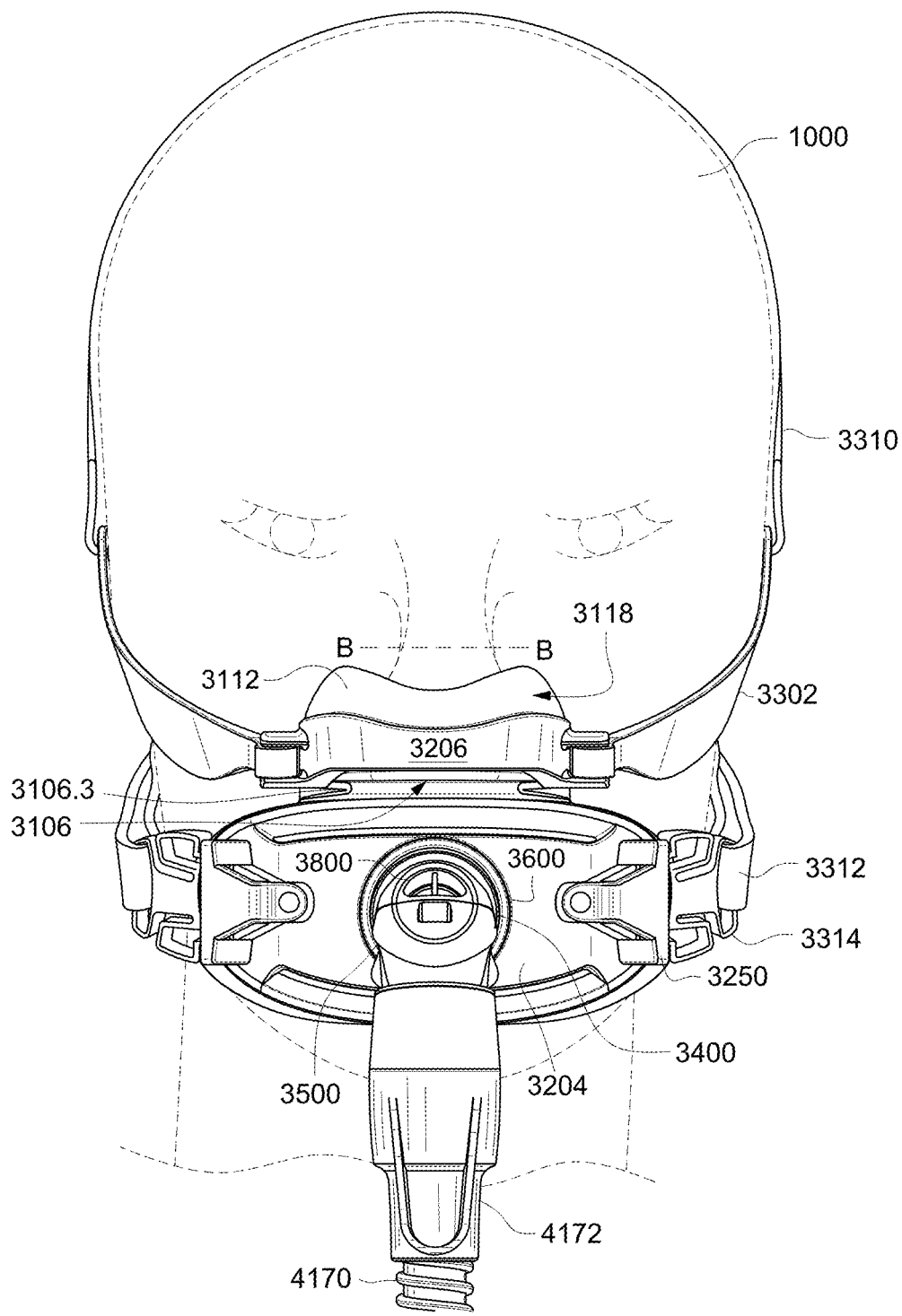

FIG. 3n shows a front view of a patient interface including a air circuit donned on a patient in accordance with an example of the present technology.

Figure 3O:
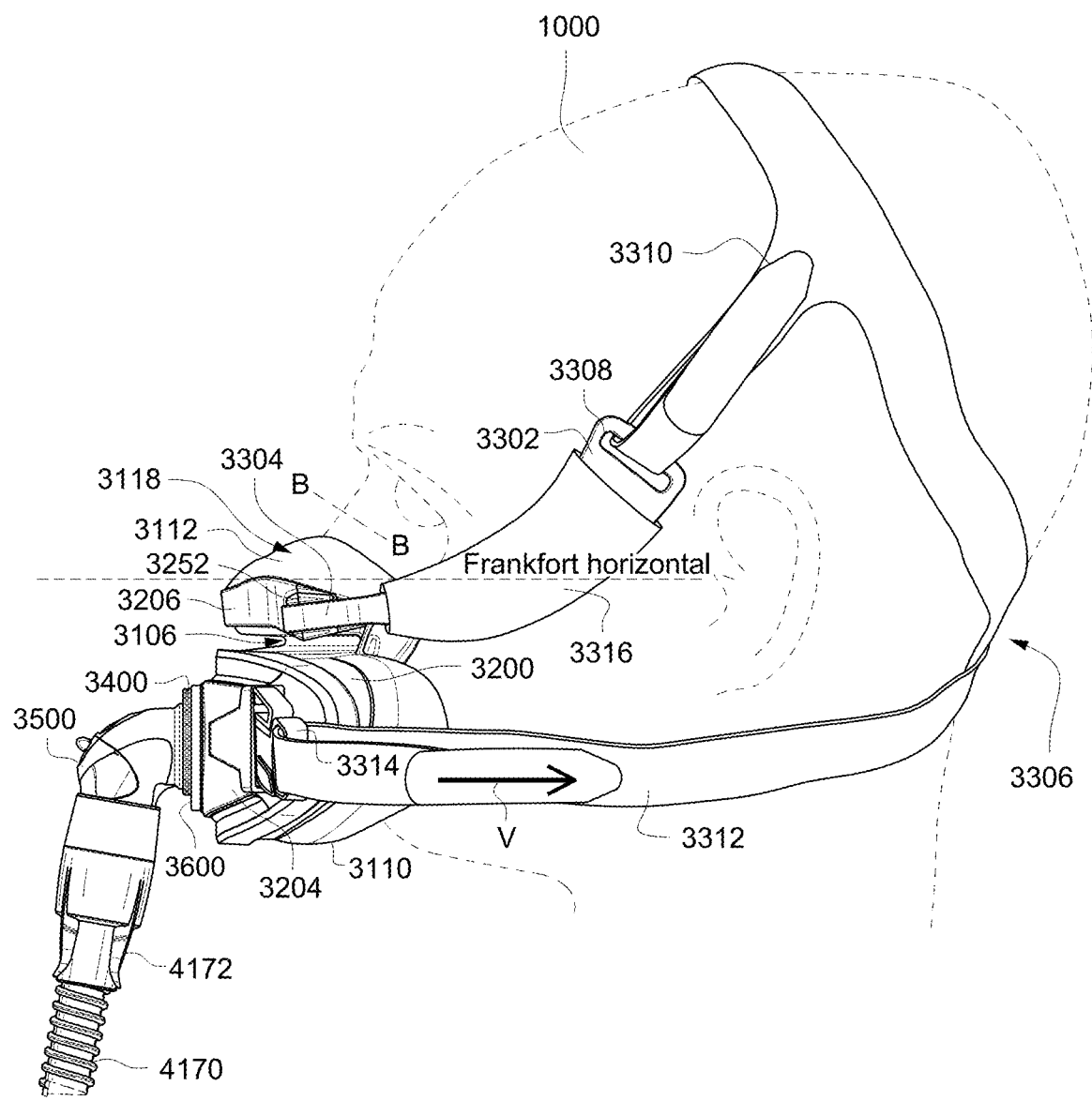

FIG. 3o shows a side view of a patient interface including a air circuit donned on a patient in accordance with an example of the present technology.

Figure 3P:
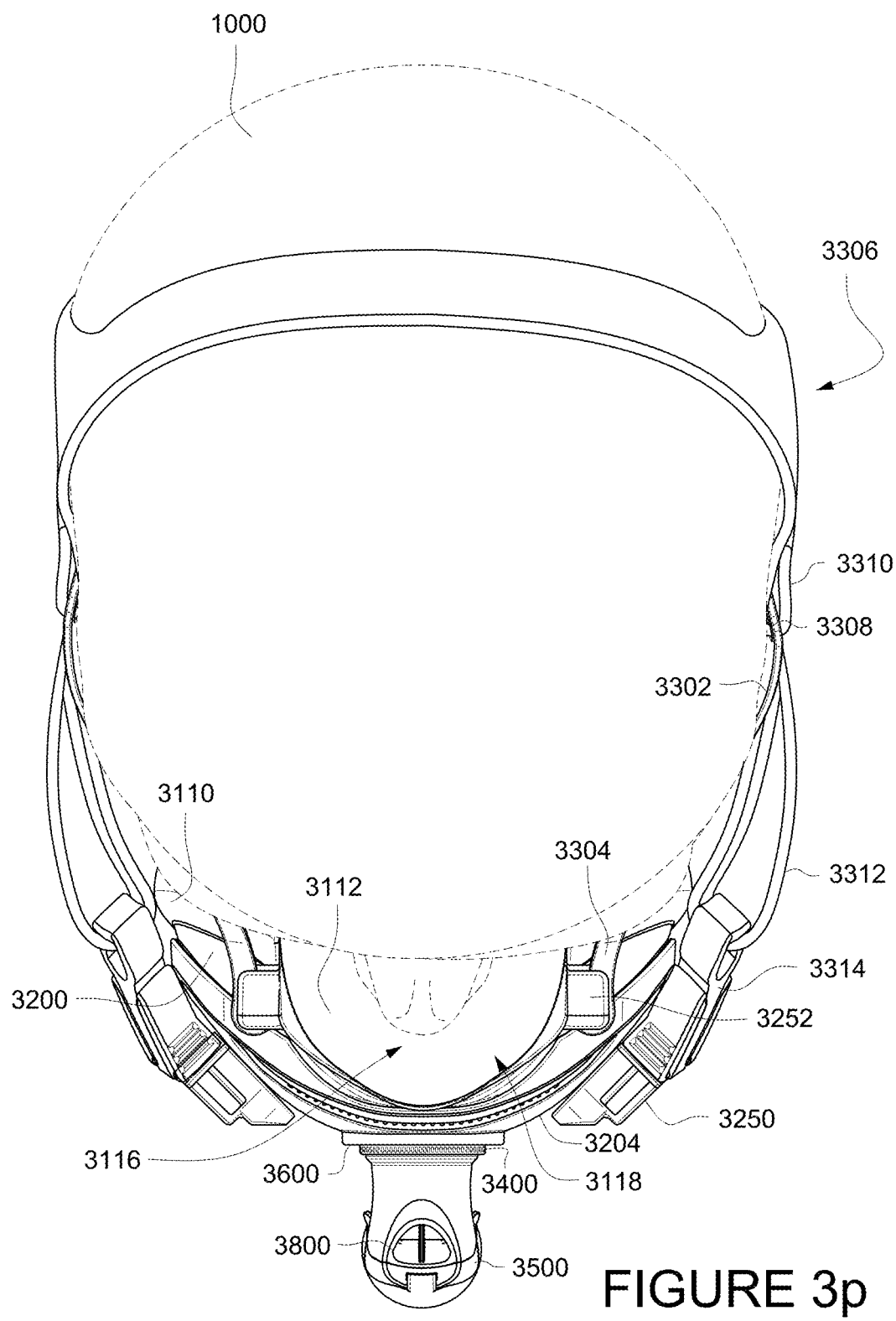

FIG. 3p shows a top view of a patient interface including a air circuit donned on a patient in accordance with an example of the present technology.

Figure 3Q:
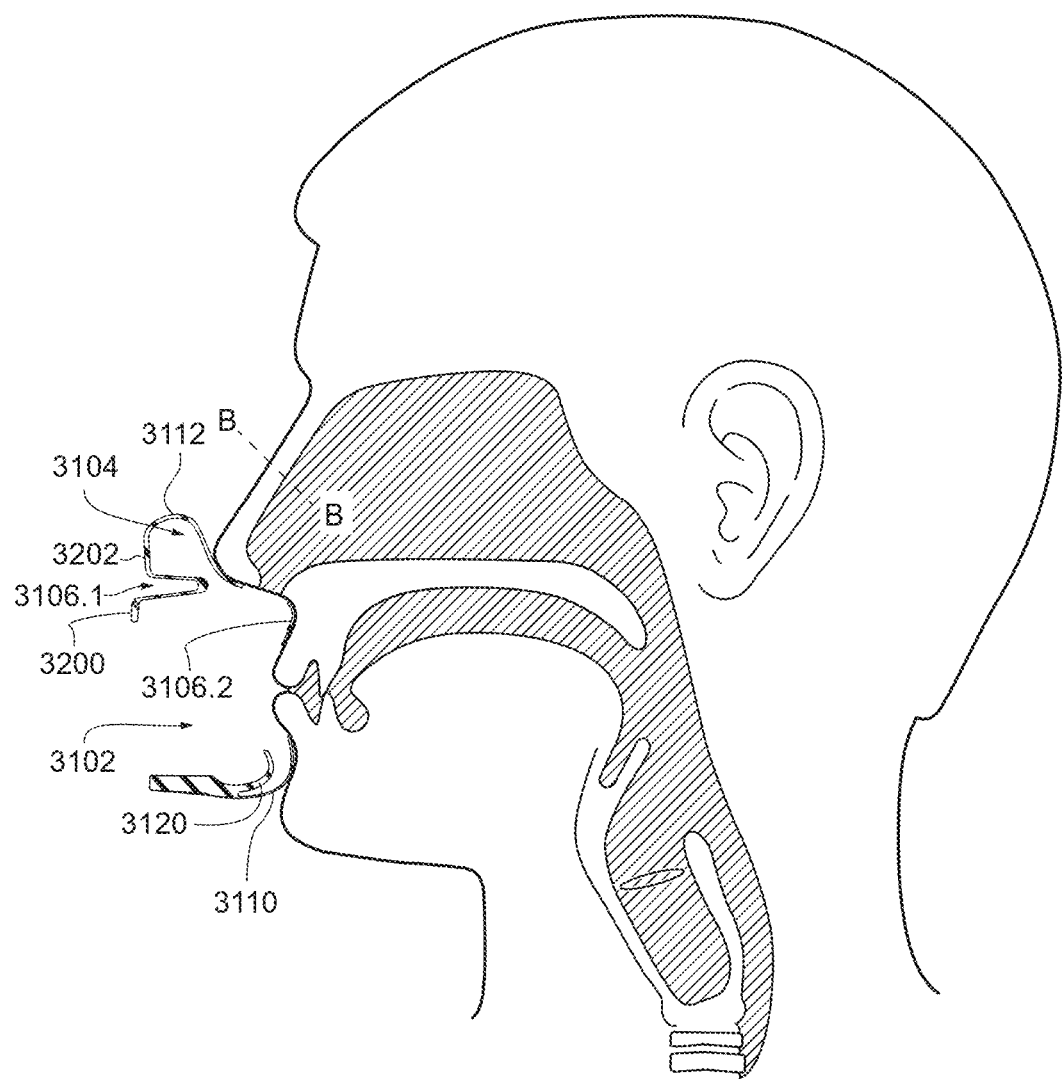

FIG. 3q shows a side cross-sectional view of a patient interface according to an example of the present technology with the patient interface located against the face of a patient. The patient is shown with a cross-section of the airways.

Figure 3R:
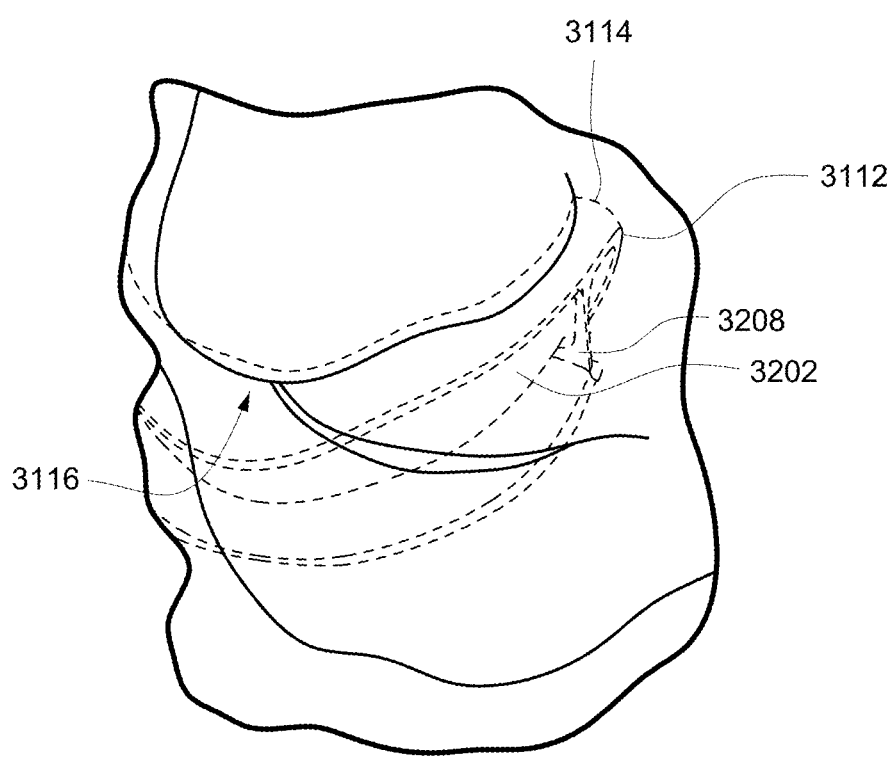

FIG. 3r shows a detailed front perspective view of a portion of a patient interface according to an example of the present technology. The patient interface is shown in dashed lines and the nose, mouth, and chin of the patient are shown in solid lines.

Figure 3S:
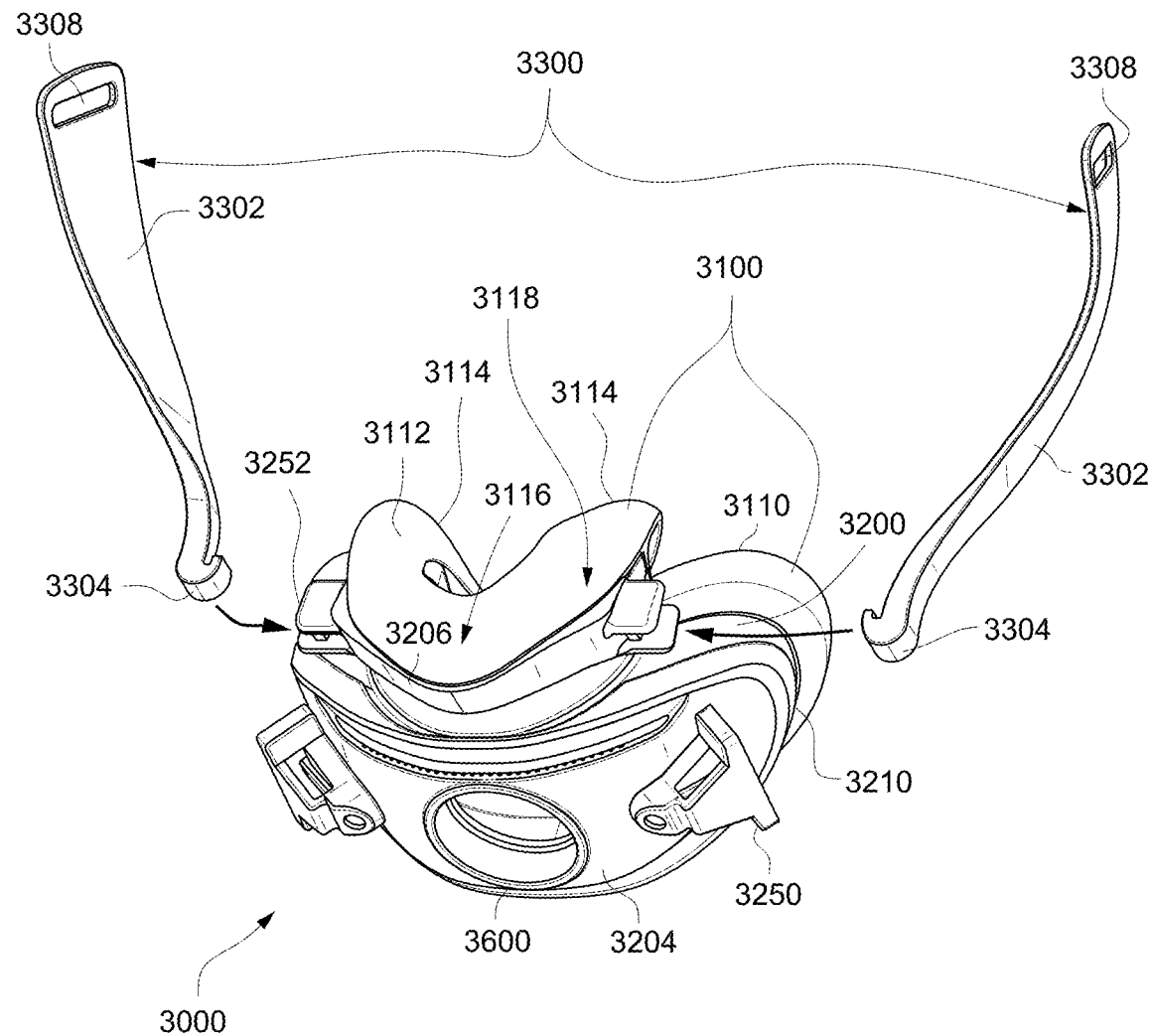

FIG. 3s shows an exploded perspective view of a patient interface in accordance with an example of the present technology.

Figure 3T:
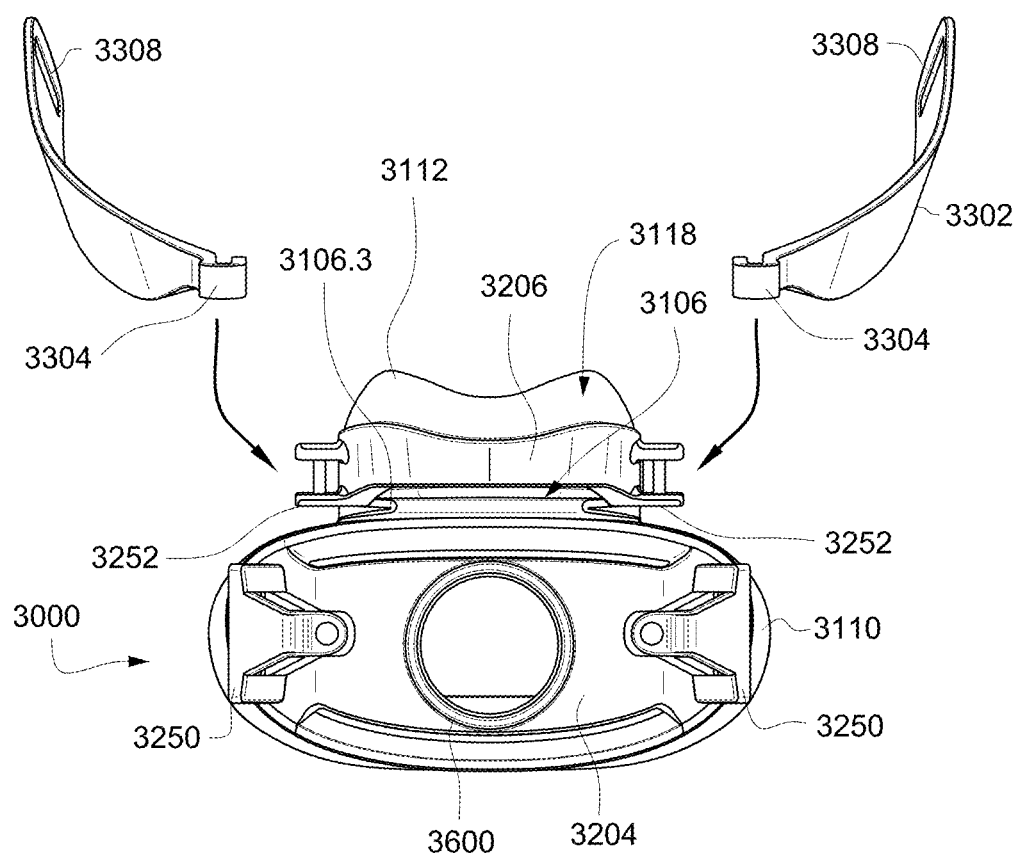

FIG. 3t shows an exploded front view of a patient interface in accordance with an example of the present technology.

Figure 3U:
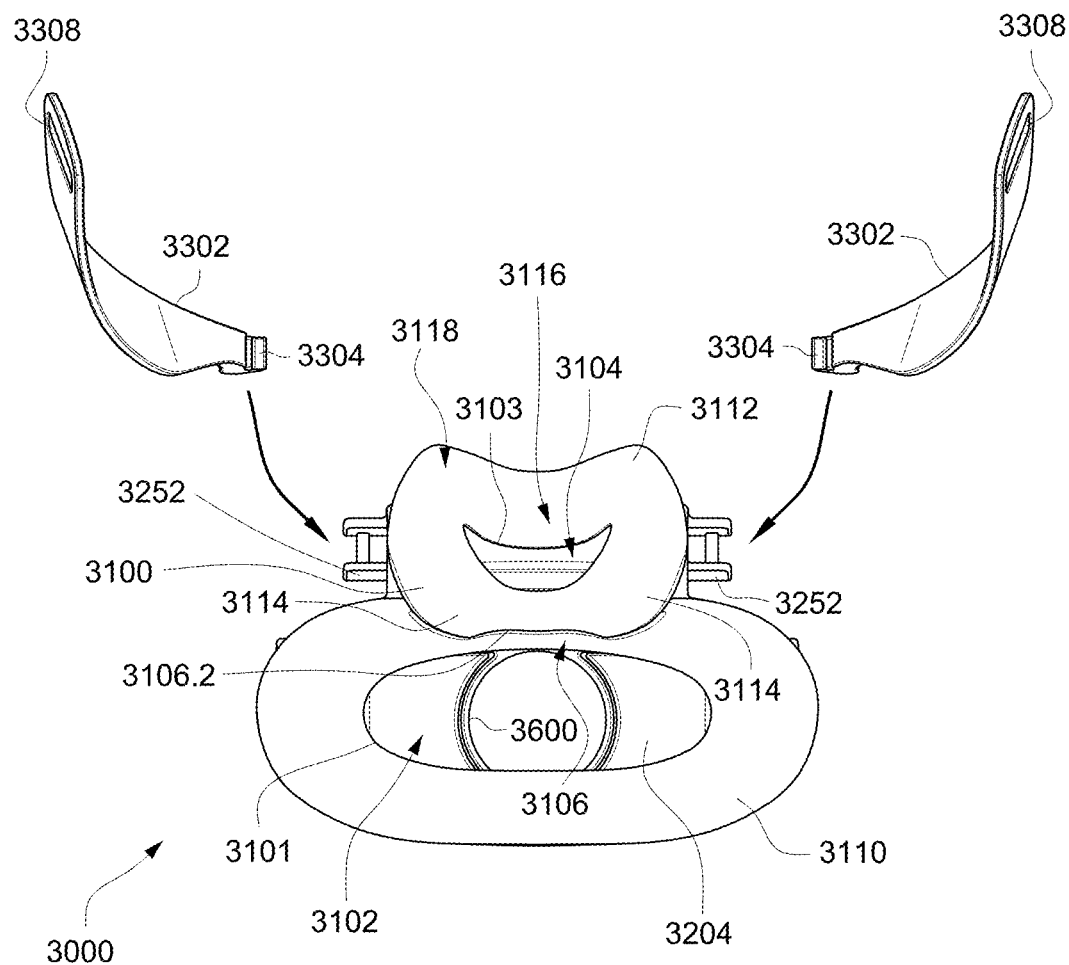

FIG. 3u shows an exploded rear view of a patient interface in accordance with an example of the present technology.

Figure 4A:
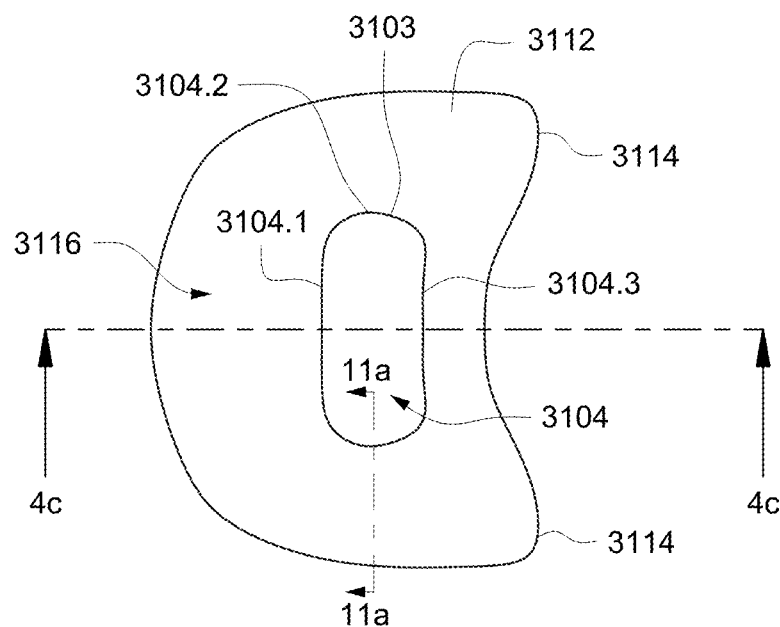

FIG. 4a shows a top view of a nasal cradle cushion of a patient interface in accordance with an example of the present technology.

Figure 4B:
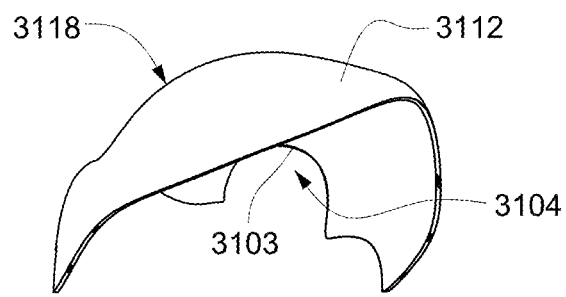

FIG. 4b shows a bottom cross-sectional view taken through line 4c-4c of FIG. 4a of a nasal cradle cushion of a patient interface in accordance with an example of the present technology.

Figure 4C:
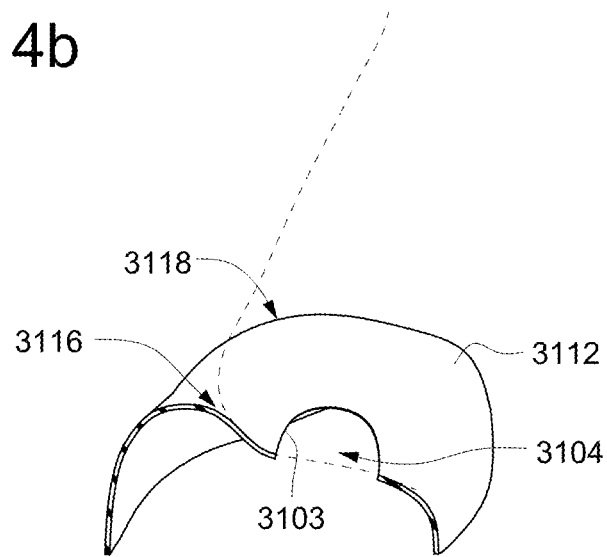

FIG. 4c shows a side cross-sectional view taken through line 4c-4c of FIG. 4a of a nasal cradle cushion of a patient interface in accordance with an example of the present technology. A patient's nose is shown in dashed lines.

Figure 5A:
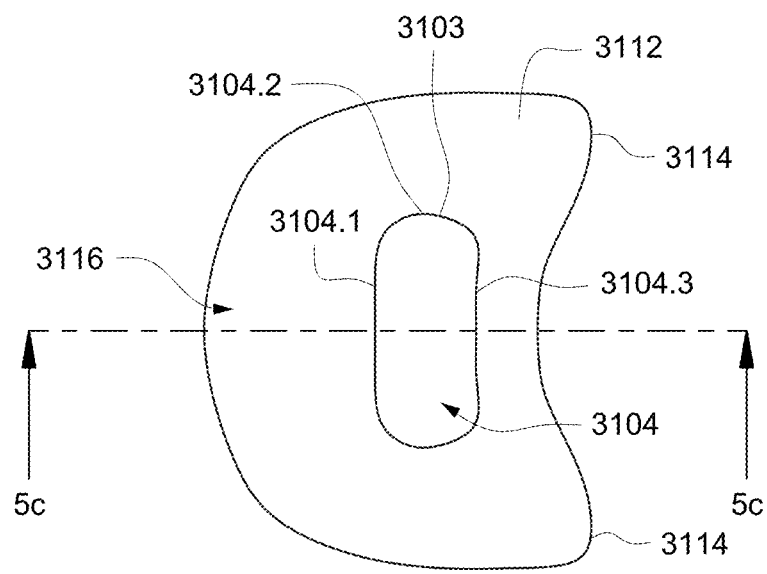

FIG. 5a shows a top view of another nasal cradle cushion of a patient interface in accordance with another example of the present technology.

Figure 5B:
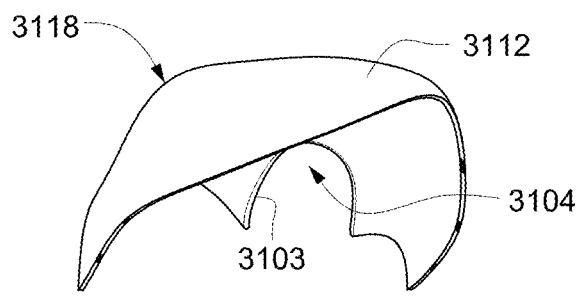

FIG. 5b shows a bottom cross-sectional view taken through line 5c-5c of FIG. 5a of another nasal cradle cushion of a patient interface in accordance with another example of the present technology.

Figure 5C:
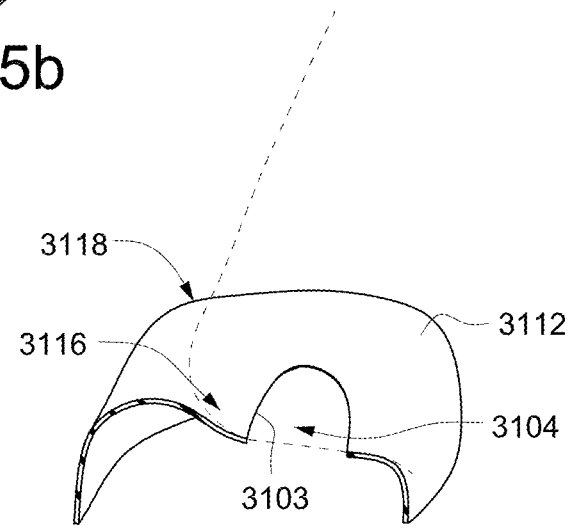

FIG. 5c shows a side cross-sectional view taken through line 5c-5c of FIG. 5a of another nasal cradle cushion of a patient interface in accordance with an example of the present technology. A patient's nose is shown in dashed lines.

Figure 6A:
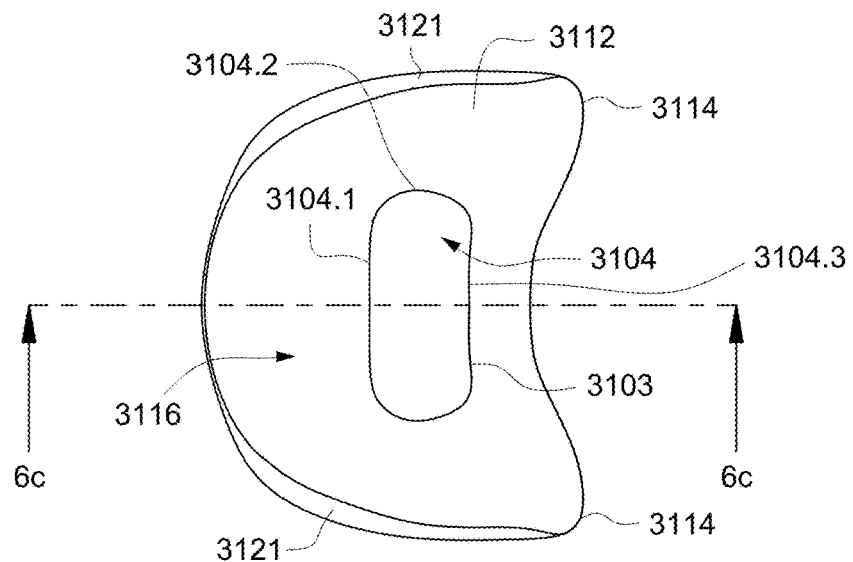

FIG. 6a shows a top view of another nasal cradle cushion of a patient interface in accordance with another example of the present technology.

Figure 6B:
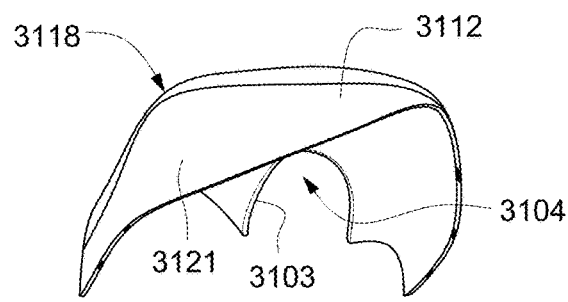

FIG. 6b shows a bottom cross-sectional view taken through line 6c-6c of FIG. 6a of another nasal cradle cushion of a patient interface in accordance with another example of the present technology.

Figure 6C:
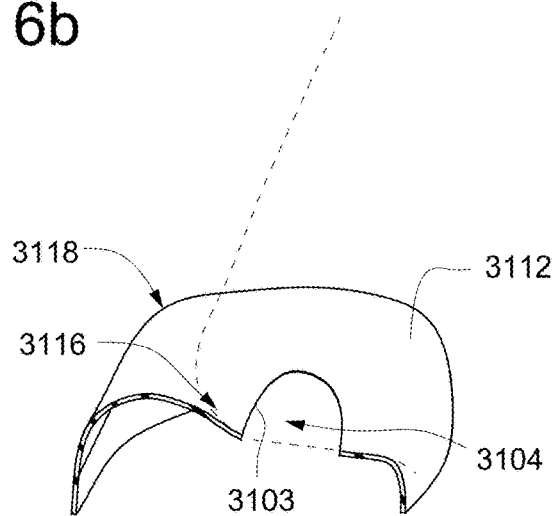

FIG. 6c shows a side cross-sectional view taken through line 6c-6c of FIG. 6a of another nasal cradle cushion of a patient interface in accordance with another example of the present technology. A patient's nose is shown in dashed lines.

Figure 7A:
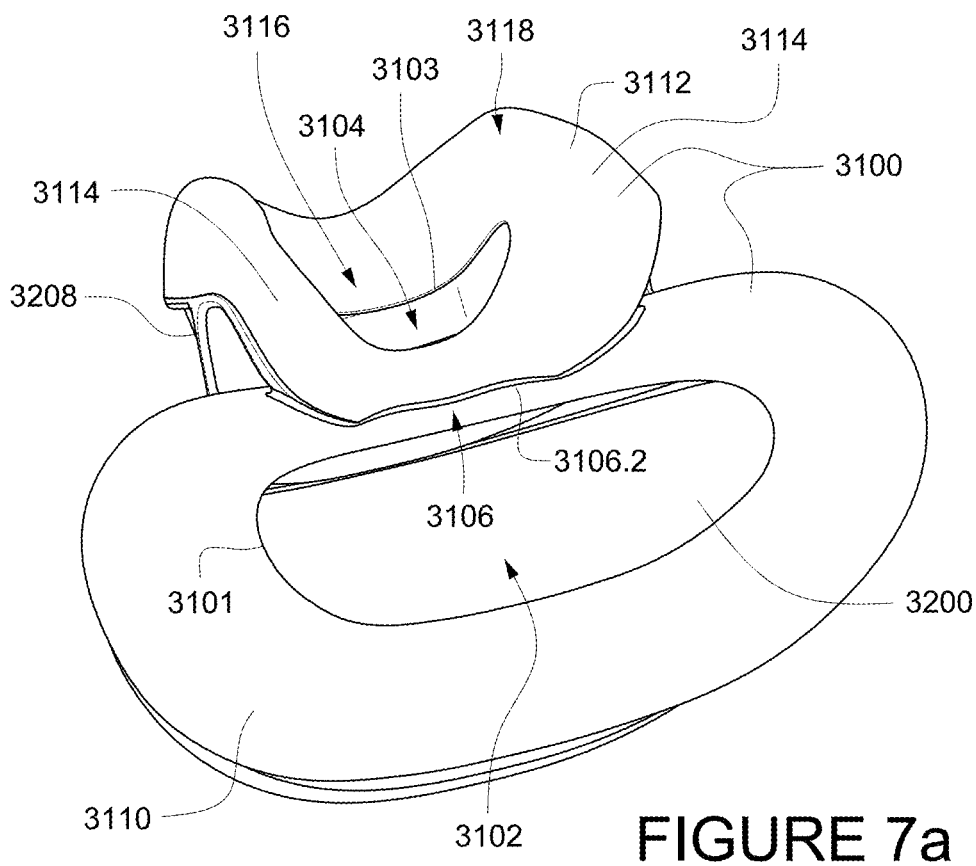

FIG. 7a shows a rear perspective view of a plenum chamber assembly of a patient interface in accordance with an example of the present technology.

Figure 7B:
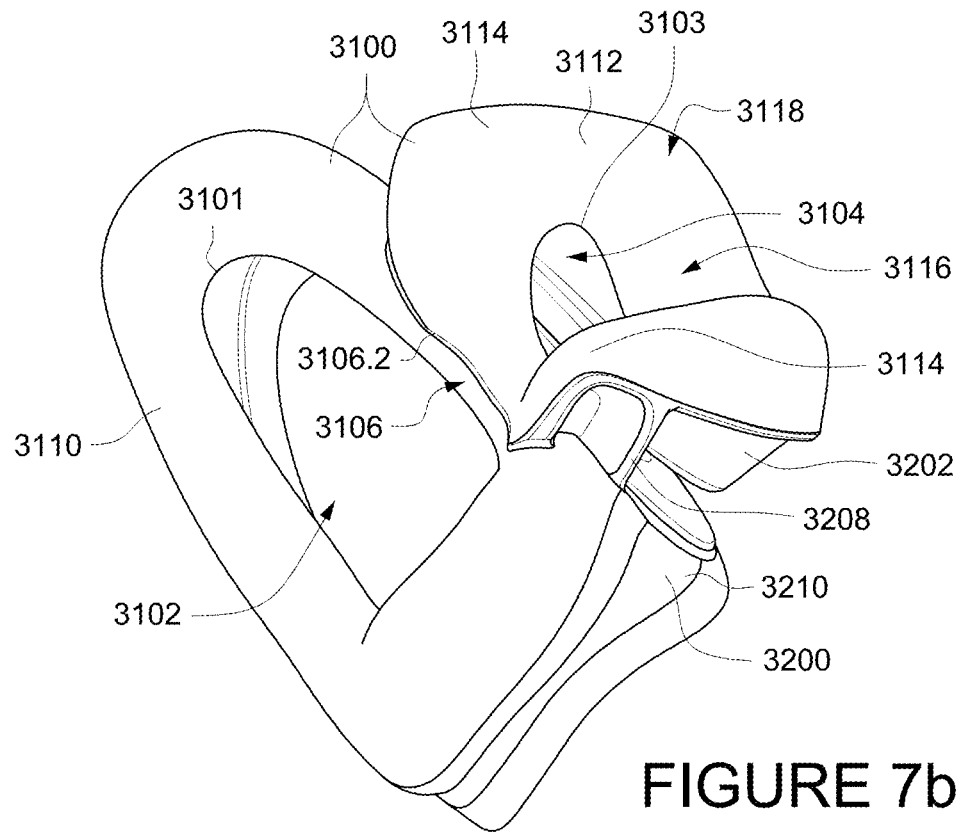

FIG. 7b shows a side perspective view of a plenum chamber assembly of a patient interface in accordance with an example of the present technology.

Figure 7C:
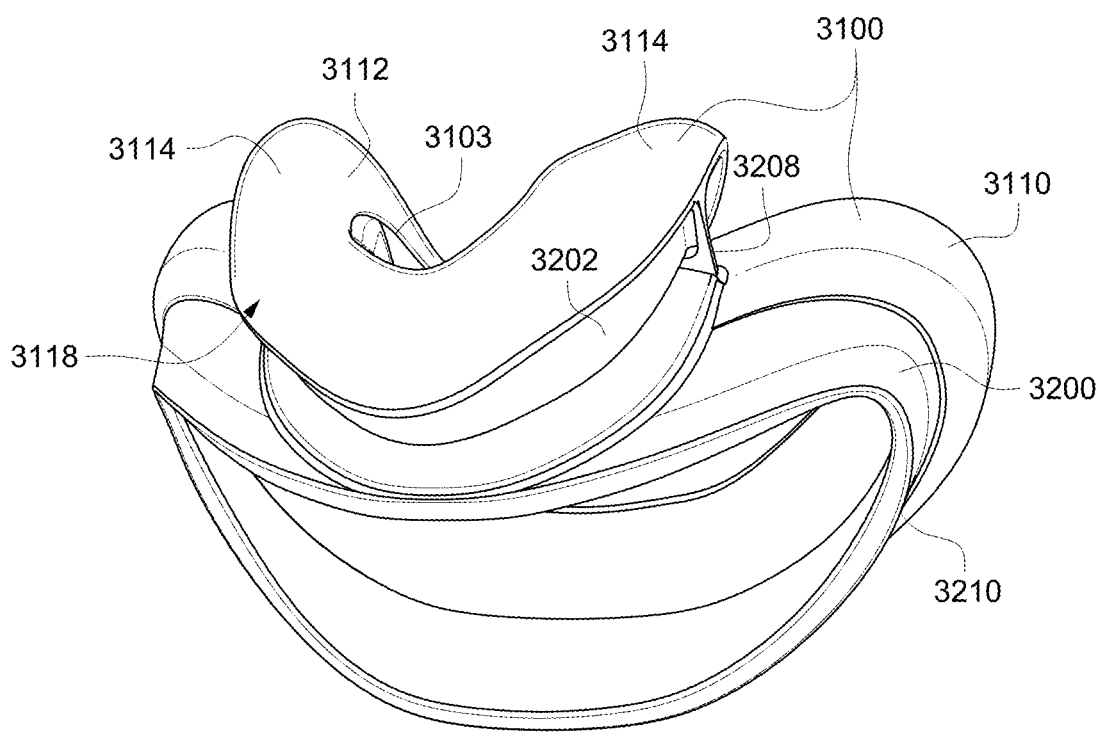

FIG. 7c shows a front perspective view of a plenum chamber assembly of a patient interface in accordance with an example of the present technology.

Figure 7D:
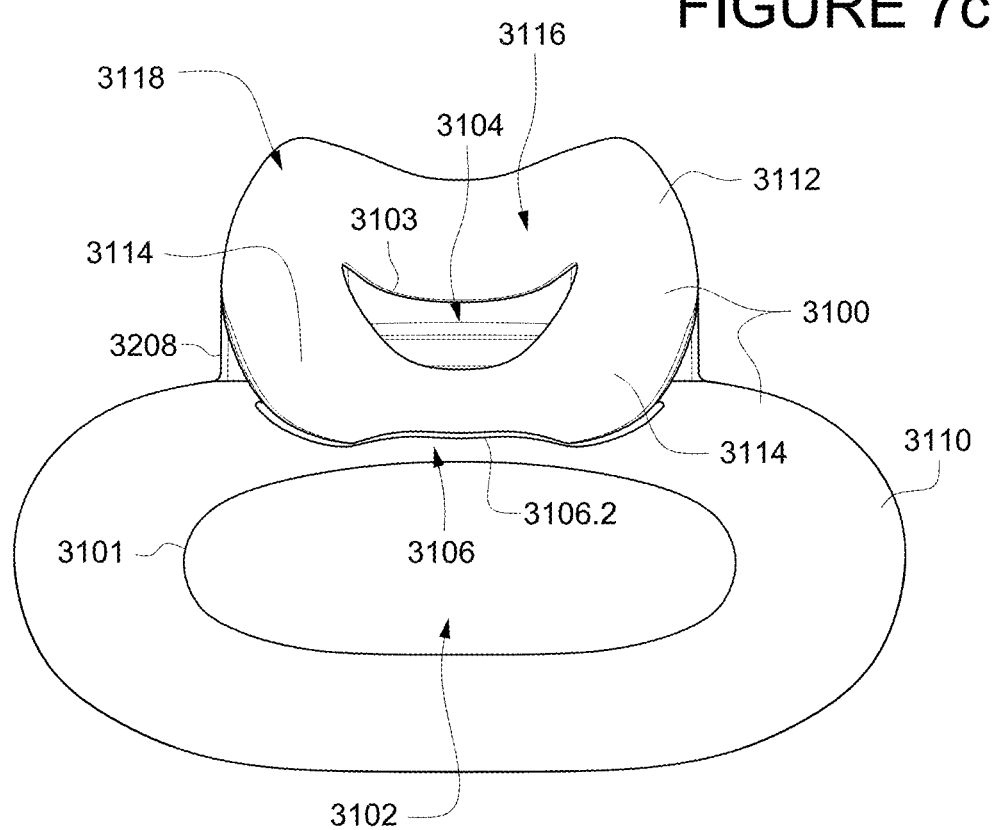

FIG. 7d shows a rear view of a plenum chamber assembly of a patient interface in accordance with an example of the present technology.

Figure 7E:
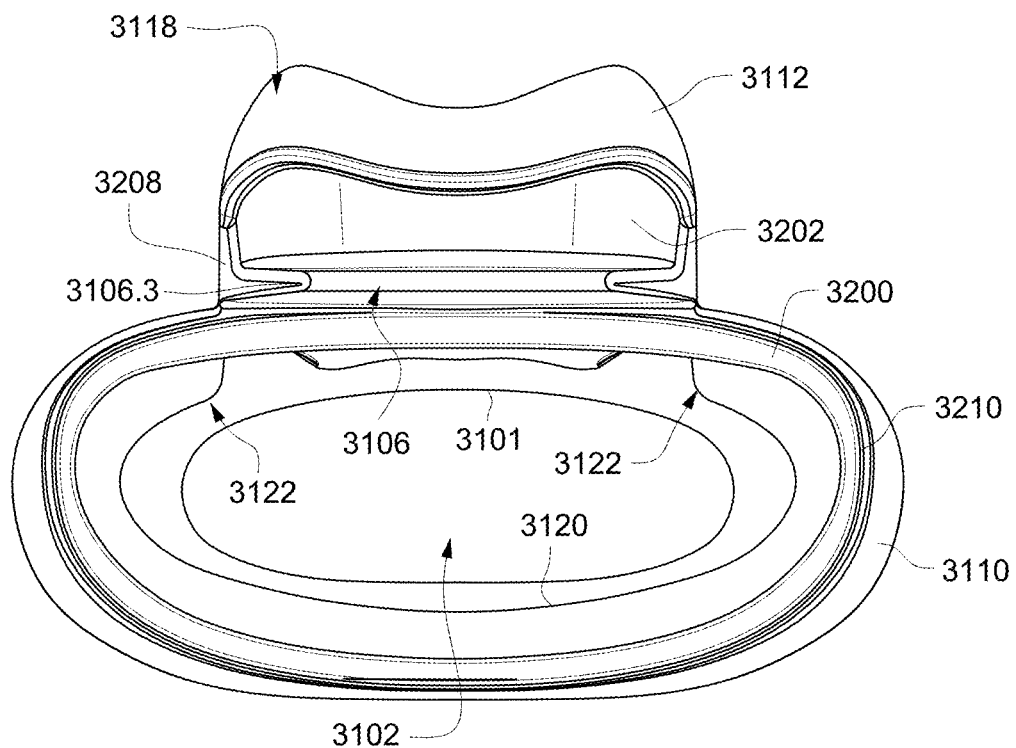

FIG. 7e shows a front view of a plenum chamber assembly of a patient interface in accordance with an example of the present technology.

Figure 7F:
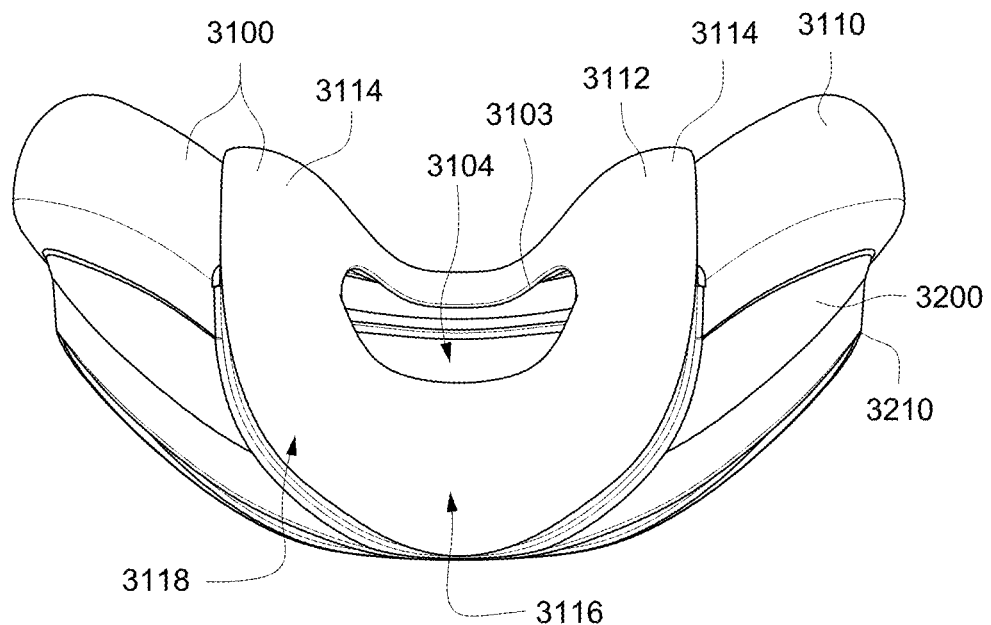

FIG. 7f shows a top view of a plenum chamber assembly of a patient interface in accordance with an example of the present technology.

Figure 7G:
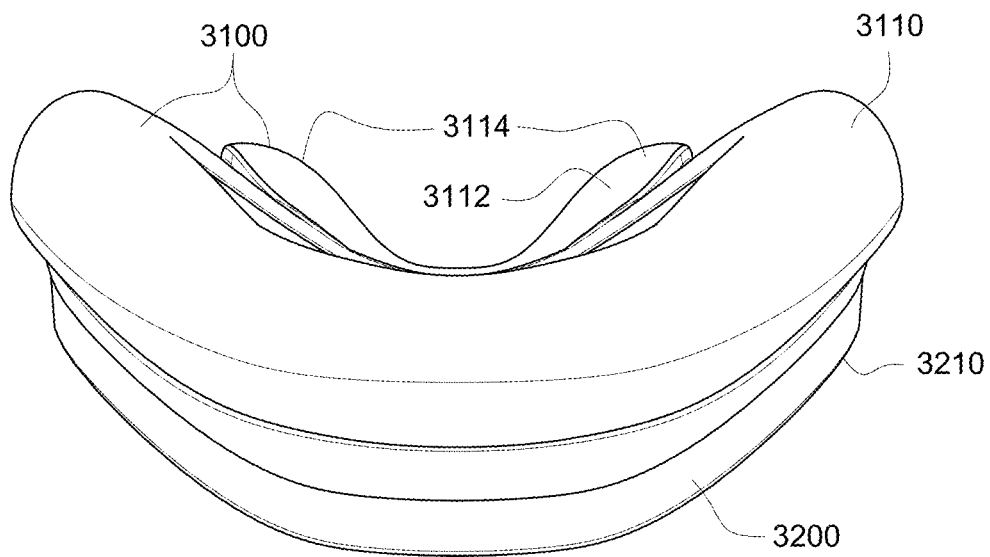

FIG. 7g shows a bottom view of a plenum chamber assembly of a patient interface in accordance with an example of the present technology.

Figure 7H:
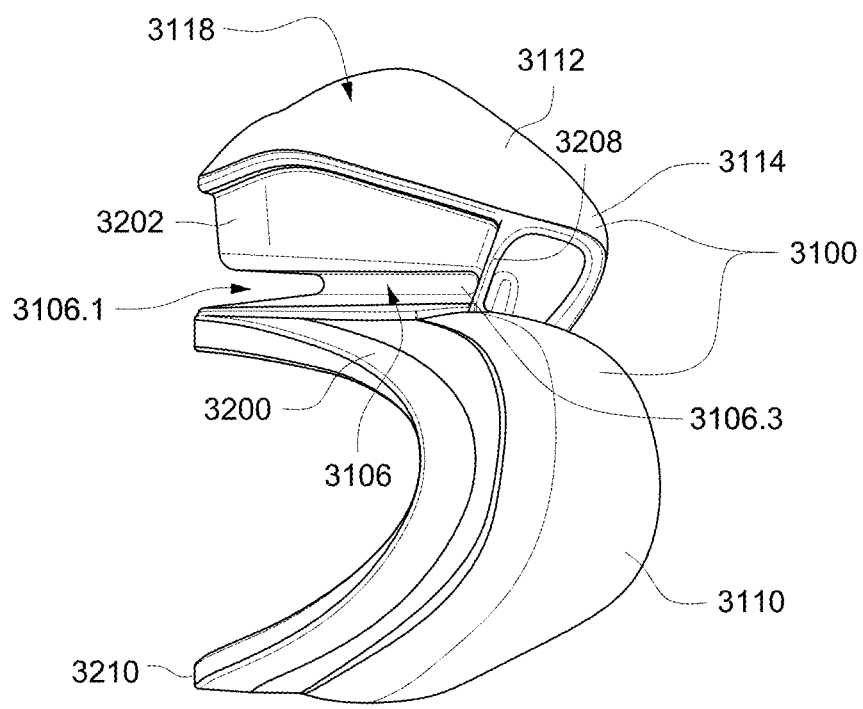

FIG. 7h shows a side view of a plenum chamber assembly of a patient interface in accordance with an example of the present technology.

Figure 8A:
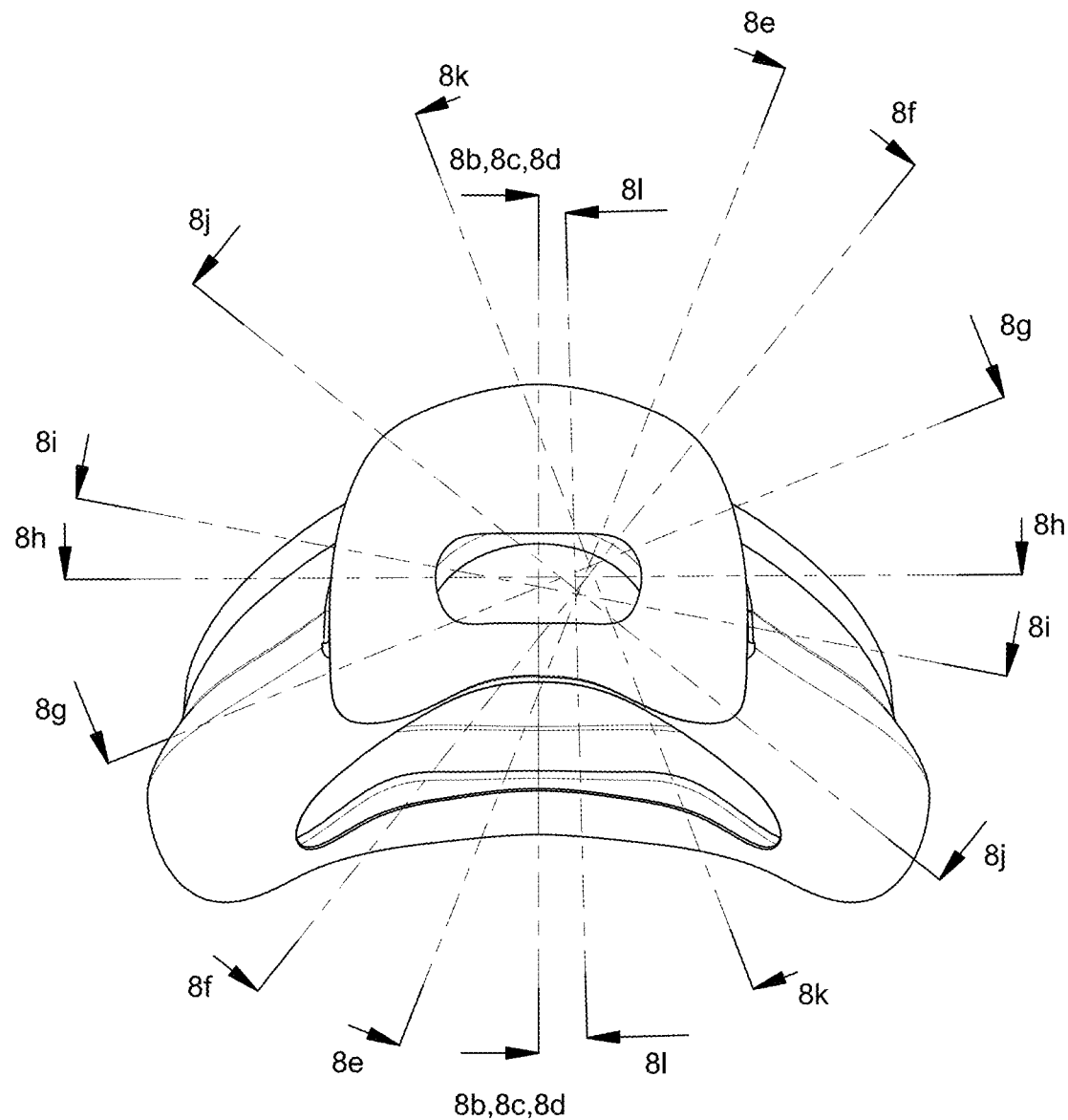

FIG. 8a shows a top view of a plenum chamber assembly of a patient interface in accordance with an example of the present technology and includes several lines defining various cross-sections.

Figure 8C:
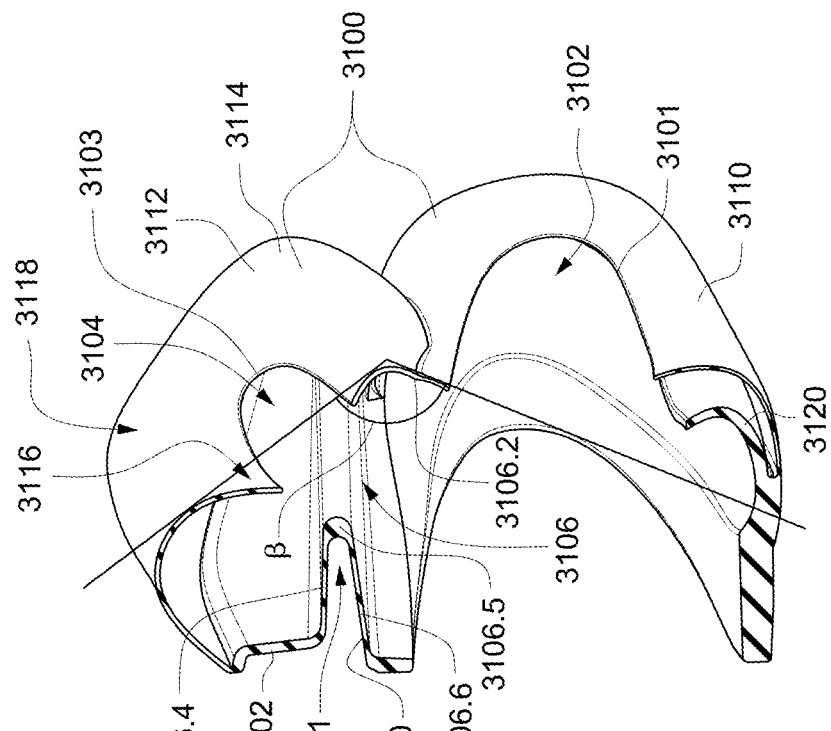
Figure 8B:
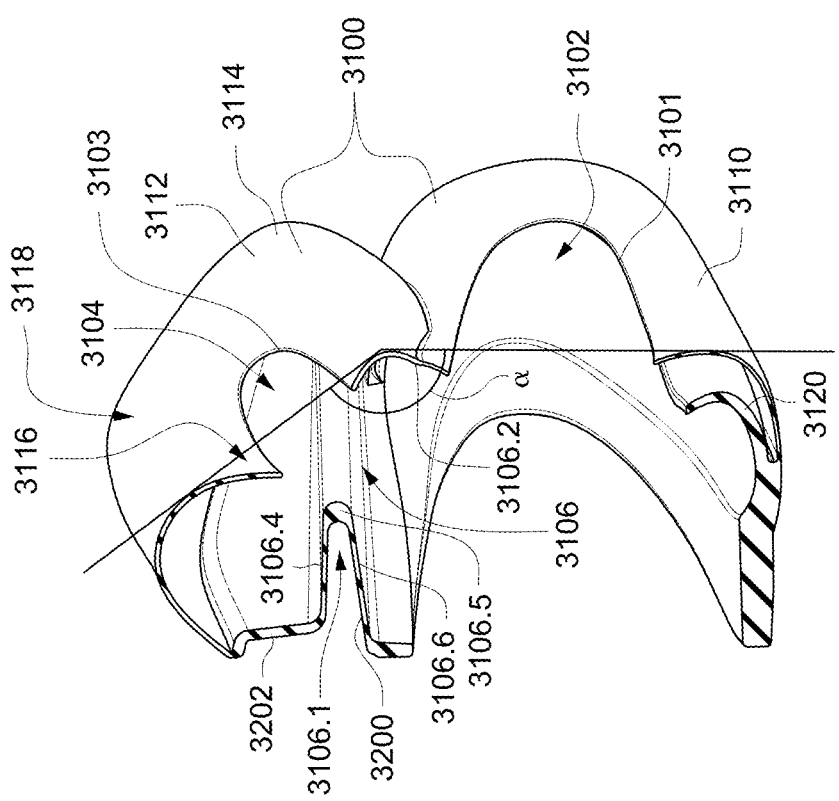

FIG. 8b shows a side cross-sectional view taken through line 8b-8b of FIG. 8a of a plenum chamber assembly of a patient interface in accordance with an example of the present technology.

FIG. 8c shows a side cross-sectional view taken through line 8c-8c of FIG. 8a of a plenum chamber assembly of a patient interface in accordance with an example of the present technology.

Figure 8D:
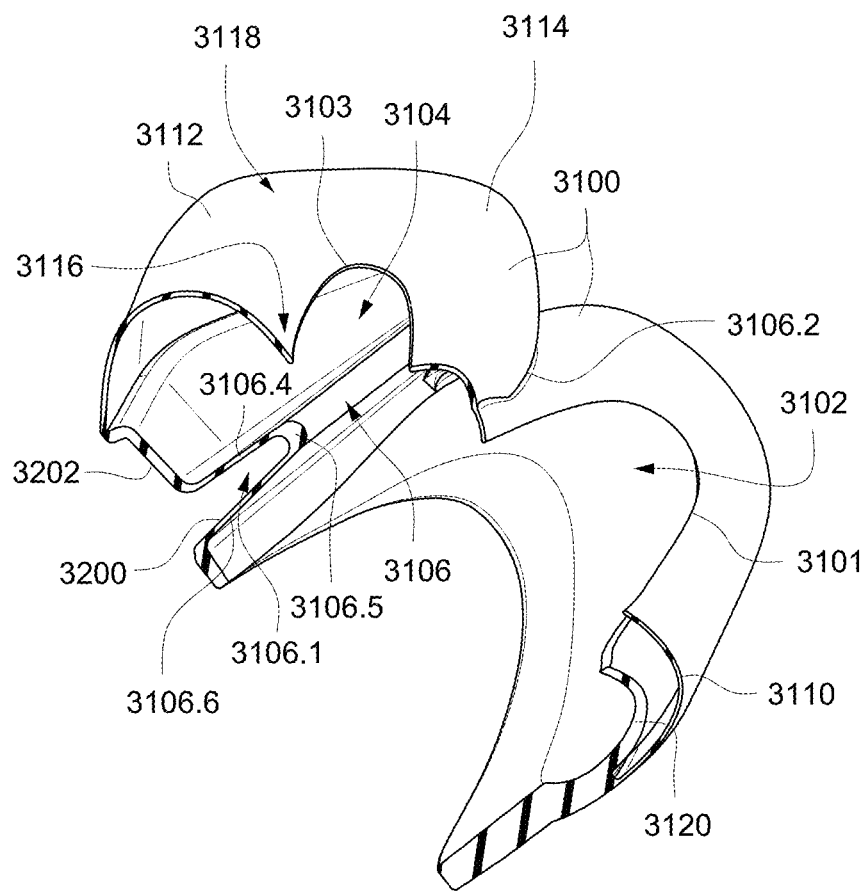

FIG. 8d shows a side cross-sectional view taken through line 8d-8d of FIG. 8a of a plenum chamber assembly of a patient interface in accordance with an example of the present technology.

Figure 8E:
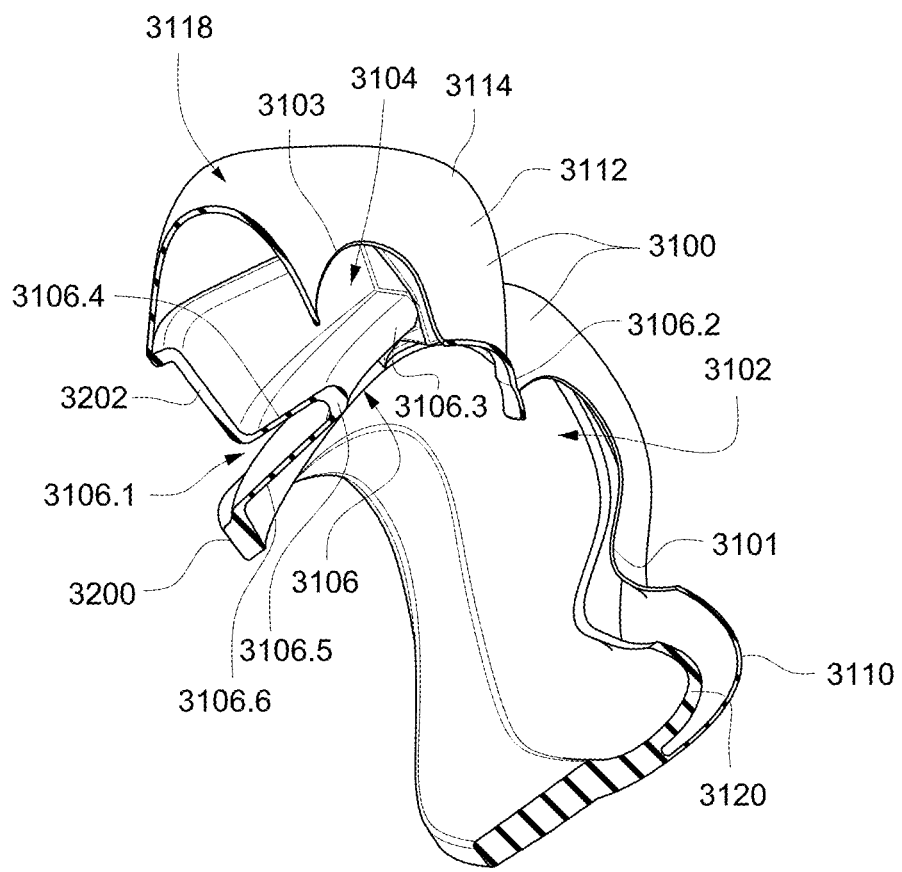

FIG. 8e shows a side cross-sectional view taken through line 8e-8e of FIG. 8a of a plenum chamber assembly of a patient interface in accordance with an example of the present technology.

Figure 8F:
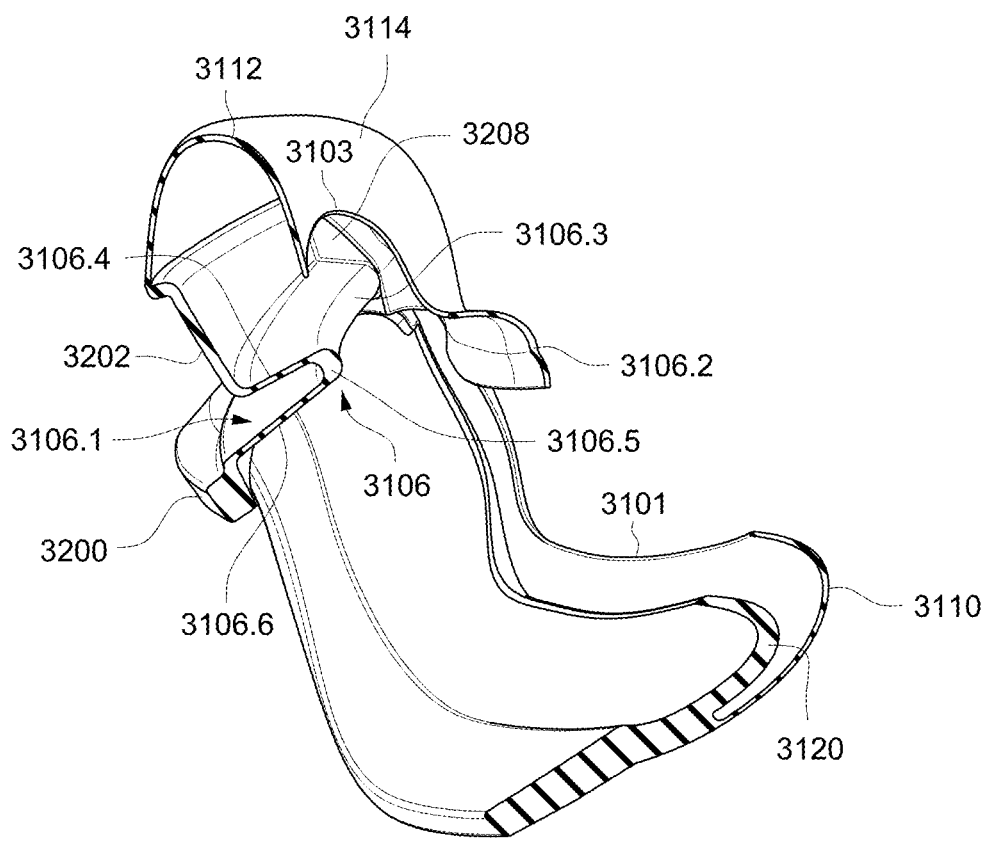

FIG. 8f shows a side cross-sectional view taken through line 8f-8f of FIG. 8a of a plenum chamber assembly of a patient interface in accordance with an example of the present technology.

Figure 8G:
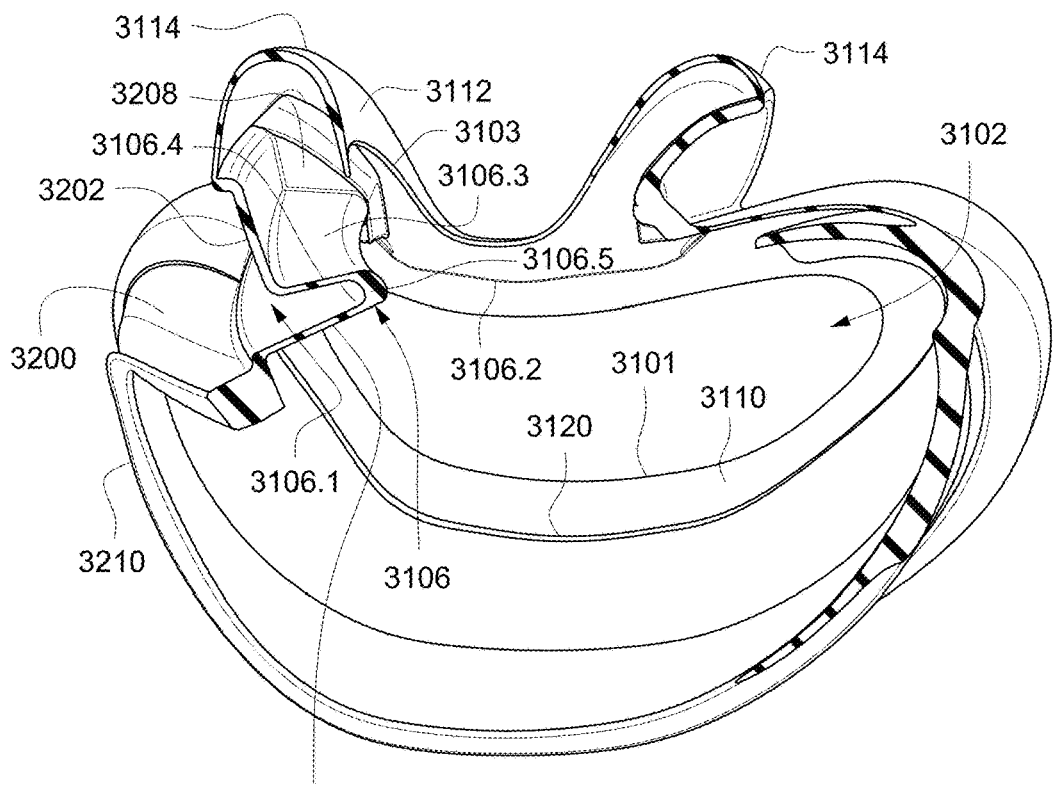

FIG. 8g shows a front cross-sectional view taken through line 8g-8g of FIG. 8a of a plenum chamber assembly of a patient interface in accordance with an example of the present technology.

Figure 8H:
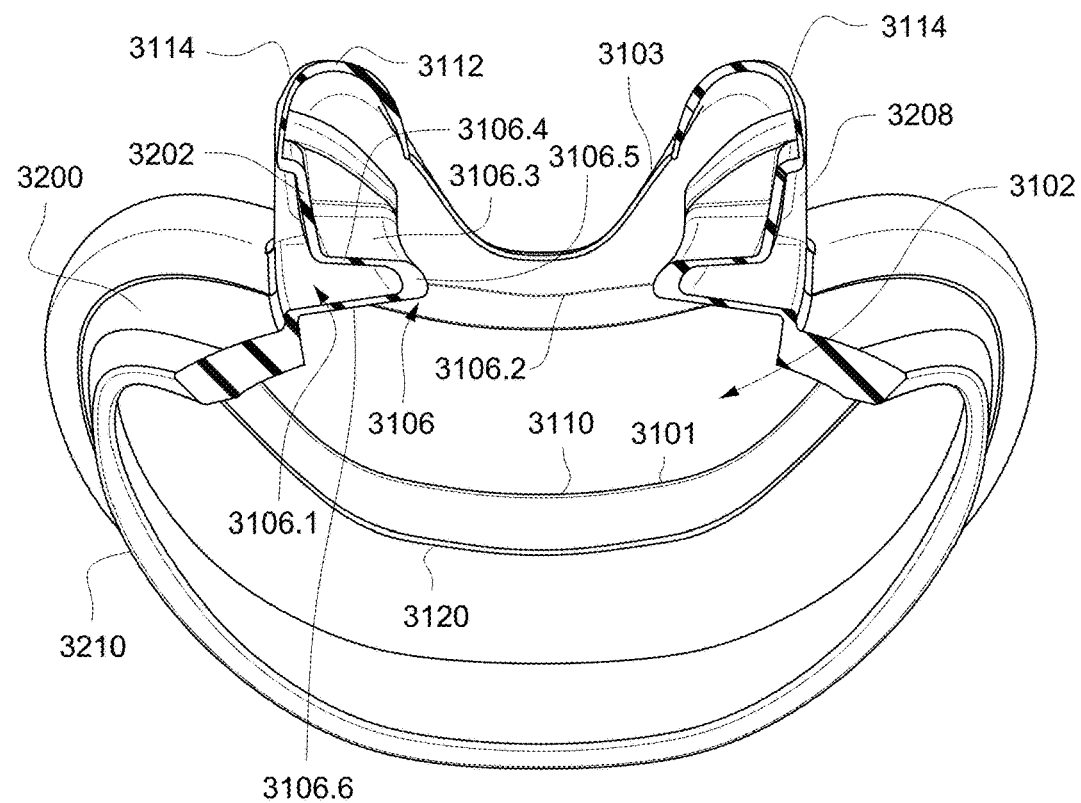

FIG. 8h shows a front cross-sectional view taken through line 8h-8h of FIG. 8a of a plenum chamber assembly of a patient interface in accordance with an example of the present technology.

Figure 8I:
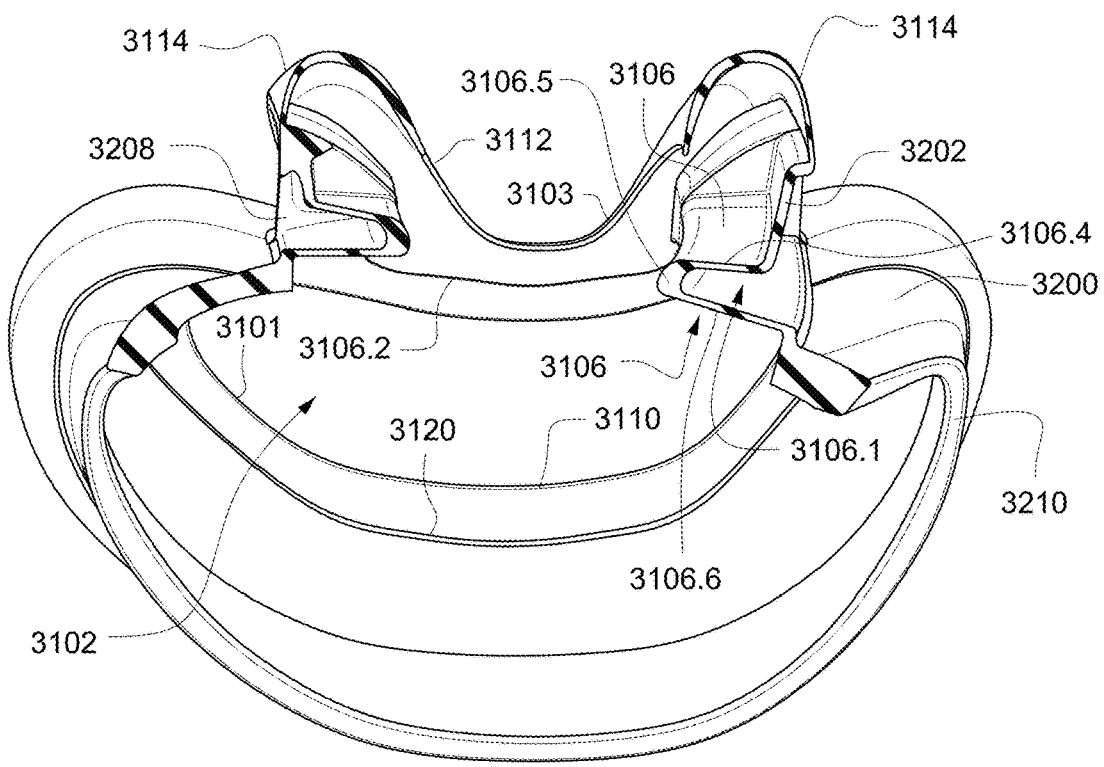

FIG. 8i shows a front cross-sectional view taken through line 8i-8i of FIG. 8a of a plenum chamber assembly of a patient interface in accordance with an example of the present technology.

Figure 8J:
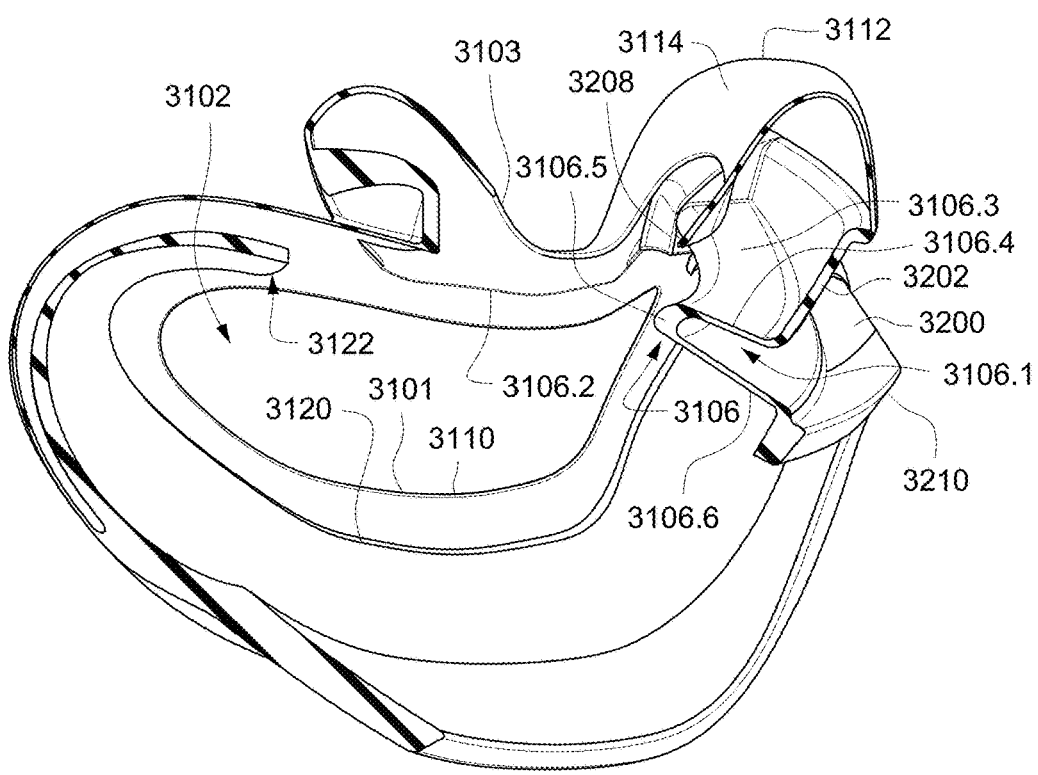

FIG. 8j shows a front perspective cross-sectional view taken through line 8j-8j of FIG. 8a of a plenum chamber assembly of a patient interface in accordance with an example of the present technology.

Figure 8K:
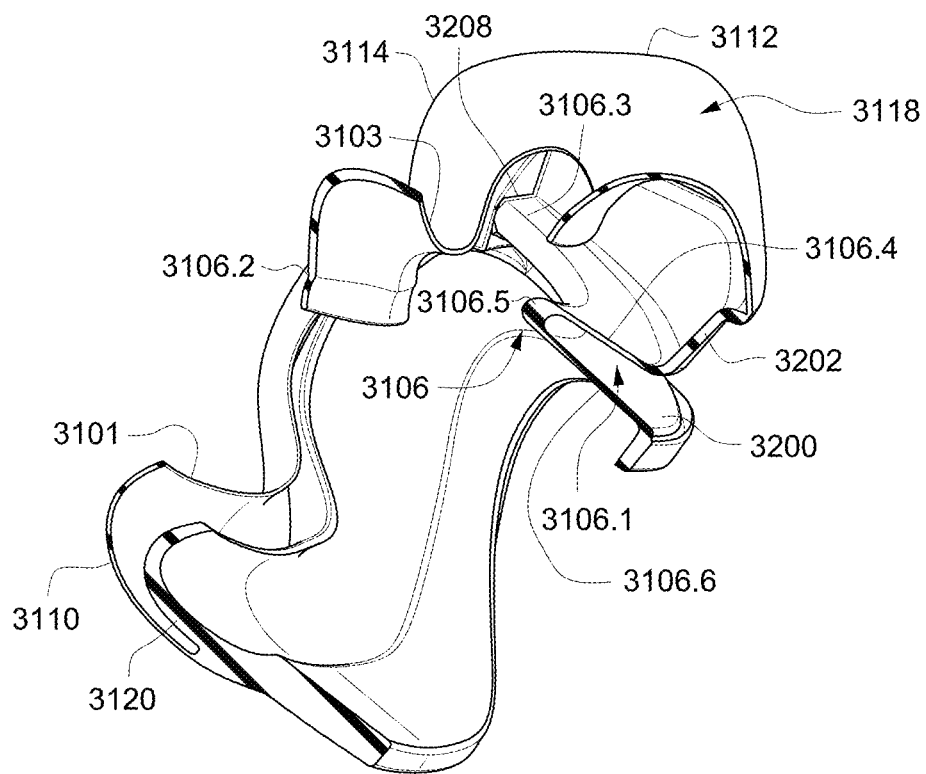

FIG. 8k shows a side cross-sectional view taken through line 8k-8k of FIG. 8a of a plenum chamber assembly of a patient interface in accordance with an example of the present technology.

Figure 8L:
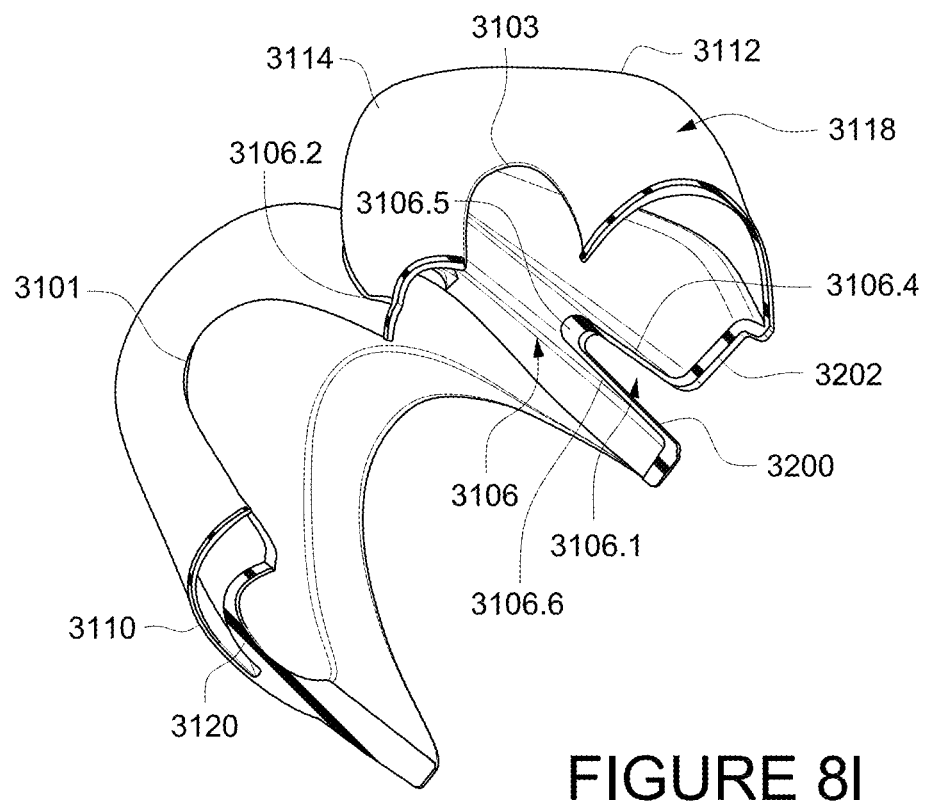

FIG. 8l shows a side cross-sectional view taken through line 8l-8l of FIG. 8a of a plenum chamber assembly of a patient interface in accordance with an example of the present technology.

Figure 9A:
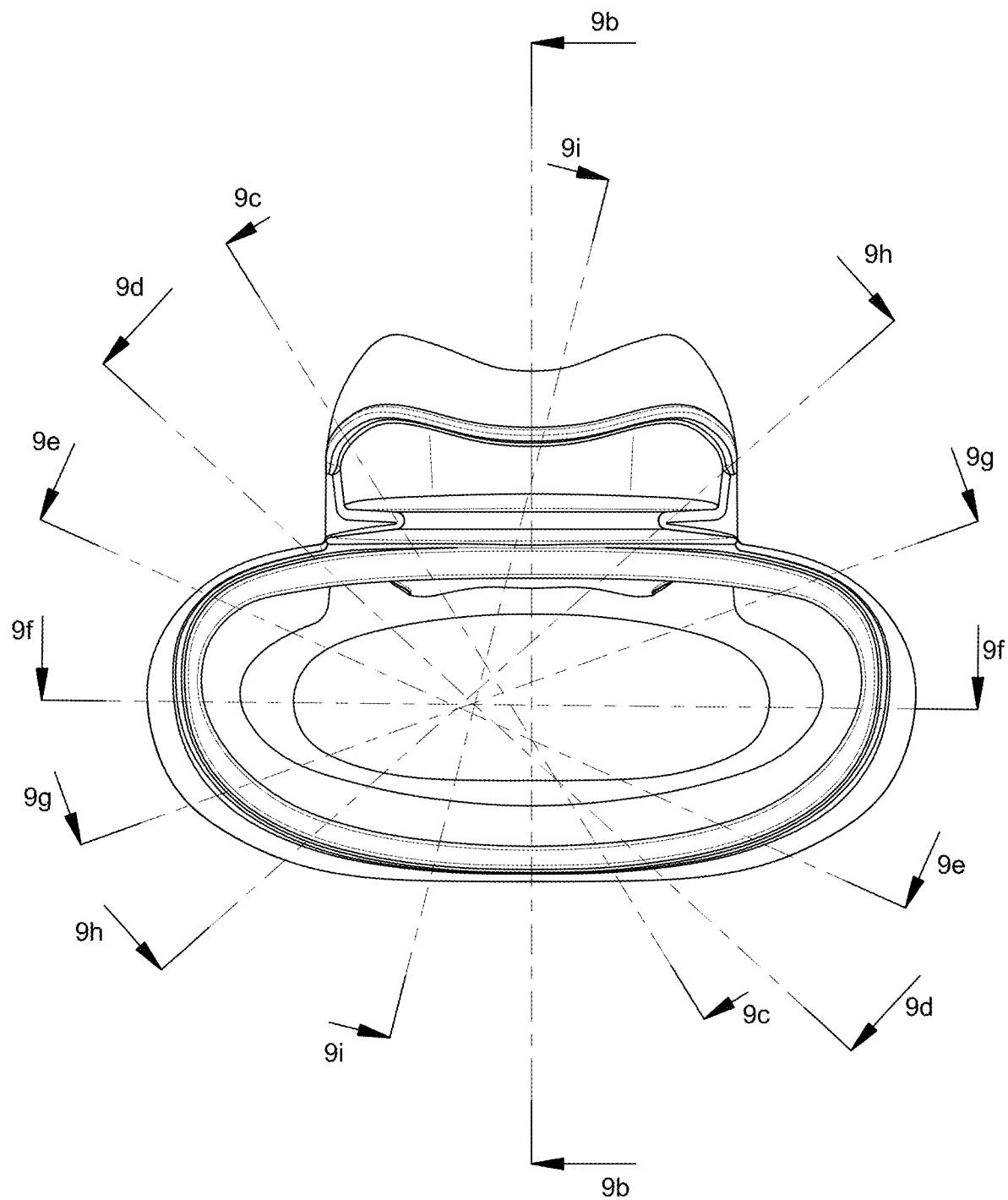

FIG. 9a shows a front view of a plenum chamber assembly of a patient interface in accordance with an example of the present technology and includes several lines defining various cross-sections.

Figure 9C:
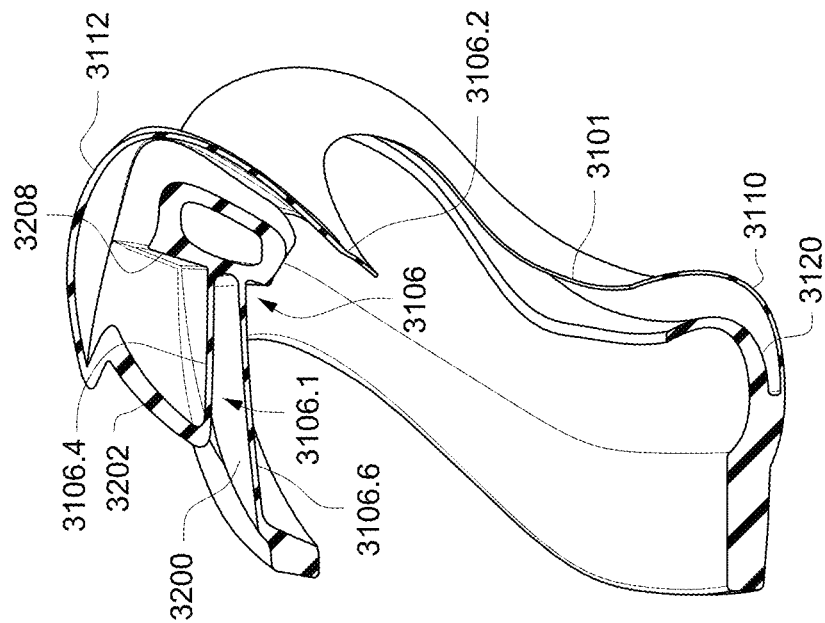
Figure 9B:
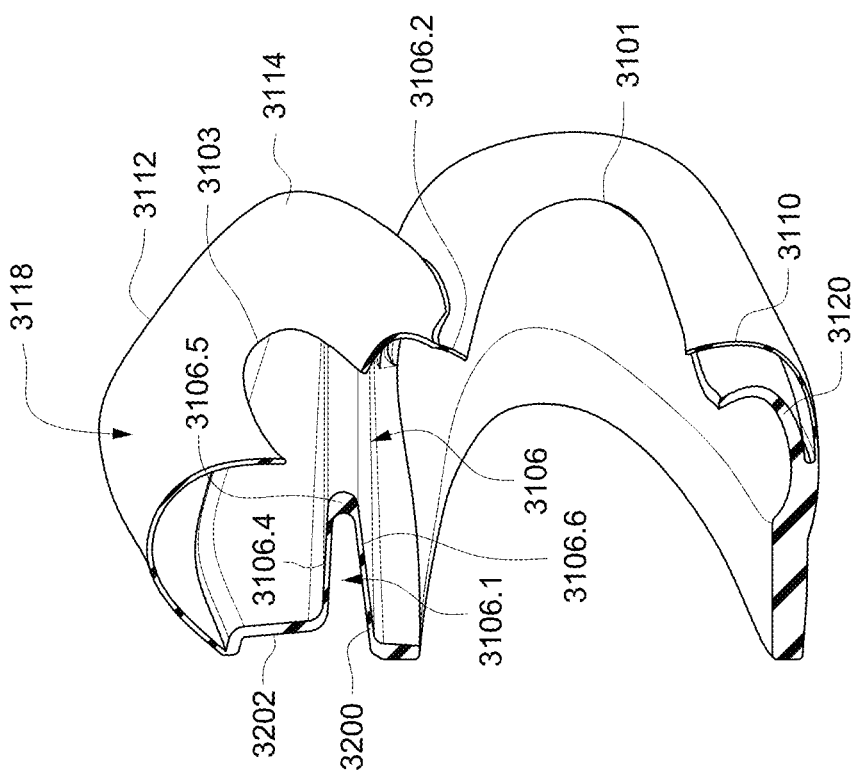

FIG. 9b shows a side cross-sectional view taken through line 9b-9b of FIG. 9a of a plenum chamber assembly of a patient interface in accordance with an example of the present technology.

FIG. 9c shows a side cross-sectional view taken through line 9c-9c of FIG. 9a of a plenum chamber assembly of a patient interface in accordance with an example of the present technology.

Figure 9E:
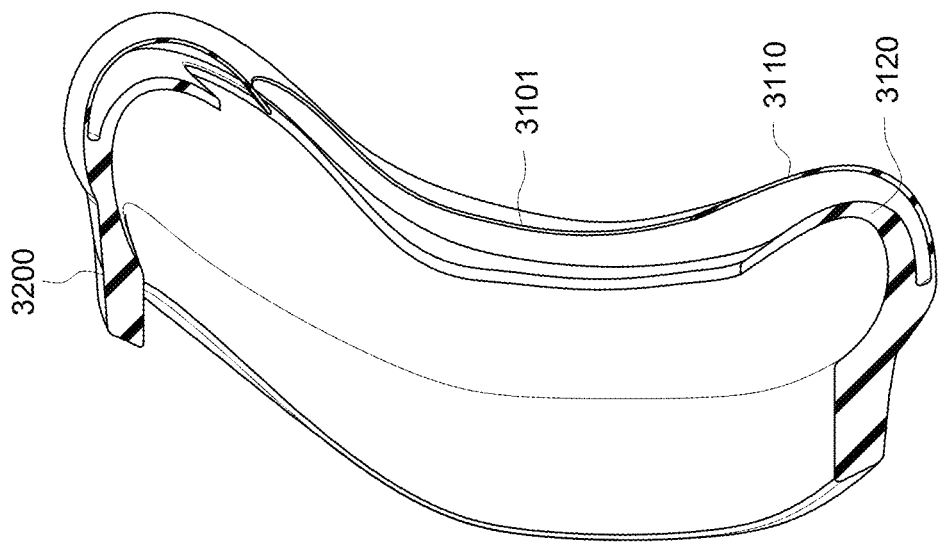
Figure 9D:
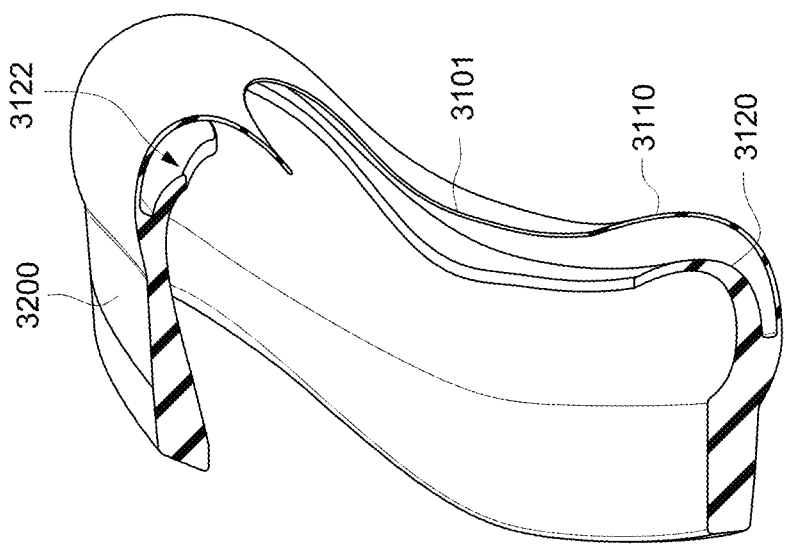

FIG. 9d shows a side cross-sectional view taken through line 9d-9d of FIG. 9a of a plenum chamber assembly of a patient interface in accordance with an example of the present technology.

FIG. 9e shows a side cross-sectional view taken through line 9e-9e of FIG. 9a of a plenum chamber assembly of a patient interface in accordance with an example of the present technology.

Figure 9G:
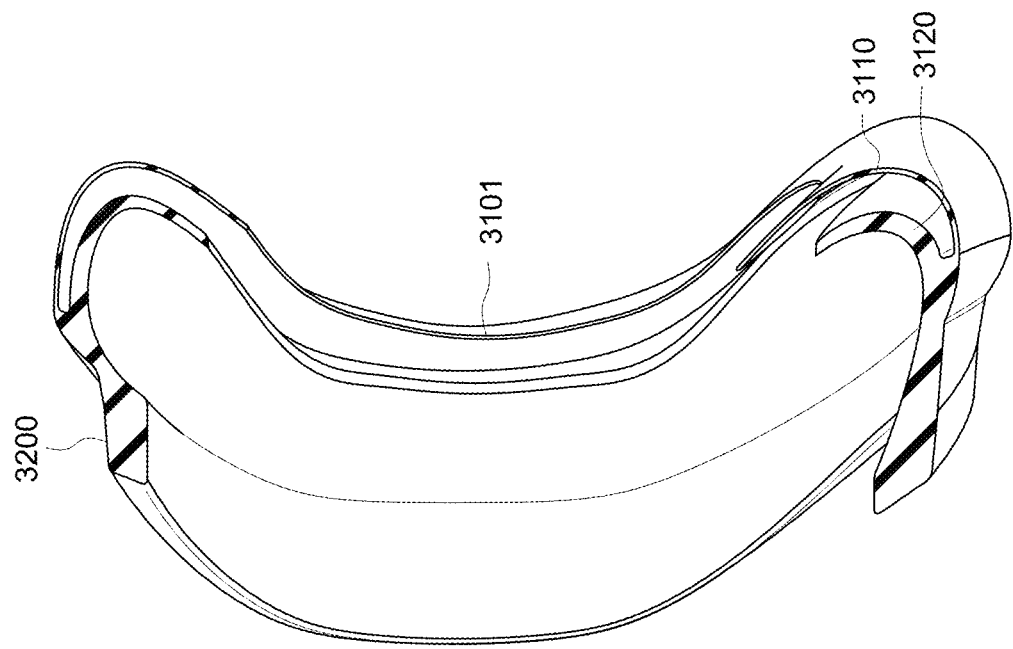
Figure 9F:
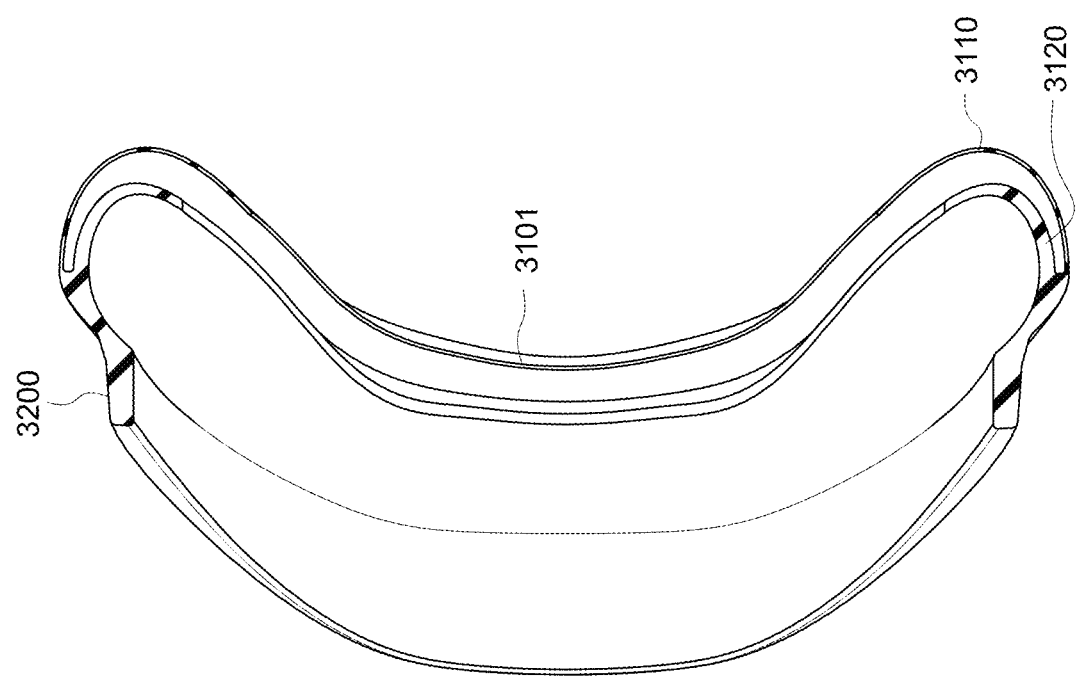

FIG. 9f shows a side cross-sectional view taken through line 9f-9f of FIG. 9a of a plenum chamber assembly of a patient interface in accordance with an example of the present technology.

FIG. 9g shows a side cross-sectional view taken through line 9g-9g of FIG. 9a of a plenum chamber assembly of a patient interface in accordance with an example of the present technology.

FIG. 9h shows a side cross-sectional view taken through line 9h-9h of FIG. 9a of a plenum chamber assembly of a patient interface in accordance with an example of the present technology.

FIG. 9i shows a side cross-sectional view taken through line 9i-9i of FIG. 9a of a plenum chamber assembly of a patient interface in accordance with one form of the present technology.

FIG. 10a shows a top view of a nasal cushion of a patient interface in accordance with an example of the present technology.

FIG. 10b shows a top view of a nasal cushion of a patient interface in accordance with another example of the present technology.

FIG. 10c shows a top view of a nasal cushion of a patient interface in accordance with another example of the present technology.

FIG. 10d shows a top view of a nasal cushion of a patient interface in accordance with another example of the present technology.

Figure 11C:
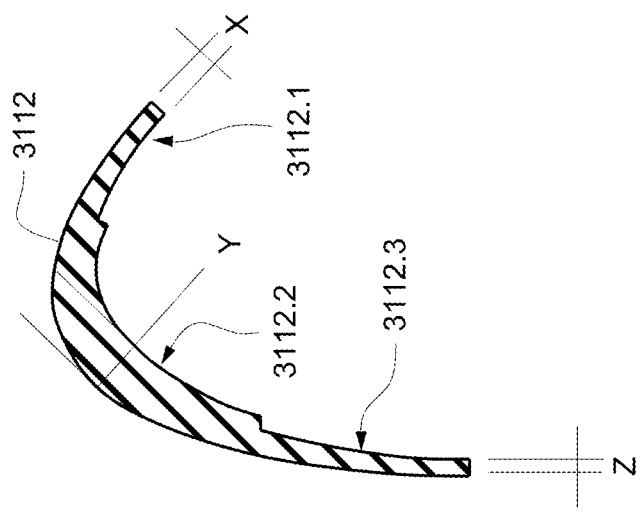
Figure 11B:
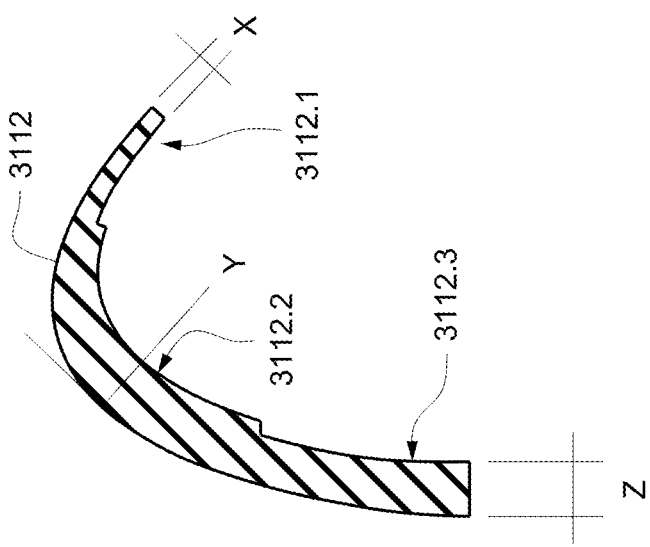
Figure 11A:
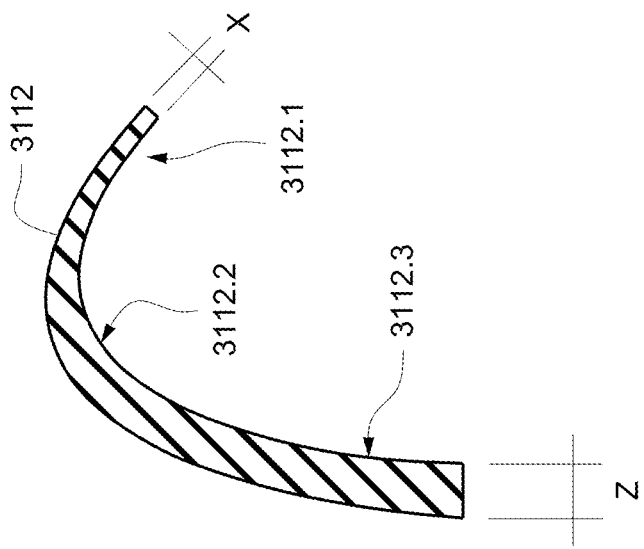

FIG. 11a shows a cross-section of a nasal cushion taken through line 11a-11a of FIG. 4a according to an example of the present technology.

Figure 13:
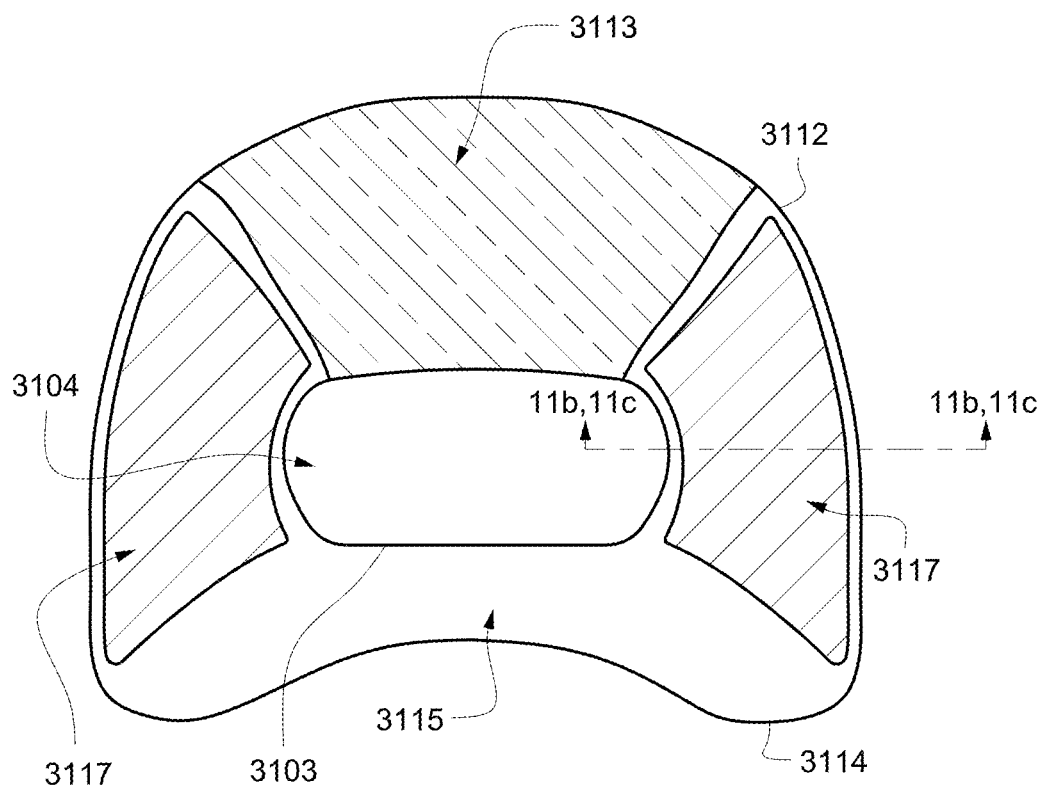

FIG. 11b shows a cross-section of a nasal cushion taken through line 11b, c of FIG. 13 according to an example of the present technology.

FIG. 11c shows a cross-section of a nasal cushion taken through line 11b, c of FIG. 13 according to an example of the present technology.

Figure 12A:
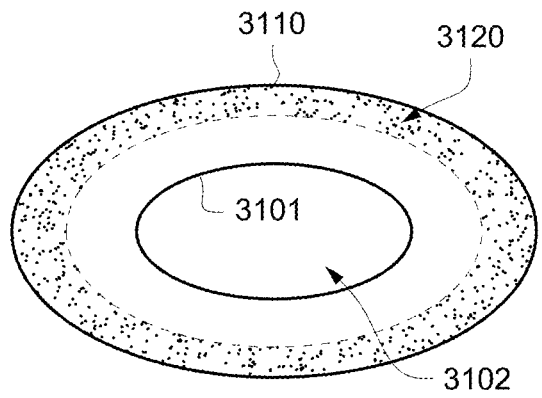

FIG. 12a shows a rear view of an oral cushion with an undercushion of an exemplary seal-forming structure according to the present technology.

Figure 12B:
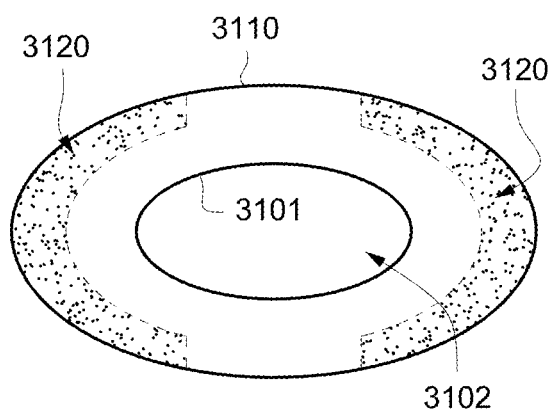

FIG. 12b shows a rear view of an oral cushion with an undercushion of another exemplary seal-forming structure according to the present technology.

Figure 12C:
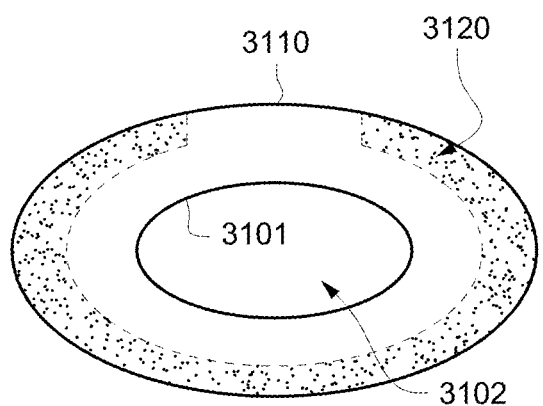

FIG. 12c shows a rear view of an oral cushion with an undercushion of another exemplary seal-forming structure according to the present technology.

Figure 12D:
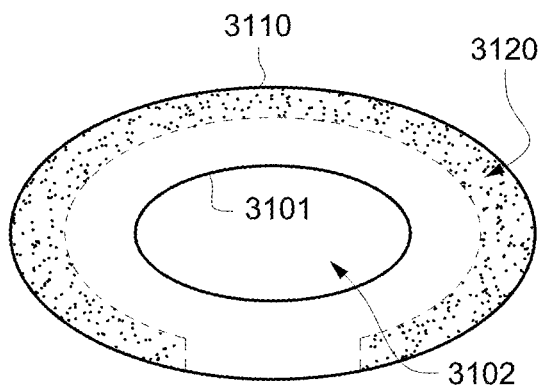

FIG. 12d shows a rear view of an oral cushion with an undercushion of another exemplary seal-forming structure according to the present technology.

FIG. 13 shows a top view of a nasal cradle cushion of a patient interface in accordance with an example of the present technology.

Figure 14:
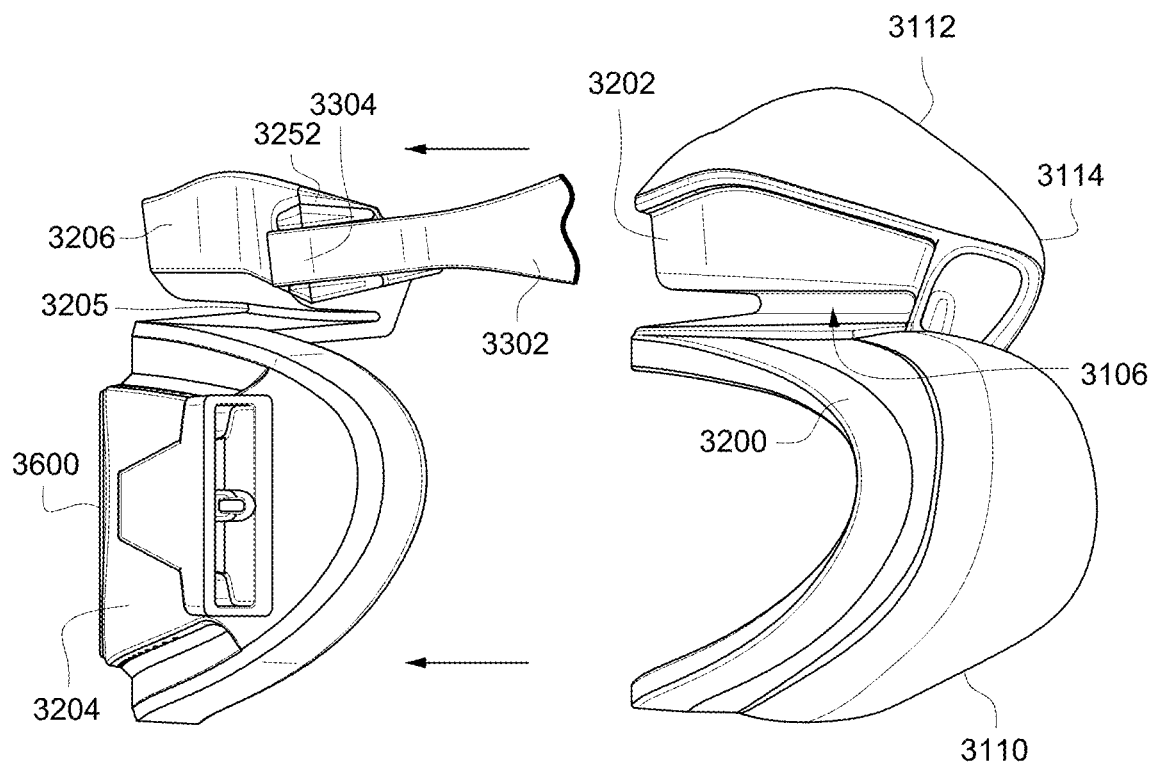

FIG. 14 shows an exploded side view of a patient interface in accordance with an example of the present technology.

Figure 15A:
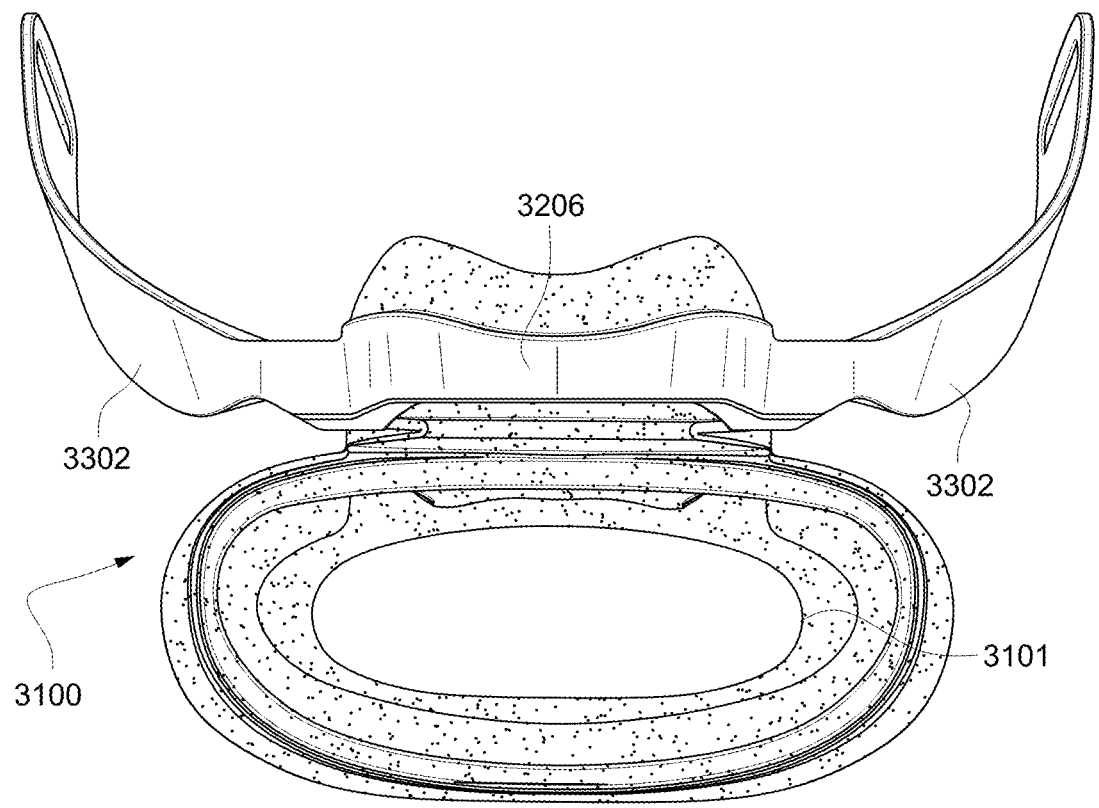

FIG. 15a shows a front view of a seal-forming structure, top plate, and rigidiser arms in accordance with an example of the present technology.

Figure 15B:
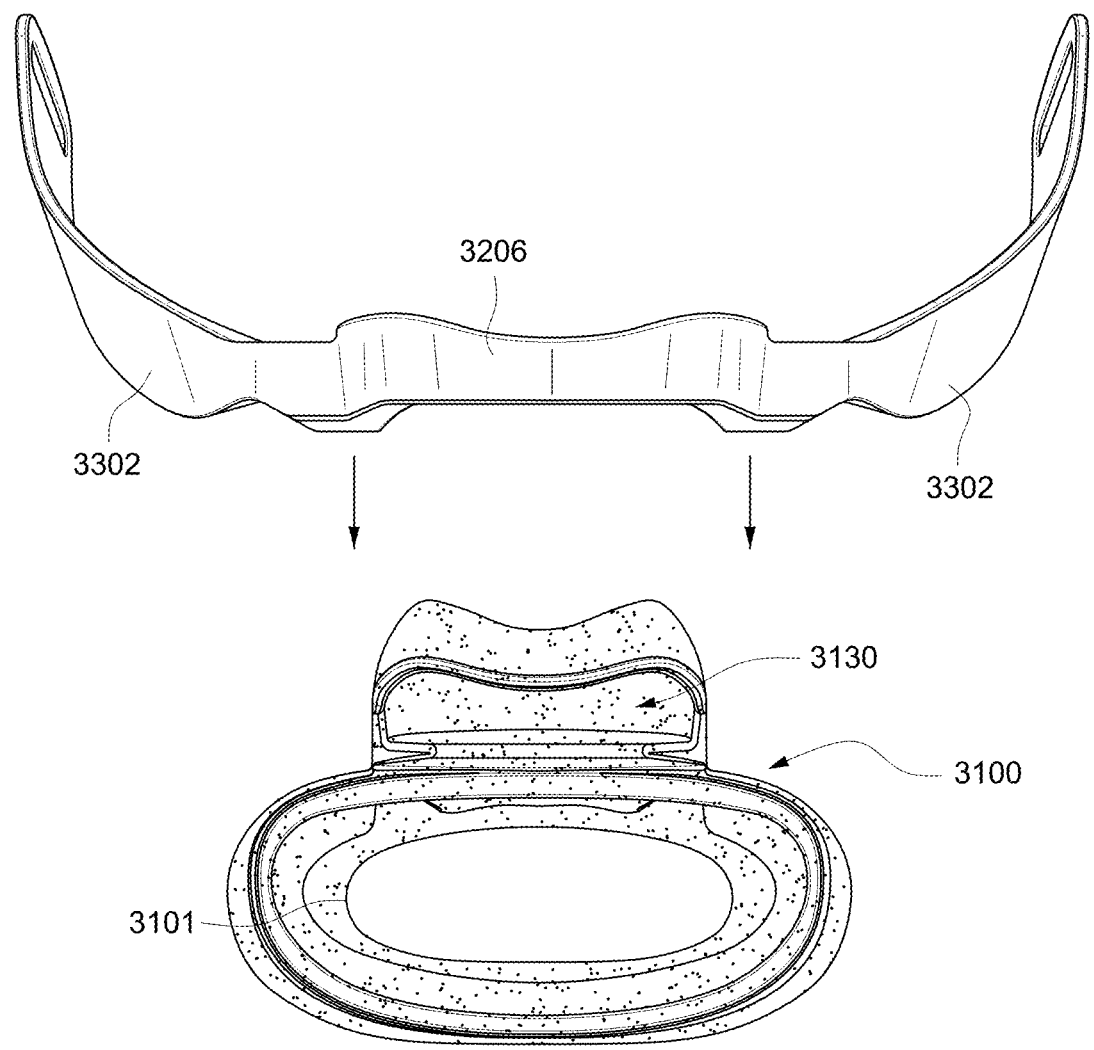

FIG. 15b shows a front view of a seal-forming structure, top plate, and rigidiser arms in accordance with another example of the present technology.

Figure 15C:
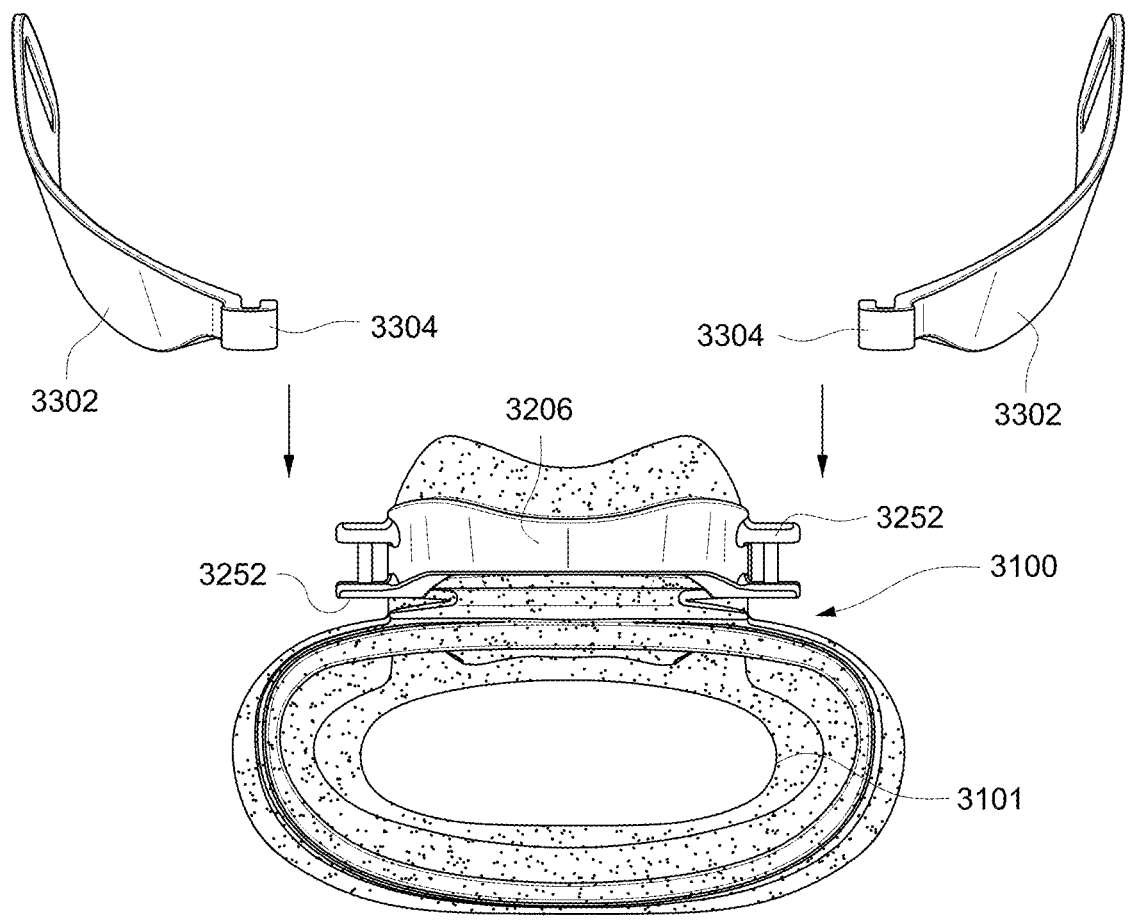

FIG. 15c shows a front view of a seal-forming structure, top plate, and rigidiser arms in accordance with an example of the present technology.

Figure 15D:
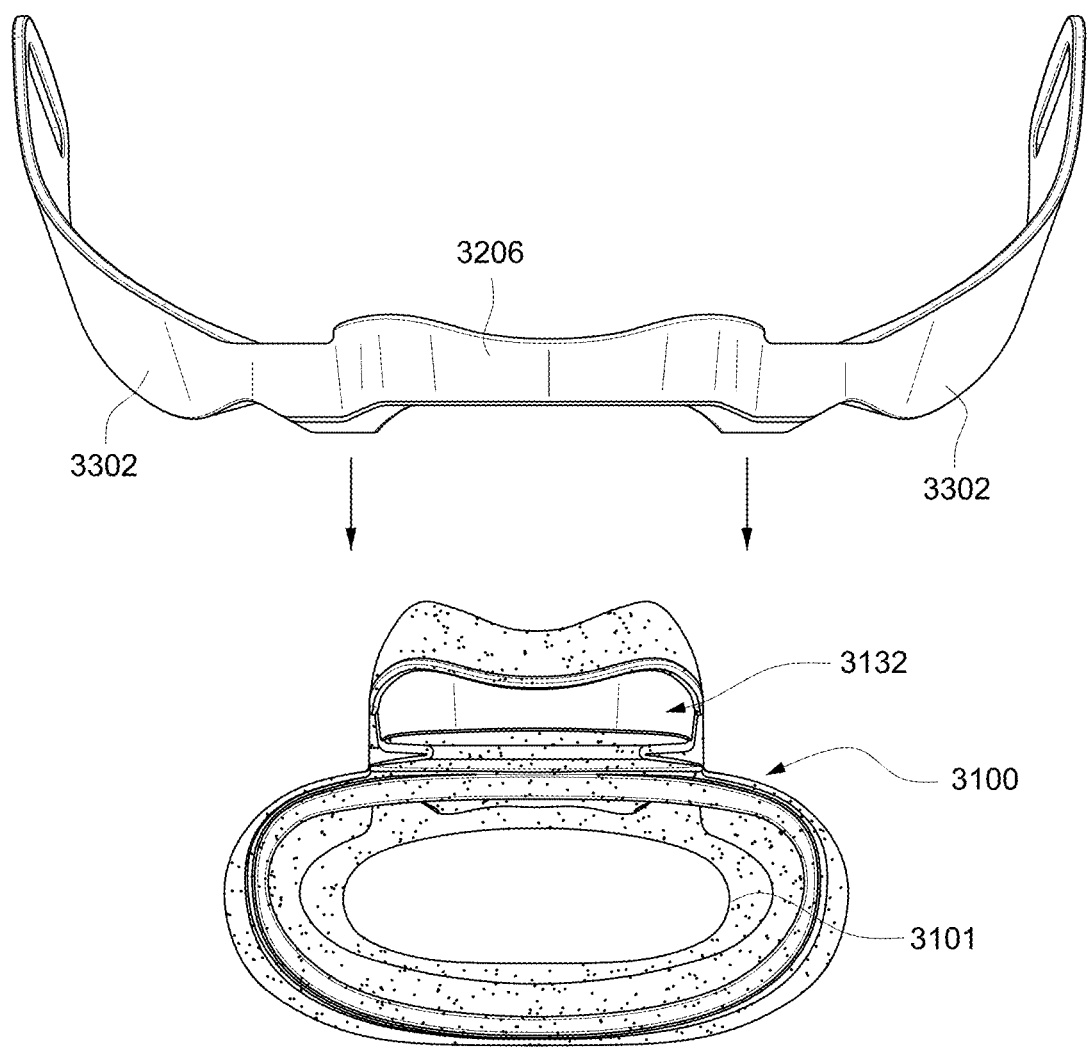

FIG. 15d shows a front view of a seal-forming structure, top plate, and rigidiser arms in accordance with an example of the present technology.

Figure 15E:
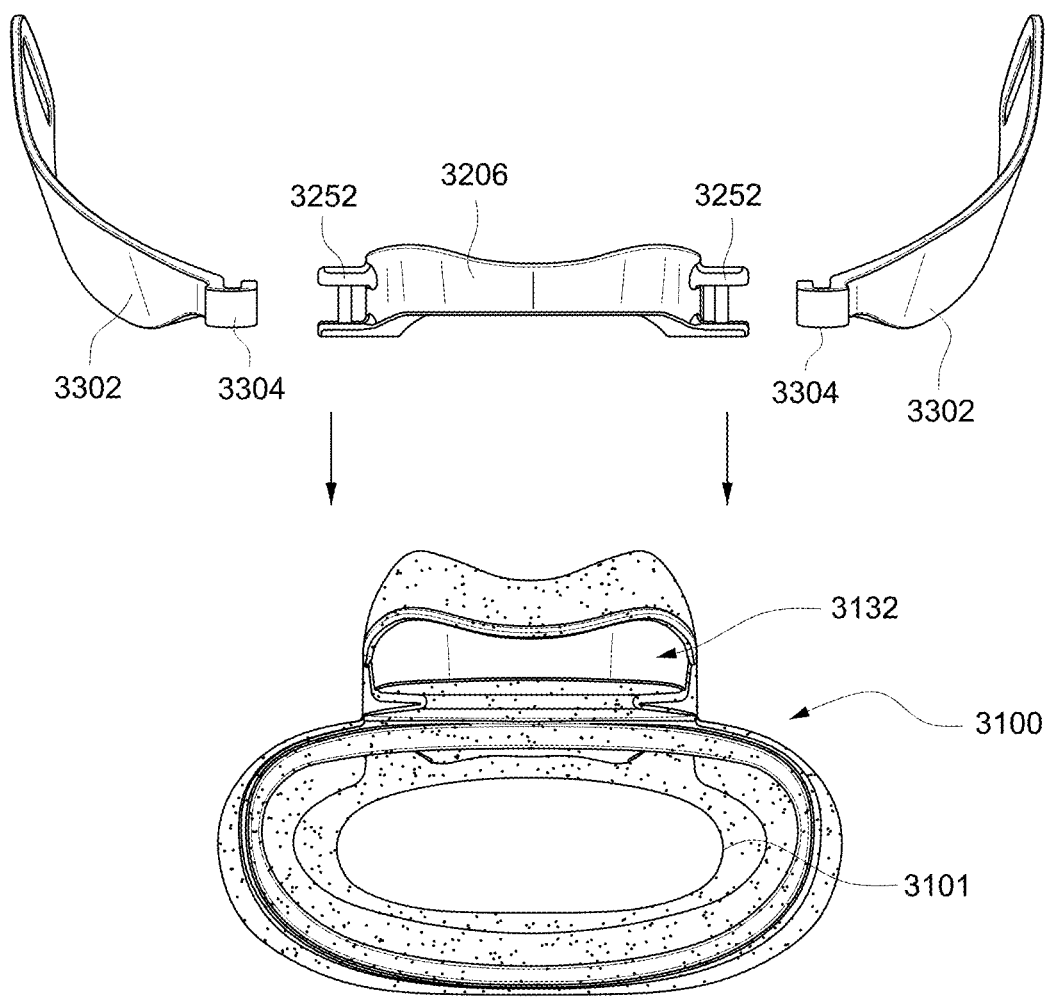

FIG. 15e shows a front view of a seal-forming structure, top plate, and rigidiser arms in accordance with an example of the present technology.

Figure 16A:
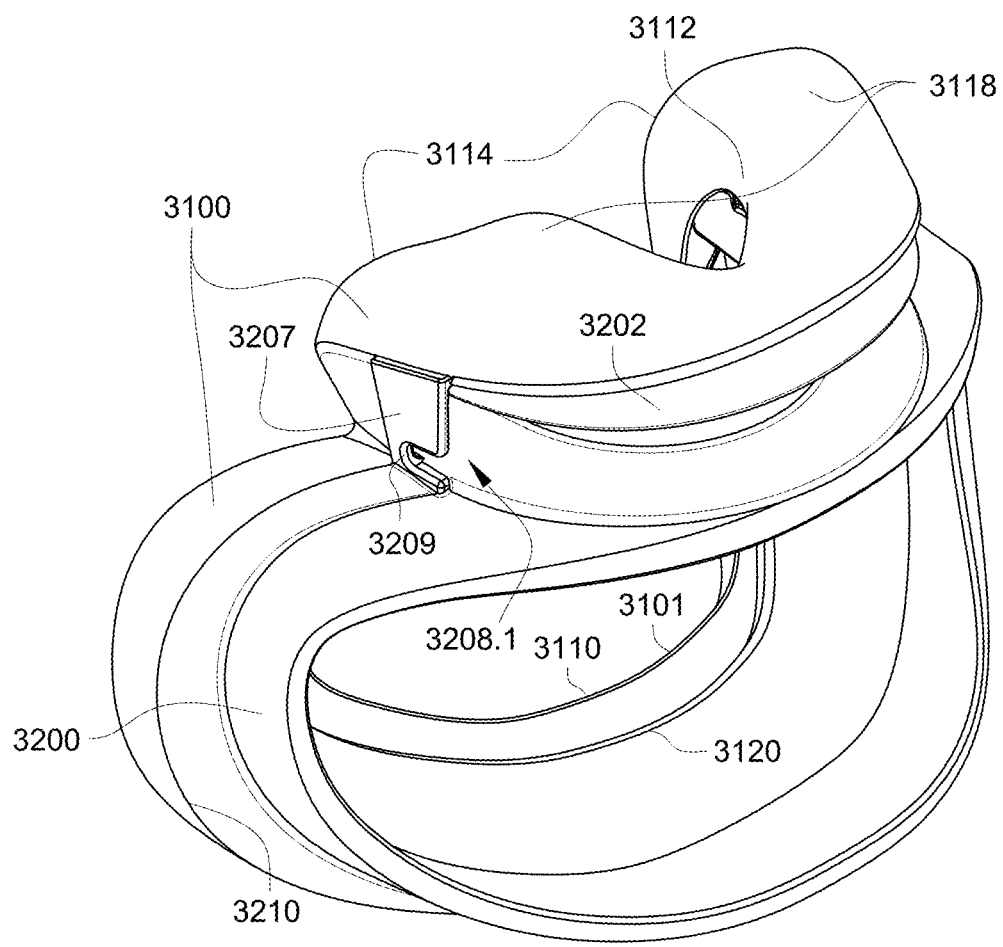

FIG. 16a shows a top perspective view of a seal-forming structure and plenum chamber according to an example of the present technology.

Figure 16B:
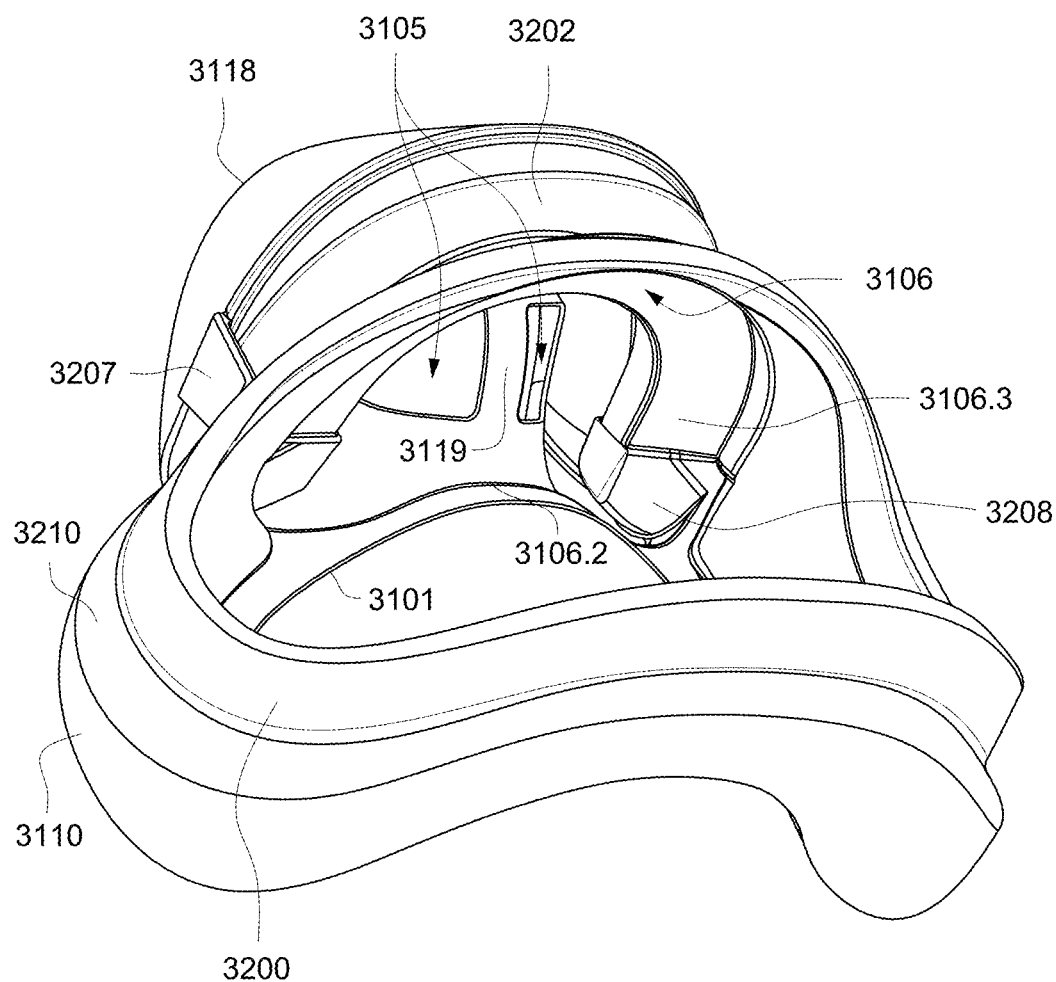

FIG. 16b shows a bottom perspective view of a seal-forming structure and plenum chamber according to an example of the present technology.

Figure 16C:
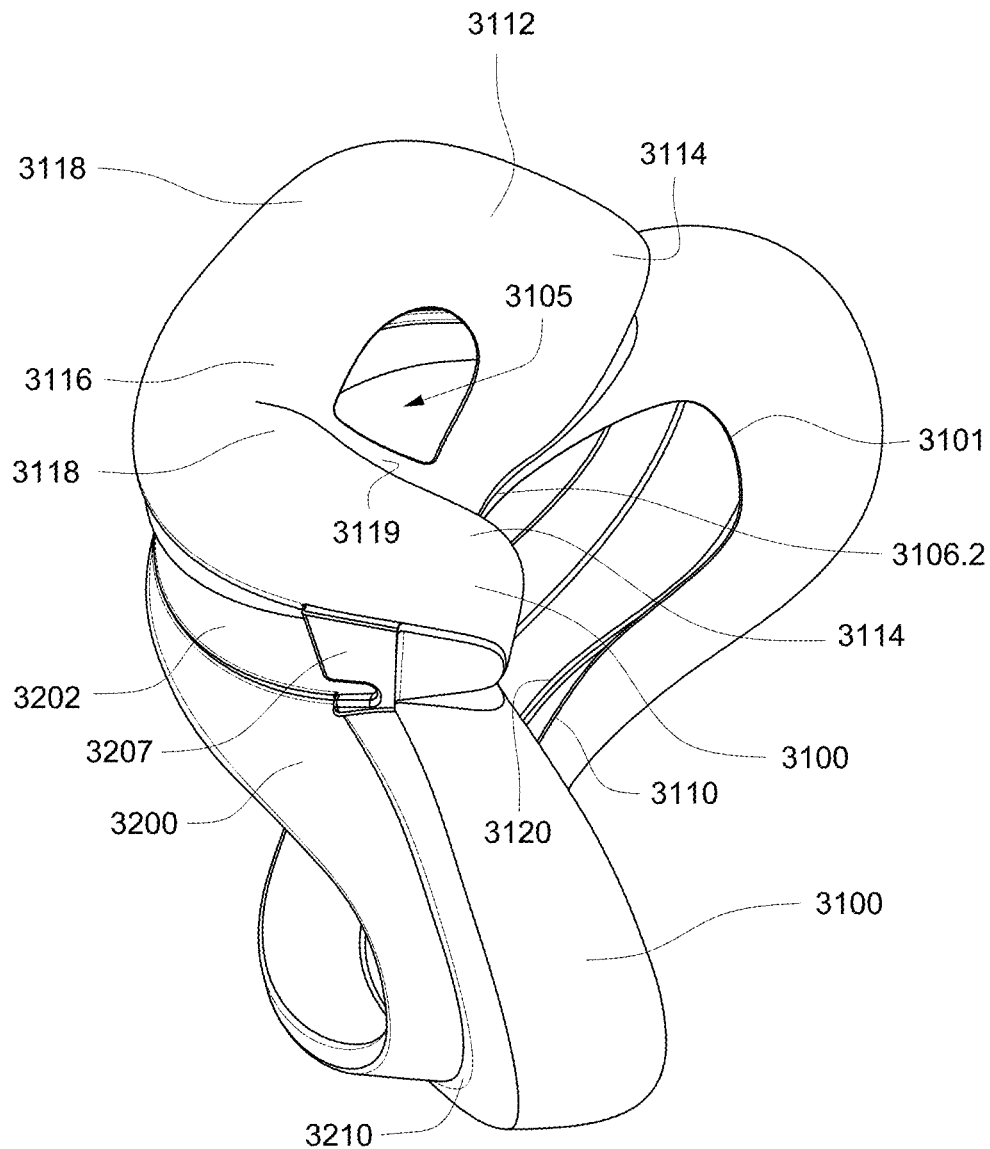

FIG. 16c shows a further top perspective view of a seal-forming structure and plenum chamber according to an example of the present technology.

Figure 16D:
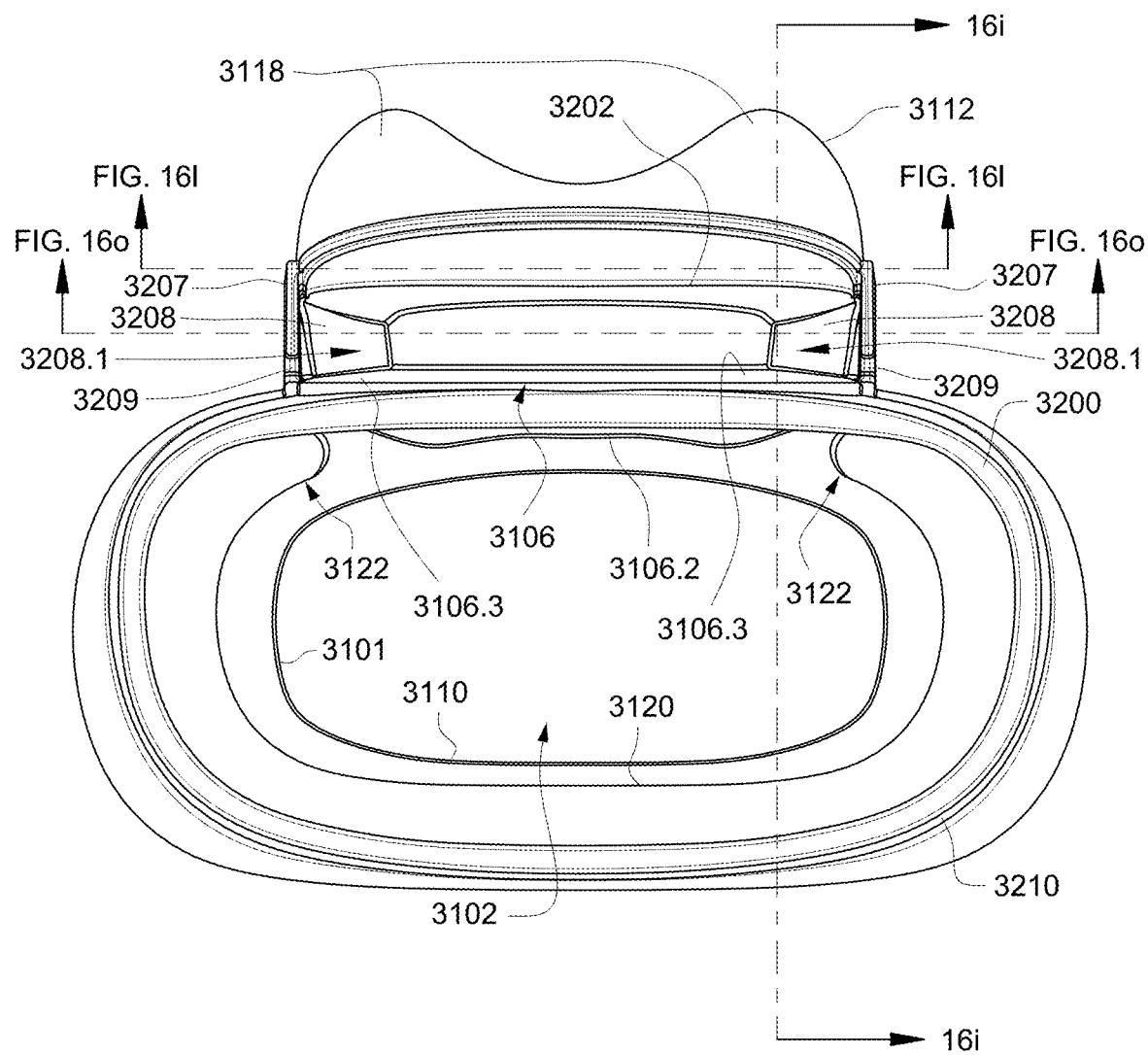

FIG. 16d shows a front view of a seal-forming structure and plenum chamber according to an example of the present technology.

Figure 16E:
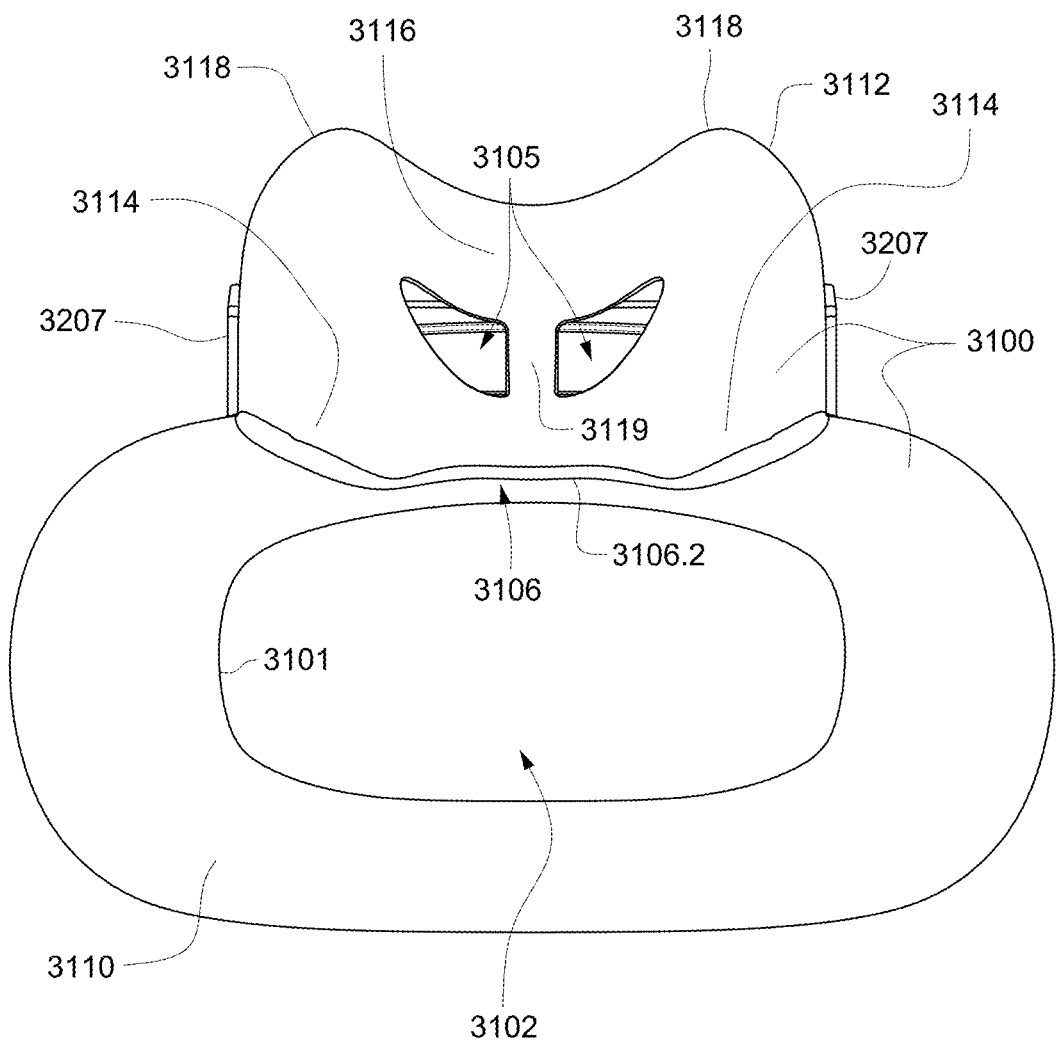

FIG. 16e shows a rear view of a seal-forming structure and plenum chamber according to an example of the present technology.

Figure 16F:
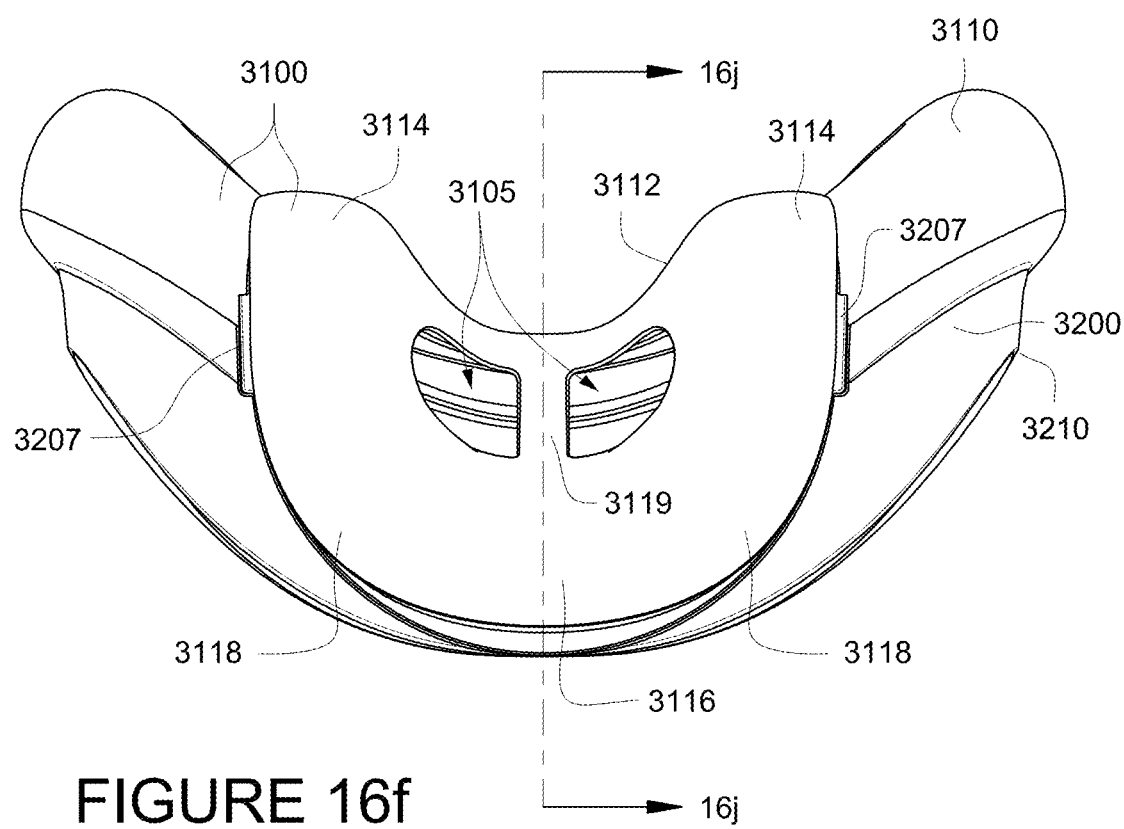

FIG. 16f shows a top view of a seal-forming structure and plenum chamber according to an example of the present technology.

Figure 16G:
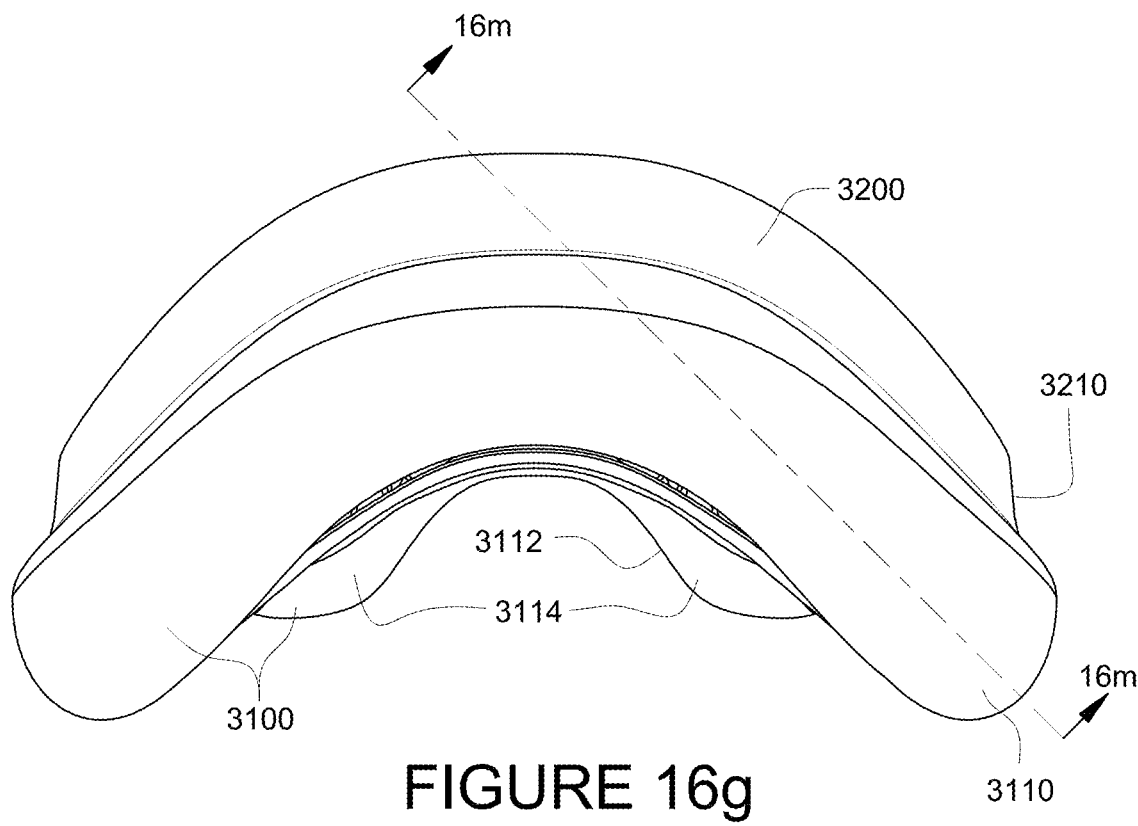

FIG. 16g shows a bottom view of a seal-forming structure and plenum chamber according to an example of the present technology.

Figure 16H:
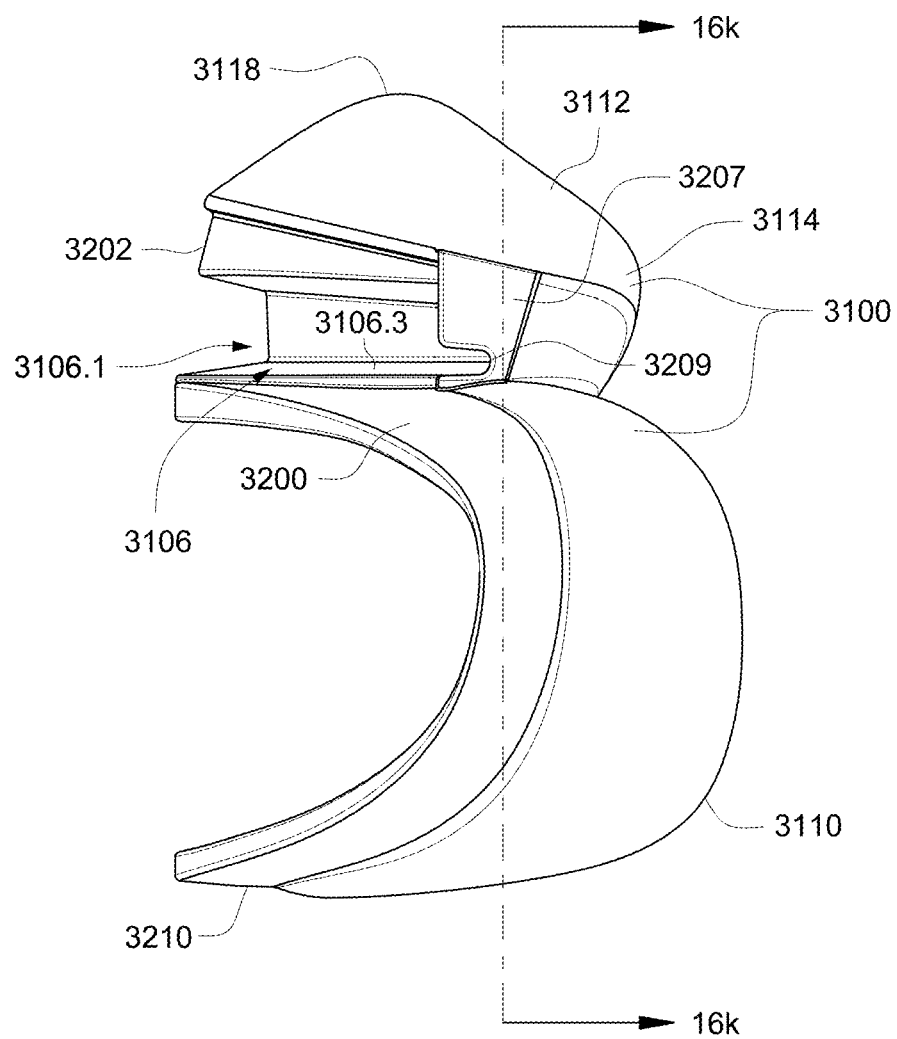

FIG. 16h shows a side view of a seal-forming structure and plenum chamber according to an example of the present technology.

Figure 16I:
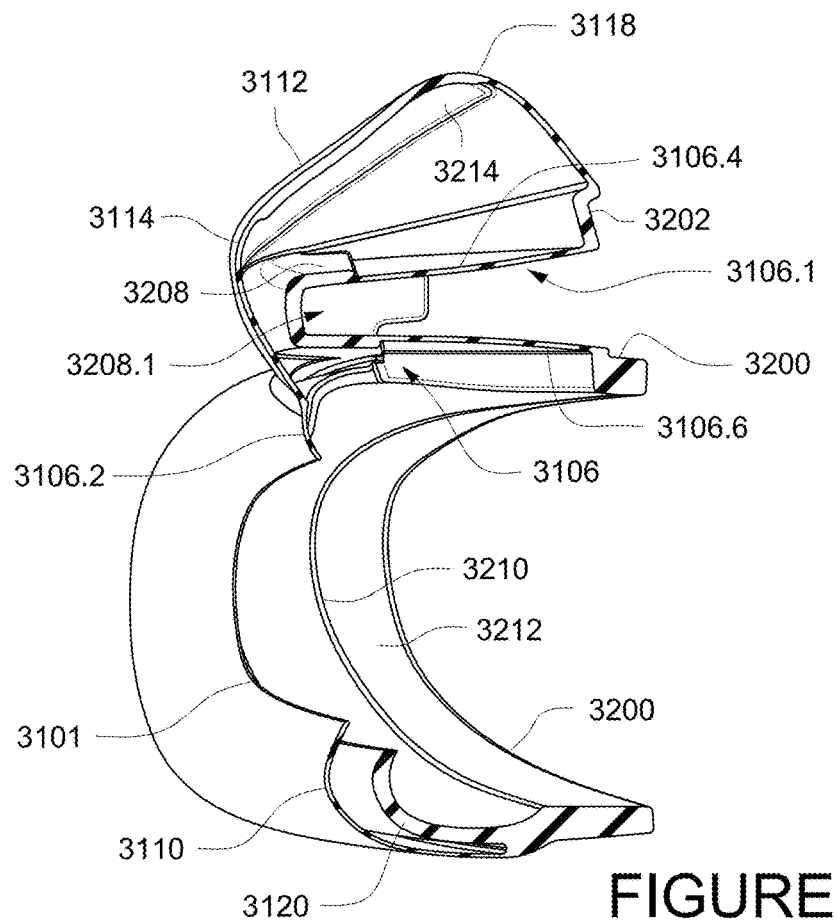

FIG. 16i shows a cross-sectional view of a seal-forming structure and plenum chamber taken through line 16i-16i of FIG. 16d according to an example of the present technology.

Figure 16J:
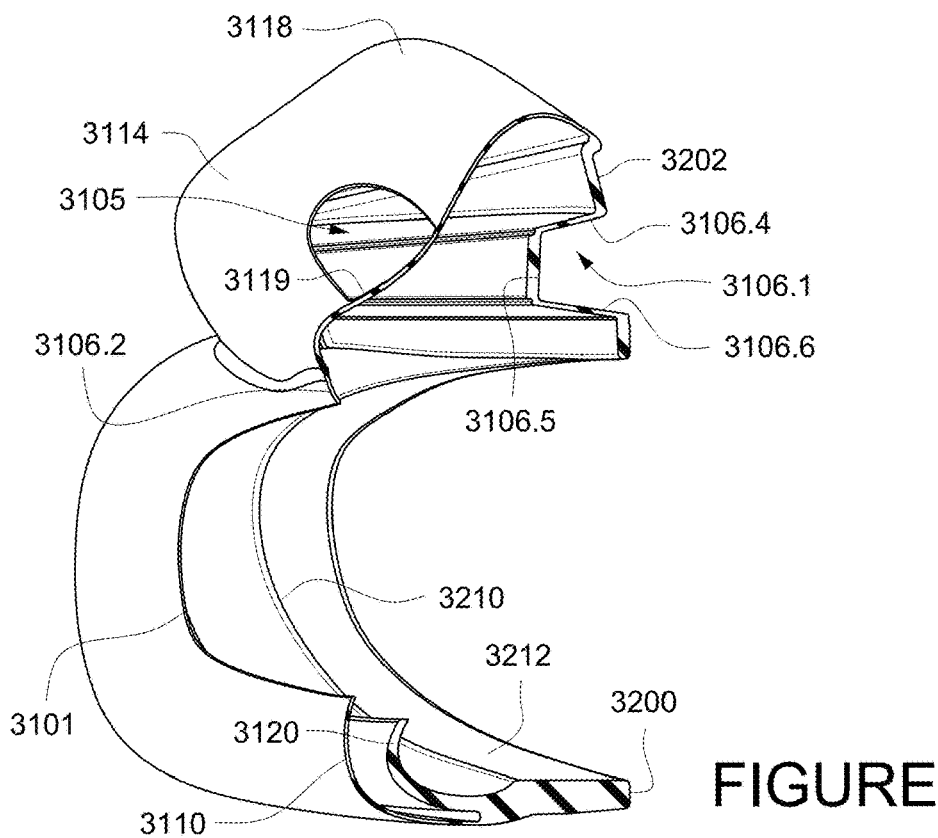

FIG. 16j shows a cross-sectional view of a seal-forming structure and plenum chamber taken through line 16j-16j of FIG. 16f according to an example of the present technology.

Figure 16K:
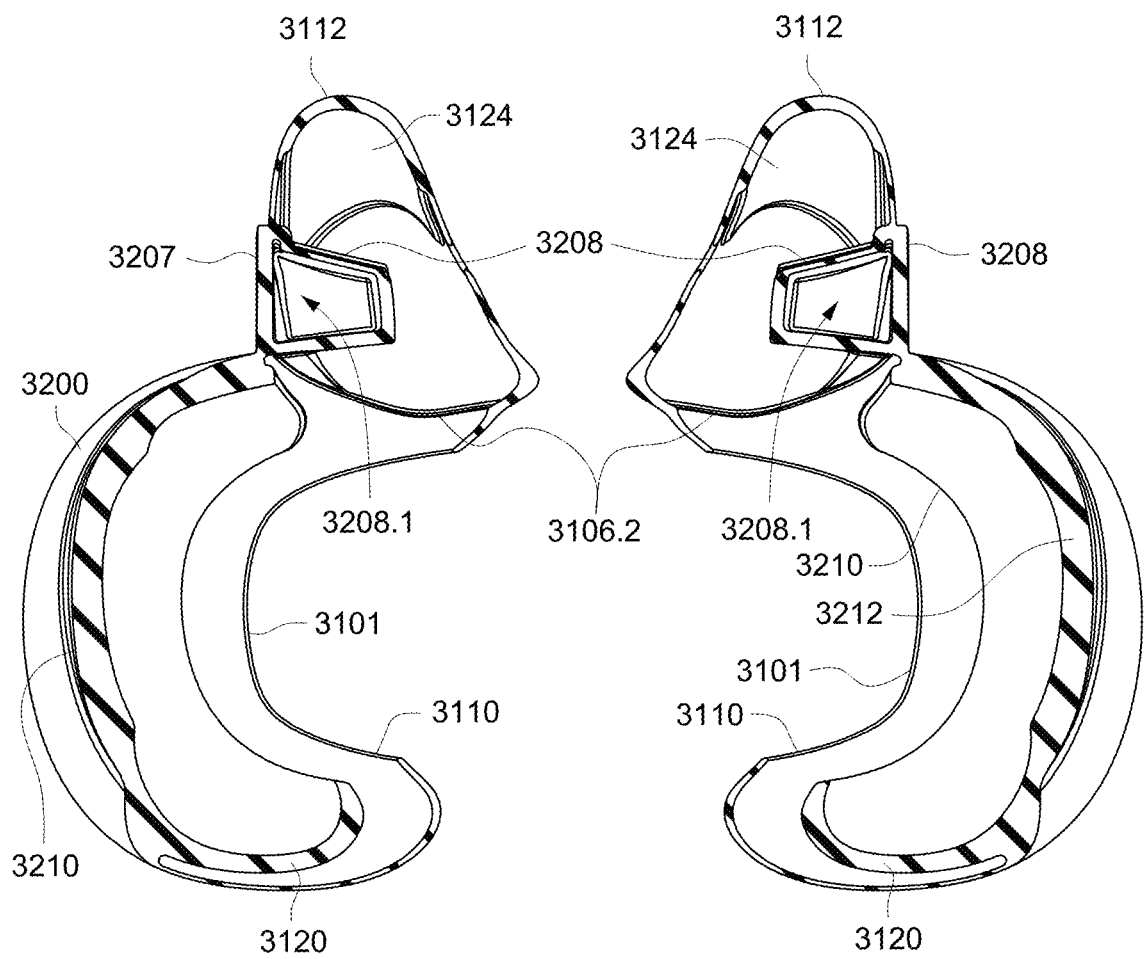

FIG. 16k shows a cross-sectional view of a seal-forming structure and plenum chamber taken through line 16k-16k of FIG. 16h according to an example of the present technology.

Figure 16L:
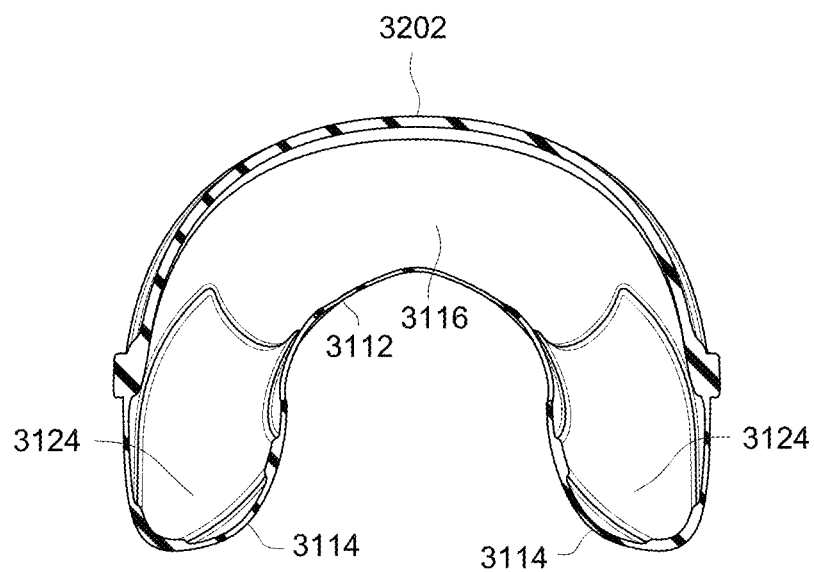

FIG. 16l shows a cross-sectional view of a seal-forming structure and plenum chamber taken through line 16l-16l of FIG. 16d according to an example of the present technology.

Figure 16M:
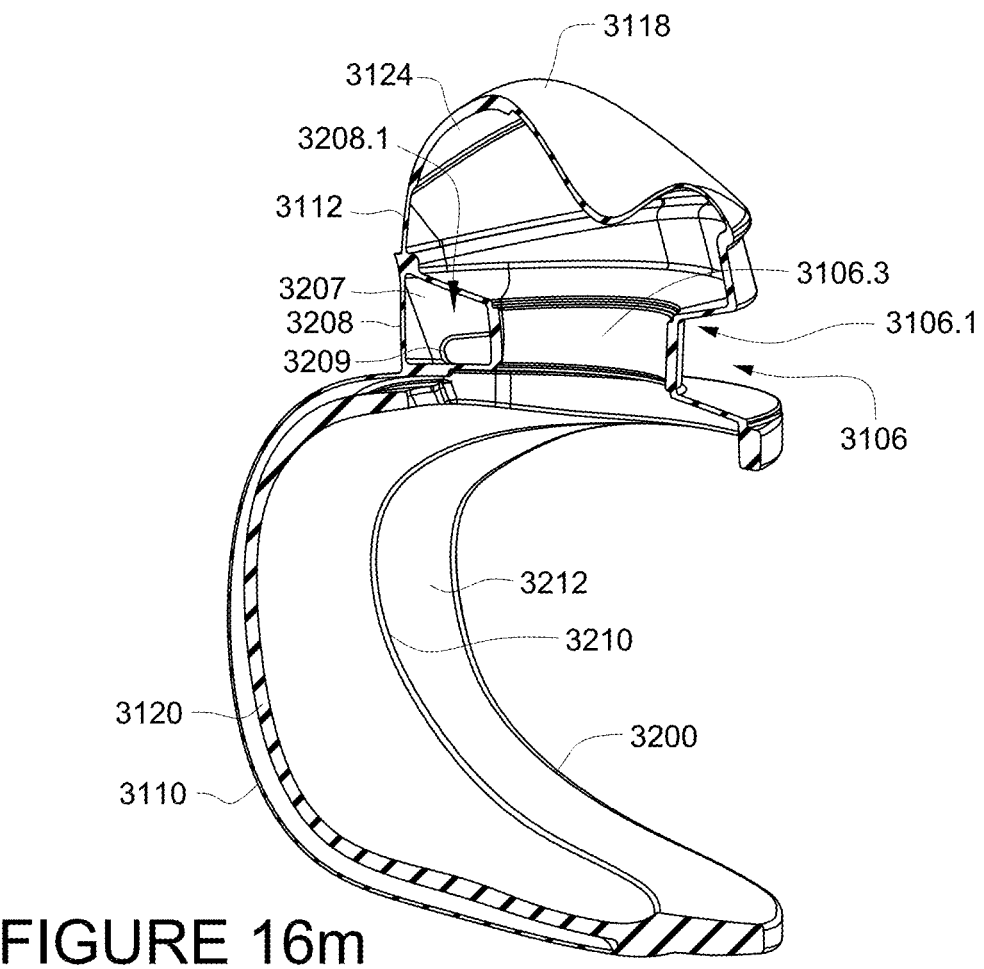

FIG. 16m shows a cross-sectional view of a seal-forming structure and plenum chamber taken through line 16m-16m of FIG. 16g according to an example of the present technology.

Figure 16N:
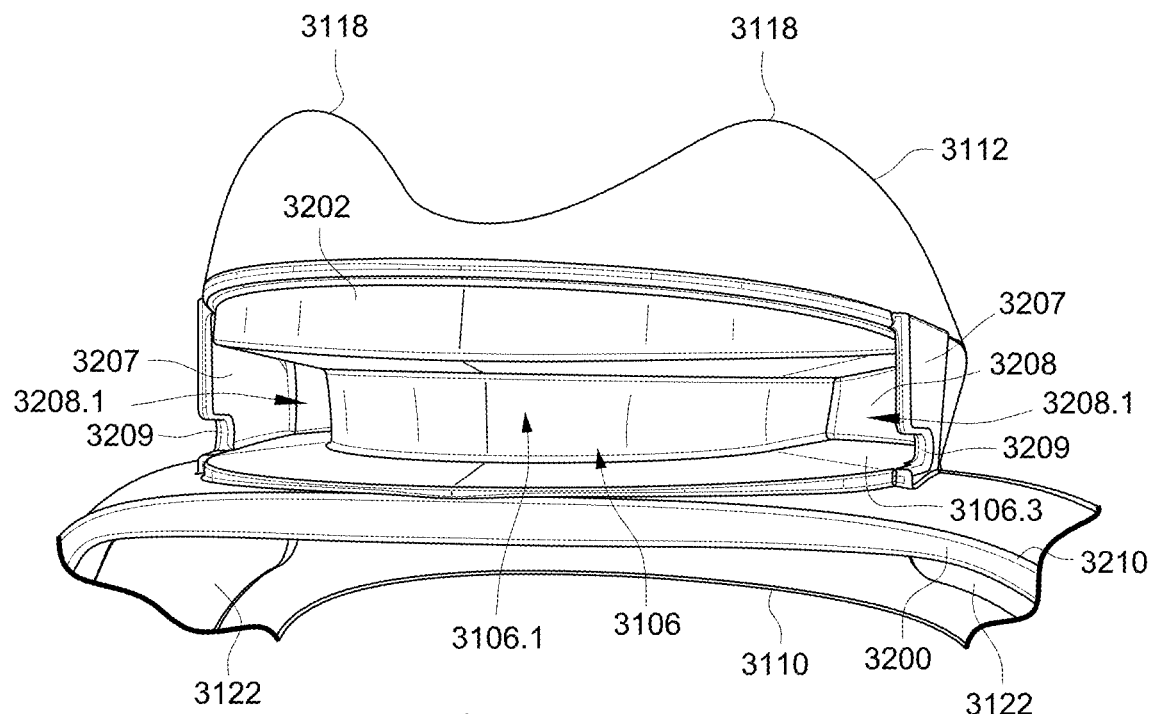

FIG. 16n shows a detailed front perspective view of a seal-forming structure and plenum chamber according to an example of the present technology.

Figure 16O:
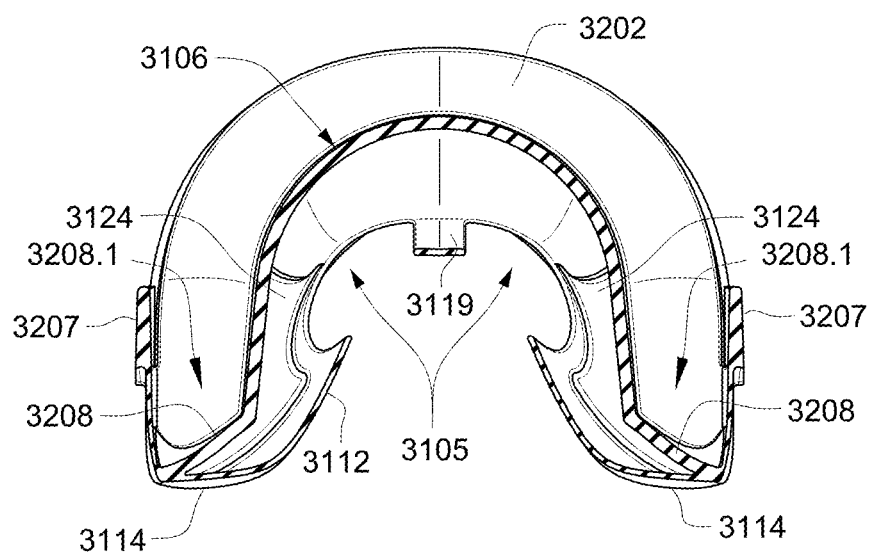

FIG. 16o shows a cross-sectional view of a seal-forming structure and plenum chamber taken through line 16o-16o of FIG. 16d according to an example of the present technology.

Figure 17A:
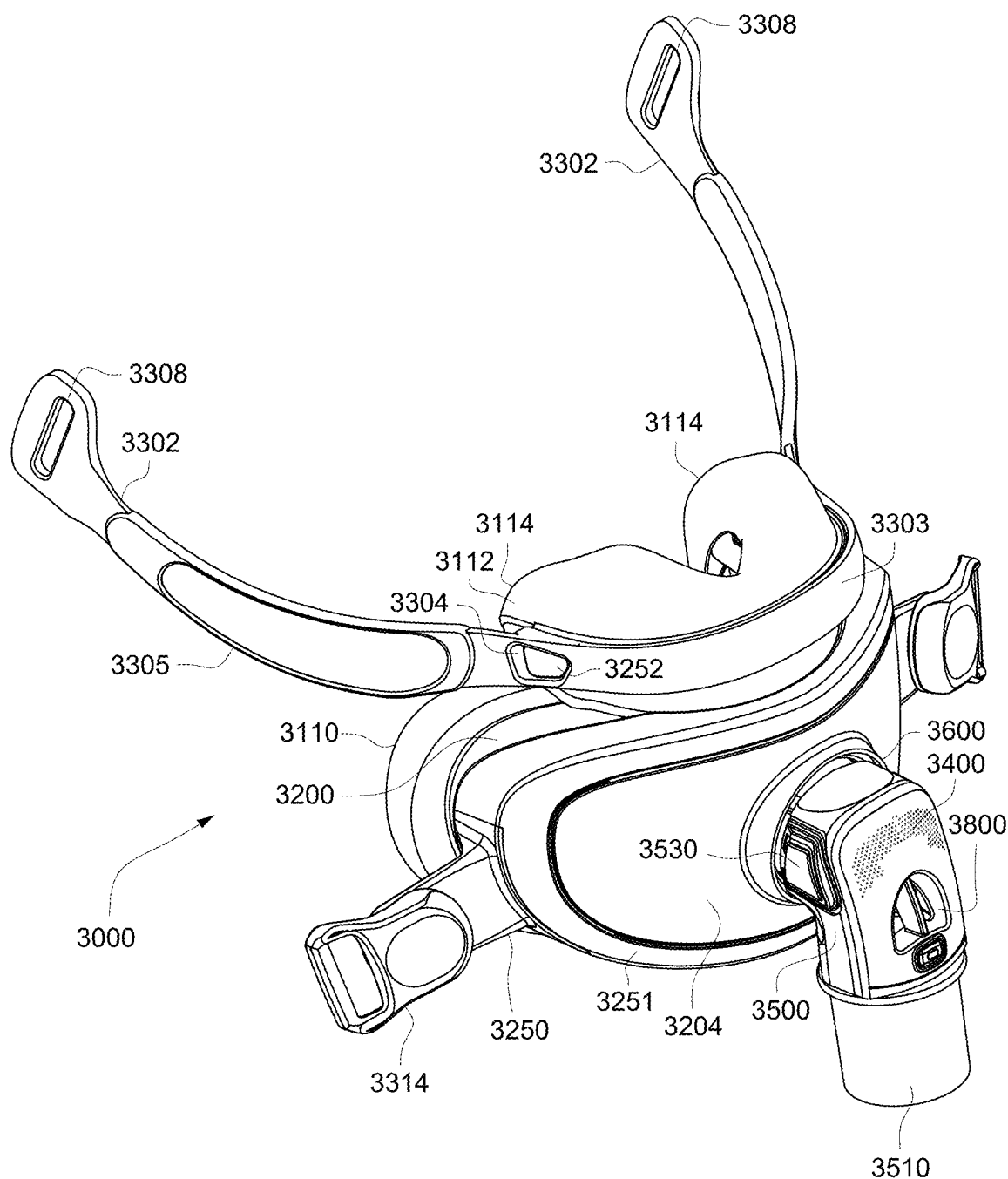

FIG. 17a shows a perspective view of a patient interface according to an example of the present technology.

Figure 17B:
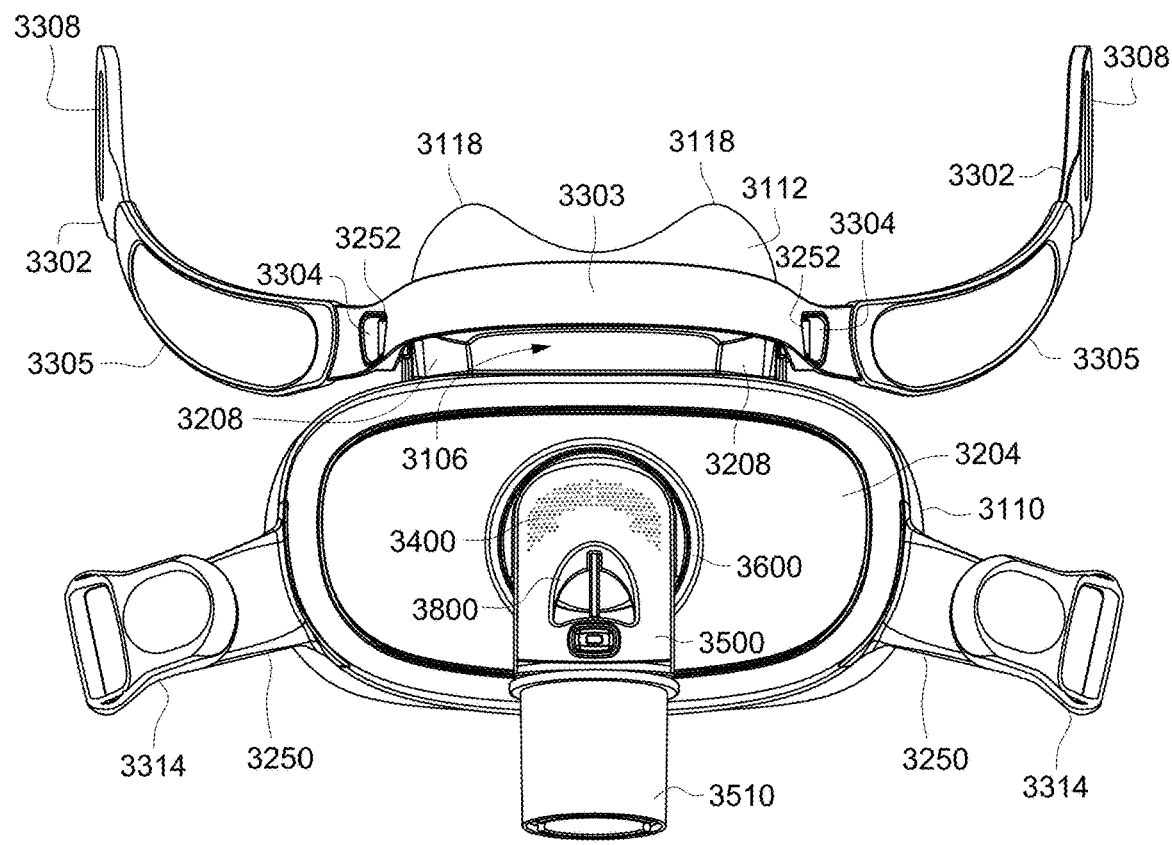

FIG. 17b shows a front view of a patient interface according to an example of the present technology.

Figure 17C:
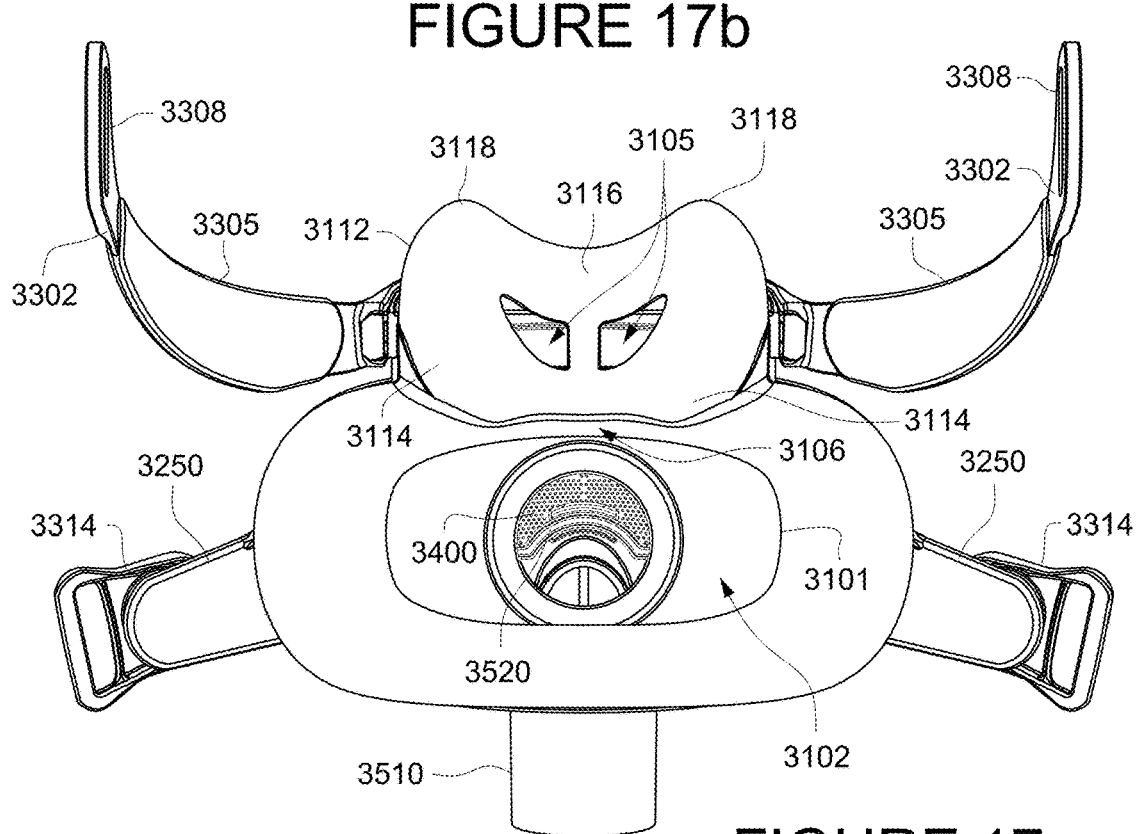

FIG. 17c shows a rear view of a patient interface according to an example of the present technology.

Figure 17D:
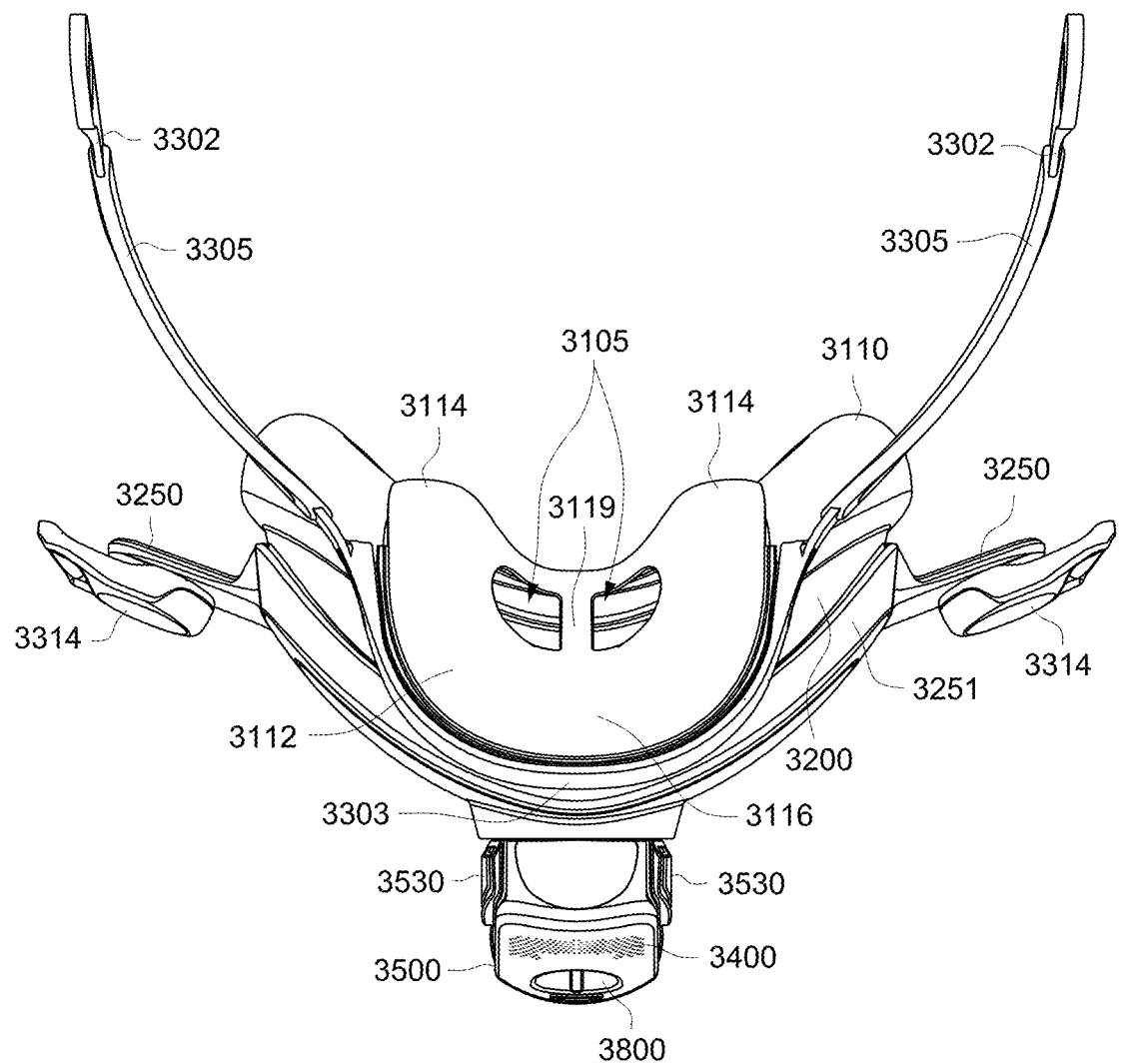

FIG. 17d shows a top view of a patient interface according to an example of the present technology.

Figure 17E:
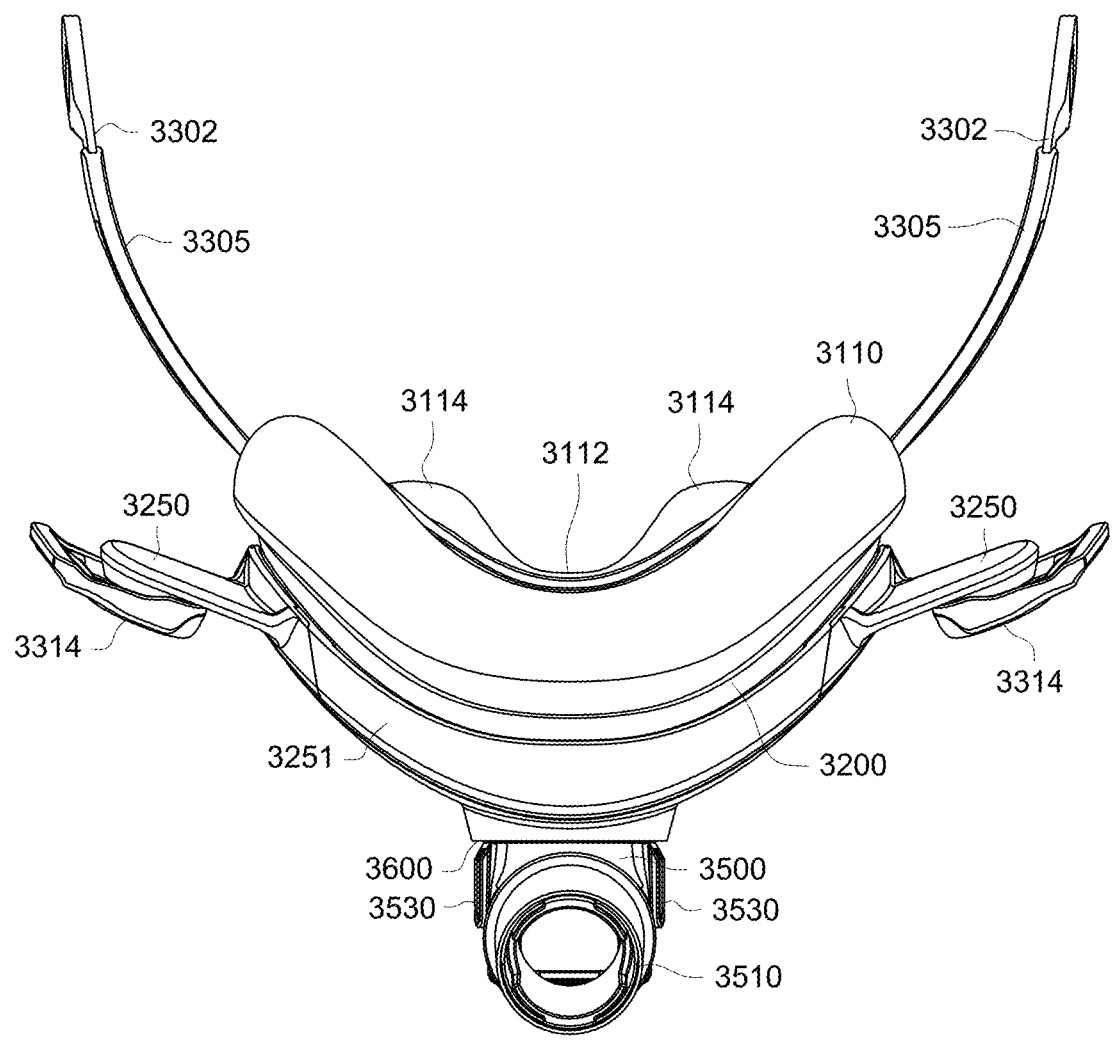

FIG. 17e shows a bottom view of a patient interface according to an example of the present technology.

Figure 17F:
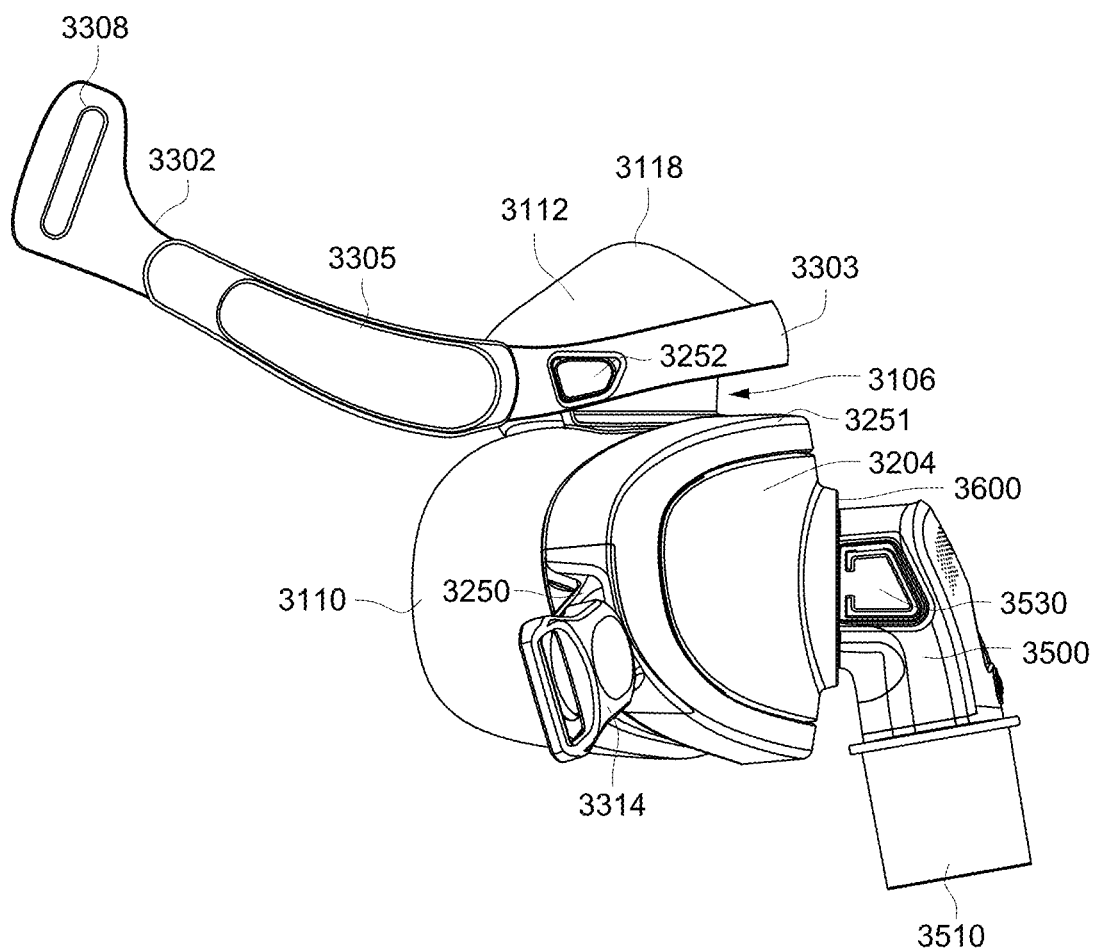

FIG. 17f shows a side view of a patient interface according to an example of the present technology.

Figure 18A:
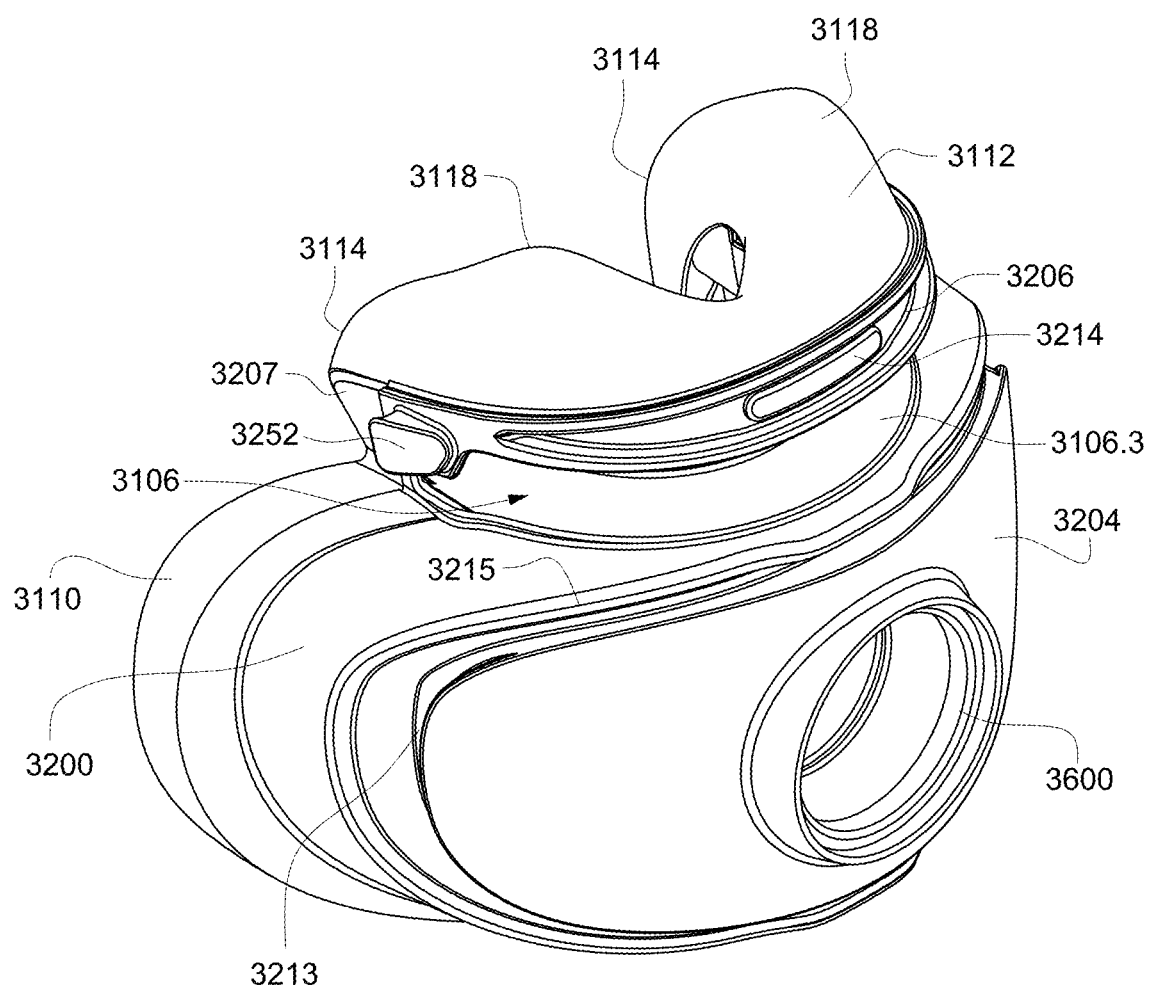

FIG. 18a shows a perspective view of a seal-forming structure with a top plate and a faceplate according to an example of the present technology.

Figure 18B:
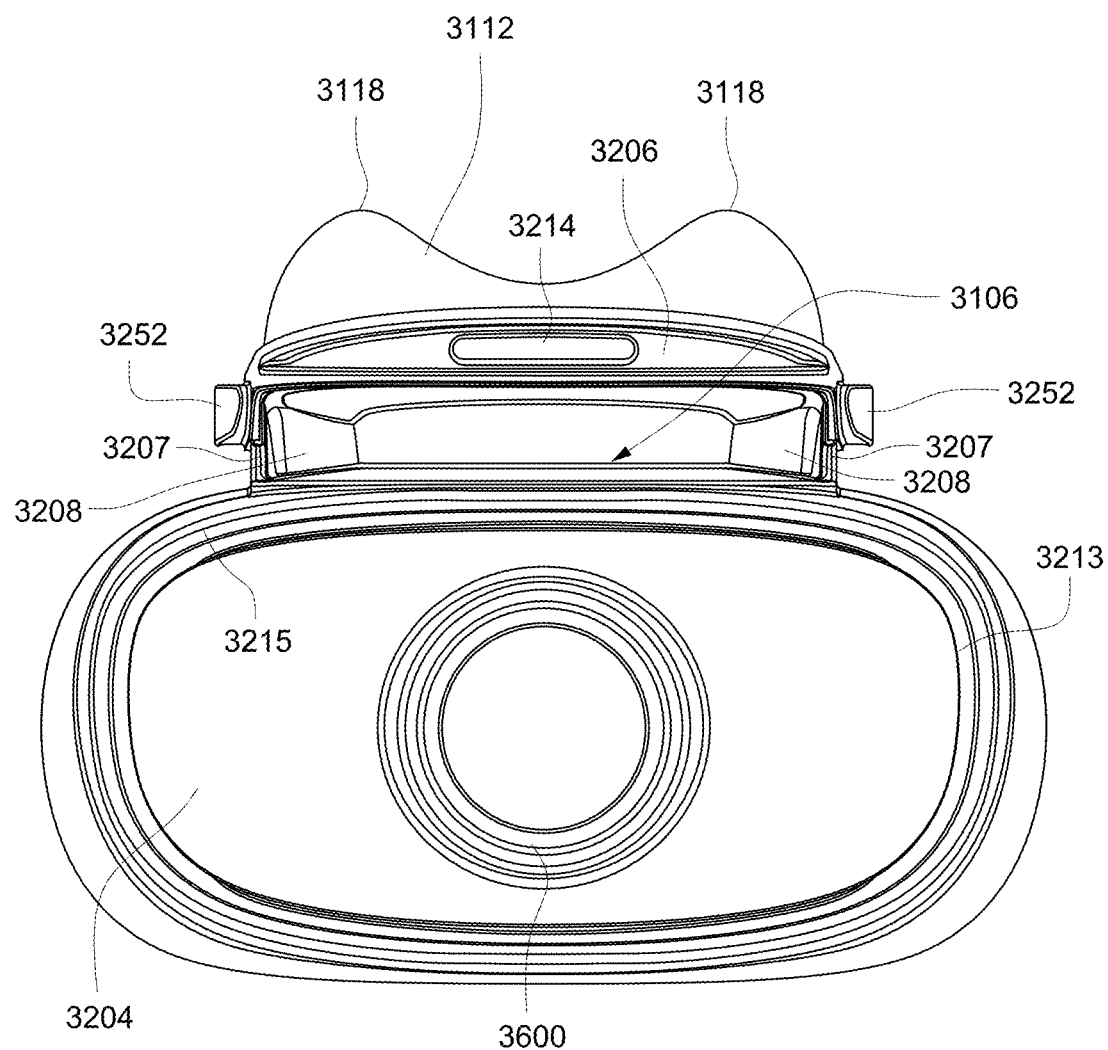

FIG. 18b shows a front view of a seal-forming structure with a top plate and a faceplate according to an example of the present technology.

Figure 18C:
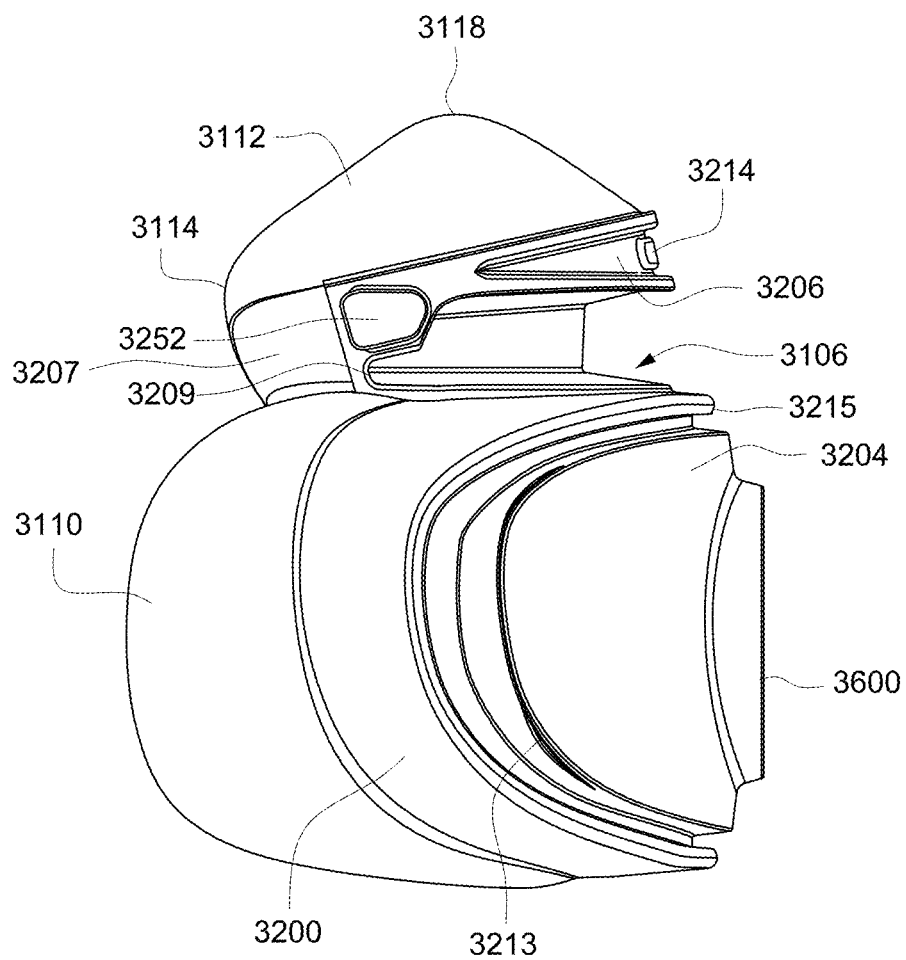

FIG. 18c shows a side view of a seal-forming structure with a top plate and a faceplate according to an example of the present technology.

Figure 18D:
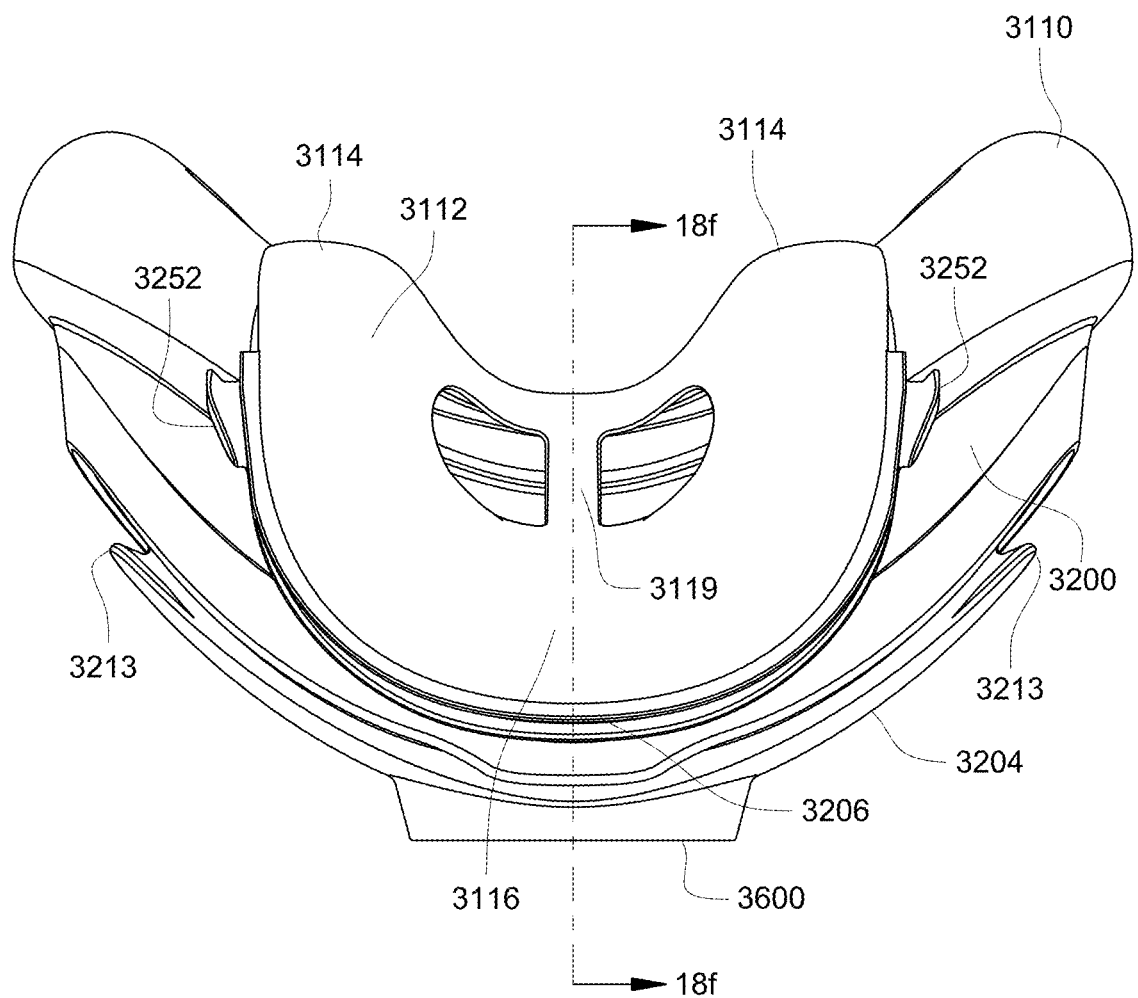

FIG. 18d shows a top view of a seal-forming structure with a top plate and a faceplate according to an example of the present technology.

Figure 18E:
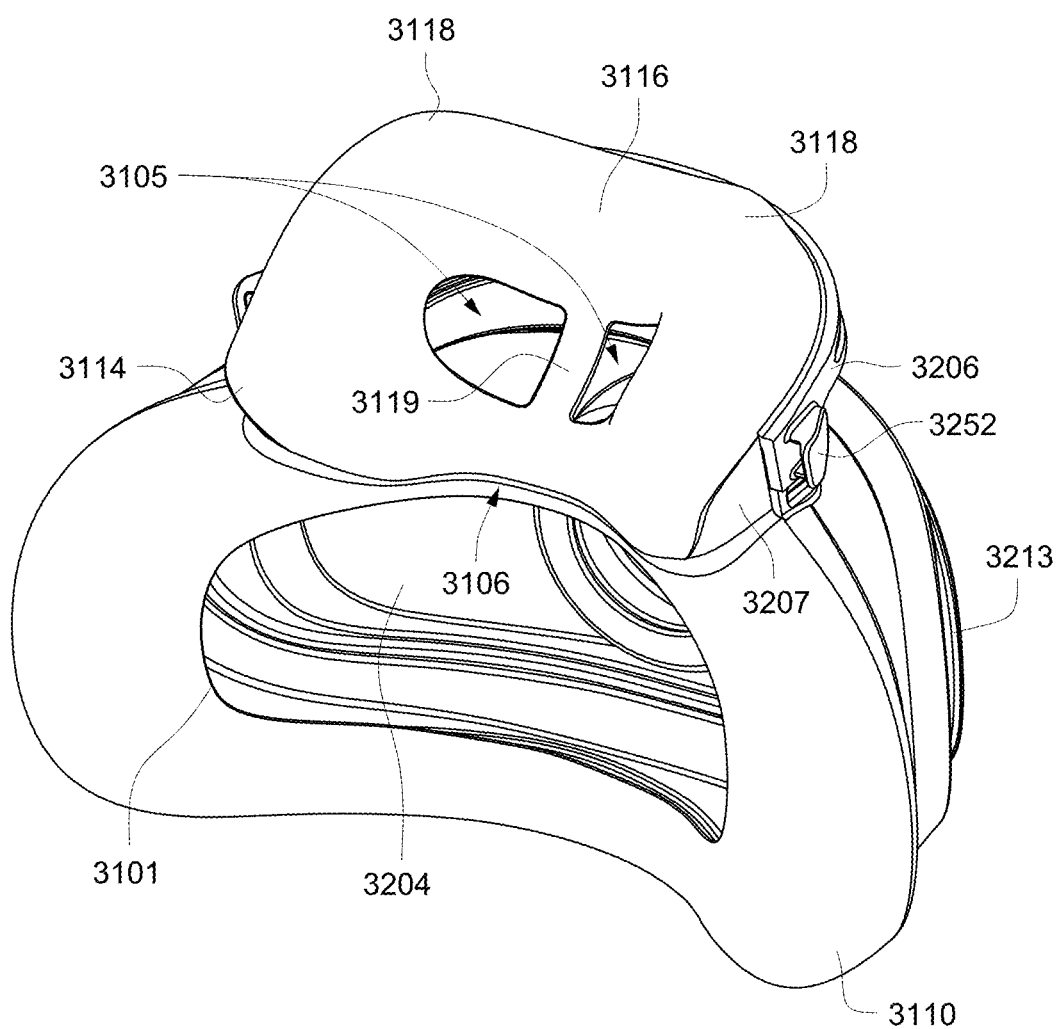

FIG. 18e shows a rear perspective view of a seal-forming structure with a top plate and a faceplate according to an example of the present technology.

Figure 18F:
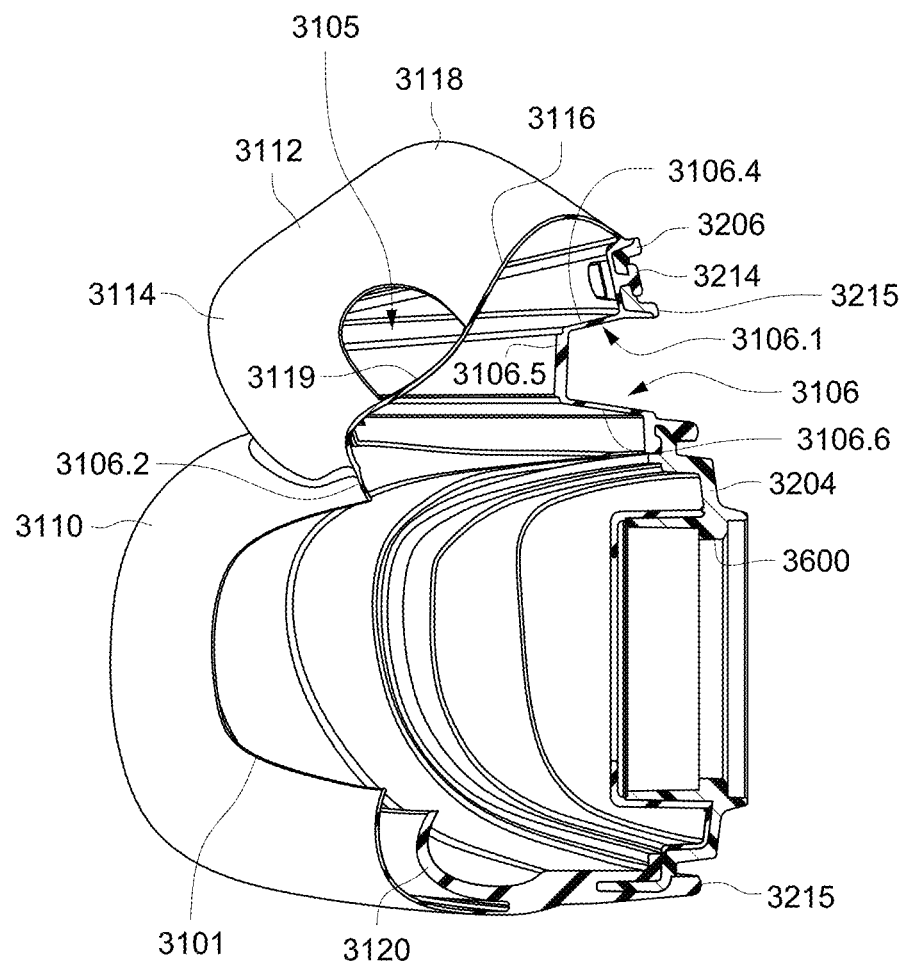

FIG. 18f shows a cross-sectional view taken through line 18f-18f of FIG. 18d of a seal-forming structure with a top plate and a faceplate according to an example of the present technology.

Figure 19A:
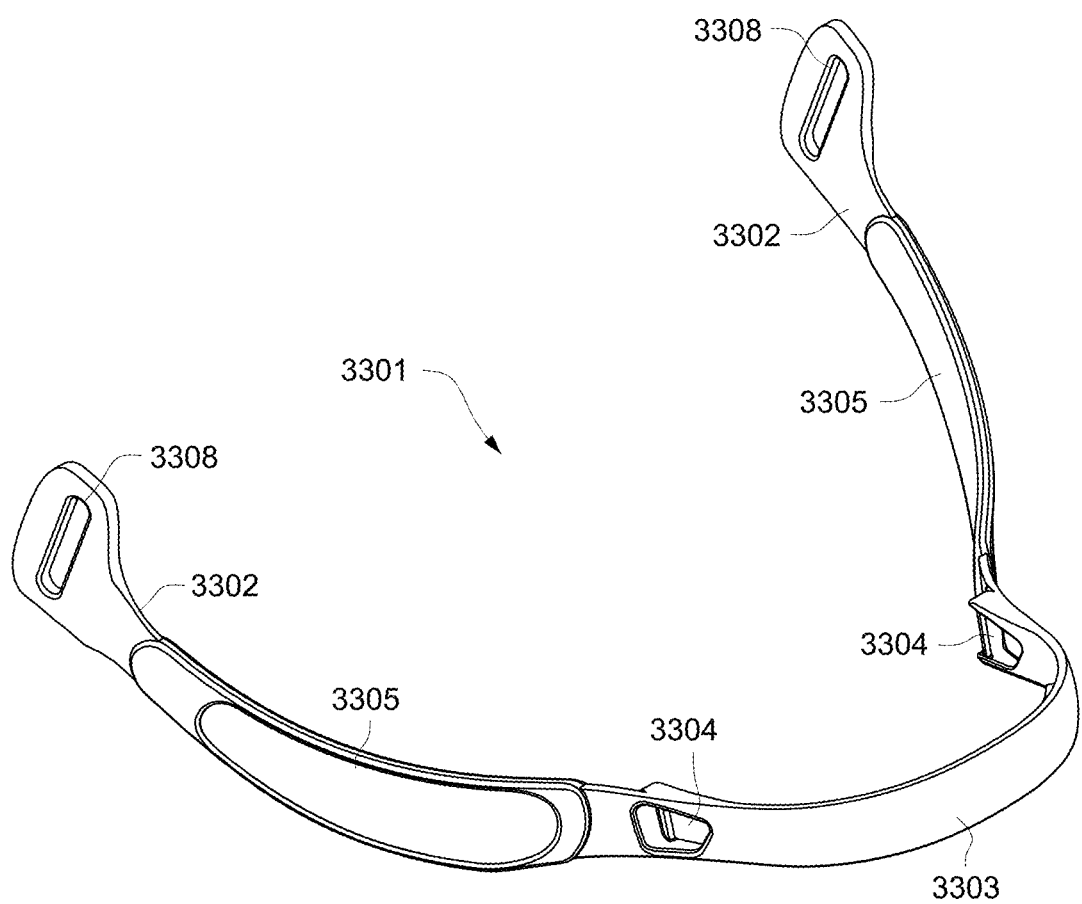

FIG. 19a shows a perspective view of a rigidiser arm assembly according to an example of the present technology.

Figure 19B:
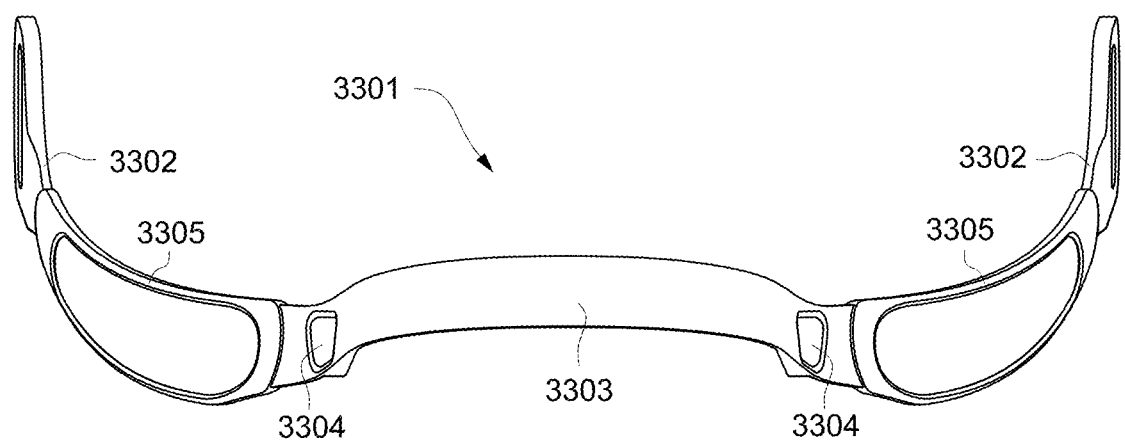

FIG. 19b shows a front view of a rigidiser arm assembly according to an example of the present technology.

Figure 19C:
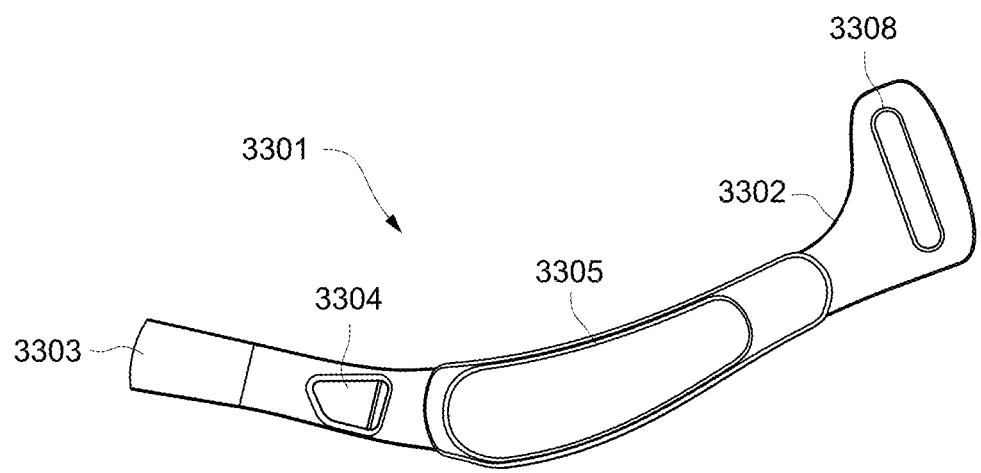

FIG. 19c shows a side view of a rigidiser arm assembly according to an example of the present technology.

Figure 19D:
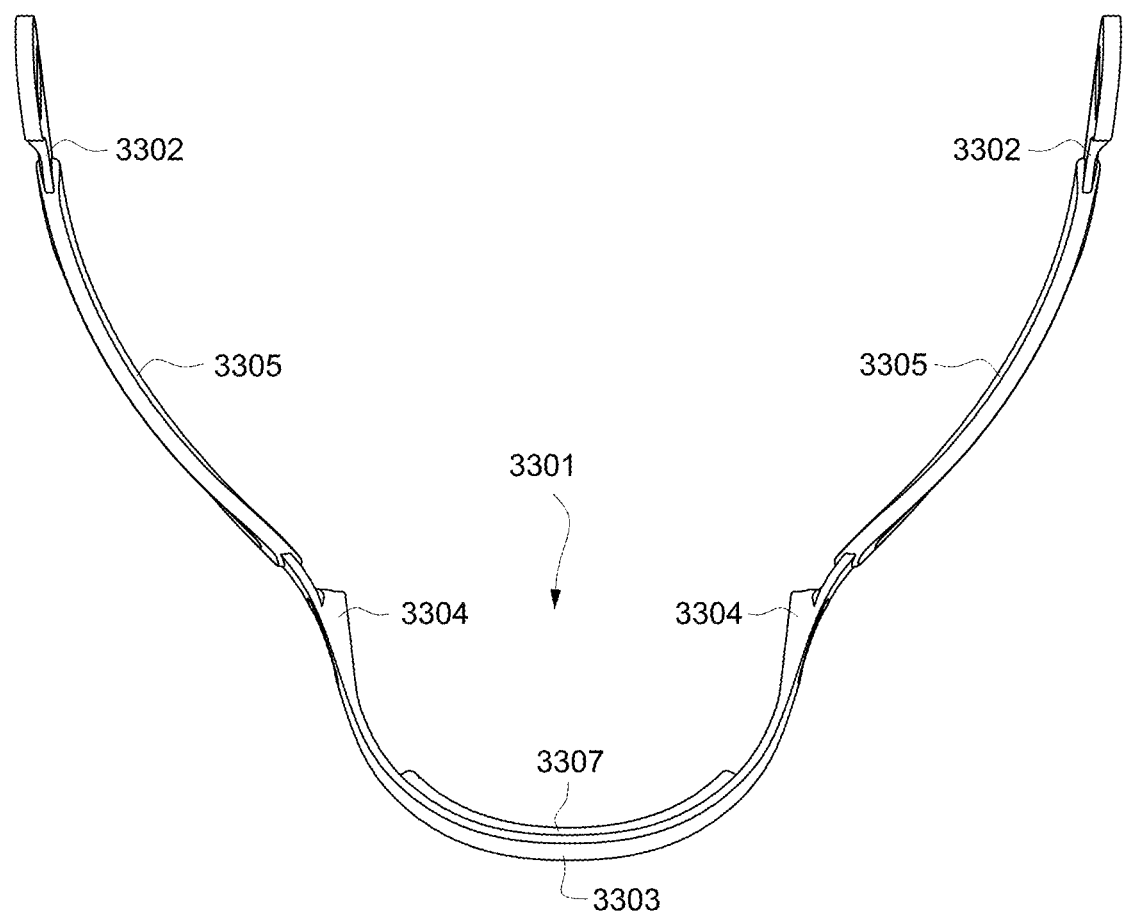

FIG. 19d shows a top view of a rigidiser arm assembly according to an example of the present technology.

Figure 19E:
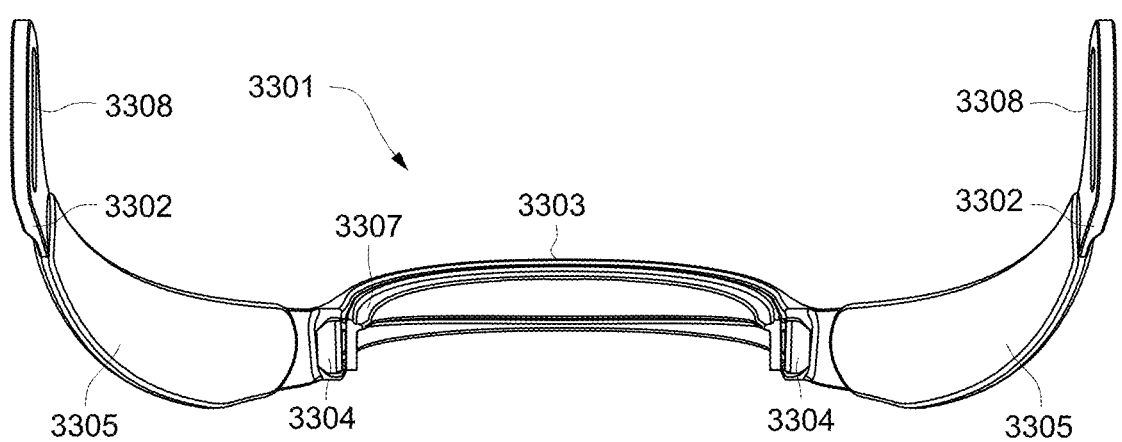

FIG. 19e shows a rear view of a rigidiser arm assembly according to an example of the present technology.

Figure 19F:
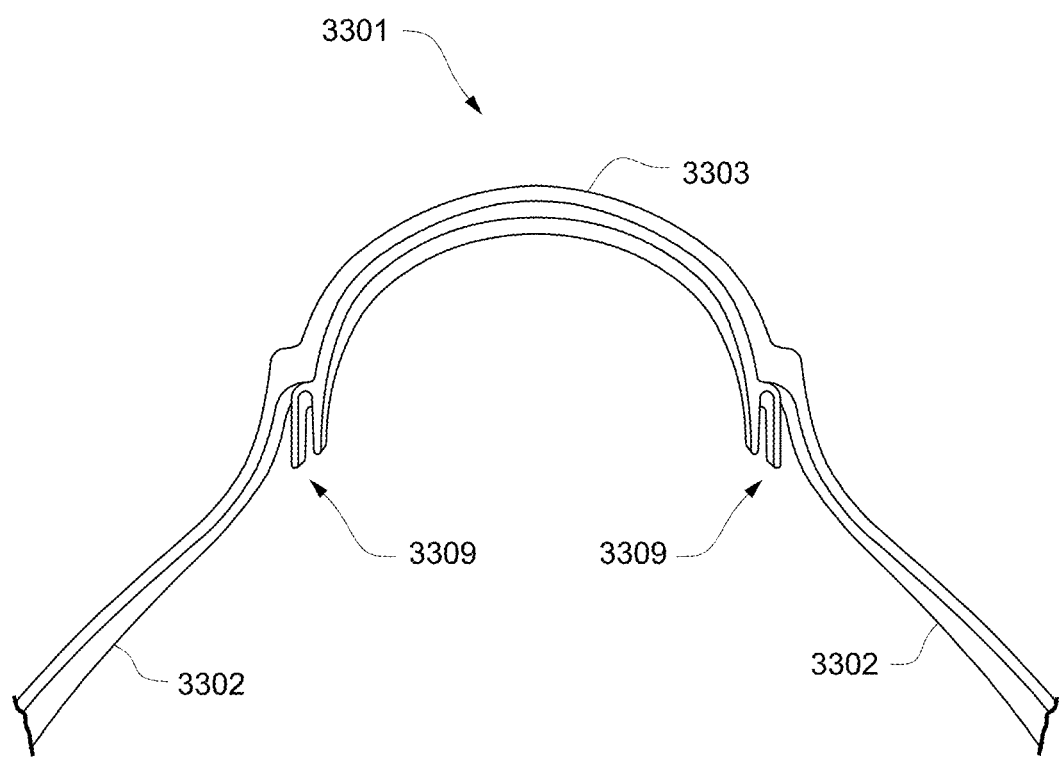

FIG. 19f shows a top view of a rigidiser arm assembly according to an example of the present technology.

Figure 19G:
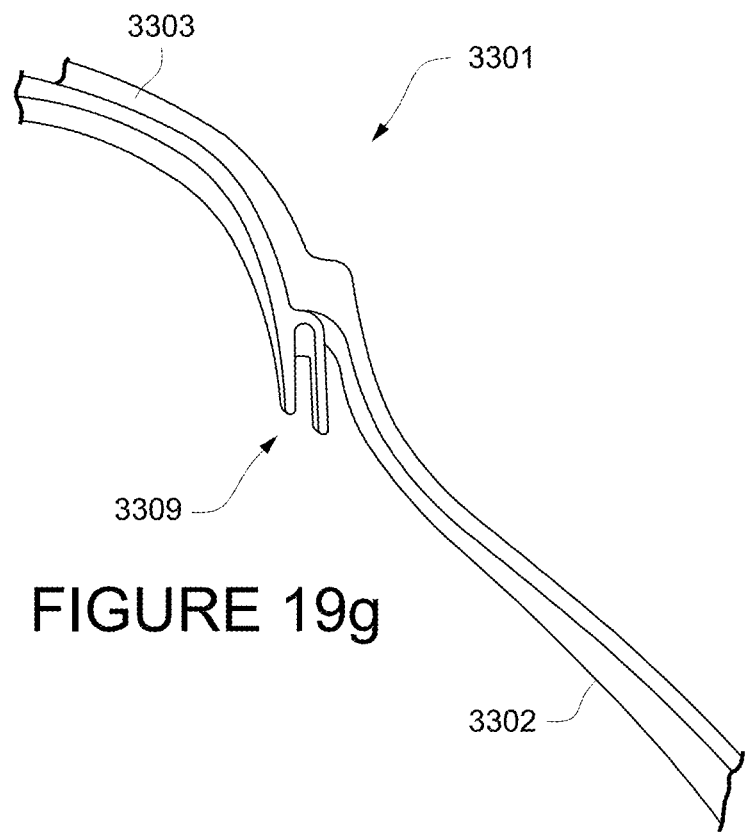

FIG. 19g shows another top view of a rigidiser arm assembly according to an example of the present technology.

Figure 19H:
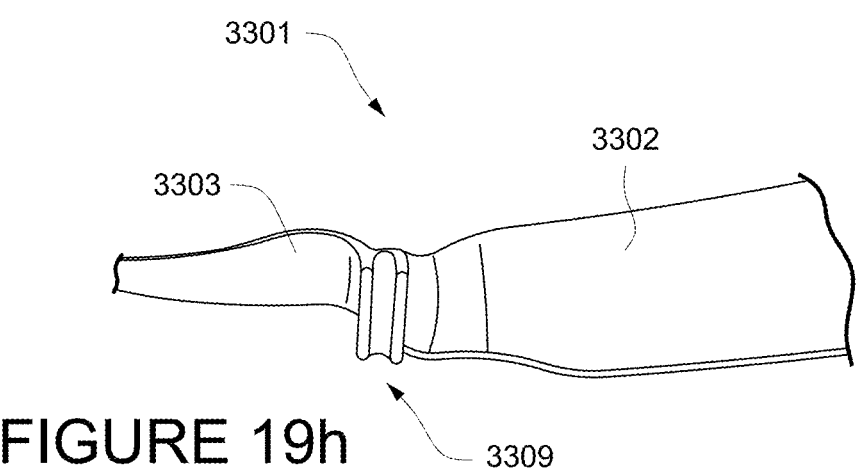

FIG. 19h shows a rear view of a rigidiser arm assembly according to an example of the present technology.

Figure 20A:
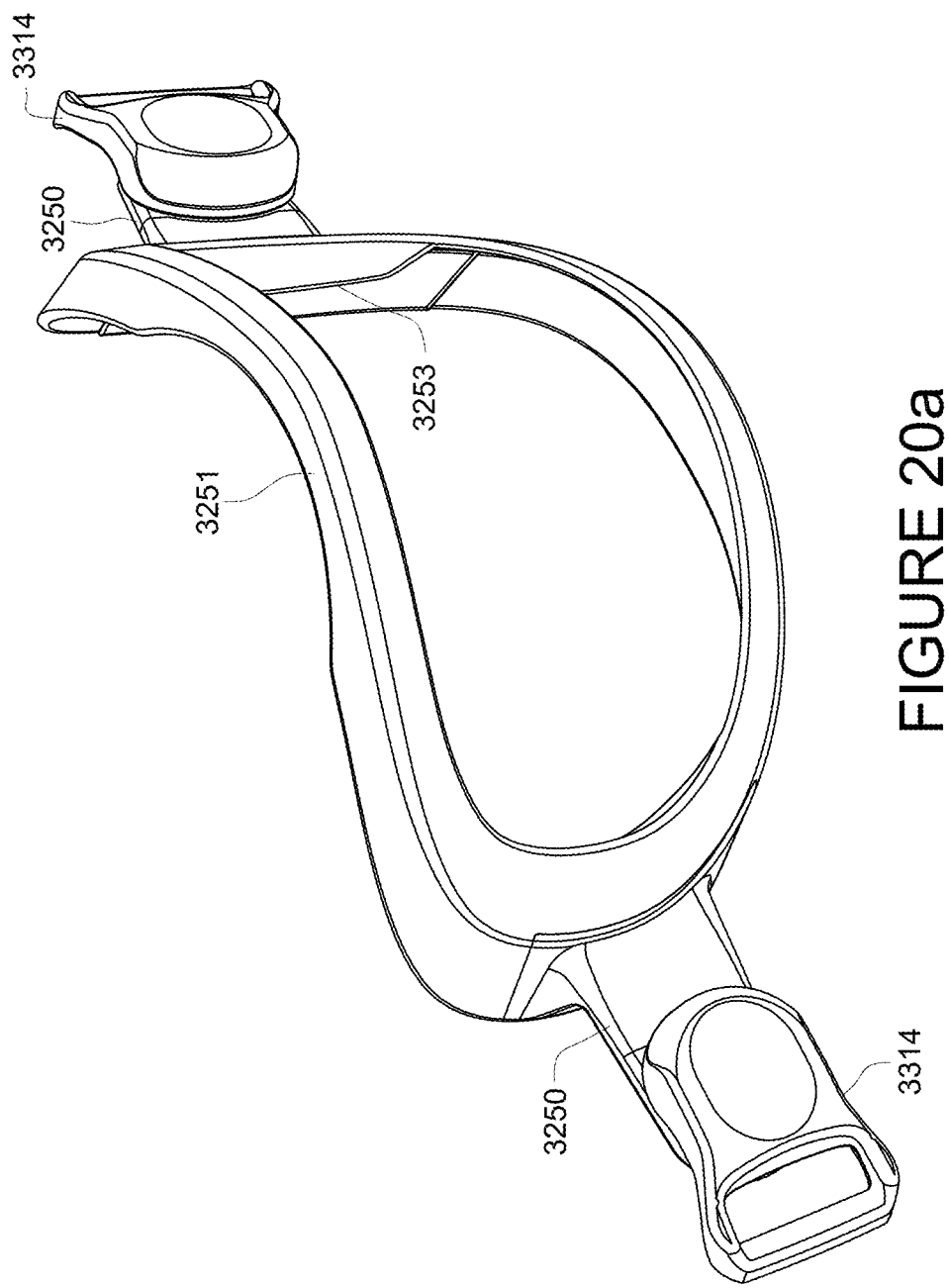

FIG. 20a shows a perspective view of a faceplate frame, lower attachment features, and clips according to an example of the present technology.

Figure 20B:
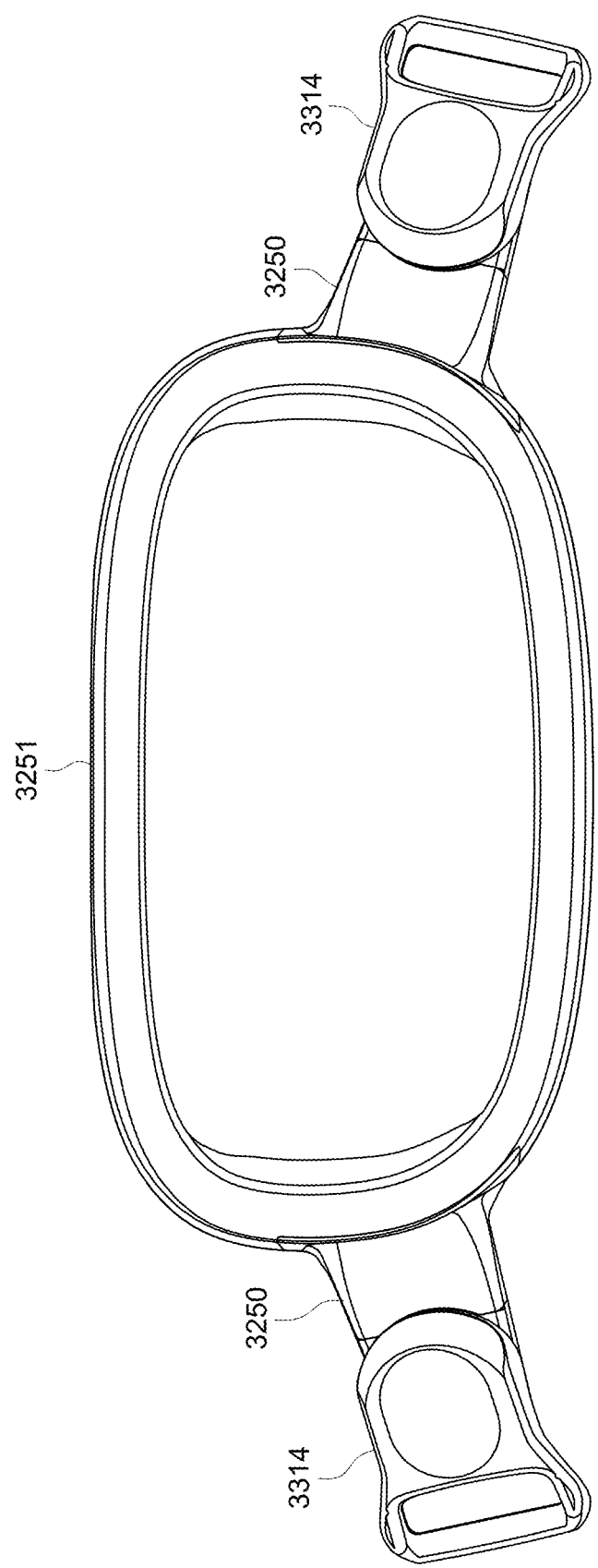

FIG. 20b shows a front view of a faceplate frame, lower attachment features, and clips according to an example of the present technology.

Figure 20C:
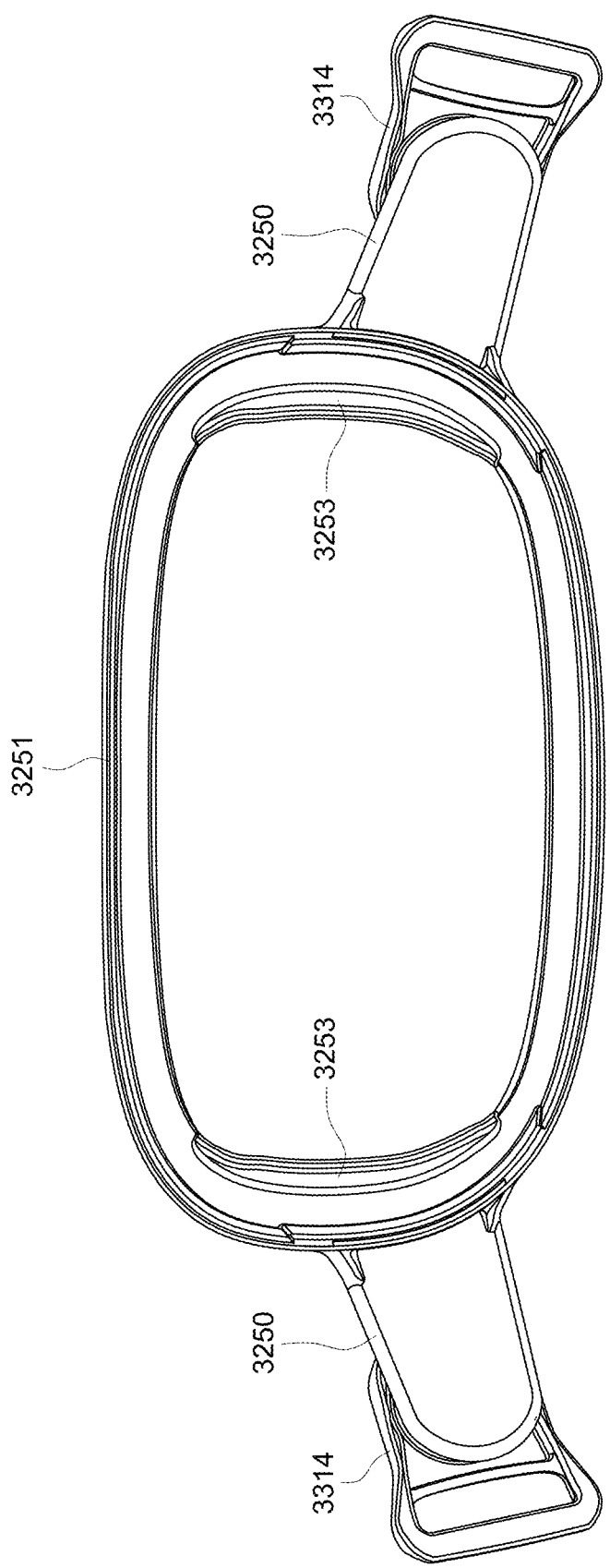

FIG. 20c shows a rear view of a faceplate frame, lower attachment features, and clips according to an example of the present technology.

Figure 20D:
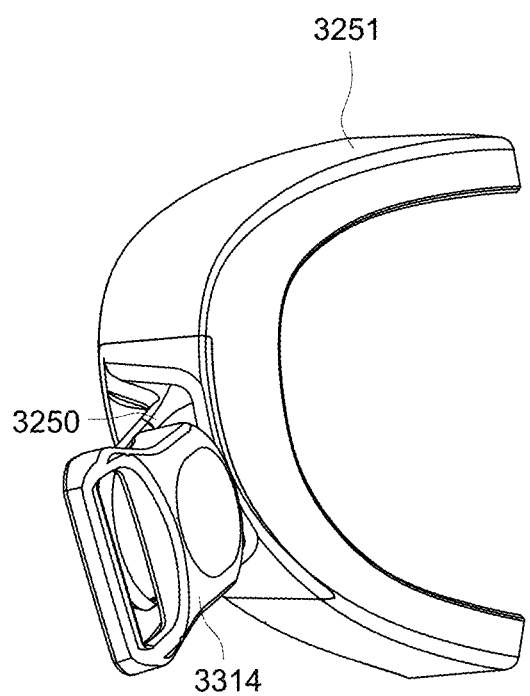

FIG. 20d shows a side view of a faceplate frame, lower attachment features, and clips according to an example of the present technology.

Figure 20E:
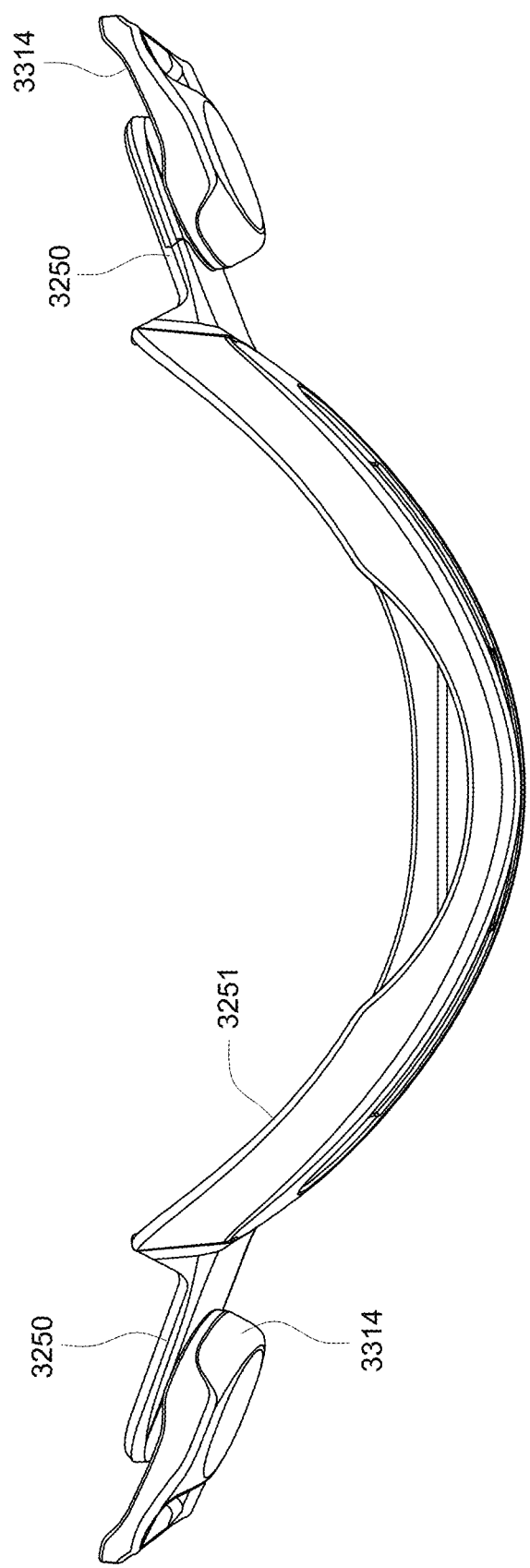

FIG. 20e shows a top view of a faceplate frame, lower attachment features, and clips according to an example of the present technology.

Figure 20F:
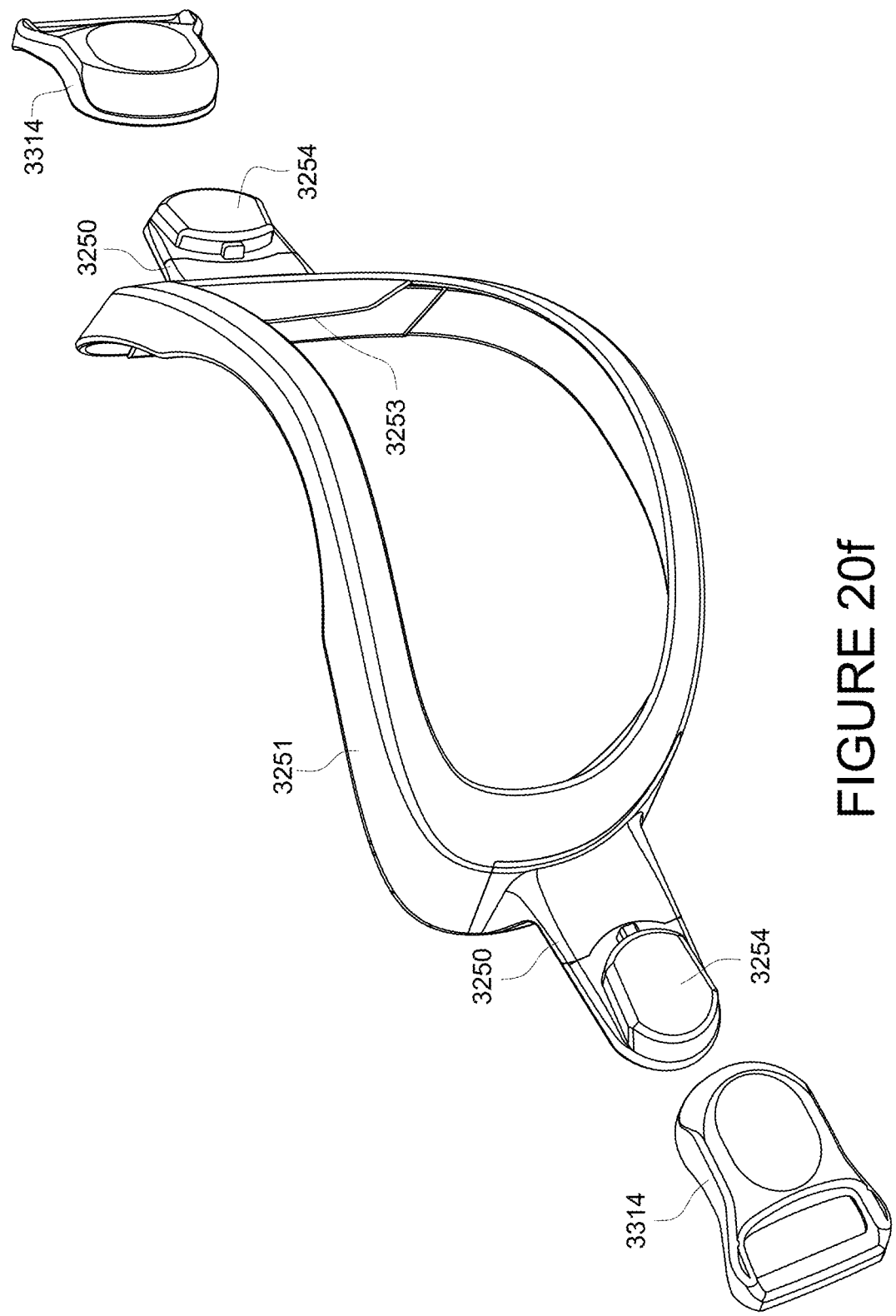

FIG. 20f shows a partially exploded perspective view of a faceplate frame, lower attachment features, and clips according to an example of the present technology.

Figure 20G:
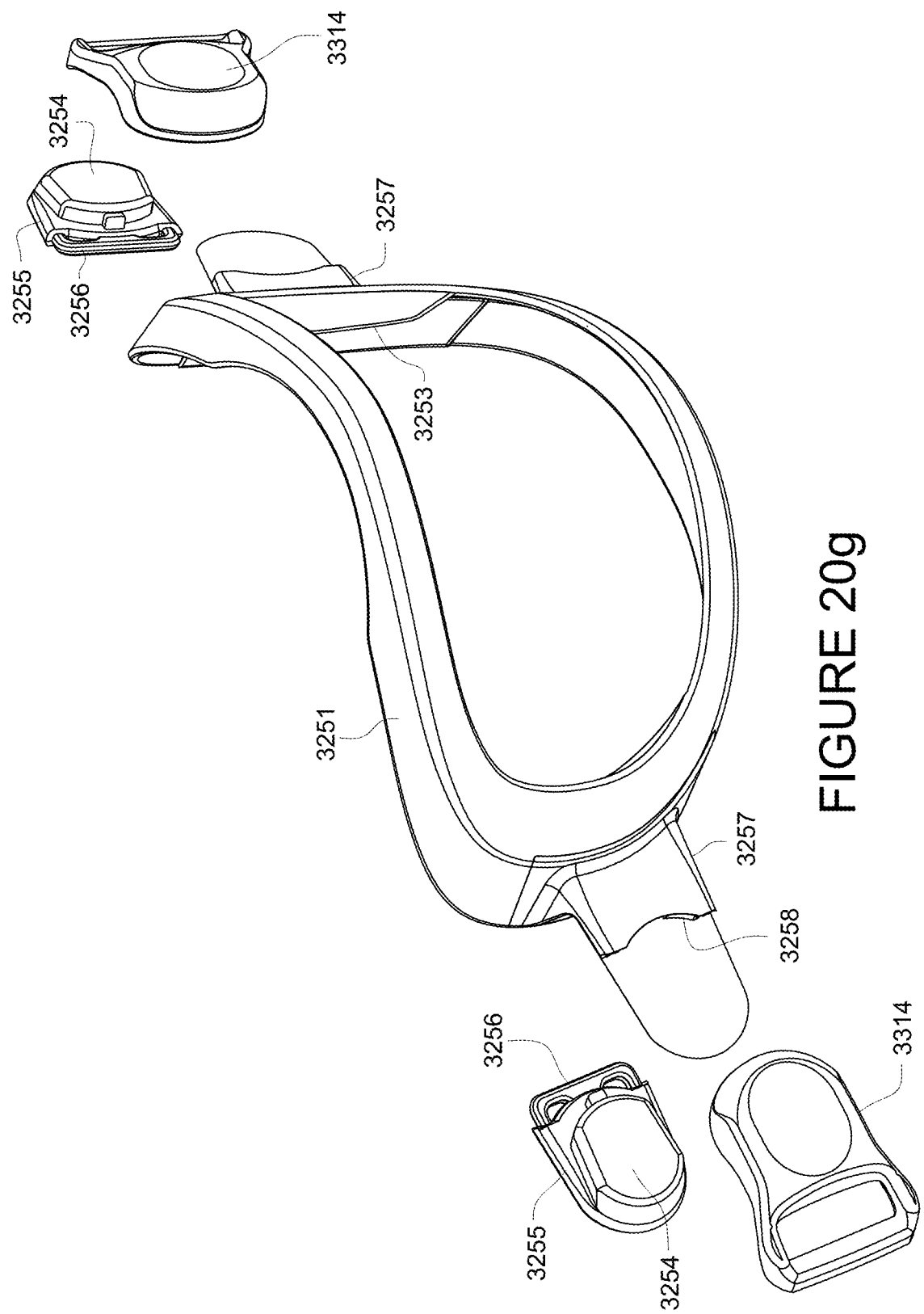

FIG. 20g shows another partially exploded perspective view of a faceplate frame, lower attachment features, and clips according to an example of the present technology.

Figure 20H:
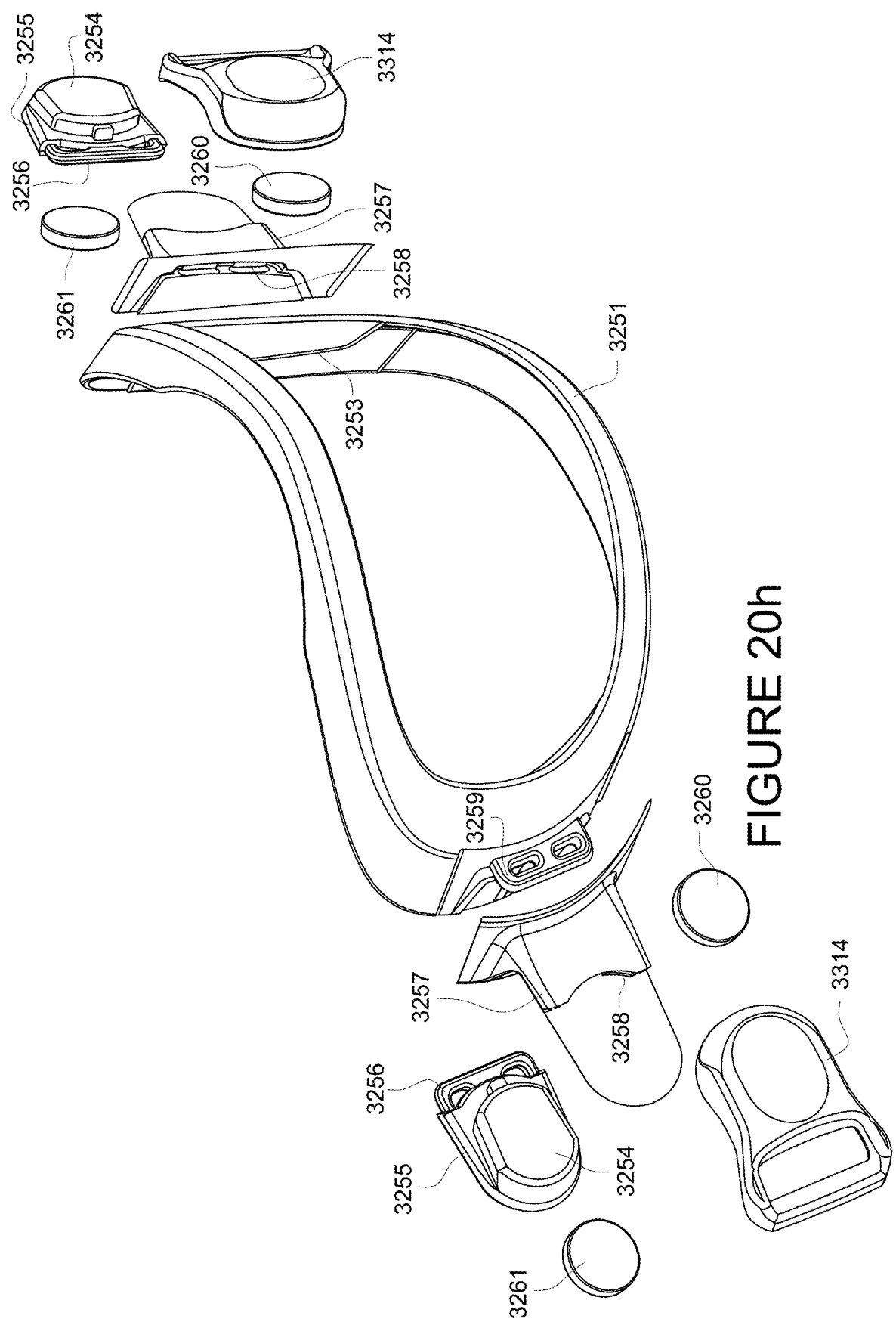

FIG. 20h shows an exploded perspective view of a faceplate frame, lower attachment features, and clips according to an example of the present technology.

Figure 20I:
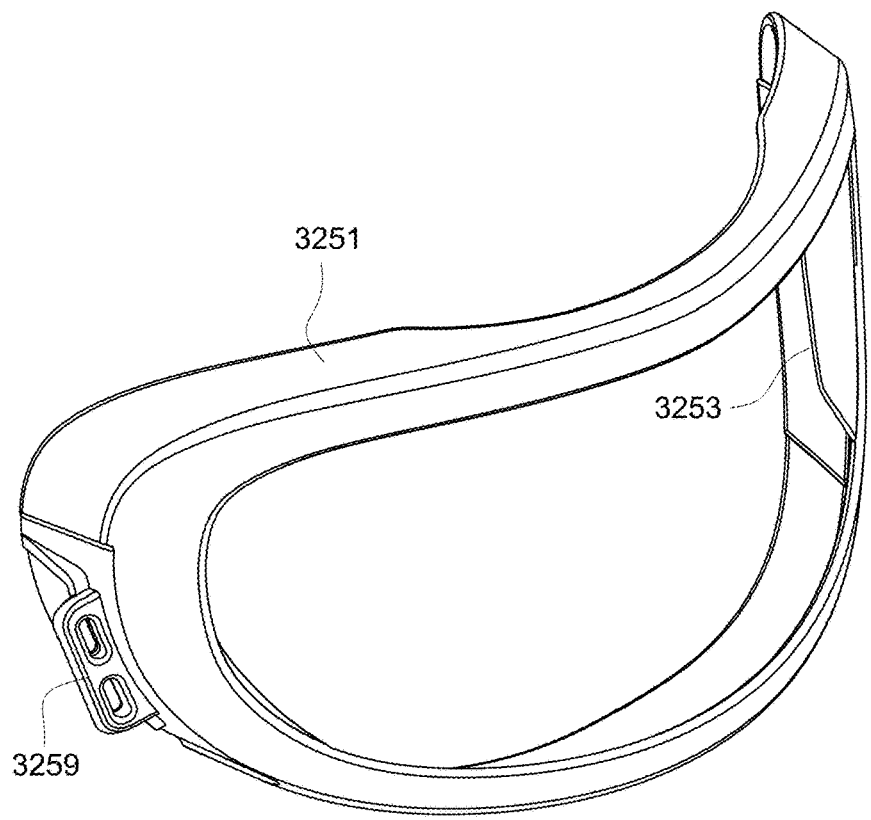

FIG. 20i shows a perspective view of a faceplate frame according to an example of the present technology.

Figure 20J:
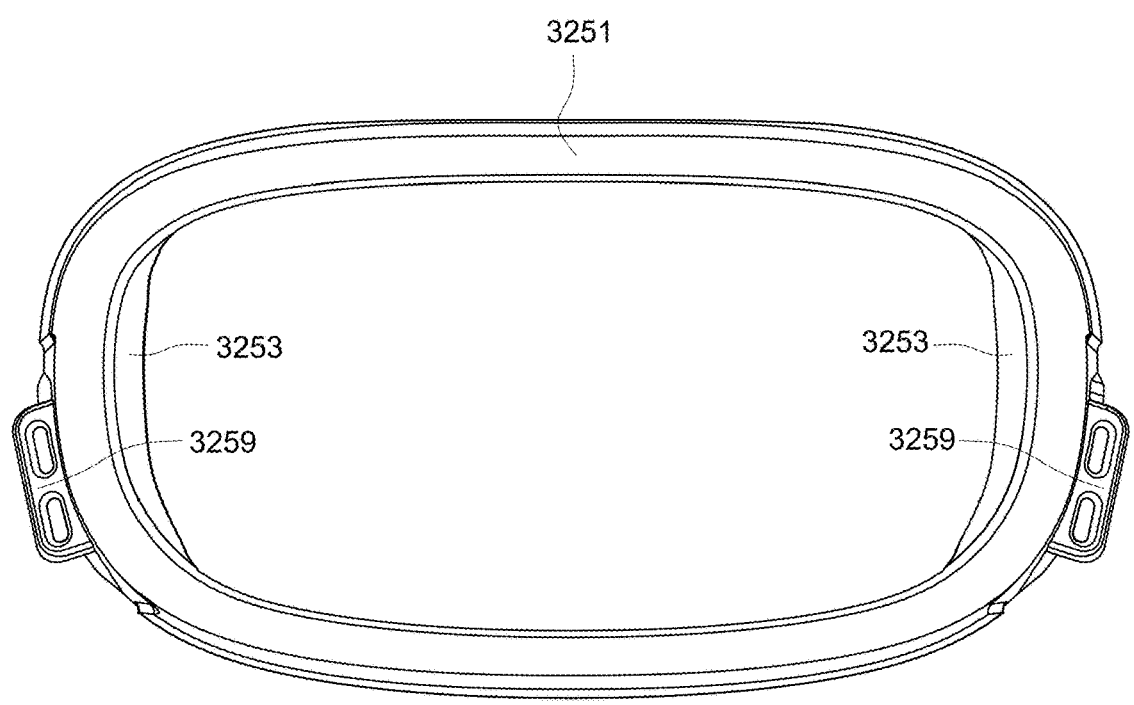

FIG. 20j shows a front view of a faceplate frame according to an example of the present technology.

Figure 20K:
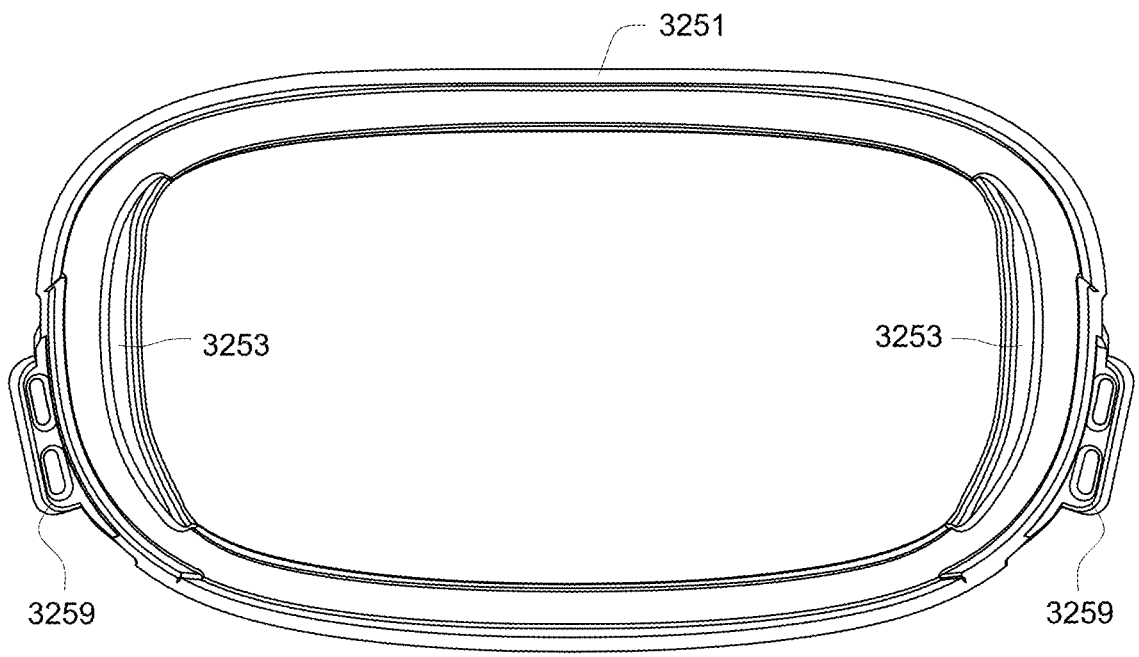

FIG. 20k shows a rear view of a faceplate frame according to an example of the present technology.

Figure 20L:
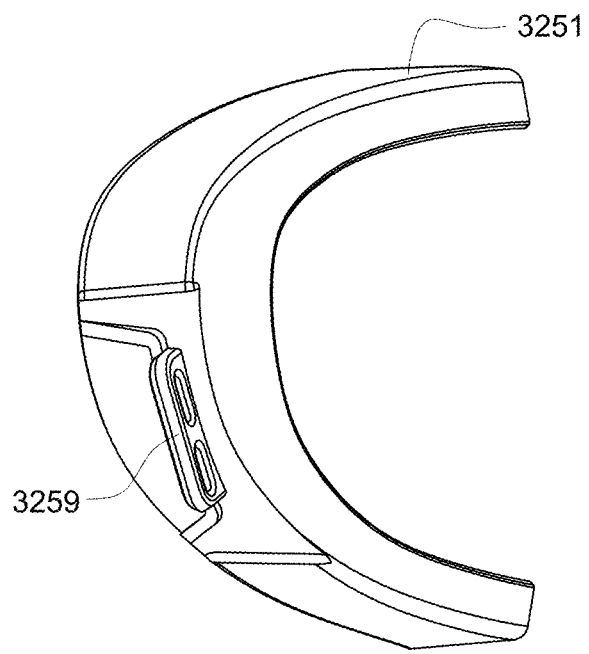

FIG. 20l shows a side view of a faceplate frame according to an example of the present technology.

FIG. 20m shows a top view of a faceplate frame according to an example of the present technology.

Figure 20N:
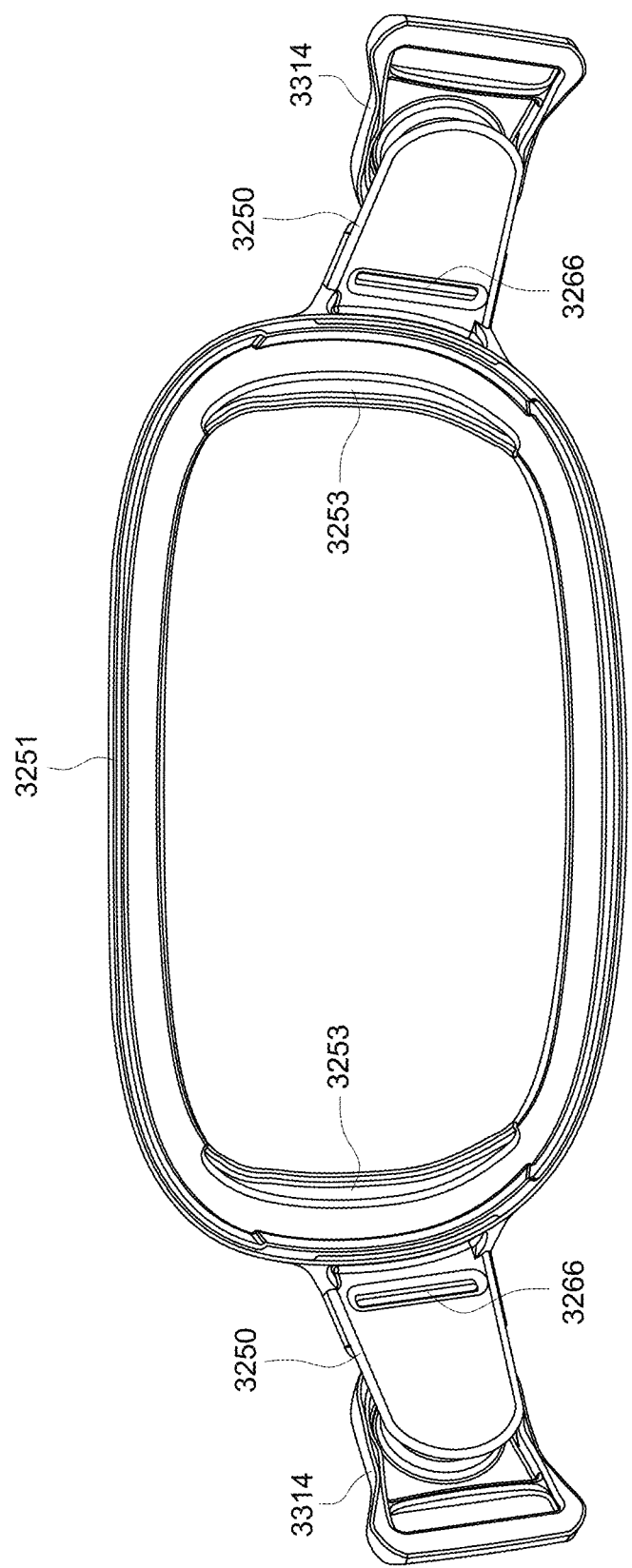

FIG. 20n shows a rear view of a faceplate frame according to an example of the present technology.

Figure 20O:
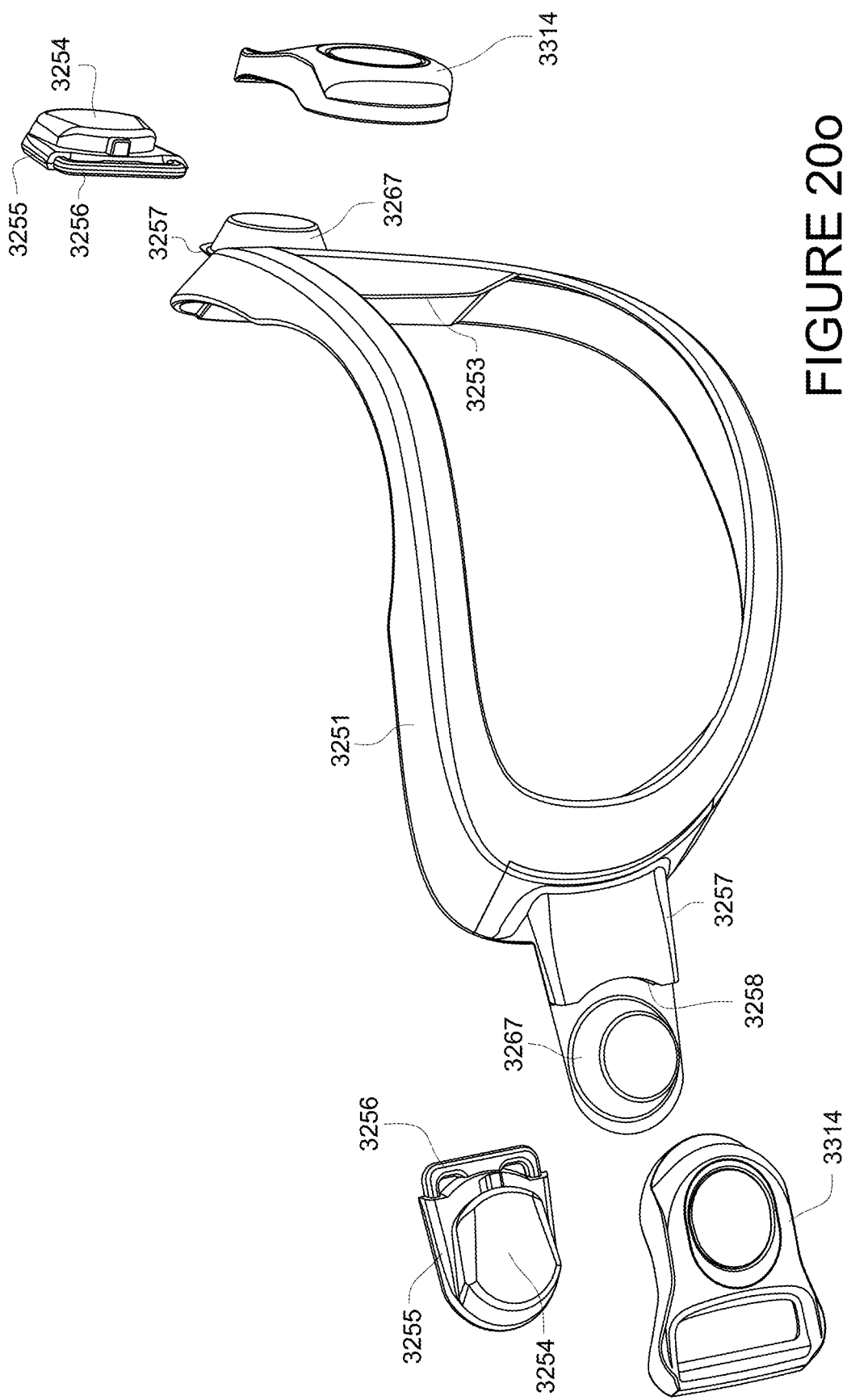

FIG. 20o shows another partially exploded perspective view of a faceplate frame, lower attachment features, and clips according to an example of the present technology.

Figure 20P:
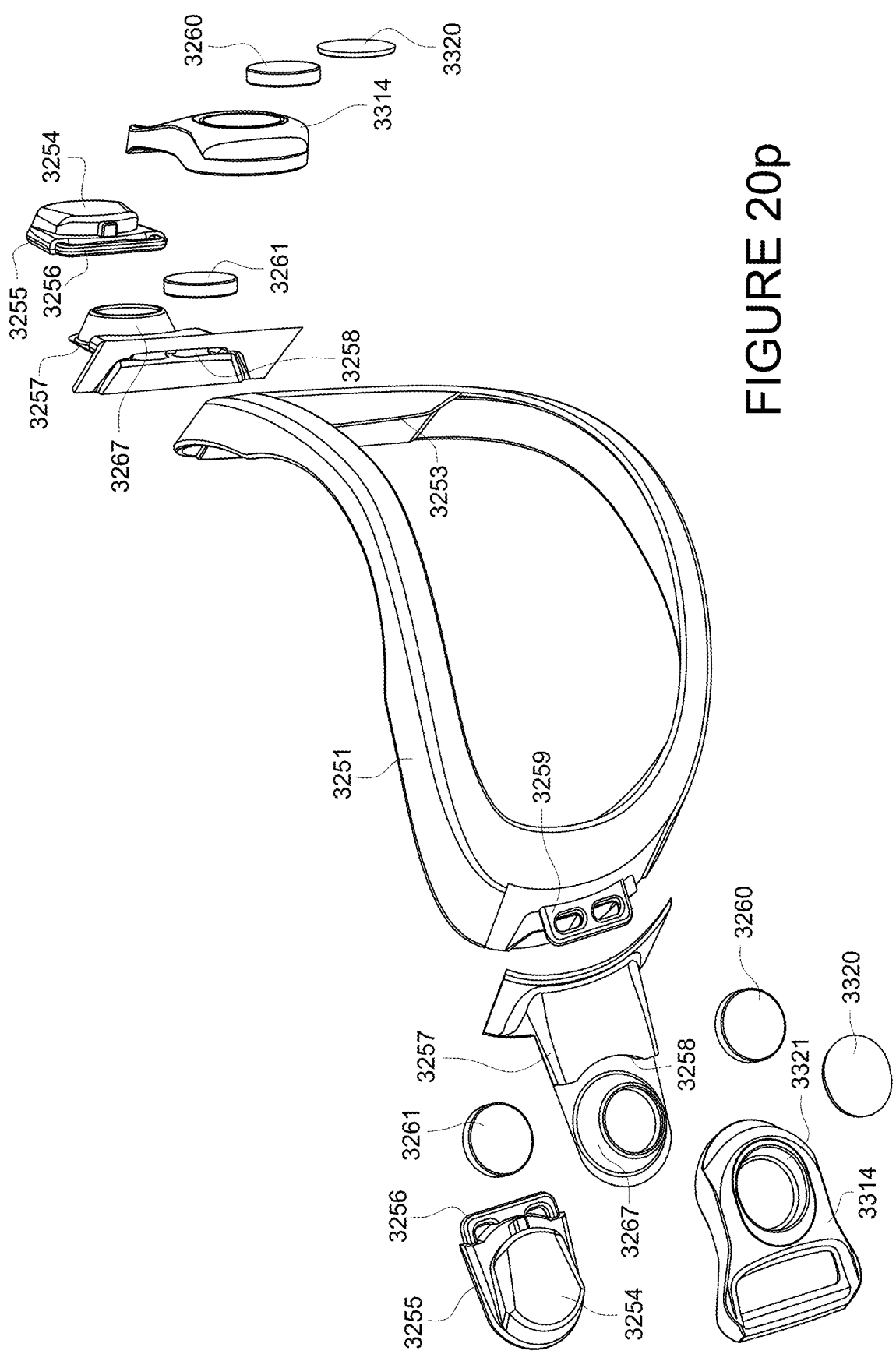

FIG. 20p shows an exploded perspective view of a faceplate frame, lower attachment features, and clips according to an example of the present technology.

Figure 20Q:
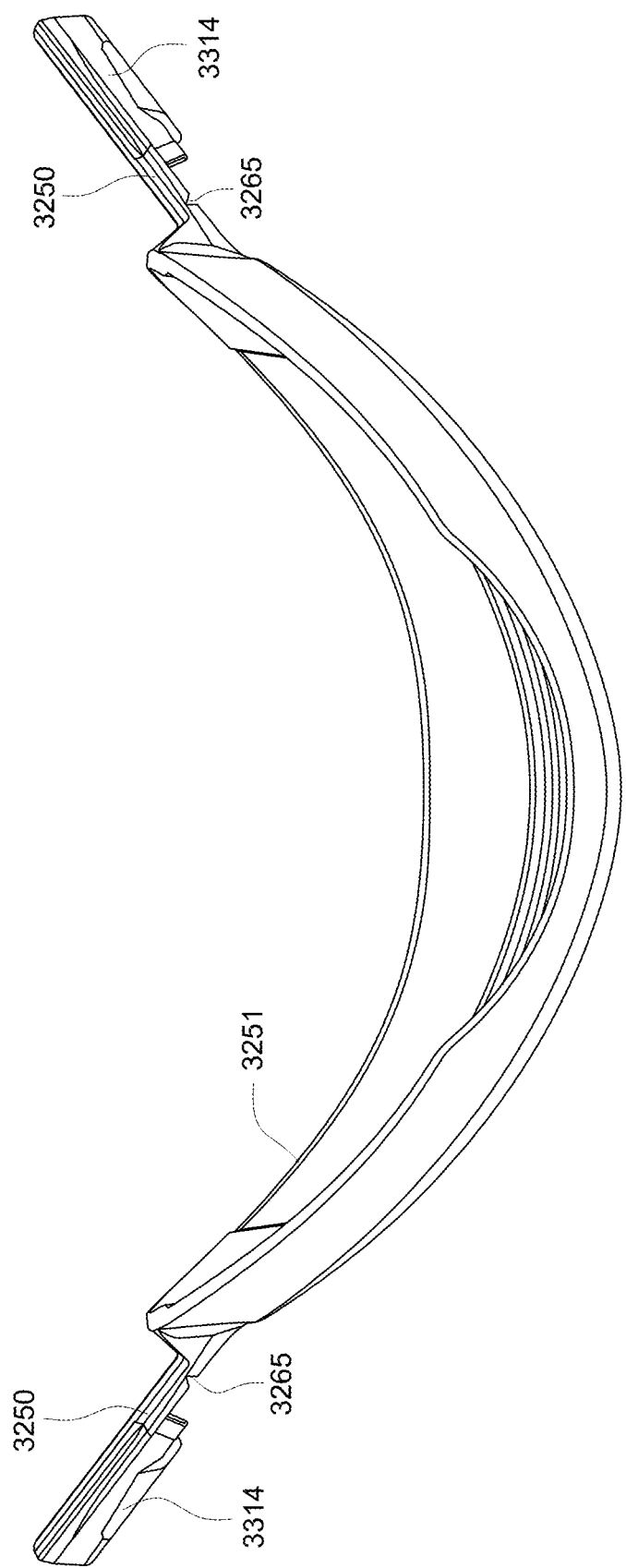

FIG. 20q shows a top view of a faceplate frame according to an example of the present technology.

Figure 20R:
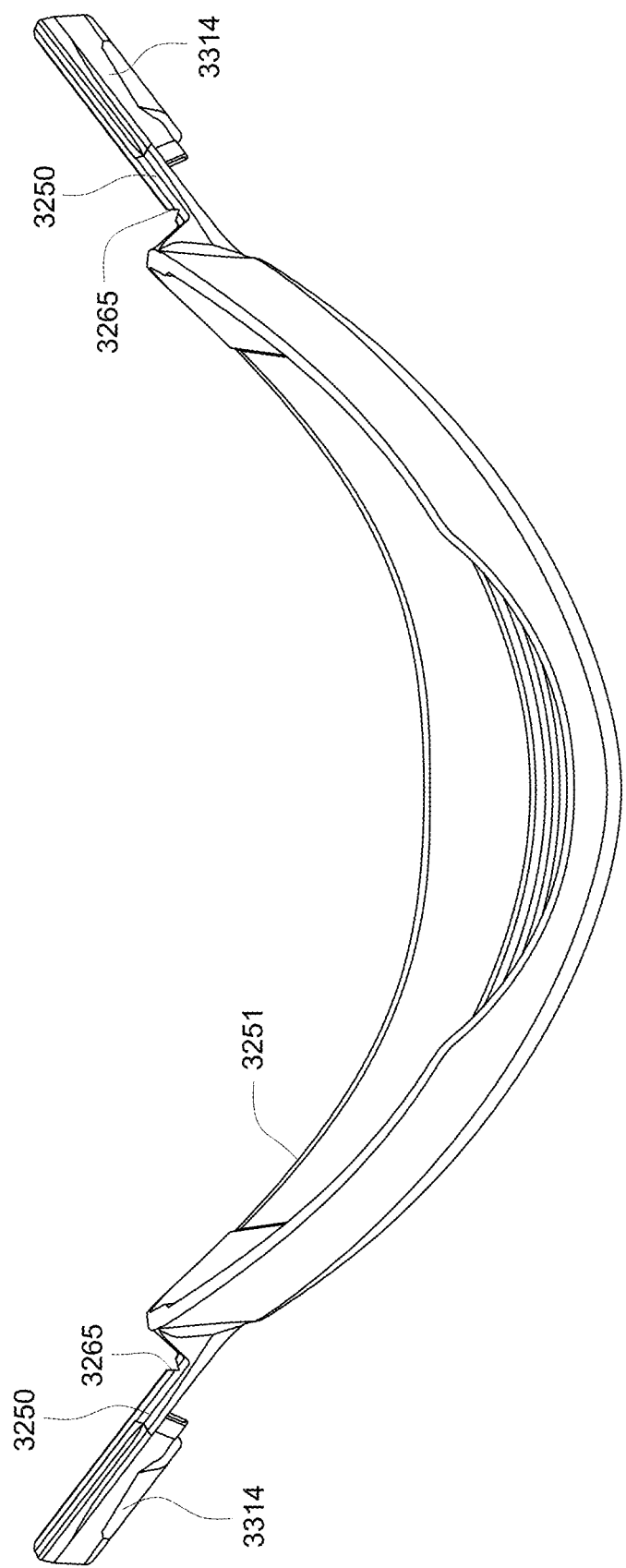

FIG. 20r shows a top view of a faceplate frame according to an example of the present technology.

Figure 20S:
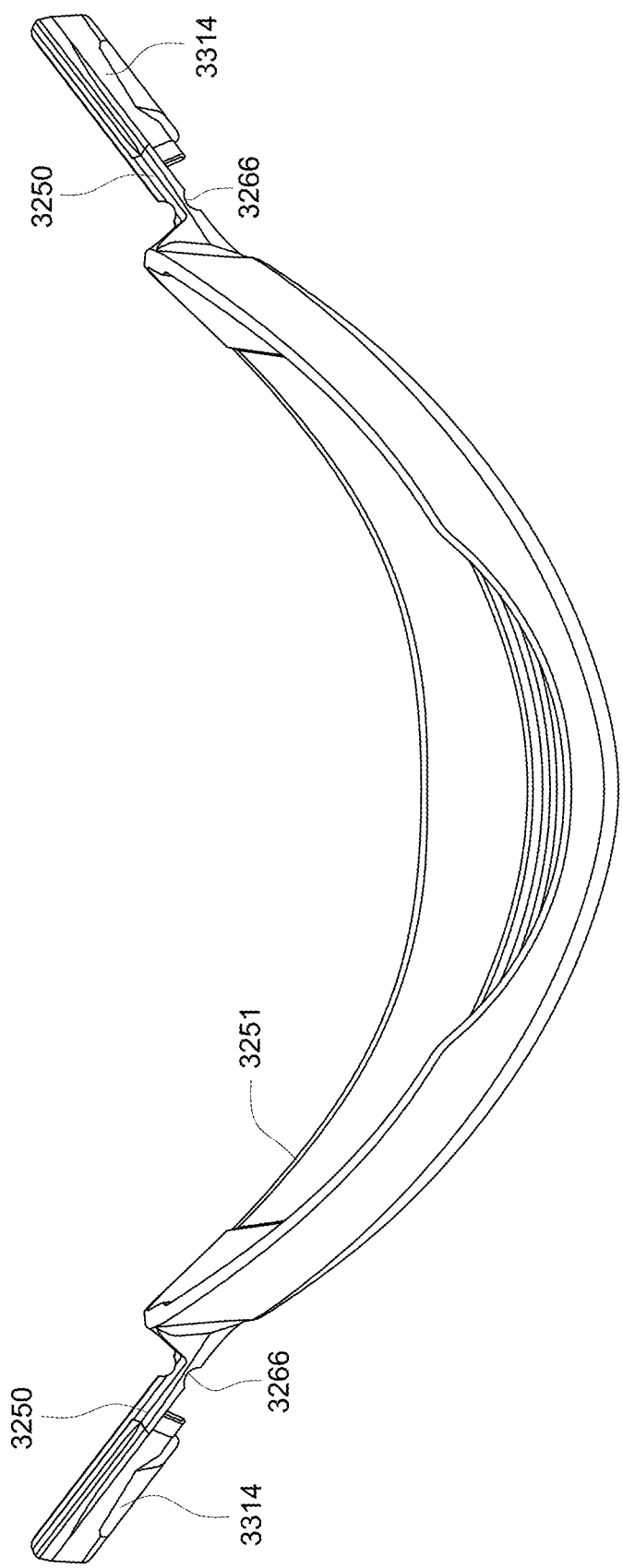

FIG. 20s shows a top view of a faceplate frame according to an example of the present technology.

Figure 21A:
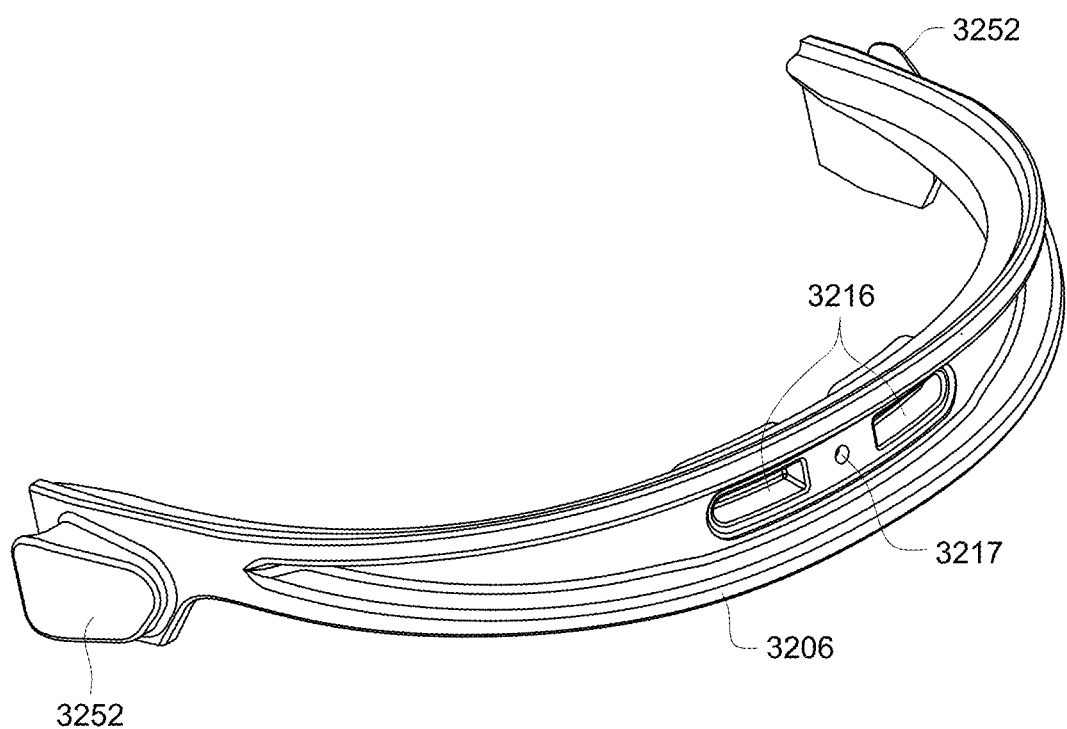

FIG. 21a shows a perspective view of a top plate according to an example of the present technology.

Figure 21B:
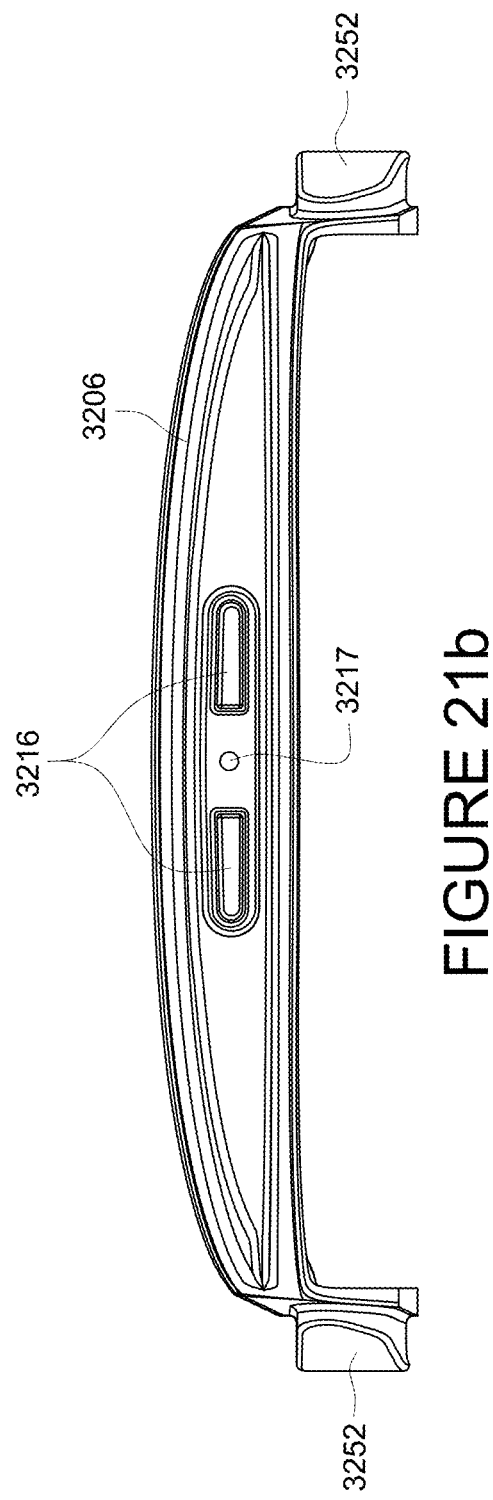

FIG. 21b shows a front view of a top plate according to an example of the present technology.

Figure 21C:
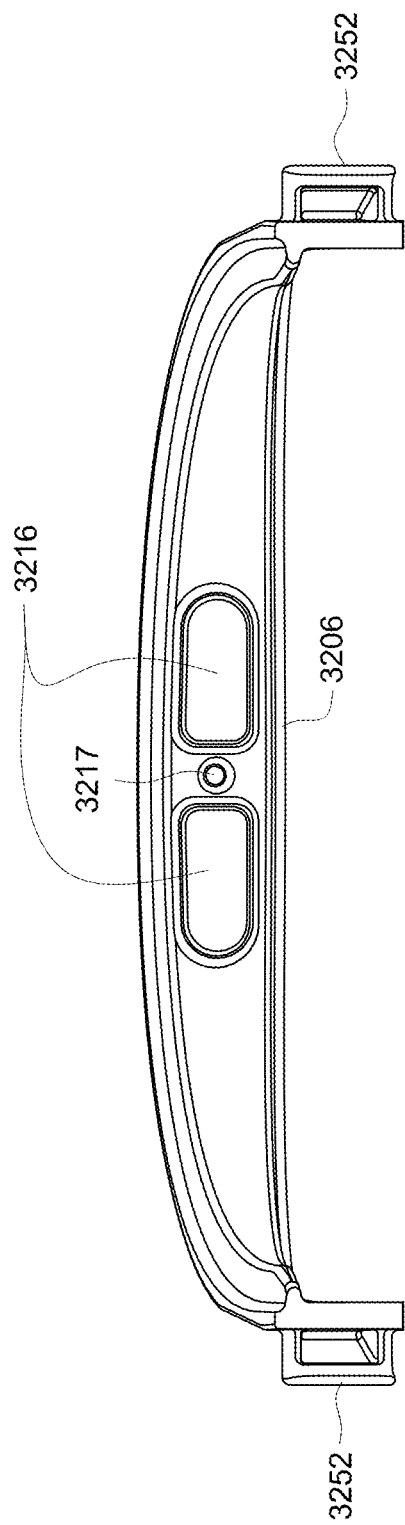

FIG. 21c shows a rear view of a top plate according to an example of the present technology.

Figure 21D:
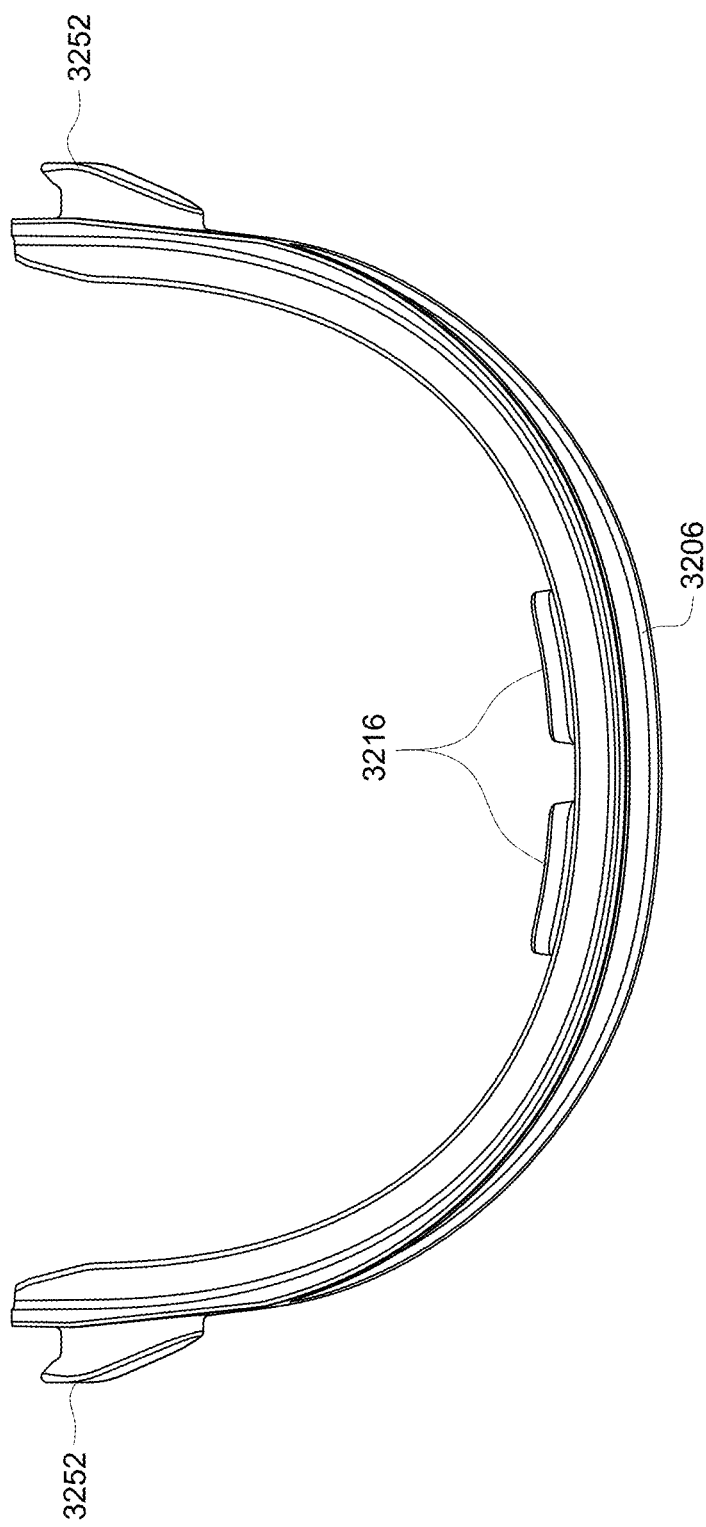

FIG. 21d shows a top view of a top plate according to an example of the present technology.

Figure 21E:
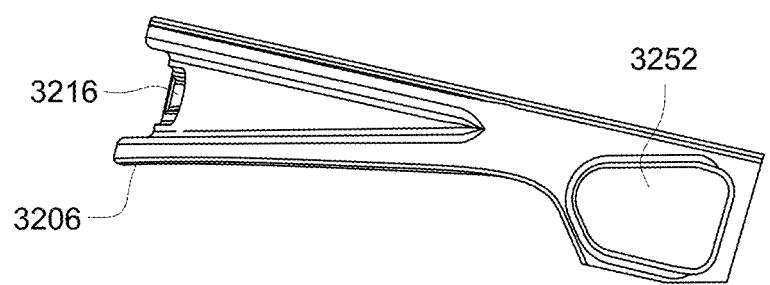

FIG. 21e shows a side view of a top plate according to an example of the present technology.

Figure 22A:
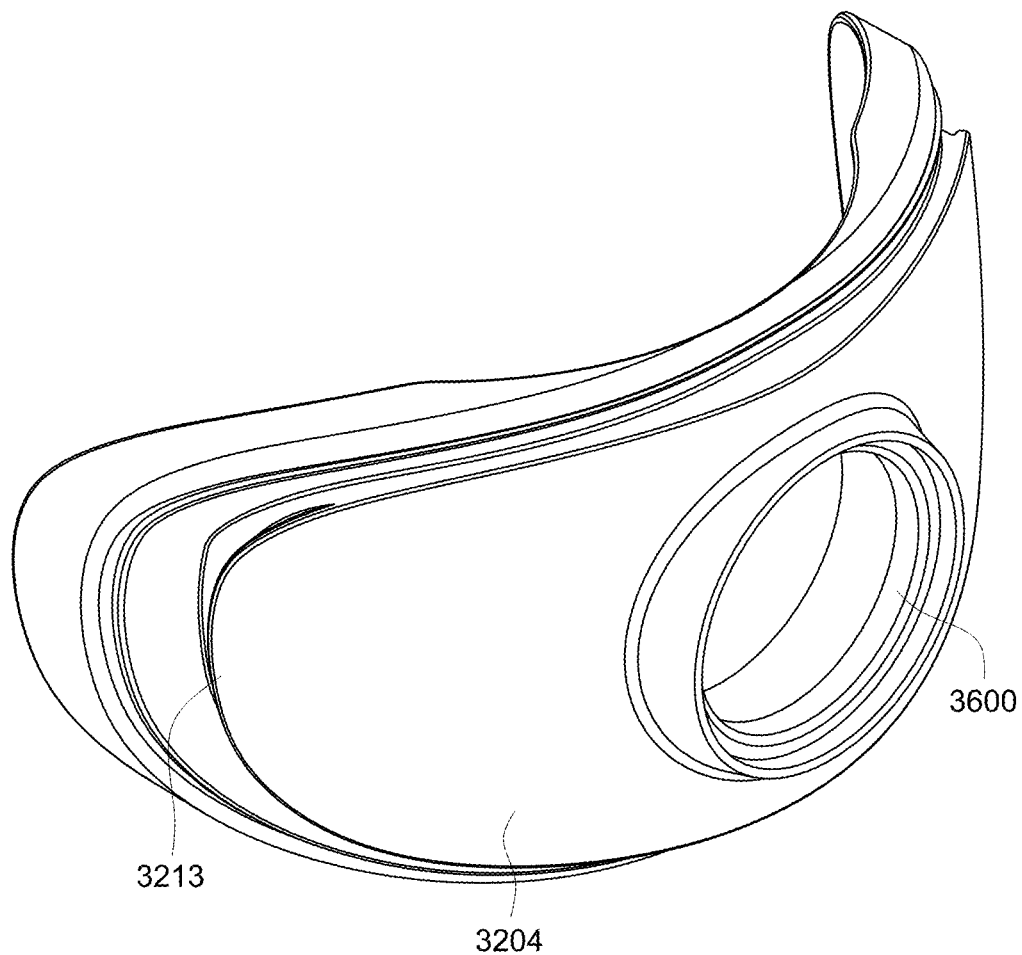

FIG. 22a shows a perspective view of a faceplate according to an example of the present technology.

Figure 22B:
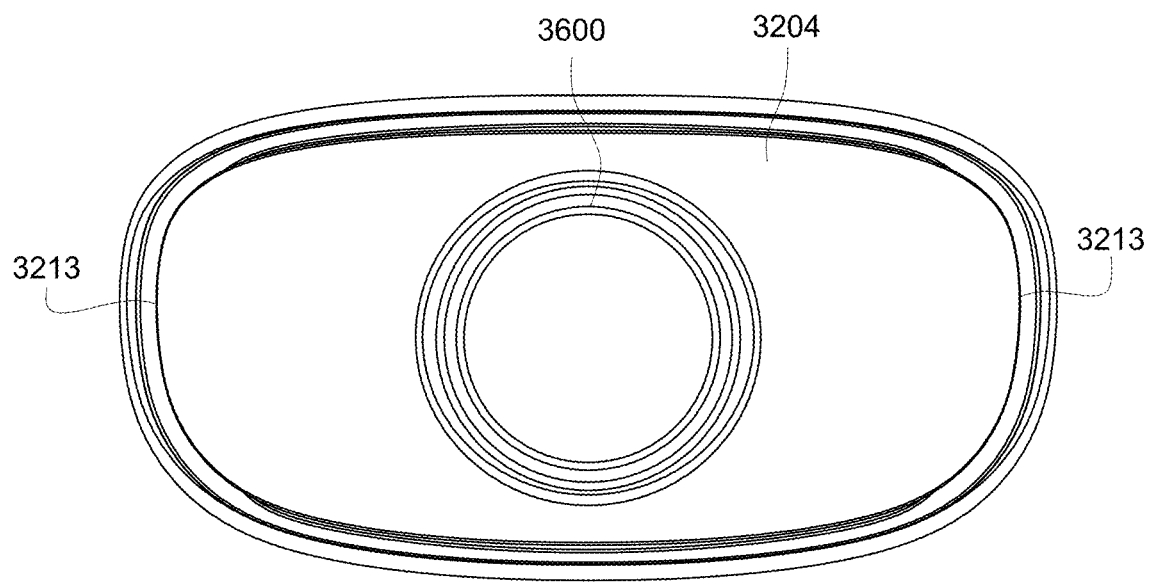

FIG. 22b shows a front view of a faceplate according to an example of the present technology.

Figure 22C:
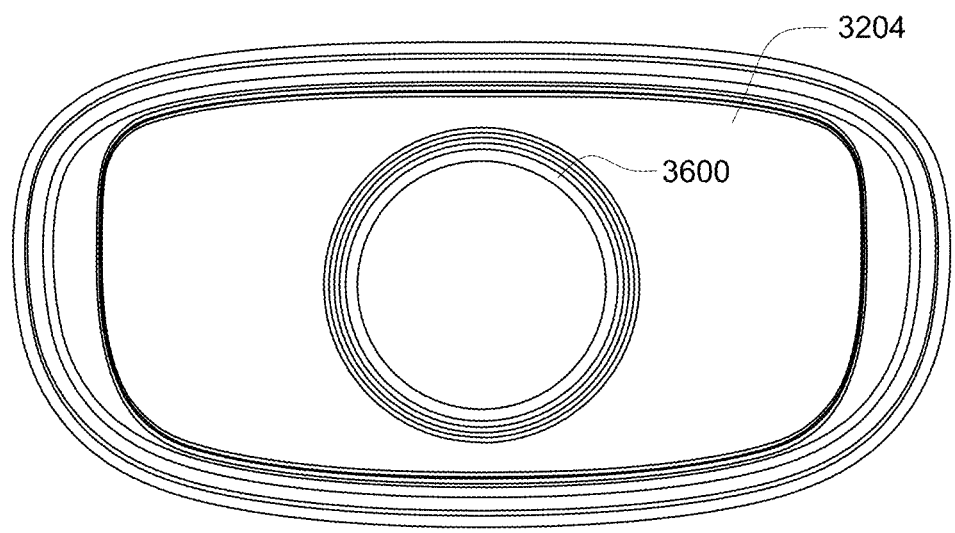

FIG. 22c shows a rear view of a faceplate according to an example of the present technology.

Figure 22D:
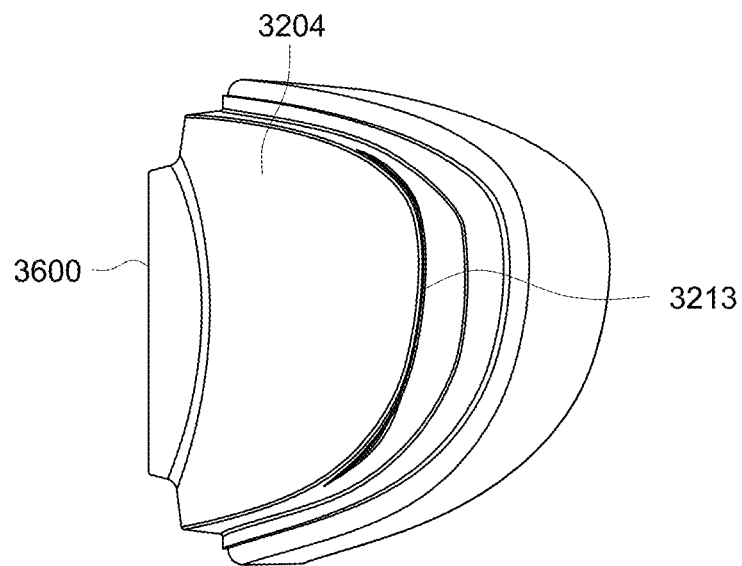

FIG. 22d shows a side view of a faceplate according to an example of the present technology.

Figure 22E:
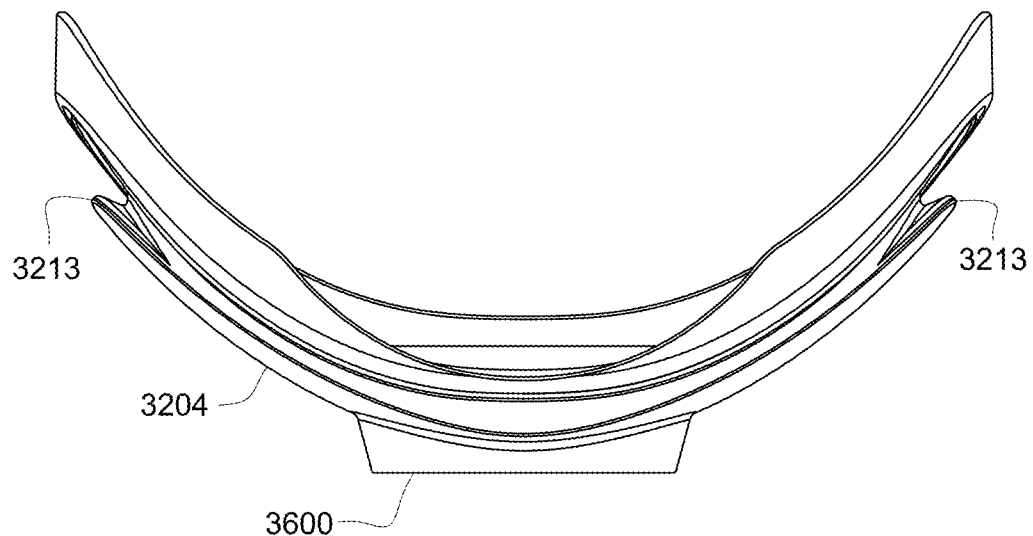

FIG. 22e shows a top view of a faceplate according to an example of the present technology.

Figure 23A:
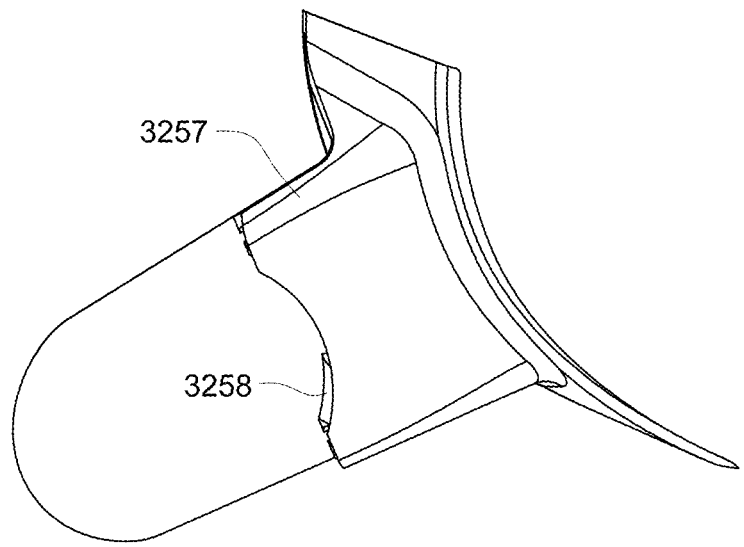

FIG. 23a shows a front perspective view of a lower attachment feature support according to an example of the present technology.

Figure 23B:
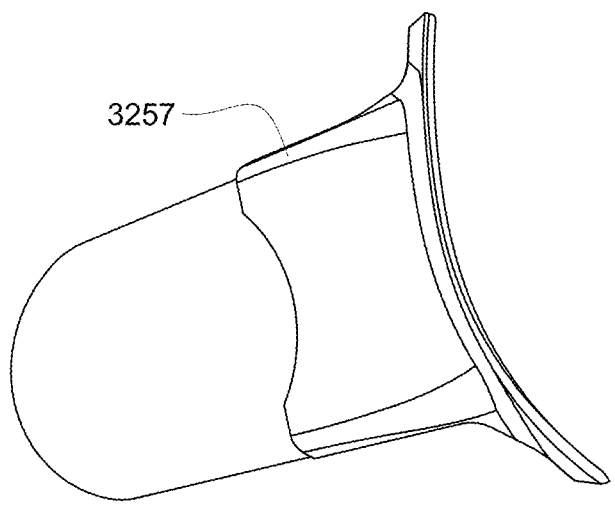

FIG. 23b shows another front perspective view of a lower attachment feature support according to an example of the present technology.

Figure 23C:
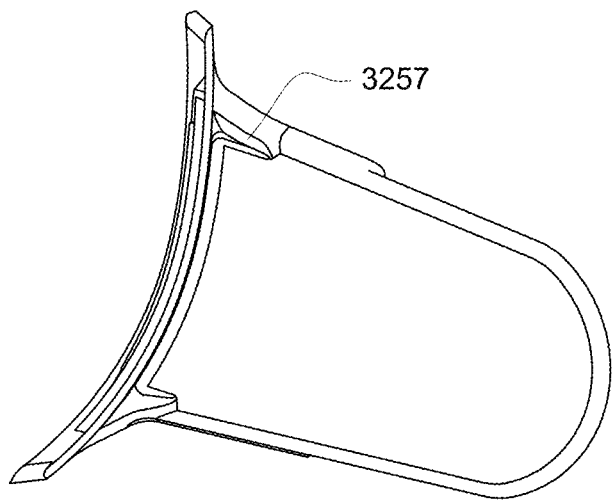

FIG. 23c shows a rear view of a lower attachment feature support according to an example of the present technology.

Figure 23D:
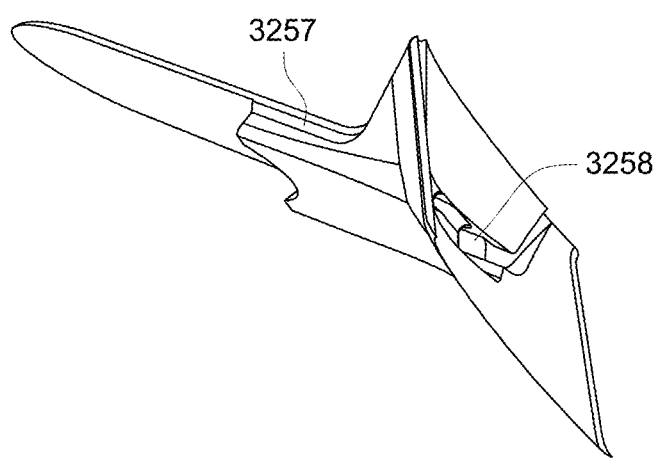

FIG. 23d shows a top perspective view of a lower attachment feature support according to an example of the present technology.

FIG. 23e shows a side perspective view of a lower attachment feature support according to an example of the present technology.

FIG. 23f shows another side perspective view of a lower attachment feature support according to an example of the present technology.

FIG. 23g shows a front view of a lower attachment feature according to an example of the present technology.

Figure 23H:
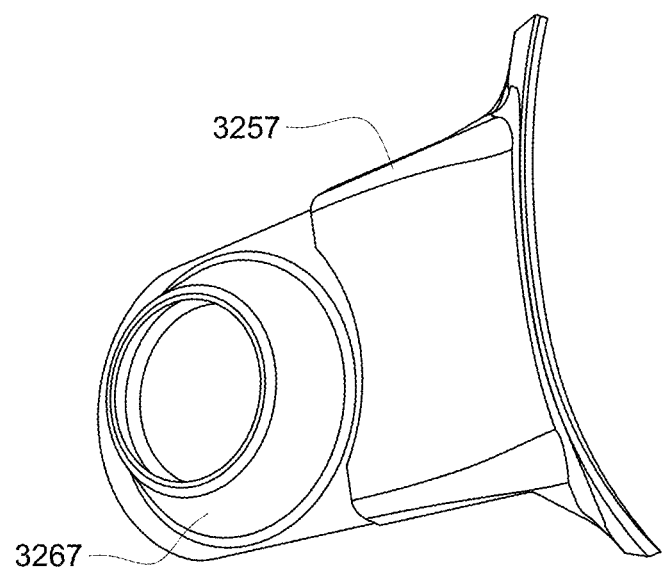

FIG. 23h shows another front view of a lower attachment feature according to an example of the present technology.

Figure 23I:
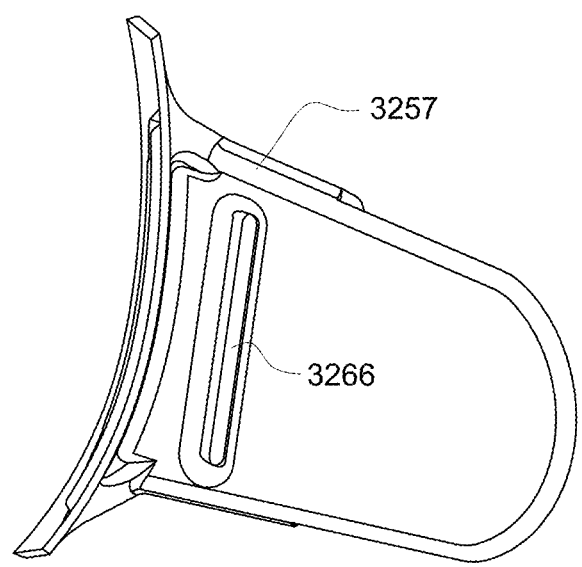

FIG. 23i shows a rear view of a lower attachment feature according to an example of the present technology.

Figure 23J:
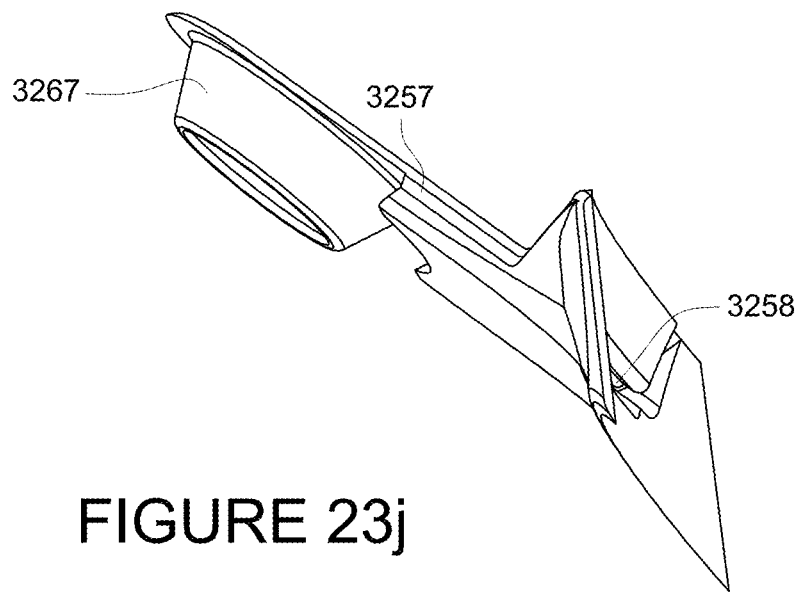

FIG. 23j shows a top view of a lower attachment feature according to an example of the present technology.

Figure 23K:
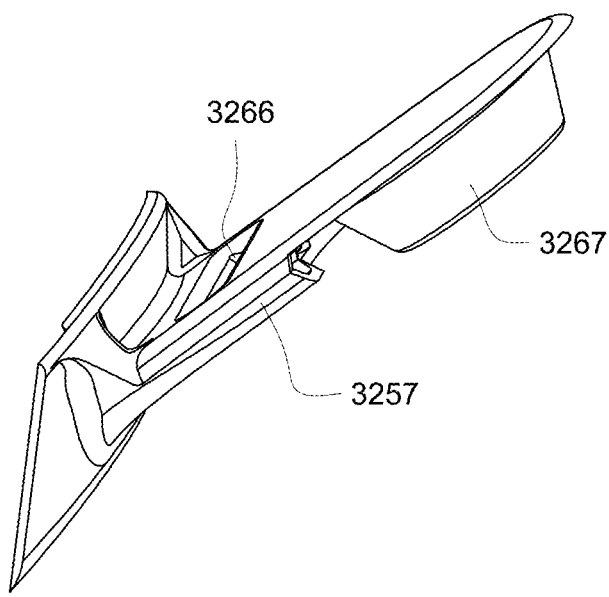

FIG. 23k shows a bottom view of a lower attachment feature according to an example of the present technology.

Figure 23L:
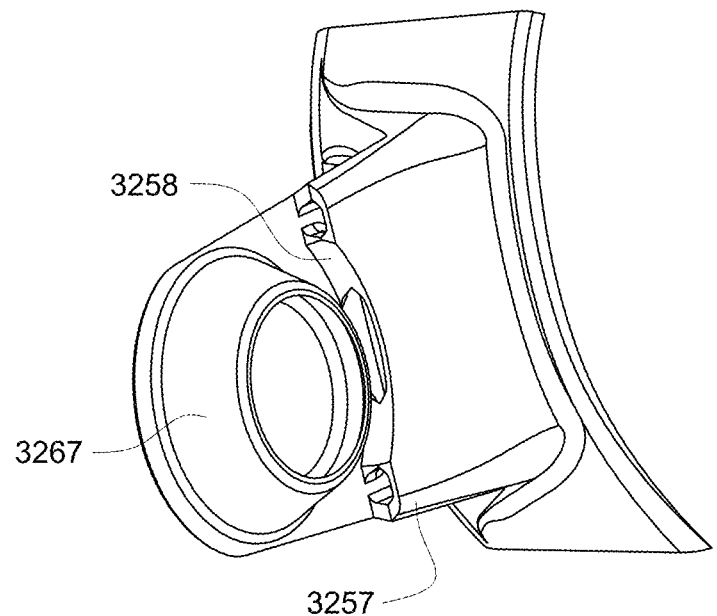

FIG. 23l shows a front perspective view of a lower attachment feature according to an example of the present technology.

Figure 23M:
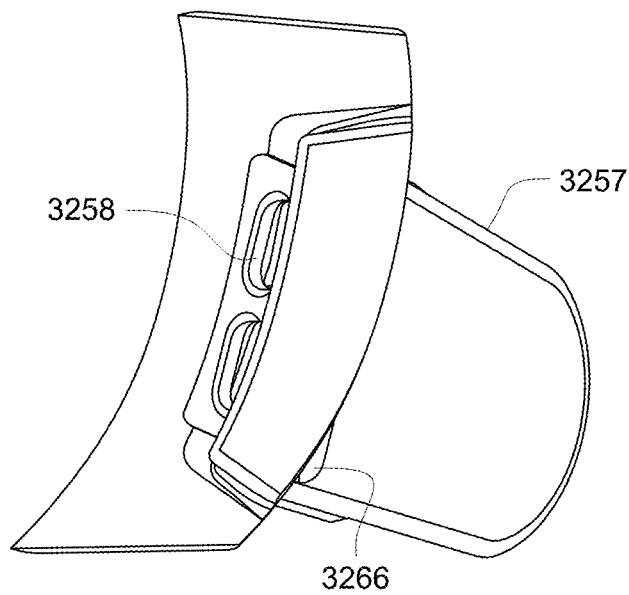

FIG. 23m shows a rear perspective view of a lower attachment feature according to an example of the present technology.

Figure 24A:
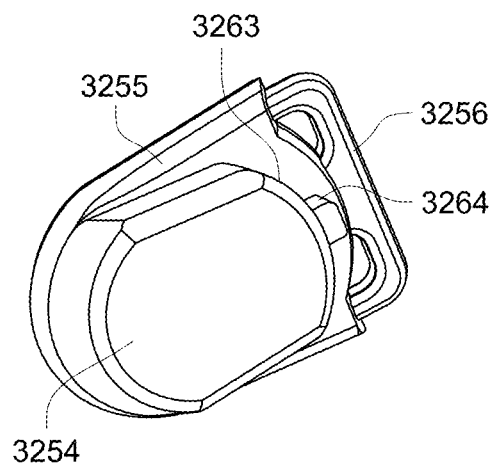

FIG. 24a shows a front perspective view of a connector of a lower attachment feature according to an example of the present technology.

Figure 24B:
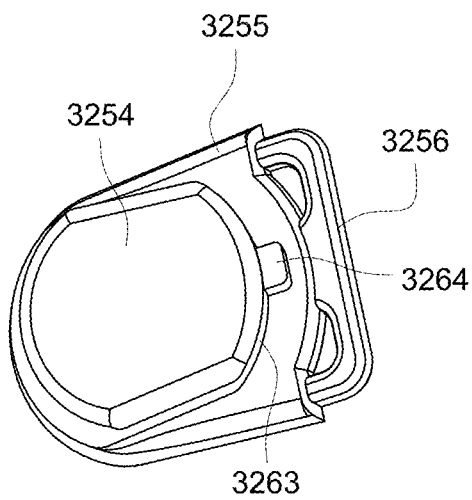

FIG. 24b shows another front perspective view of a connector of a lower attachment feature according to an example of the present technology.

Figure 24C:
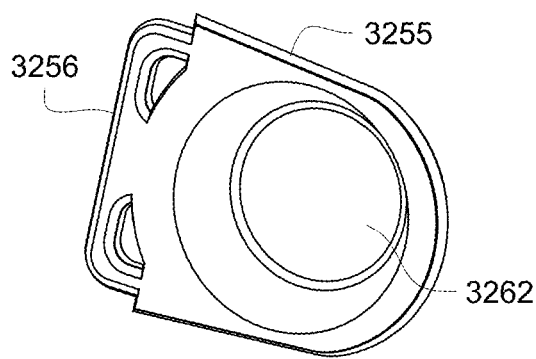

FIG. 24c shows a rear view of a connector of a lower attachment feature according to an example of the present technology.

Figure 24D:
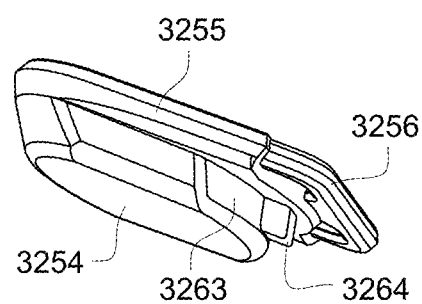

FIG. 24d shows a top perspective view of a connector of a lower attachment feature according to an example of the present technology.

Figure 24E:
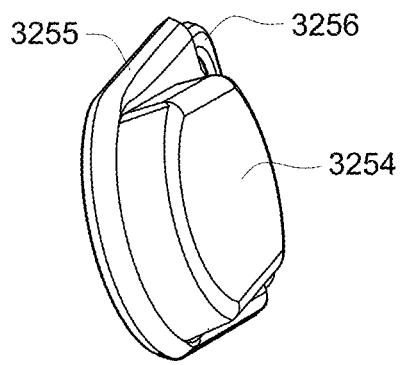

FIG. 24e shows a side perspective view of a connector of a lower attachment feature according to an example of the present technology.

Figure 24F:
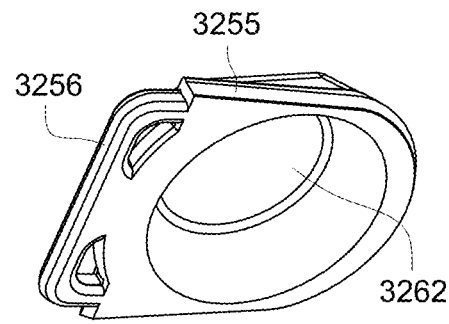

FIG. 24f shows another rear perspective view of a connector of a lower attachment feature according to an example of the present technology.

Figure 25A:
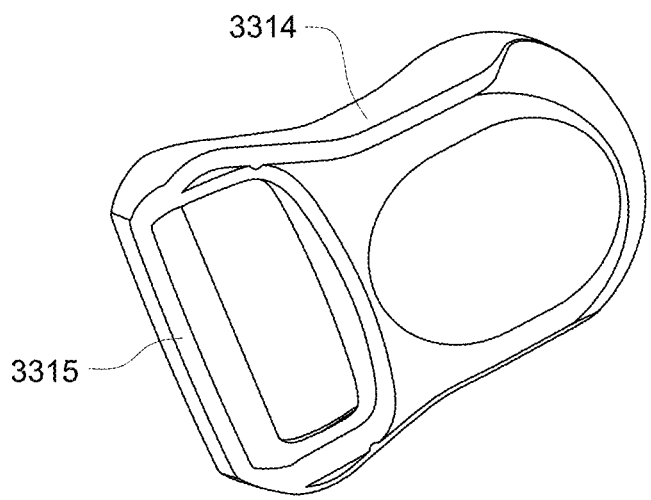

FIG. 25a shows a front perspective view of a clip according to an example of the present technology.

Figure 25B:
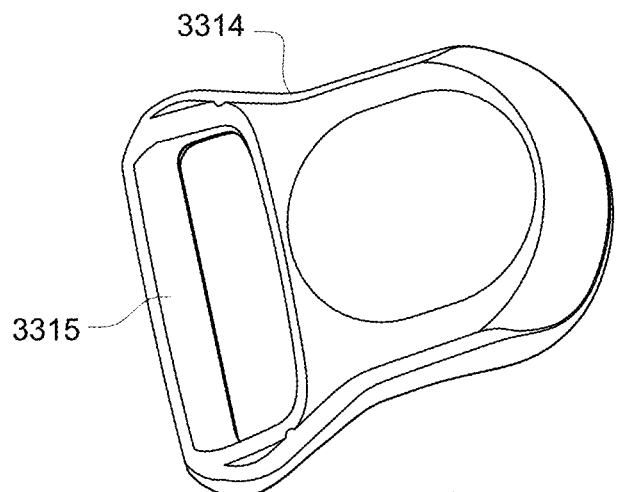

FIG. 25b shows another front perspective view of a clip according to an example of the present technology.

Figure 25C:
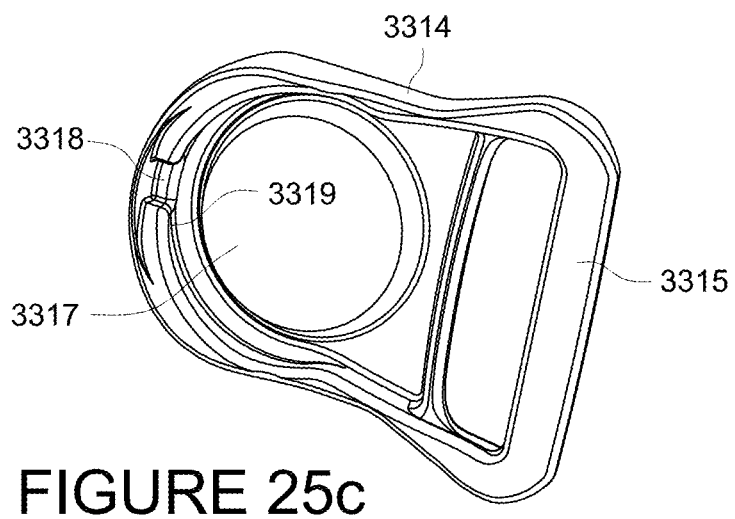

FIG. 25c show a rear perspective view of a clip according to an example of the present technology.

Figure 25D:
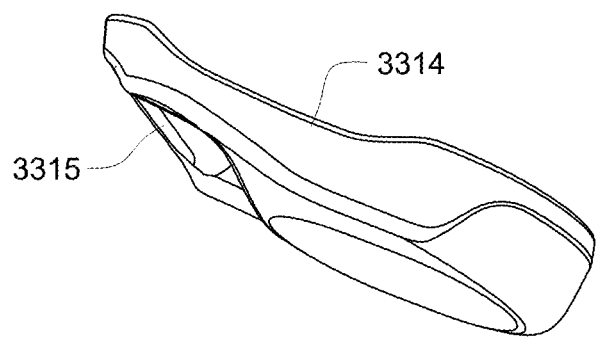

FIG. 25d shows a top perspective view of a clip according to an example of the present technology.

Figure 25E:
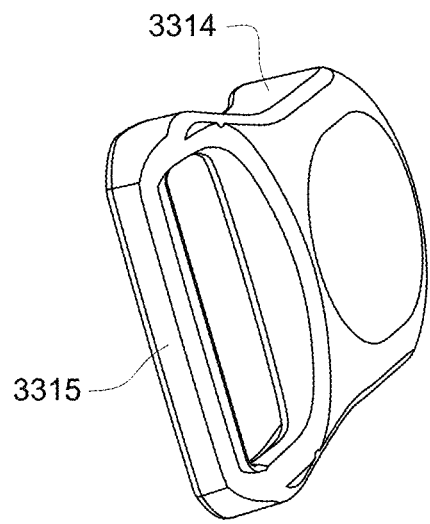

FIG. 25e shows a side perspective view of a clip according to an example of the present technology.

Figure 25F:
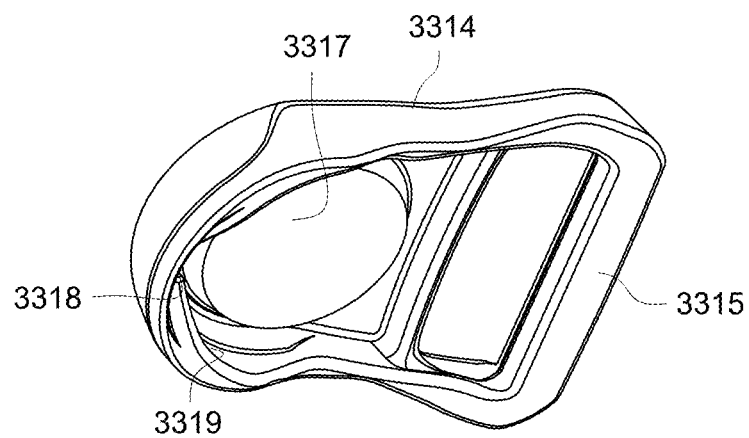

FIG. 25f shows another rear perspective view of a clip according to an example of the present technology.

Figure 25G:
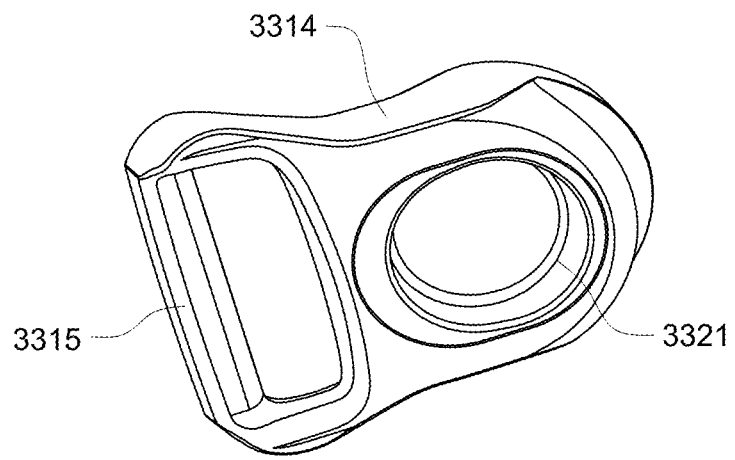

FIG. 25g shows a front perspective view of a clip according to an example of the present technology.

Figure 25H:
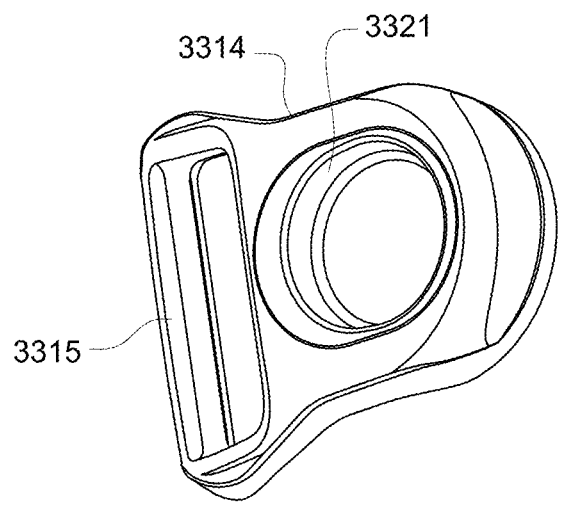

FIG. 25h shows another front perspective view of a clip according to an example of the present technology.

Figure 25I:
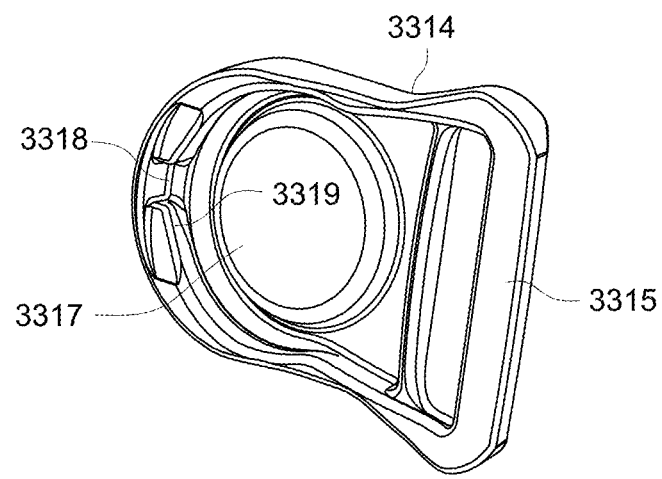

FIG. 25i show a rear perspective view of a clip according to an example of the present technology.

Figure 25J:
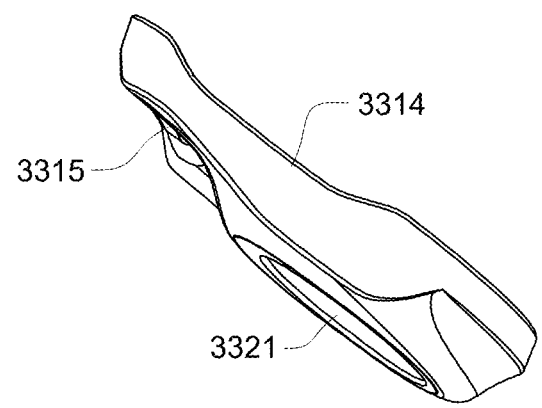

FIG. 25j shows a top perspective view of a clip according to an example of the present technology.

Figure 25K:
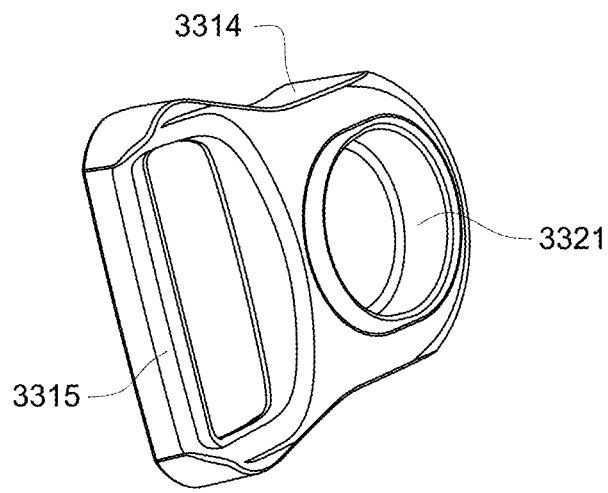

FIG. 25k shows a side perspective view of a clip according to an example of the present technology.

Figure 25L:
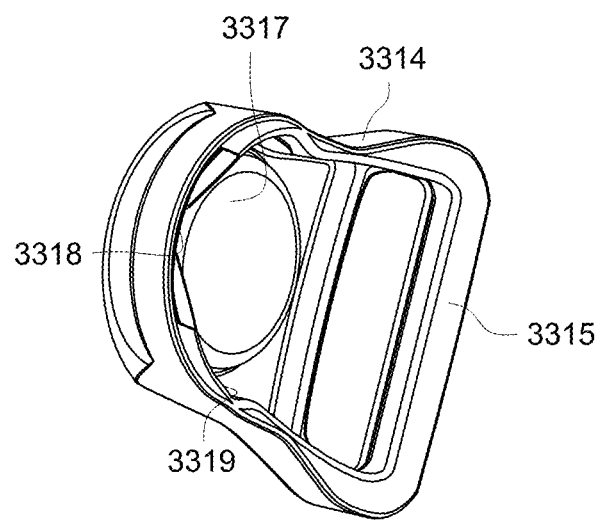

FIG. 25l shows another rear perspective view of a clip according to an example of the present technology.

Figure 26A:
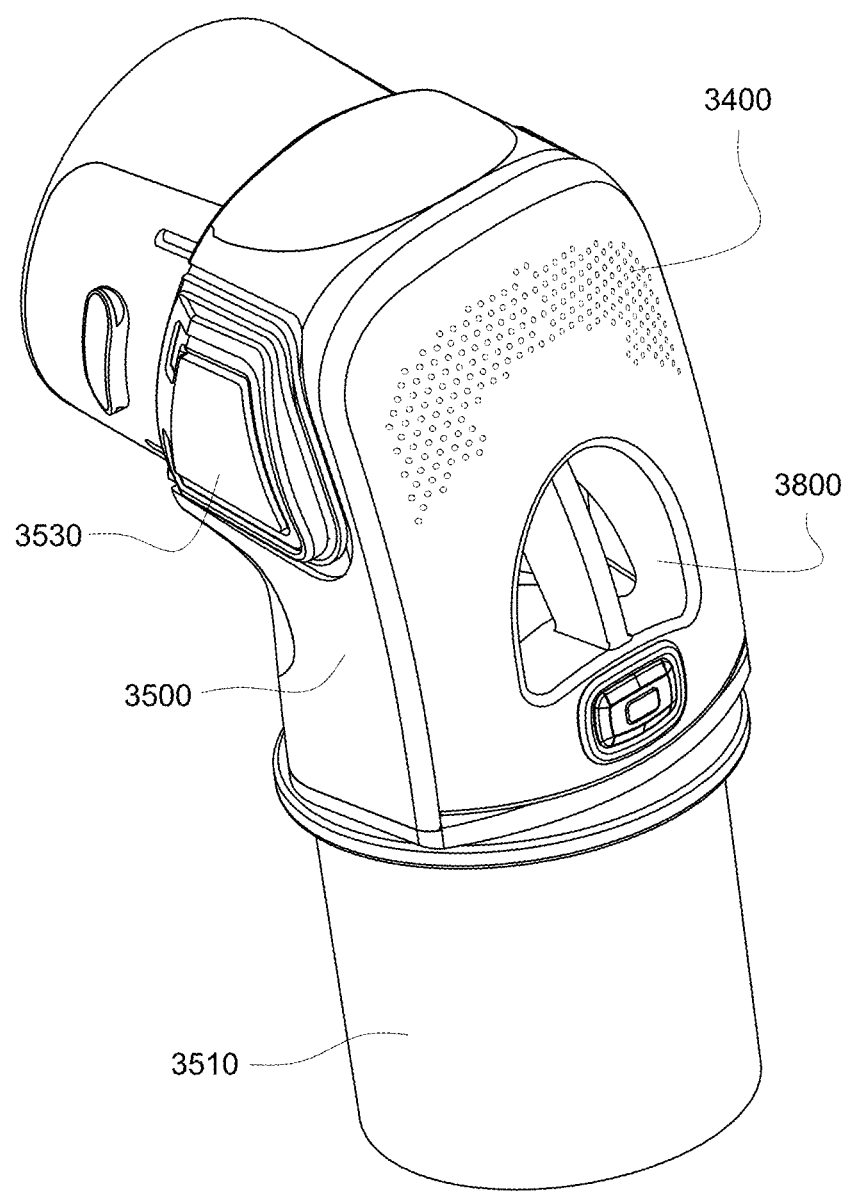

FIG. 26a shows a perspective view of a tube decoupling structure according to an example of the present technology.

Figure 26B:
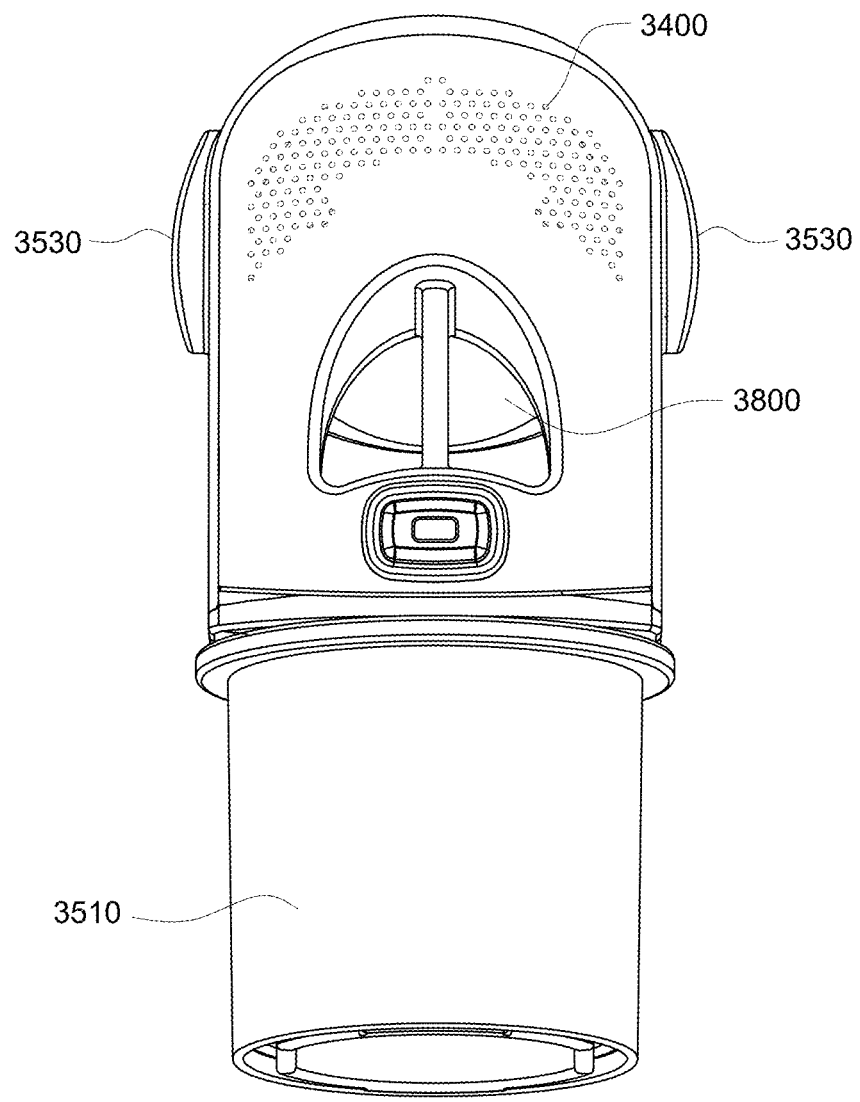

FIG. 26b shows a front view of a tube decoupling structure according to an example of the present technology.

Figure 26C:
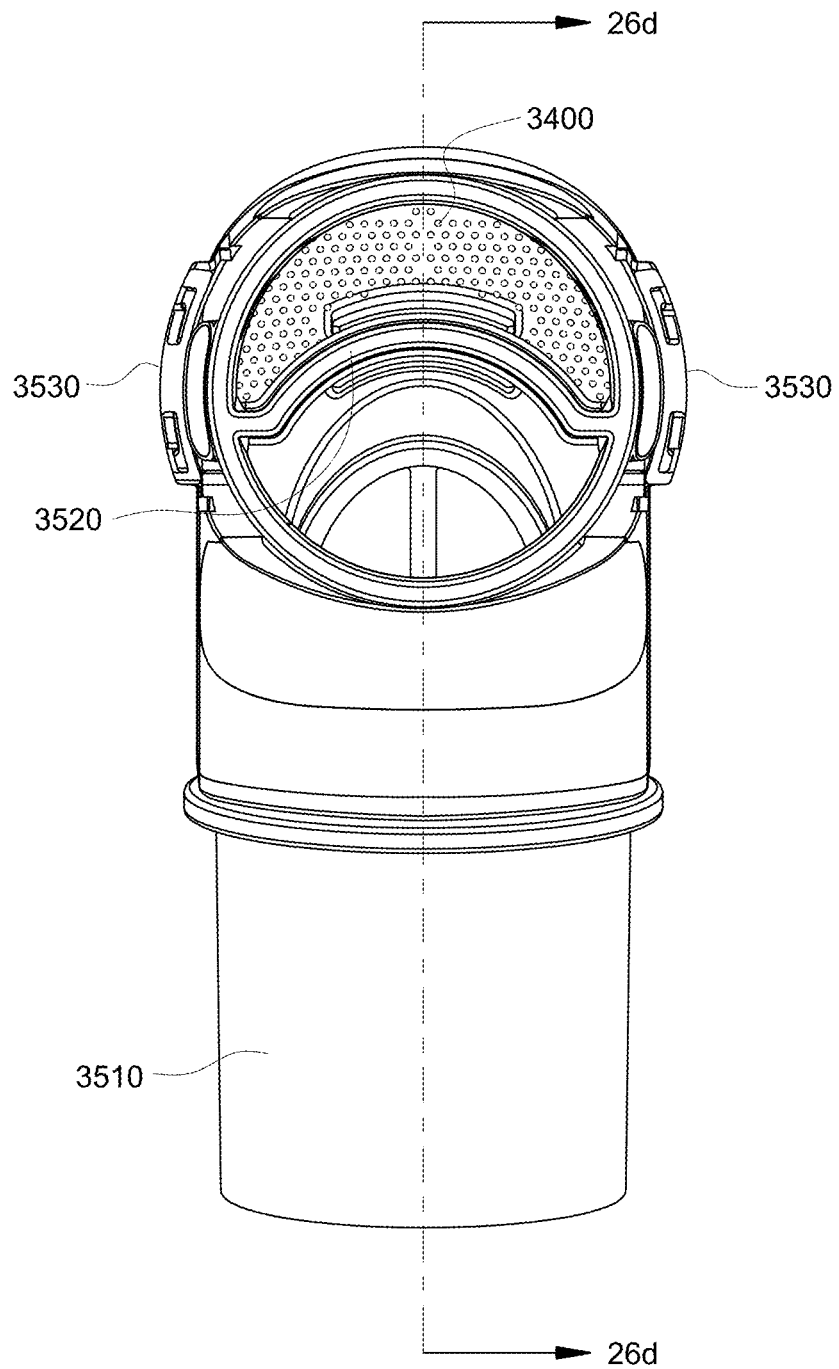

FIG. 26c shows a rear view of a tube decoupling structure according to an example of the present technology.

Figure 26D:
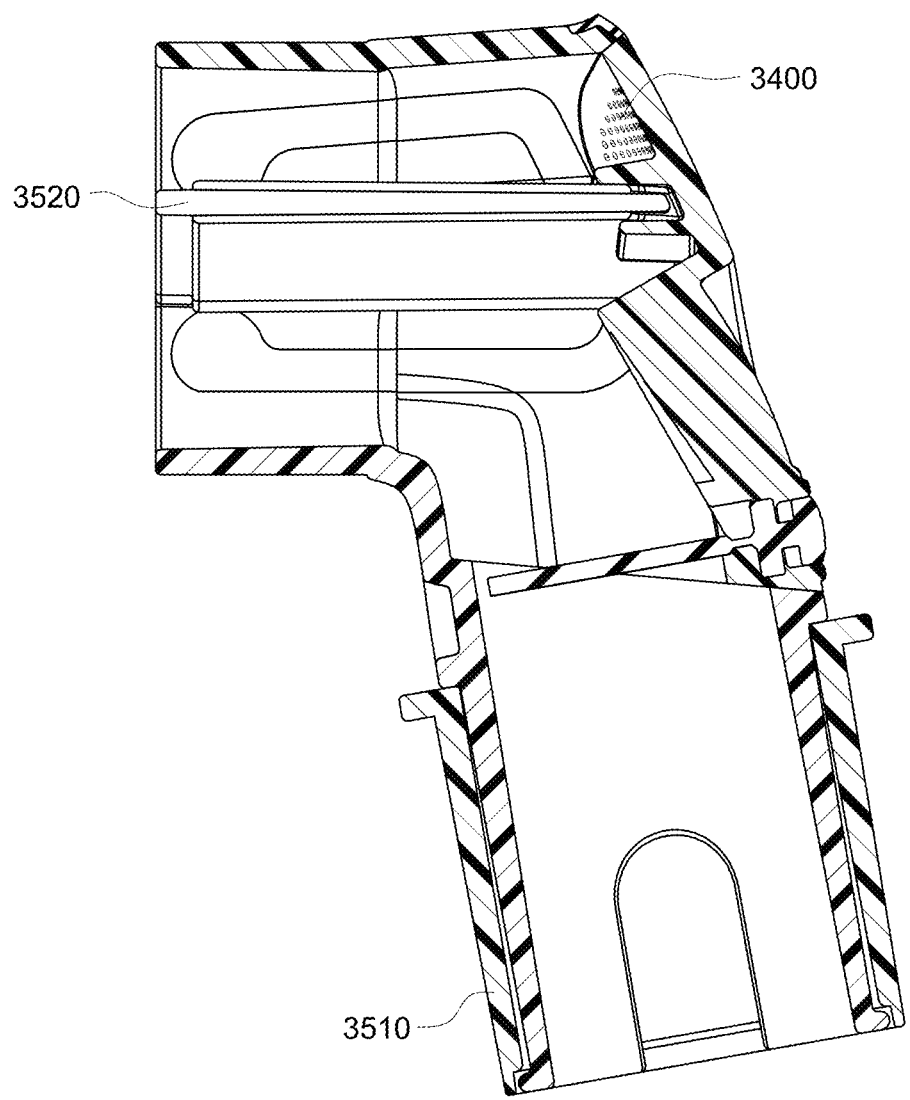

FIG. 26d shows a cross-sectional view of a tube decoupling structure taken through line 26d-26d of FIG. 26c according to an example of the present technology.

Figure 27A:
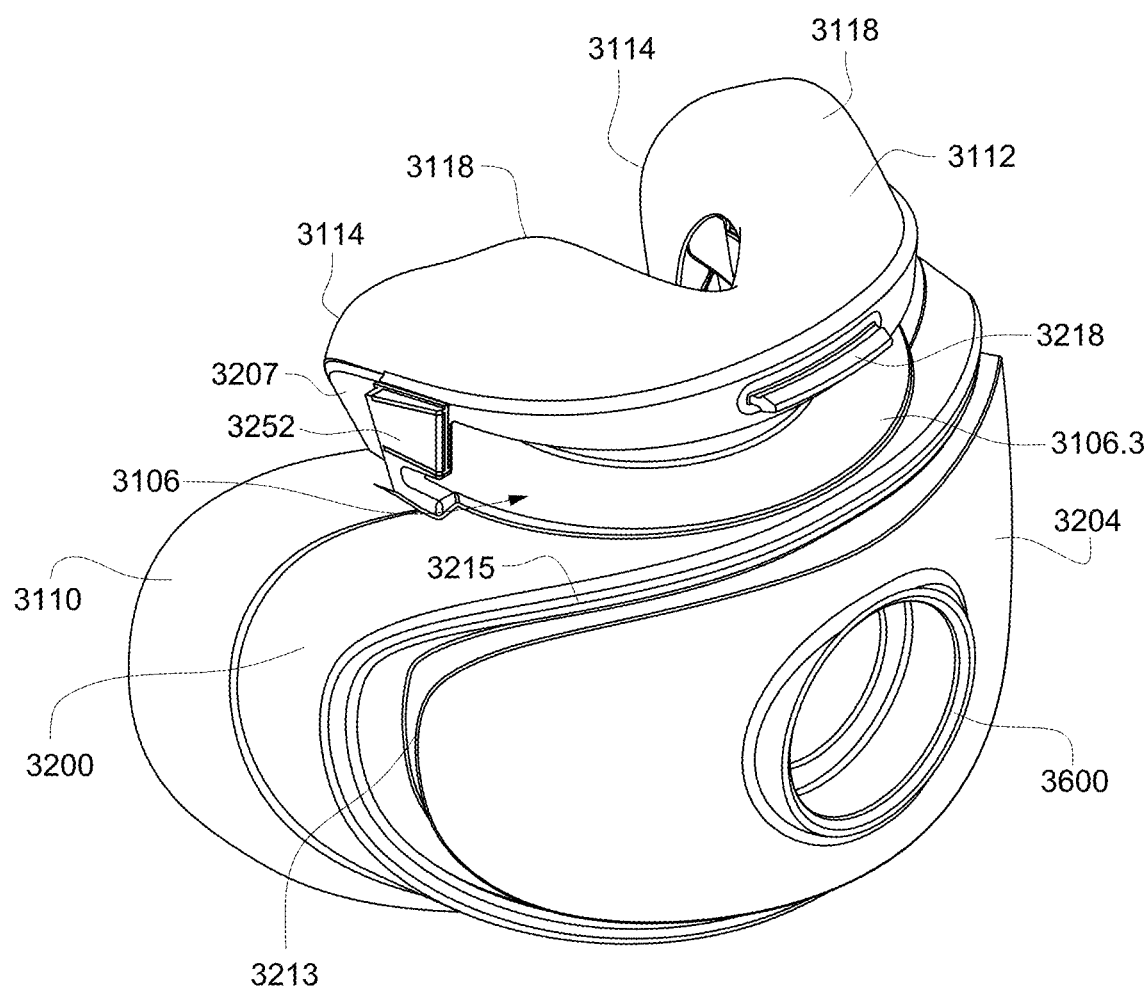

FIG. 27a shows a perspective view of a seal-forming structure with a top plate and a faceplate according to an example of the present technology.

Figure 27B:
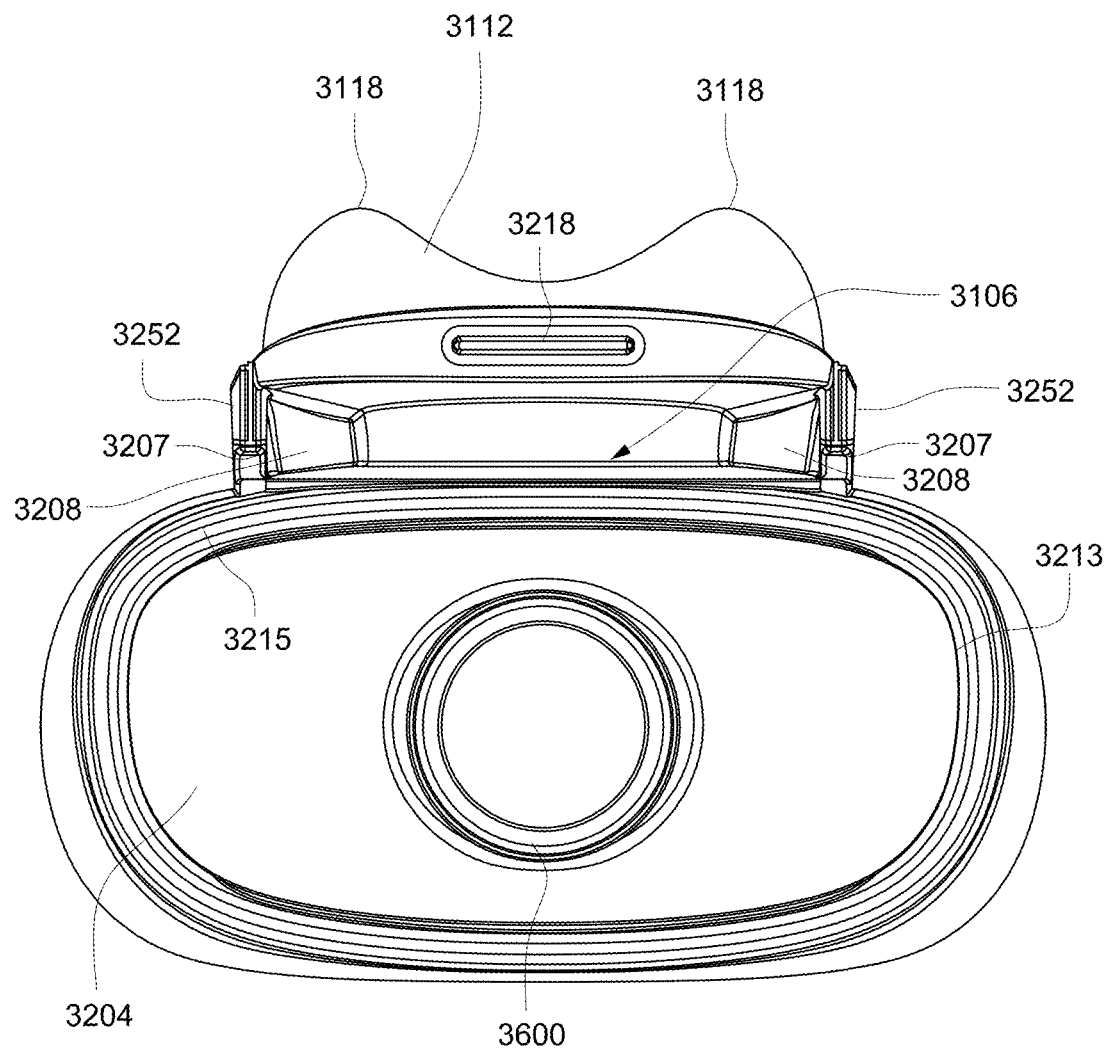

FIG. 27b shows a front view of a seal-forming structure with a top plate and a faceplate according to an example of the present technology.

Figure 27C:
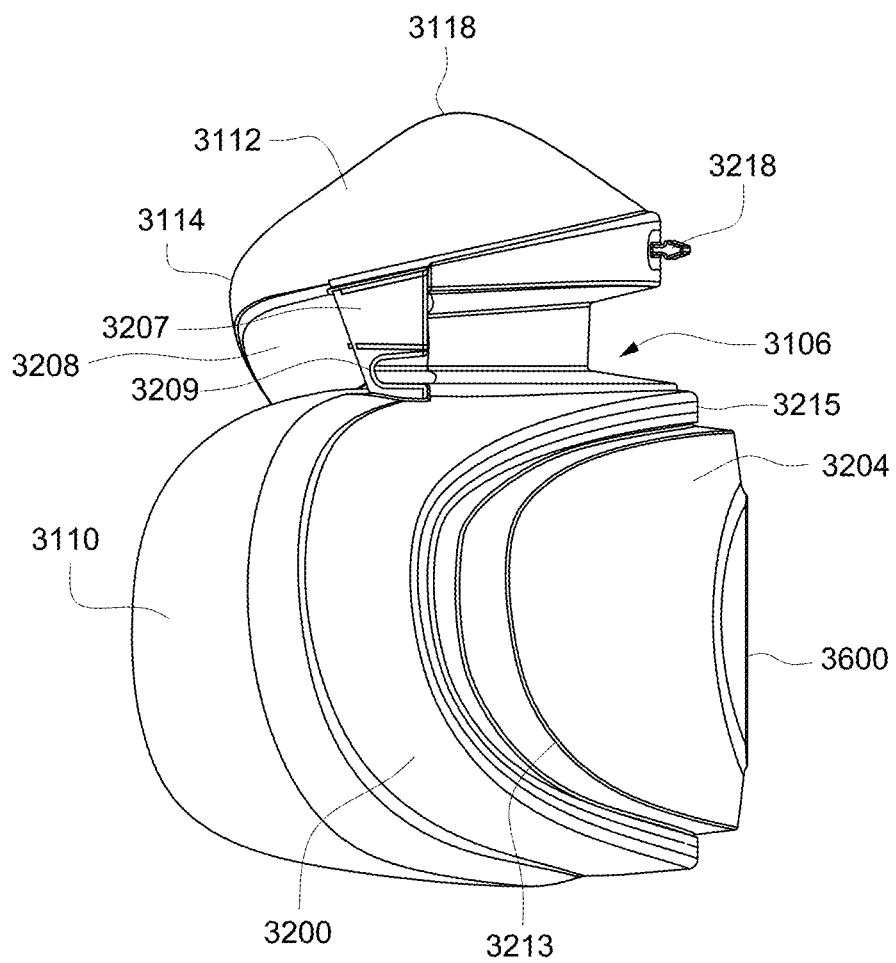

FIG. 27c shows a side view of a seal-forming structure with a top plate and a faceplate according to an example of the present technology.

Figure 27D:
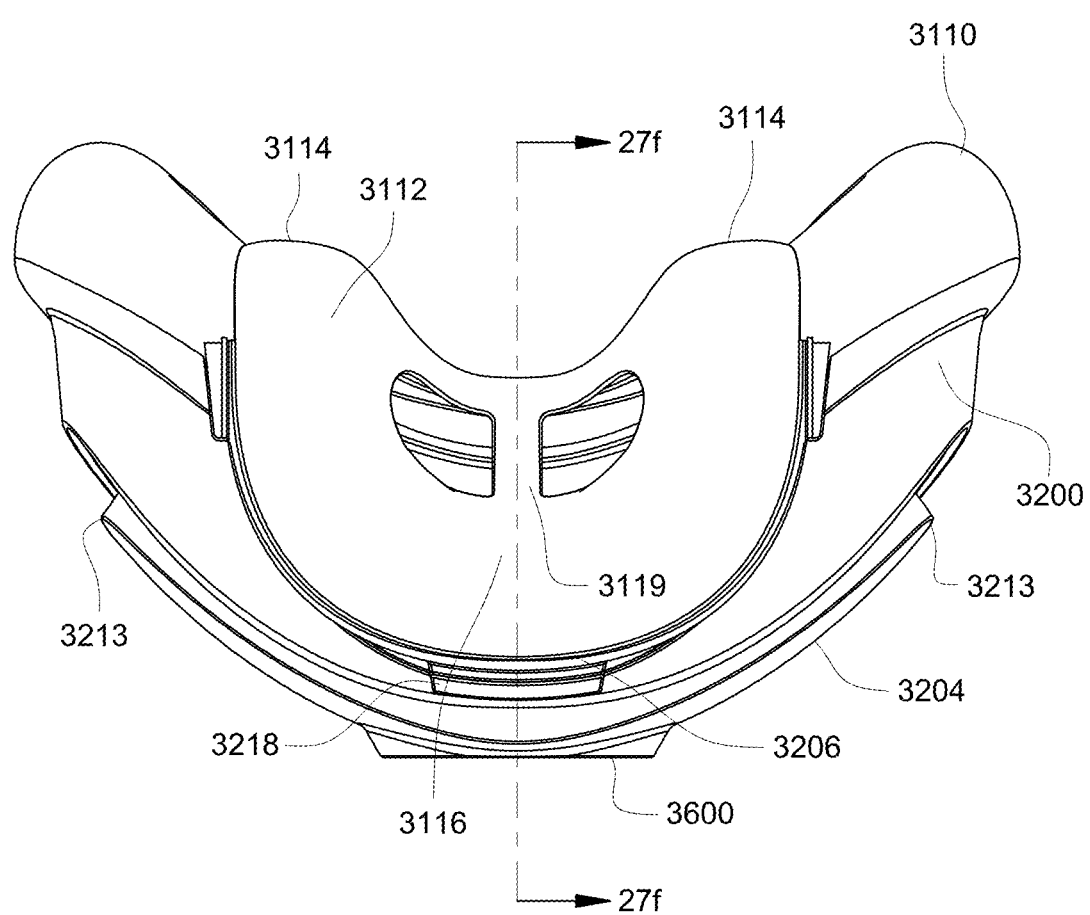

FIG. 27d shows a top view of a seal-forming structure with a top plate and a faceplate according to an example of the present technology.

Figure 27E:
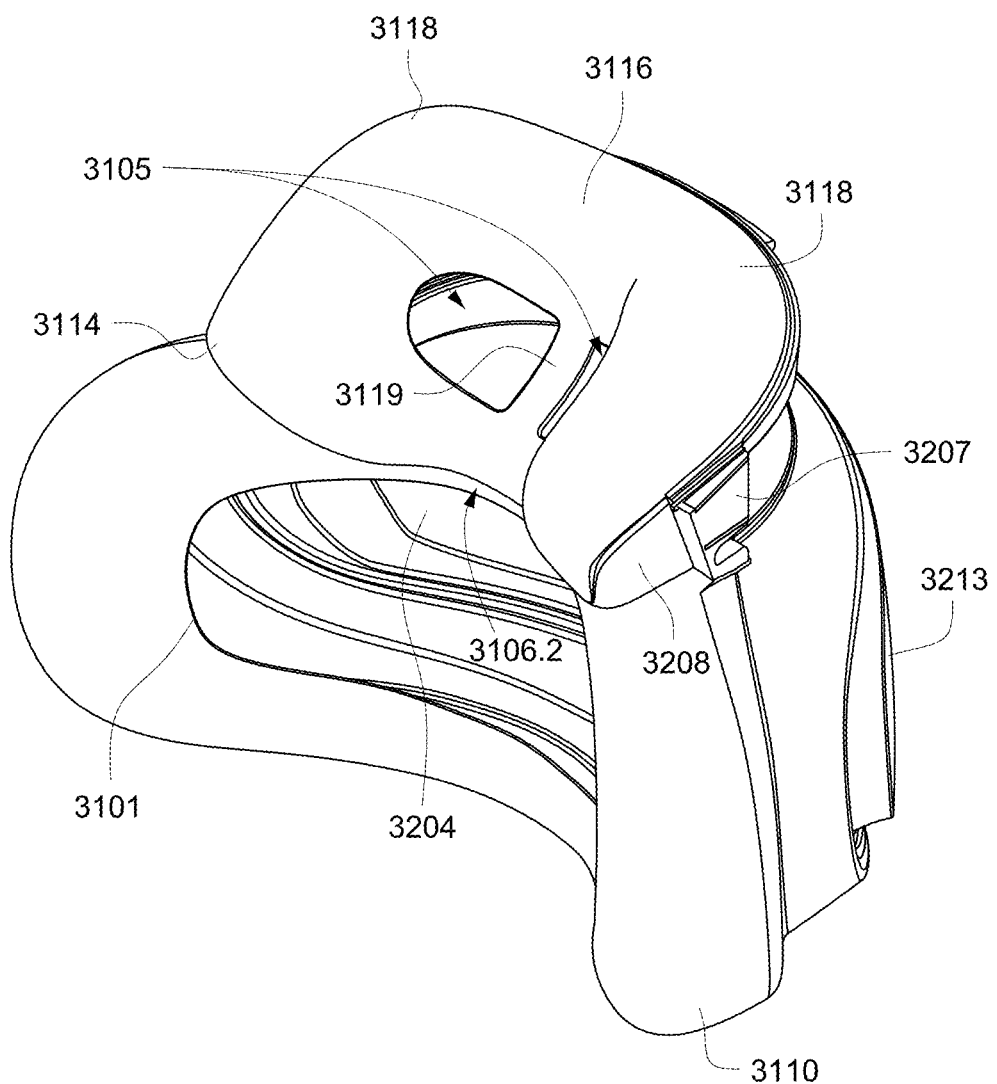

FIG. 27e shows a rear perspective view of a seal-forming structure with a top plate and a faceplate according to an example of the present technology.

Figure 27F:
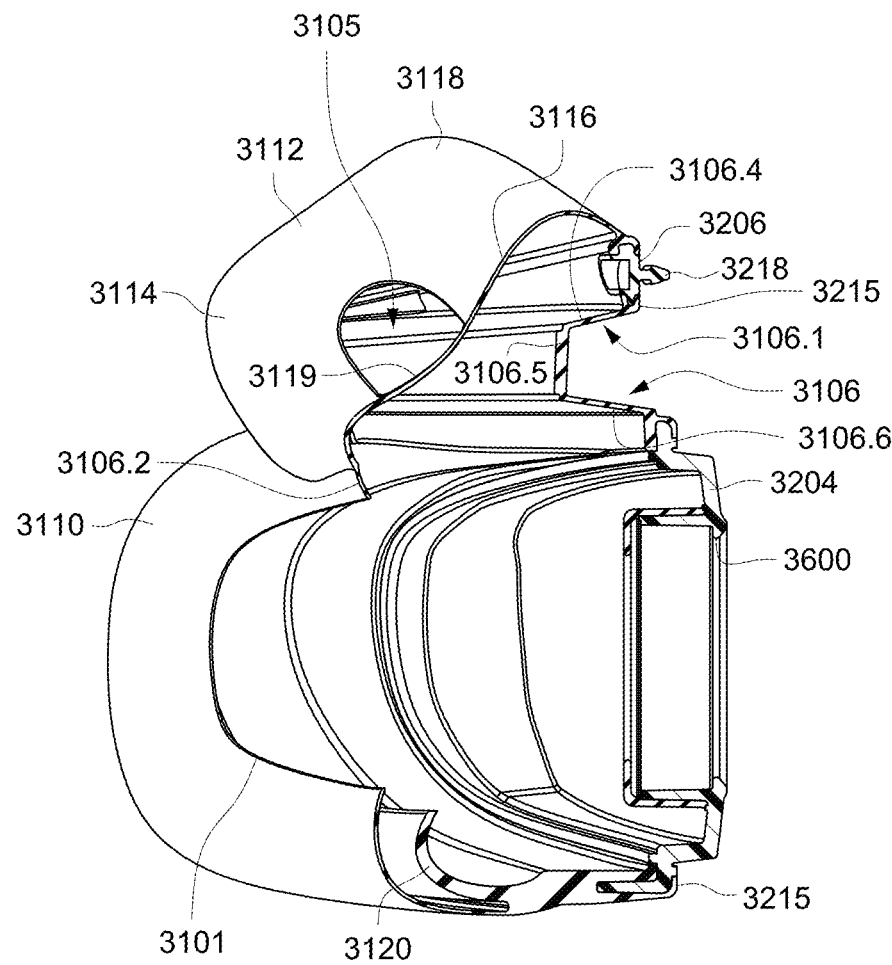

FIG. 27f shows a cross-sectional view taken through line 27f-27f of FIG. 27d of a seal-forming structure with a top plate and a faceplate according to an example of the present technology.

Figure 28A:
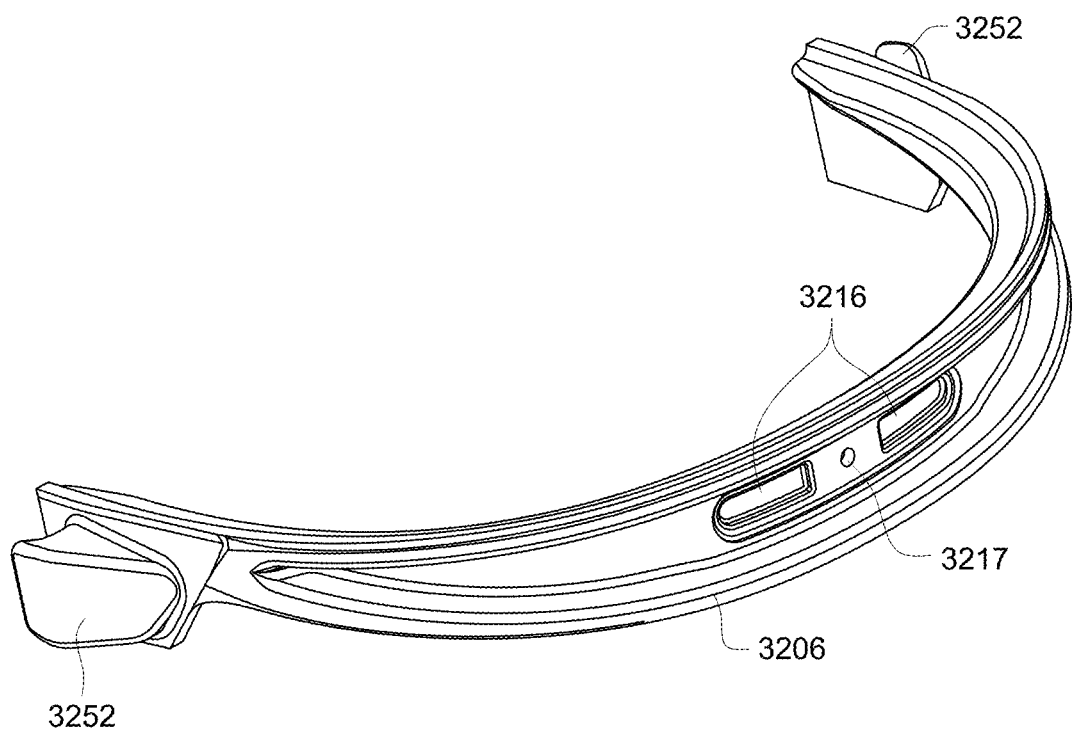

FIG. 28a shows a perspective view of a top plate according to an example of the present technology.

Figure 28B:
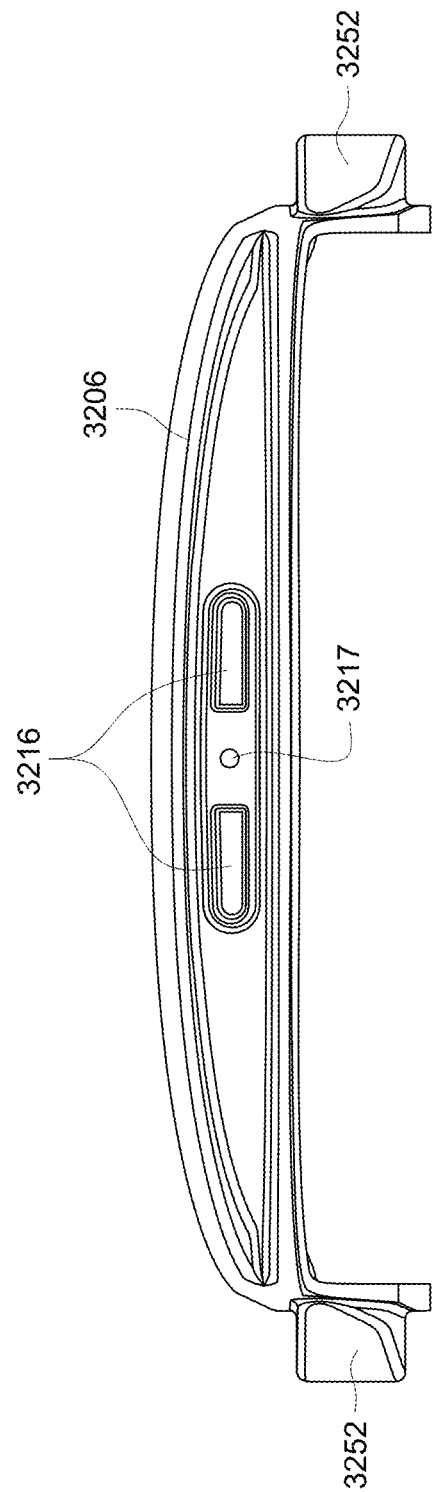

FIG. 28b shows a front view of a top plate according to an example of the present technology.

Figure 28C:
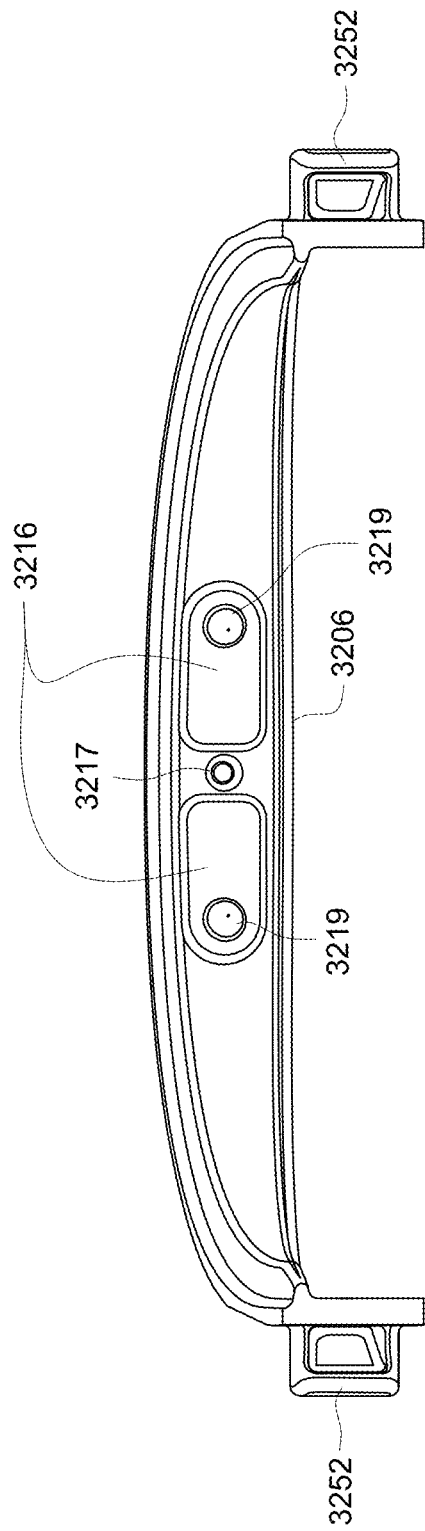

FIG. 28c shows a rear view of a top plate according to an example of the present technology.

Figure 28D:
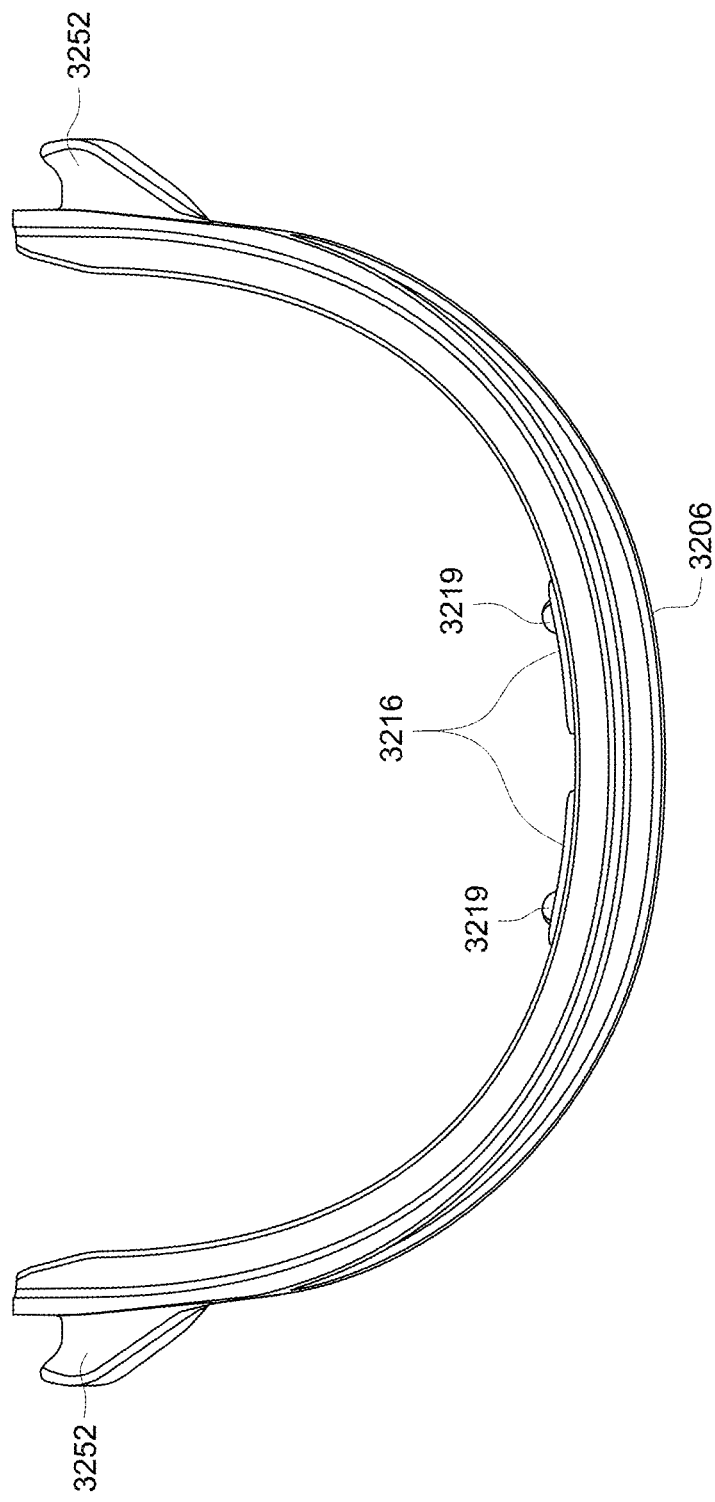

FIG. 28d shows a top view of a top plate according to an example of the present technology.

Figure 28E:
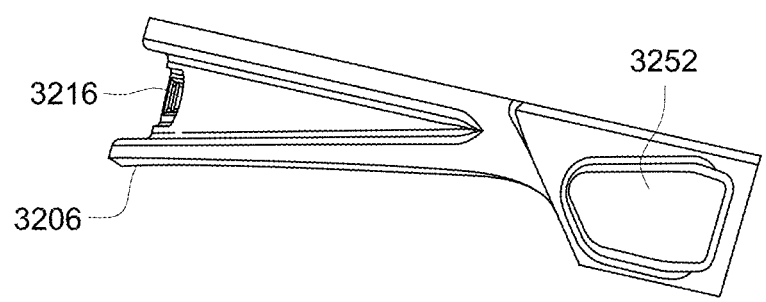

FIG. 28e shows a side view of a top plate according to an example of the present technology.

Figure 29A:
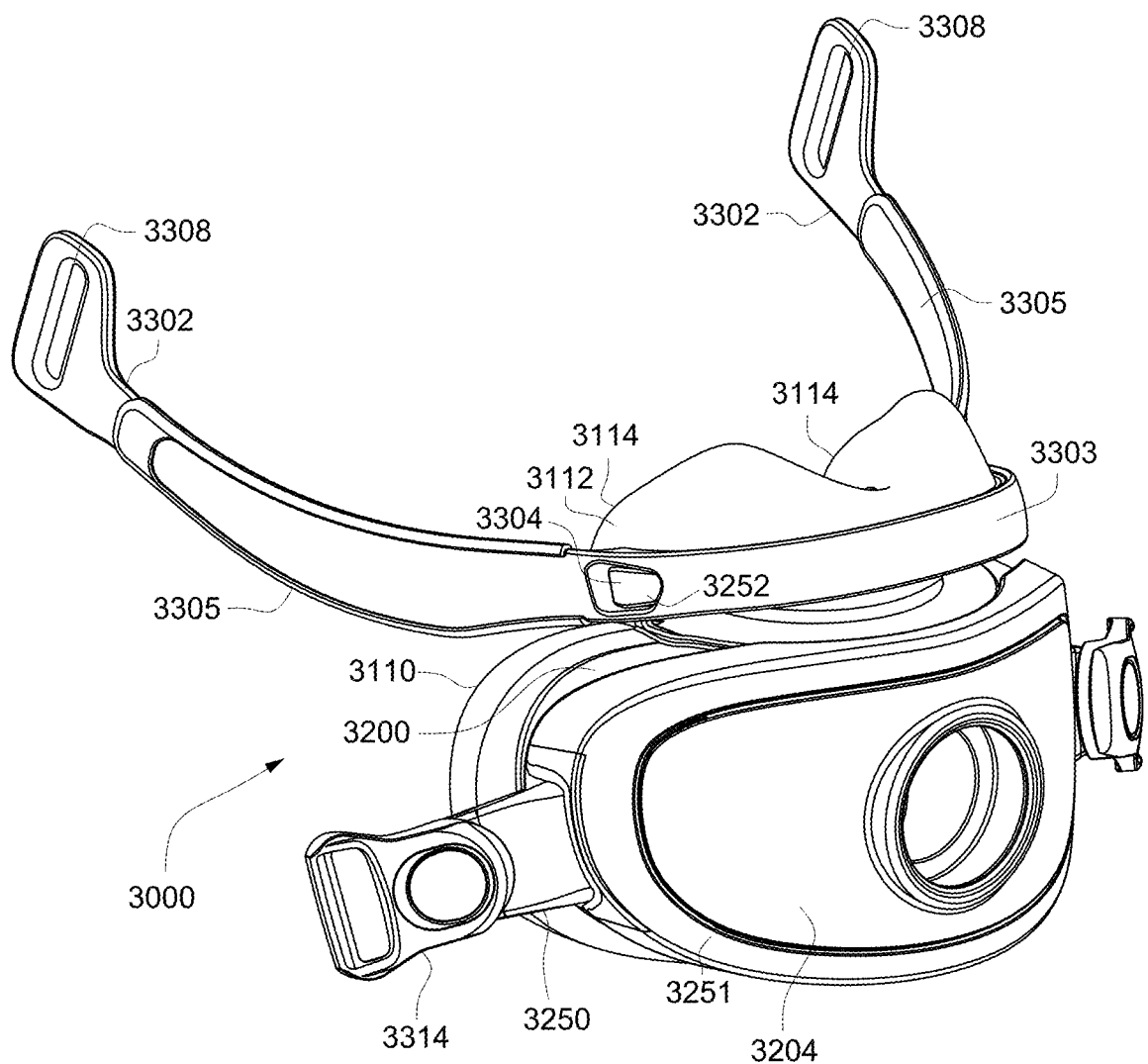

FIG. 29a shows a perspective view of a patient interface according to an example of the present technology.

Figure 29B:
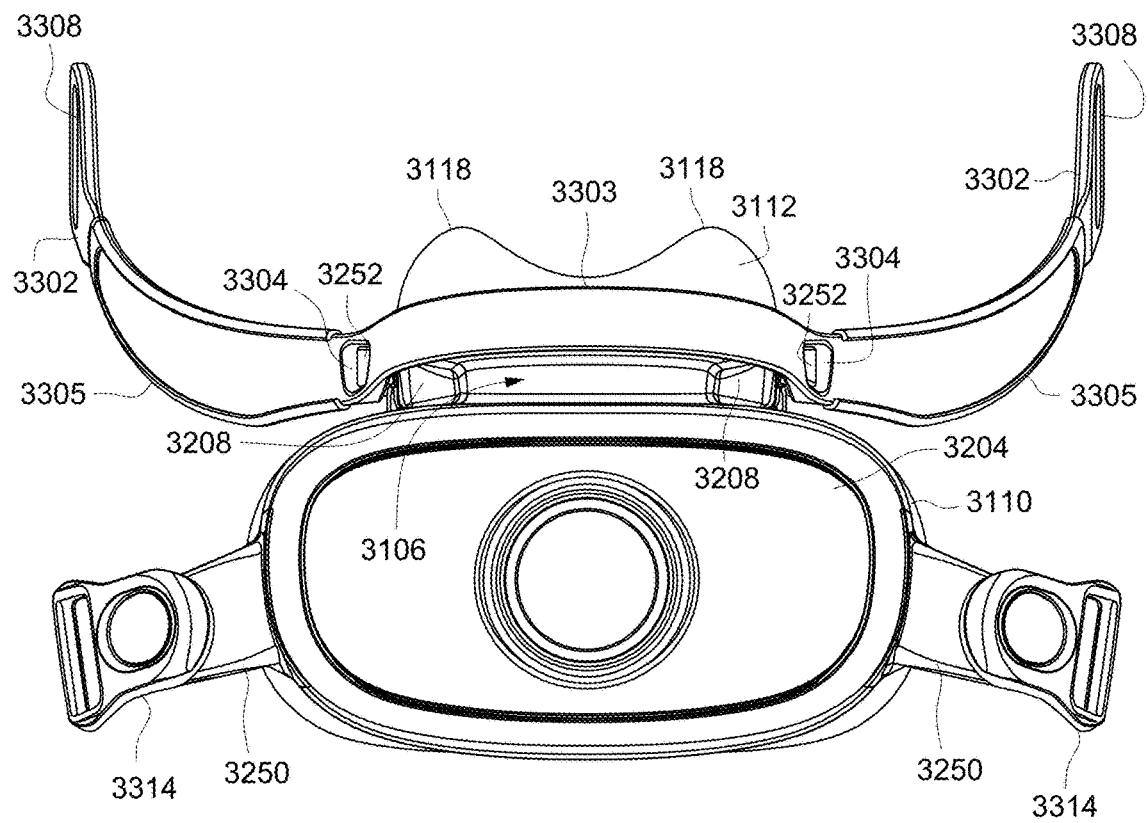

FIG. 29b shows a front view of a patient interface according to an example of the present technology.

Figure 29C:
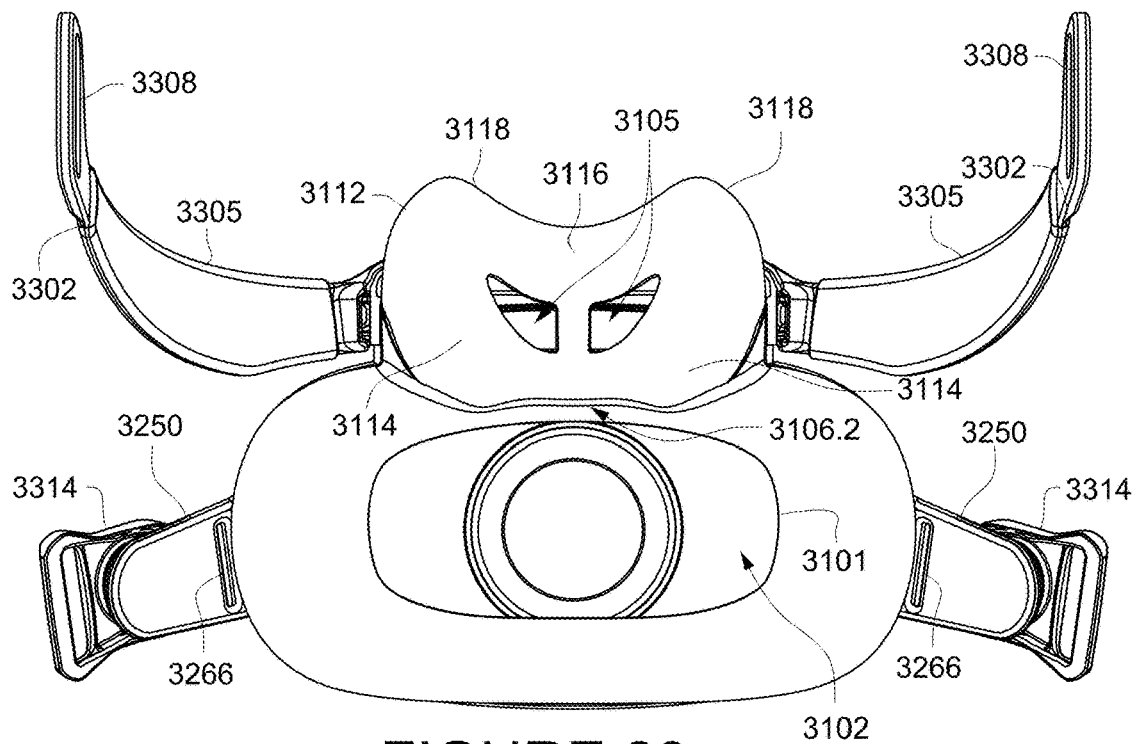

FIG. 29c shows a rear view of a patient interface according to an example of the present technology.

Figure 29D:
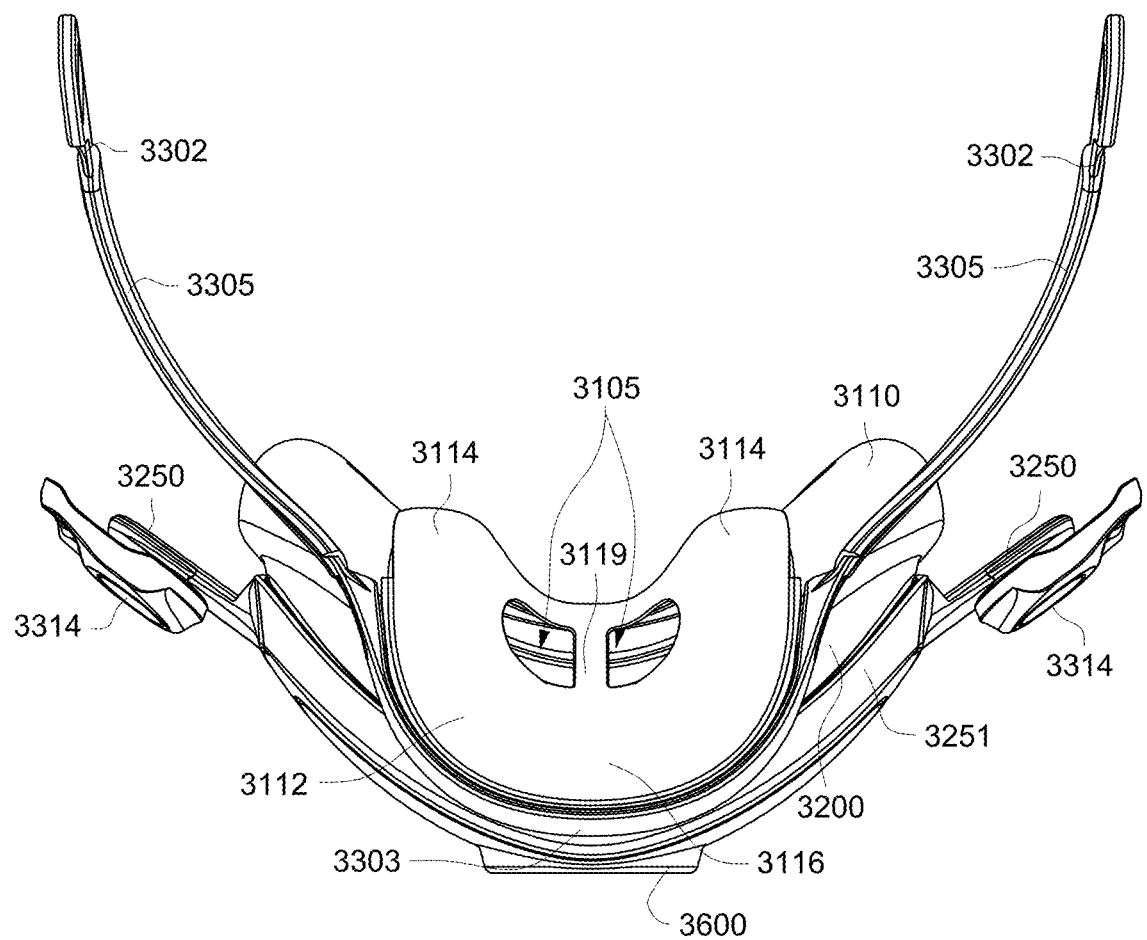

FIG. 29d shows a top view of a patient interface according to an example of the present technology.

Figure 29E:
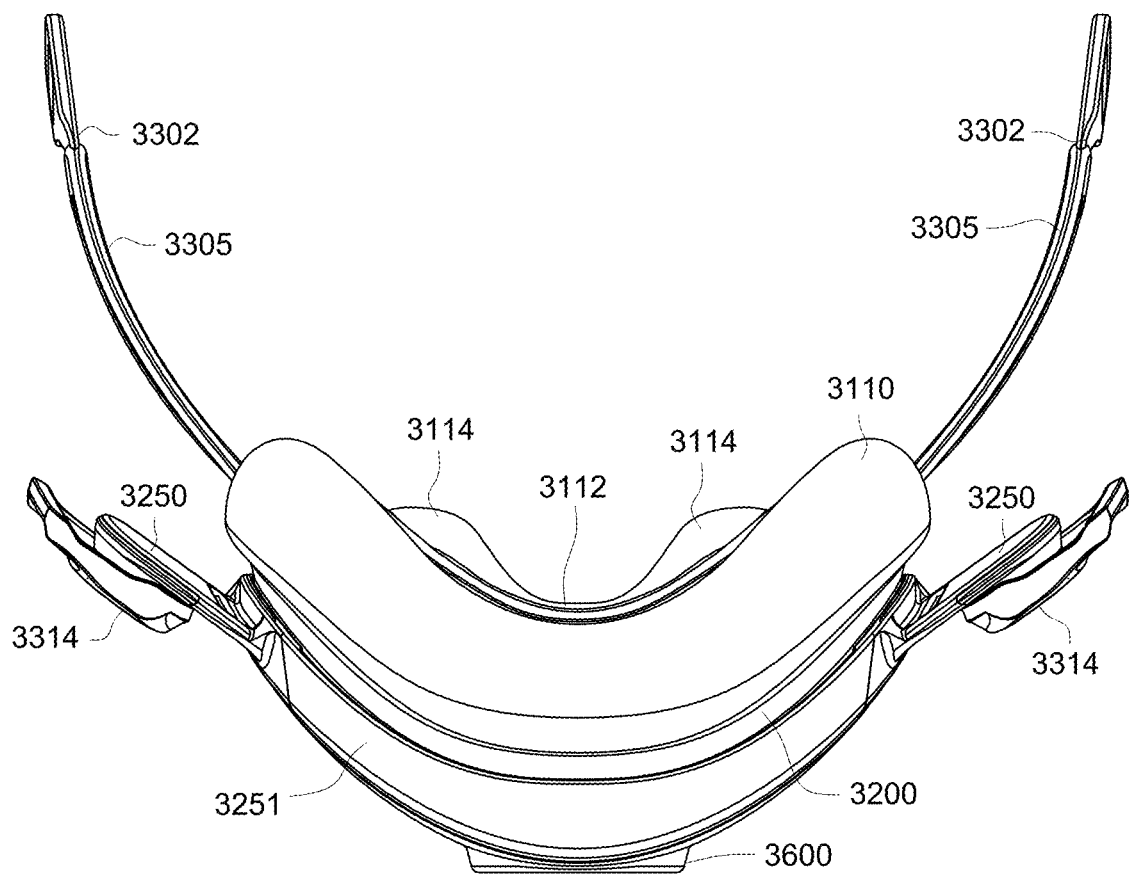

FIG. 29e shows a bottom view of a patient interface according to an example of the present technology.

Figure 29F:
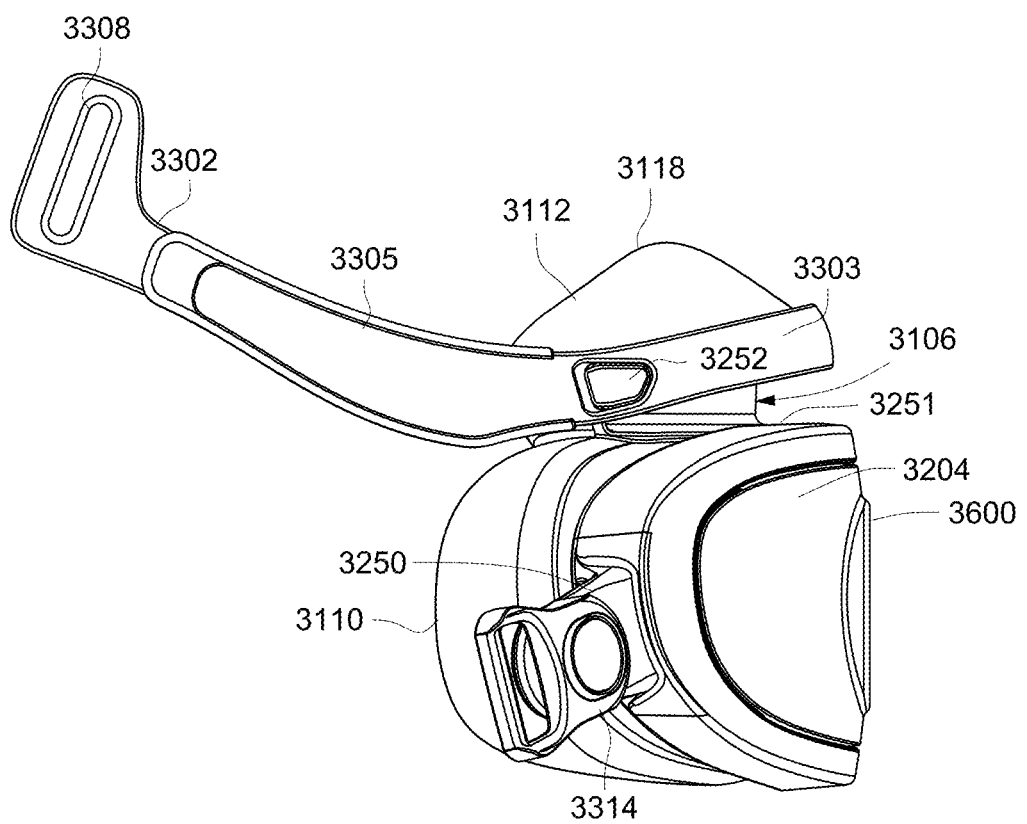

FIG. 29f shows a side view of a patient interface according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Treatment Systems

In one form, the present technology comprises apparatus for treating a respiratory disorder. In an example, the apparatus comprises a flow generator or blower for supplying pressurised respiratory gas, such as air, to the patient 1000 via an air delivery tube leading to a patient interface 3000.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

5.3 Patient Interface

A non-invasive patient interface in accordance with one aspect of the present technology comprises the following functional aspects: a seal-forming structure, a plenum chamber, a positioning and stabilising structure and a connection port for connection to an air circuit. In some forms a functional aspect may be provided by one or more physical components. In some forms, one physical component may provide one or more functional aspects. In use the seal-forming structure is arranged to surround an entrance to the airways of the patient so as to facilitate the supply of air at positive pressure to the airways.

FIG. 3a shows a front perspective view of a patient interface 3000 according to an example of the present technology. The patent interface 3000 may include a seal-forming structure 3100, an oral plenum chamber 3200, a nasal plenum chamber 3202, and components of a positioning and stabilising structure 3300.

5.3.1 Plenum Chamber and Seal-Forming Structure

Also shown in FIG. 3a, the upper portion of the seal-forming structure 3100 may include a nasal cushion or flange 3112 to seal around the lower portion of the nose of the patient, particularly around the ala and tip of the nose. This nasal cushion 3112 may define, at least in part, an upper gas chamber, which will be discussed in greater detail below.

FIG. 3a also shows that the seal-forming structure 3100 may also include an oral cushion or flange 3110 to seal around the mouth of the patient. The oral cushion 3110 may be attached to the oral plenum chamber 3200 around a perimeter 3210 of the oral plenum chamber 3200.

The rear view in FIG. 3c shows the portions of the seal-forming structure 3100 that may contact the face of the patient during use. The nasal cushion 3112 is shown connected to an upper portion of the oral cushion 3110 by a decoupling structure 3106. The decoupling structure 3106 may be understood to be an intermediate structure that joins the nasal cushion 3112 and the oral cushion 3110. The decoupling structure 3106 may allow the nasal cushion 3112 and the oral cushion 3110 to move relative to one another, while maintaining a pneumatic flow path therebetween. The nasal cushion 3112 may define a nasal gas chamber 3104 and a nasal gas chamber opening 3103 in the nasal cushion 3112 may receive a portion of the nose of the patient in use. During therapy, breathable gas may be provided to the patient from the patient interface 3000 to the nose through the nasal gas chamber 3104. The oral cushion 3110 may also include an oral gas chamber 3102 and an oral gas chamber opening 3101 to provide breathable gas to the patient's mouth during therapy. Through the oral gas chamber 3102 of the oral cushion 3110, the faceplate 3204 and the port 3600 can be seen. It should be understood that when the patient interface 3000 is donned on a patient, the faceplate 3204, the plenum chamber 3200, the oral cushion 3110, the nasal cushion 3112, and the decoupling structure 3106 may at least partially, along with the face of the patient, define the nasal gas chamber 3104 and the oral gas chamber 3102 through which breathable gas may be provided to the patient at positive pressure.

In FIG. 3d, a protruding end 3114 can be seen on either side of the nasal cushion 3112. When donned on the patient each protruding end 3114 may be shaped to extend from the patient interface 3000 so as to seal within the gap between the respective alae and nasolabial sulci of the patient. FIG. 2c, which depicts superficial features of the face, indicates the location of the alae and the nasolabial sulci. The details of the seal provided by the protruding ends 3114 will be described in greater detail below. The protruding ends 3114 may partially inflate and/or deform to seal in this area.

FIG. 3r shows how the exemplary patient interface 3000 may seal against a patient, particularly the nose. In this detailed front perspective view, the nose, mouth, and chin of a patient are shown in solid lines with the nasal cushion 3112 shown against the nose in dashed lines. It should be understood that the nasal cushion 3112 may be concave in shape to cradle the nose of the patient. The recessed portion 3116 is shown receiving the tip of the nose and the protruding end 3114 can be seen sealing in the region of the ala and nasolabial sulcus. The nasal undercushion support wall 3208 may support the nasal cushion 3112 in the region of the protruding end 3114 to aid in maintaining the seal in this region, and may function like an undercushion. The nasal plenum chamber 3202 is also shown. The oral components of the patient interface 3000 are not shown in this view for the sake of clarity.

FIG. 3d also shows a recessed portion 3116 that may be included on the nasal cushion 3112. This recessed portion 3116 may comprise an inwardly shaped section that extends into the nasal gas chamber 3104 to receive the tip of the nose of the patient when donned by the patient. The recessed portion 3116 may provide enhanced sealing around and under the tip of the nose of the patient during therapy by allowing the shape of the nasal cushion 3112 to better conform to the patient's nose. The recessed portion 3116 will also be described in greater detail below.

In FIGS. 3m and 3n it can be seen that the oral cushion 3110 surrounds the perimeter of the mouth of the patient 1000. The oral gas chamber 3102 may be formed by the oral cushion 3110 that surrounds the mouth of the patient 1000, the oral plenum chamber 3200, and the faceplate 3204. In use, the air circuit 4170 may be connected to a PAP device 4000 (not shown in this view) to provide breathable gas to the patient 1000 via the oral gas chamber 3102 of the patient interface 3000 through the patient's mouth.

This view also shows the nasal cushion 3112 surrounding a portion of the nose, specifically the nose tip, of the patient 1000. The nasal gas chamber 3104 is thus formed by the nasal cushion 3112 and the face of the patient. In this example, breathable gas from the air circuit 4170 may pass through the oral gas chamber 3102, then through the opening defined by the decoupling structure 3106 and into the nasal gas chamber 3104. The line B-B shown in FIG. 3m is intended to indicate the transition between the nasal bone and the cartilaginous portion of the nose extending from the bone structure of the nose of the patient 1000. The nasal cushion 3112 depicted with this exemplary patient interface 3000 is designed to seal about the periphery of the nose of the patient and below the line B-B with respect to the nose. In other words, the nasal cushion 3112 may seal below the bridge of the nose.

The patient interface 3000, according to an example of the present technology, has a 4896 $mm^2$ surface area footprint on the face which is less obtrusive than a conventional full face mask (for example, the ResMed Quattro FX full face mask has a 7007.89 $mm^2$ surface area footprint on the face) by about 30%. For some patients, it may also feel less claustrophobic. Also, the specific areas of reduced obstruction are important because these areas are found to have significant beneficial psychological impact on a bed partner when looking at the mask because it looks less medical and "opens up" the face. From the patient's perspective, the exemplary patient interface 3000 is not in, or significantly reduced from, their field of vision because the nasal cushion 3112 seals below the bridge of the nose. This allows the patient to wear spectacles when reading a book or watching television after donning the patient interface 3000 before they fall asleep. By sealing below the nose bridge, irritation may be avoided in an area that has thin skin, is pressure sensitive, and/or has high chance of skin breakdown due to blood flow constriction. Another advantage may be that anthropometric variations between patients above the nose bridge do not need to be considered and focus for the mask fit range can be directed towards anthropometric variations around the upper lip area. Also, unlike some other full face masks, the patient interface 3000 may not require a forehead support which is required for providing pressure point relief. This may also avoid the problem of the forehead support being a source of a pressure point and/or skin break down.

Anatomically, FIGS. 2h and 2i may be referenced for an indication as to the location of the transitional region between the nasal bone and the cartilage. Thus, the exemplary nasal cushion 3112 is intended to seal about the periphery of the nose of the patient in contact with the softer tissues of the nose, e.g., fatty tissue and cartilage. By forming a seal with the nose on these softer tissues it may be possible to avoid irritation of the skin of the patient that would otherwise occur were the seal to be formed around/ over the harder nasal structures, i.e., bone. In other words, patient discomfort may be minimised by sealing below the bridge of the nose. Also, locating the seal of the nasal cushion 3112 around this region of the nose may allow for a better seal to be formed because the nasal tissues and the nasal cushion 3112 may conform to one another to form the seal. The nasal cushion 3112 should conform to the nose predominantly.

A sealing feature described above that may be seen in FIG. 3*m* is the location of the protruding end 3114 against the face of the patient 1000. Specifically, the protruding end 3114 may be an extended portion of the nasal cushion 3112 that seals in the region between the nasolabial sulcus and ala. These anatomical features may be seen in FIG. 2*c*. Depending on the individual facial structure of the patient, this region may represent a recessed portion 3116 such that an extension from the nasal cushion 3112 may be necessary to form an adequate seal about the nose of the patient. The protruding ends 3114, as depicted in FIG. 3*m*, may advantageously serve this function.

Another sealing feature of the depicted exemplary patient interface 3000 can be seen in FIG. 3*p*. The nasal cushion 3112 includes, as discussed above, a recessed portion 3116 to receive the tip of the nose of the patient 1000 when donned by the patient. Specifically, at the region where the recessed portion 3116 is located, the tip of the nose of the patient 1000 can be seen in dashed lines. This view also shows how the nasal cushion 3112 may be shaped to seal against the perimeter of the nose at its underside. In other words, the seal formed by the nasal cushion 3112 against the nose may be characterized as against an inferior and peripheral portion of the nose. Thus, it may be understood from this view that the sealing surface of the nasal cushion 3112, as a whole, may be concave or form a pocket to receive the nose and it may further include the recessed portion 3116 to receive the tip of the nose.

FIG. 3*q* depicts the various points of contact that may be made by the patient interface 3000 to seal against the face of a patient. The patient interface 3000 is shown in a side cross-sectional view. Specifically, the nasal cushion 3112, nasal plenum chamber 3202, oral cushion 3110, and the oral plenum chamber 3200 are shown in cross-section. Reference may also be made to FIGS. 2*b-f* for description of the relevant anatomical features. The nasal cushion 3112 is shown sealing against the nose of the patient at the tip. A connection region 3106.2 between the oral cushion 3110 and nasal cushion 3112 is shown sealing against the lip superior of the patient. It should be noted that connection region 3106.2 may be arranged to seal against the lip superior of the patient in a region that is below the naris and above the mouth so as not block airflow into the airways. The connection region 3106.2 may connect the posterior portions of the oral cushion 3110 and the nasal cushion 3112. The connection region 3106.2 may be structured and positioned to maintain a seal against the lip superior of the patient and below the naris, while allow for relative movement between structures of the oral gas chamber 3102 and the nasal gas chamber 3104 (e.g., the oral cushion 3110 and the nasal cushion 3112, respectively). The connection region 3106.2 may function cooperatively with the decoupling structure 3106 to facilitate this relative movement as well.

The nasal gas chamber 3104 may be seen defined, at least in part, by the nasal cushion 3112, nasal plenum chamber 3202, and the patient's nose to provide a sealed path for breathable gas to enter the patient's airways via the naris or nostril. A gap 3106.1 can also be seen between the oral plenum chamber 3200 and the nasal plenum chamber 3202. The gap 3106.1 will be discussed in greater detail below, however, it should be understood that the gap 3106.1 may facilitate, in part, maintenance of the seals against the nose and mouth in spite of independent movement of the nasal cushion 3112 and the oral cushion 3110. It may be advantageous to maintain the seal of the nasal cushion 3112 against the nose, the connection region 3106.2 against the lip superior, and the oral cushion 3110 around the mouth while allowing these components to move independently of one another and also to accommodate anthropometric variance and a large range of patients.

As shown in FIG. 3*q*, the oral gas chamber 3102 may be seen defined, at least in part, by the oral cushion 3110, oral plenum chamber 3200, and the mouth of the patient to provide a sealed path for breathable gas to enter the patient's airways via the mouth. A seal and/or contact at the lip inferior of the patient may be made by the oral cushion 3110. Although not shown in this view, it should be understood that the oral undercushion 3120 may support the thinner oral cushion 3110 against the lip inferior when a positioning and stabilising 3300 structure urges the patient interface 3000 against the face of the patient. In such a situation, the oral undercushion 3120 would be urged into contact with a corresponding portion of the oral cushion 3110.

In one form of the present technology, a seal-forming structure 3100 provides a sealing-forming surface, and may additionally provide a cushioning function.

In an example, a seal-forming structure 3100 in accordance with the present technology is constructed from a soft, flexible, resilient material such as silicone.

In another example of the present technology, the seal-forming structure 3100, e.g., the oral cushion 3110, the nasal cushion 3112 and/or their respective undercushions, may be formed from foam.

In an example, the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter 3210 of the plenum chamber 3200.

FIGS. 7*a-h* depict several views of the seal-forming structure 3100 and the plenum chamber 3200. These views show the seal-forming structure 3100 and the plenum chamber 3200 without the top plate 3206 and the faceplate 3204, as well as without any of the associated positioning and stabilising structure 3300.

FIG. 7*a* shows a rear perspective view of the seal-forming structure 3100 and plenum chamber 3200. The exemplary seal-forming structure 3100 shown in this view includes the oral cushion 3110 and the nasal cushion 3112. The connection region 3106.2 can be seen in this view connecting the oral cushion 3110 and the nasal cushion 3112. Also, the location of the decoupling structure 3106 is shown between the oral cushion 3110 and the nasal cushion 3112.

The oral cushion 3110 and the oral plenum chamber 3200 can be seen partially defining the oral gas chamber 3102. The opening 3101 to the oral gas chamber 3102 defined by the oral cushion 3110 can also be seen.

Also visible in FIG. 7*a* is the nasal plenum chamber 3202 that partly defines the nasal gas chamber 3104 along with the nasal cushion 3112. This exemplary nasal cushion 3112 can also be seen, including the protruding ends 3114 at either side. The recessed portion 3116 that receives the tip of the nose can also be seen. A nasal undercushion support wall 3208 is shown in this view as well. The nasal undercushion support wall 3208 is associated with a respective protruding end 3114 and may provide support for the protruding end 3114 as it seals against the ala and nasolabial sulcus of the patient.

FIG. 7*b* shows a side perspective view of the exemplary seal-forming structure 3100 and plenum chamber 3200. FIG. 7*b* depicts similar features to those shown in FIG. 7*a*. This view, however, also depicts that the connection region 3106.2 may have a concave shape. In other examples, the connection region 3106.2 may have a non-concave shape. By forming the connection region 3106.2 with a concave shape, the oral cushion 3110 may be able to better seal around the mouth of the patient and the nasal cushion may be able to better seal around and under the nose of the patient. Alternatively, a fully convex cushion may also function similarly. In this view, a portion of the perimeter 3210 of the oral plenum chamber 3200 can also be seen. Also, the location of the decoupling structure 3106 is indicated.

FIG. 7*b* shows the nasal undercushion support wall 3208 associated with the respective protruding end 3114 of the nasal cushion 3112. The nasal undercushion support wall 3208 extends out to beyond the perimeter of the nasal plenum chamber 3202. Such a configuration may allow the nasal undercushion support wall 3208 to provide sufficient support for the protruding end 3114 to seal against the patient's face. The bottom half of the nasal undercushion support wall 3208 may act as a hinge or pivot point for the decoupling structure 3106. The top half of the nasal undercushion support wall 3208 may help locate the top plate 3206.

FIG. 7*c* shows a front perspective view of the exemplary seal-forming structure 3100 and plenum chamber 3200. This view depicts particularly well the anterior portion of the nasal plenum chamber 3202 as well as the nasal undercushion support wall 3208 that supports the protruding ends 3114 of the nasal cushion 3112.

FIG. 7*d* shows a rear view of the exemplary seal-forming structure 3100 and plenum chamber 3200. This view shows features similar to those shown in FIG. 7*a*. On either side of the nasal cushion 3112 a portion of each nasal undercushion support wall 3208 can be seen. Also, this view shows how the connection region 3106.2 may connect the oral cushion 3110 to the nasal cushion 3112. Also, the location of the decoupling structure 3106 is indicated.

FIG. 7*e* shows a front view of the exemplary seal-forming structure 3100 and plenum chamber 3200. This view shows especially well the oral cushion 3110 disposed about the perimeter 3210 of the oral plenum chamber 3200. Further, the oral gas chamber 3102 can be seen defined by the oral cushion 3110 and the oral plenum chamber 3200. Also, this view shows the anterior portion of the decoupling structure 3106 that connects the nasal cushion 3112 to the oral cushion 3110. Nasal undercushion support walls 3208 can be seen on either side of the nasal cushion 3112. From this view, the oral undercushion 3120 is also visible. This view also shows that the oral undercushion 3120 may terminate at a tapered region 3122 near either side of the nasal cushion 3112. Thus, there may be no undercushion at the connection region 3106.2 (not shown in this view) between the oral cushion 3110 and the nasal cushion 3112. Advantageously, this may allow greater flexibility in the connection region 3106.2 such that the seal against the lip superior that is shown in FIG. 3*q* may be easily maintained despite movement of the oral and nasal cushions 3110, 3112.

FIGS. 12*a-d* show further exemplary arrangements of the oral undercushion 3120 in accordance with the present technology. These Figures show the oral cushion 3110 and the opening 3101 to the oral gas chamber 3102 with various configurations of the oral undercushion 3120 shown in stippling. For the sake of simplicity additional features associated with the seal-forming structure 3100 have been omitted from these drawings.

FIG. 12*a* depicts an example of the oral cushion 3110 where the oral undercushion 3120 surrounds the entire perimeter of the oral cushion 3110. FIG. 12*b* depicts an example of the oral cushion 3110 where there are two portions of oral undercushion 3120, one on either side of the oral cushion. FIG. 12*c* depicts an example where the oral undercushion 3120 surrounds the entire perimeter of the oral cushion 3110 with the exception of a portion near an upper region of the oral cushion 3110. FIG. 12*d* depicts a similar example to FIG. 12*c*, however the portion of the oral cushion 3110 where there is no oral undercushion 3120 is at a lower region of the oral cushion 3110.

FIG. 7*f* shows a top view of the exemplary seal-forming structure 3100 and plenum chamber 3200. This view shows nasal cushion 3112 with its protruding ends 3114 and recessed portion 3116, as well as the nasal gas chamber 3104 defined, in part, by the nasal cushion 3112. This view also partly shows the pneumatic connection between the oral gas chamber 3102 and the nasal gas chamber 3104 that is defined by the decoupling structure 3106.

FIG. 7*g* shows a bottom view of the exemplary seal-forming structure 3100 and plenum chamber 3200. This view shows oral cushion 3110 attached to the oral plenum chamber 3200. Also, the protruding ends 3114 of the nasal cushion 3112 can be seen.

FIG. 8*a* shows another top view of the exemplary seal-forming structure 3100 and plenum chamber 3200. This view also shows a number of cross-section lines to indicate the cross-sections depicted in subsequent drawings, FIGS. 8*b*-8*l*. This view is similar to FIG. 7*f* and similar components are therefore depicted. However, to avoid confusion, reference numerals and lead lines have been excluded.

FIGS. 8*b-d* show cross-sectional views of the exemplary seal-forming structure 3100 and plenum chamber 3200 taken along line 8*b*, 8*c*, 8*d*,-8*b*, 8*c*, 8*d*. The nasal cushion 3112 can be seen connected to the oral cushion 3110 by the connection region 3106.2. The oral gas chamber 3102 can be seen defined, in part, by the oral plenum chamber 3200 and the oral cushion 3110. The nasal gas chamber 3104 can be seen defined, in part, by the nasal plenum chamber 3202 and the nasal cushion 3112. The protruding end 3114 and the recessed portion 3116 of the nasal cushion 3112 are also shown. This view also shows how the connection region 3106.2 in one example of the technology may not include an undercushion, while the oral cushion 3110 may include an oral undercushion 3120 and a nasal undercushion support wall 3208 (not shown in these views) to support the protruding end 3114. The gap 3106.1 formed by the hinge-like arrangement of the oral plenum chamber 3200, nasal plenum chamber 3202, and the decoupling structure 3106 can also be seen. In another example of the present technology, the oral undercushion 3120 may include two discontinuous side portions that are present on either side of the oral cushion 3110, but there would be no oral undercushion portion at the connection region 3106.2 or at the lower central portion of the oral cushion 3110. Alternatively, as shown in FIG. 7*e*, the oral undercushion 3120 may terminate near the nasal cushion 3112 at tapered regions 3122 on either side thereof.

FIGS. 8*b* and 8*c* also show angles $\alpha$ and $\beta$, respectively, being swept out with respect to the connection region 3106.2. FIG. 8*b* shows that $\alpha$ is the angle from the nasal cushion 3112 to a lower portion of the oral cushion 3110.

Angle α may be in the range of about 80° to about 180° and in one example of the technology a may be about 142°. FIG. 8c shows that β is the angle from the nasal cushion 3112 to an upper portion of the oral cushion 3110. Angle β may be in the range of about 80° to about 170° and in one example of the technology β may be about 120°. The cushions 3110, 3112 and plenum chambers 3200, 3202 may be formed as one-piece.

FIG. 8e shows another cross-sectional view of the exemplary seal-forming structure 3100 and plenum chamber 3200 taken along line 8e-8e. Again in this view, it can be seen that the oral cushion 3110 includes an oral undercushion 3120. The connection region 3106.2 is shown without an undercushion in accordance with this example of the technology. The gap 3106.1 formed by the hinge-like arrangement of the oral plenum chamber 3200, nasal plenum chamber 3202, and the decoupling structure 3106 can also be seen. Also, the side portion 3106.3 of the decoupling structure 3106 can be seen.

FIG. 8f shows another cross-sectional view of the exemplary seal-forming structure 3100 and plenum chamber 3200 taken along line 8f-8f. This view shows features similar to the example depicted in FIG. 8e. However, this view also shows a portion of the nasal undercushion support wall 3208 positioned to support the protruding end 3114 of the nasal cushion 3112. Here, the side portion 3106.3 of the decoupling structure 3106 can be seen proximal to the nasal undercushion support wall 3208.

FIG. 8g shows another cross-sectional view of the exemplary seal-forming structure 3100 and plenum chamber 3200 taken along line 8g-8g. FIG. 8g again shows similar features to FIGS. 8e and 8f. This view, however, also more clearly shows the nasal undercushion support wall 3208 positioned under the protruding end 3114 of the nasal cushion 3112.

FIG. 8h shows another cross-sectional view of the exemplary seal-forming structure 3100 and plenum chamber 3200 taken along line 8h-8h. This view also shows features similar to those depicted in FIG. 8g. In this view each protruding end 3114 can be seen with a respective nasal undercushion support wall 3208 positioned thereunder.

FIG. 8i shows another cross-sectional view of the exemplary seal-forming structure 3100 and plenum chamber 3200 taken along line 8i-8i. This view also shows features similar to those depicted in FIG. 8h.

FIG. 8j shows another cross-sectional view of the exemplary seal-forming structure 3100 and plenum chamber 3200 taken along line 8j-8j. This view also shows features similar to those depicted in FIG. 8f.

FIG. 8k shows another cross-sectional view of the exemplary seal-forming structure 3100 and plenum chamber 3200 taken along line 8k-8k. This view also shows features similar to those depicted in FIG. 8d. FIG. 8k also shows particularly well that in this depicted example of the technology that the connection region 3106.2 may have a concave shape to fit against the upper lip of the patient.

FIG. 8l shows another cross-sectional view of the exemplary seal-forming structure 3100 and plenum chamber 3200 taken along line 8l-8l. This view also shows features similar to those depicted in FIG. 8d.

FIG. 9a shows another front view of the exemplary seal-forming structure 3100 and plenum chamber 3200. This view also shows a number of cross-section lines to indicate the cross-sections depicted in subsequent drawings, FIGS. 9b-9i. This view is similar to FIG. 7e and similar components are therefore depicted. However, to avoid confusion, reference numerals and lead lines have been excluded.

FIG. 9b shows a cross-sectional view of the exemplary seal-forming structure 3100 and plenum chamber 3200 taken along line 9b-9b. FIG. 9b also depicts similar features to those shown in FIGS. 8b-d.

FIG. 9c shows a cross-sectional view of the exemplary seal-forming structure 3100 and plenum chamber 3200 taken along line 9c-9c. This view shows particularly well a cross-section of the nasal undercushion support wall 3208 that may be included to support the protruding end 3114 of the nasal cushion 3112.

FIG. 9d shows a cross-sectional view of the exemplary seal-forming structure 3100 and plenum chamber 3200 taken along line 9d-9d. The cross-sectional view shown here is taken at an angle such that no portion of the nasal cushion 3112 is shown. This view also depicts particularly well the oral undercushion 3120 of the oral cushion 3110. In the example shown in this view, the tapered end 3122 of the oral undercushion 3120 can be seen as well.

FIG. 9e shows a cross-sectional view of the exemplary seal-forming structure 3100 and plenum chamber 3200 taken along line 9e-9e. FIG. 9e is taken along a similar cross-section to FIG. 9d and, therefore, depicts similar features.

FIG. 9f shows a cross-sectional view of the exemplary seal-forming structure 3100 and plenum chamber 3200 taken along line 9f-9f. This view depicts particularly well the oral cushion 3110 and the oral undercushion 3120 and how these two cushions 3110, 3120 may share a similar profile to seal against the face of the patient.

FIG. 9g shows a cross-sectional view of the exemplary seal-forming structure 3100 and plenum chamber 3200 taken along line 9g-9g. FIG. 9g is taken along a similar cross-section to FIG. 9f and, therefore, depicts similar features.

FIG. 9h shows a cross-sectional view of the exemplary seal-forming structure 3100 and plenum chamber 3200 taken along line 9h-9h. FIG. 9h depicts features similar to those shown in FIG. 9c, including the cross-section of the nasal undercushion support wall 3208.

FIG. 9i shows a cross-sectional view of the exemplary seal-forming structure 3100 and plenum chamber 3200 taken along line 9i-9i. FIG. 9i depicts features similar to those shown in FIG. 9b.

FIGS. 16a to 16o show several views of another seal-forming structure 3100 and plenum chamber 3200, according to an example of the present technology.

The seal-forming structure 3100 and the plenum chamber 3200 according to this example includes pockets 3208.1 on either side of the nasal cushion 3112 near the side portions 3106.3 and under the protruding ends 3114. FIGS. 16a, 16d, 16i, 16k, and 16m-o depict examples of the pockets 3208.1. The pockets 3208.1 may be defined, at least in part, by the decoupling structure 3106, the undercushion support walls 3208, the side portions 3106.3, the nasal plenum chamber 3202, and the side supports 3207. The pockets 3208.1 may be open in an anterior direction of the seal-forming structure 3100 and the plenum chamber 3200. The pockets 3208.1 may also provide resistance to deformation of the nasal cushion 3112 in every direction. The pockets 3208.1 may provide compression resistance for the nasal cushion 3112. This compression resistance may help to reduce leak at the corners of nose area where the pockets 3208.1 may support the nasal cushion 3112 and/or the protruding ends 3114 when the nasal cushion 3112 is in contact the patient's nose. According to an example of the present technology, it may be advantageous for the nasal cushion 3112 to deform at regions other than at the protruding ends 3114 that may be supported by the pockets 3208.1. The pockets 3208.1 and the decoupling structure 3106 may help to resist deformation of the nasal cushion 3112 or may help to allow deformation to occur in targeted areas.

The side supports 3207 shown in the examples depicted by FIGS. 16a to 16o may be integrally formed with the seal-forming structure 3100 and the plenum chamber 3200. Thus, in the example where the seal-forming structure 3100 and the plenum chamber 3200 are formed from silicone, the side supports 3207 would likewise be formed of silicone. The side supports 3207 may serve a stiffening purpose to improve the seal between the seal-forming structure and the patient's face. For example, the side supports 3207 may help to support the nasal cushion 3112, at its sides, against the patient's alae and/or the side supports may help to support the protruding ends 3114 against the region of the patient's face where the alae join near the nasolabial sulci. The side supports 3207 may also control deformation of the nasal cushion 3112, so that certain areas of the nasal cushion deform before others. The side supports 3207 may also control the extent of deformation in certain areas of the nasal cushion 3112. The side supports 3207 may facilitate controlled deformation of the nasal cushion 3112 because the side supports 3207 may allow bending when compressed due to contact with the patient's face. The side supports 3207 may also strengthen the sides of the nasal cushion 3112 to decouple a compression force of the face against the nasal cushion 3112 to prevent the nasal cushion 3112 from collapsing into the decoupling structure 3106.

The side supports 3207 may each include a notch 3209. The notches 3209 of the side supports 3207 may provide a pivot point between the nasal cushion 3112 and the oral cushion 3110. The pockets 3208.1 may also serve to control the location of the pivot point.

The side supports 3207 may also provide attachment points for the top plate 3206. The top plate 3206 may be integrally and/or chemically bonded with the seal-forming structure 3100 and the plenum chamber 3200. In an example, the silicone of the seal-forming structure 3100 and the plenum chamber 3200 may be formed and/or molded around the top plate 3206. No mechanical interlock may be necessary, according to an example of the present technology, between the top plate 3206 and the seal-forming structure 3100 and the plenum chamber 3200. Alternatively, there may be no chemical and/or integral bond, such that a mechanical interlock between the top plate 3206 and the seal-forming structure 3100 and the plenum chamber 3200 would be necessary. The top plate 3206 may also define, at least in part, the pivot point between the nasal cushion 3112 and the oral cushion 3110.

It may also be desirable to strengthen or stiffen the nasal cushion 3112 to provide localized support so as to reduce or control deformation in particular regions of the nasal cushion relative other regions. Examples of stiffening may include increasing the relative thickness of the nasal cushion 3112 that are desired to be strengthened. Alternatively, reinforcement ribs or other reinforcement structures may be formed on the nasal cushion 3112 to provide the desired level and position of localized support.

FIGS. 16i, 16k-m, and 16o show that the nasal cushion 3112 may also include thickened nasal cushion sections 3124 at the sides. The thickened nasal cushion sections 3124 may be thickened portions of the nasal cushion 3112 that extend in an internal direction of the nasal cushion and generally into the nasal gas chamber 3104. These thickened nasal cushion sections 3124 may provide additional support for the nasal cushion 3112 when it is in sealing engagement with the nose and the face of the patient. The thickened nasal cushion sections 3124 may be located on opposite sides of the nasal cushion 3112 in a position such that they are proximal to the patient's nasolabial sulcus when the seal-forming structure engages the patient's face. The thickened nasal cushion sections 3124 may also help to seal around the alae of the patient's nose by preventing collapse of the nasal cushion 3112 due to sealing forces. The thickened nasal cushion sections 3124 may be formed integrally with the nasal cushion 3112. Also, the thickened nasal cushion sections 3124 may be located on the nasal cushion 3112 such that when the seal-forming structure engages the patient's nose and face the thickened nasal cushion sections 3124 may be, at least partially, urged against respective undercushion support walls 3208. The thickened nasal cushion sections 3124 may have a constant thickness throughout that is greater than the thickness of the remainder of the nasal cushion 3112. Alternatively, the thickened nasal cushion sections 3124 may have a thickness that is variable across its area.

In alternative examples of the present technology, the thickened nasal cushion sections 3124 not be provided and other structures may be provided to increase stiffness in these regions. For examples, ribs or other reinforcing structures may be provided to the nasal cushion 3112 in the regions where the thickened nasal cushion sections 3124 are shown to accomplish the function of stiffening the nasal cushion 3112 in these areas.

FIG. 16k also shows an example of the present technology where the oral plenum chamber 3200 includes thickened oral plenum chamber sections 3212. These thickened oral plenum chamber sections 3212 may provide additional support for the oral plenum chamber 3200 to help resist collapsing of the oral plenum chamber.

Also, FIGS. 16j and 16k show cross-sectional views through the seal-forming structure 3100 and the plenum chamber 3200. These views show that the connection region 3106.2 may be thicker in the examples depicted in these views relative to the connection region shown in FIGS. 8a to 8l and 9a to 9l. The thickness of the connection region 3106.2 shown in FIGS. 16j and 16k may also be consistent along its width and height. Tube torque from the air circuit 4170 may cause the oral cushion 3110 to pull on the nasal cushion 3112 via decoupling structure 3106 and extend the connection region 3106.2 in a generally vertical direction. Extension of the connection region 3106.2 may cause disruption of the seal of the nasal cushion 3112. By thickening the connection 3106.2 and making the thickness consistent throughout, this extension of the connection region 3106.2 may be resisted and disruption of the seal at the nasal cushion 3112 may be prevented and/or reduced.

FIGS. 16b, 16c, 16e, 16f, 16j, and 16o show views of the nasal cushion 3112 that include a nasal sling 3119 that divides the opening 3103 to the nasal gas chamber 3104 into nare ports 3105. The nasal sling 3119 may seal along the columella of the patient's nose (see FIG. 20 so that each nare may be sealed individually. Alternatively, the nasal sling 3119 may provide columella relief by contacting the patient's columella without forming a seal. Also, the nasal sling 3119 may prevent the tip of the patient's nose from extending through the nasal cushion 3112 and into the nasal gas chamber 3104. The nasal sling 3119 may also provide support for the nasal cushion 3112 to prevent deformation of the nasal cushion 3112 in the direction of the longitudinal axis of the nasal sling 3119.

The seal-forming structure 3100 may include a compliant region. The compliant region is not shown in these examples. Description and depiction of further examples of the compliant region is provided in PCT Application No. PCT/AU2014/000026. The compliant region may be relatively soft, flexible, and/or compliant relative to other portions of the seal-forming structure 3100. The compliant region's relative flexibility may be advantageous in that it may help to relieve discomfort to the patient in the regions of the tip of the nose and the septum. The compliant region may be relatively thin as compared to other portions of the seal-forming structure 3100 and, as such, may function like a mechanical spring to maintain an effective seal at the tip of the nose by wrapping against and/or contacting the tip of the nose. The compliant region may be located on the seal-forming structure 3100 at the upper apex where the seal-forming structure 3100 transitions to the plenum chambers 3200, 3202. The compliant region may be located on the seal-forming structure 3100 above the recessed portion 3116. The compliant region may also blend into the recessed portion 3116. The compliant region may also be located substantially centrally on the seal-forming structure 3100 in horizontal direction. The seal-forming structure 3100 may have a thickness at the compliant region that is about 0.35 mm according to an example of the present technology and may be one of the thinnest regions of the seal-forming structure 3100.

5.3.1.1 Exemplary Nasal Cushions

FIGS. 4a-c, 5a-c, and 6a-c depict various examples of the nasal cushion 3112 in accordance with the present technology.

FIG. 4a shows a top view of an exemplary nasal cushion 3112. The protruding ends 3114 can be seen at either side of the nasal cushion 3112. The nasal gas chamber 3104 and the opening 3103 thereto can also be seen. The opening 3103 to the nasal gas chamber 3104 may generally have a rectangular, lozenge or trapezoidal shape that may be curved at its respective minor and major sides 3104.2. When placed against the nose of the patient the curved minor sides 3104.2 of the nasal opening 3103 will be proximal to the respective alae of the nose. Also in this example, one of a pair of major sides, specifically a distal side 3104.1 of the nasal opening 3103, will be distal to the upper lip of the patient and near the tip of the nose, while another of the pair of major sides, a proximal side 3104.3, will be proximal to the upper lip of the patient. The recessed portion 3116 that is shaped to receive the tip of the nose is also shown.

FIG. 4b shows a bottom view of the exemplary nasal cushion 3112 sectioned along line 4c-4c of FIG. 4a. This view also shows the nasal gas chamber 3104 and its associated opening 3103.

FIG. 4c shows a side perspective view of the exemplary nasal cushion 3112 sectioned along line 4c-4c of FIG. 4a. This view again shows the nasal gas chamber 3104 and the opening 3103 thereto. The recessed portion 3116 is also indicated. Of particular note in this view is the profile of the nasal cushion 3112 along the section line 4c-4c. The nasal cushion 3112 can be seen to curve slightly upward as it approaches the distal side 3104.1 of the opening 3103 to the nasal gas chamber 3104 from the recessed portion 3116. Also, it can be seen in this view, as well as FIG. 4b, that the anterior upper portion of the nasal cushion 3112 that is near the recessed portion 3116 includes a slight dip or concave region at its center where line 4c-4c passes, such that the nasal cushion 3112 is higher at its sides than in the middle. This view also shows the outline of a nose in dashed lines to indicate how the nose of the patient may be located relative to the nasal cushion 3112. The peak 3118 in the cushion 3112 may be tasked with sealing the anterior of the nares. The peak 3118 sits further toward the posterior but transitions more gradually for creating the balloon effect. The distal side 3104.1 may flick up from the cushion 3112 and may improve the seal at the nose tip because it makes contact with the nose sooner and causes both a compressive and pneumatic seal by cradling the nose. The recessed portion 3116 that is shaped to receive the tip of the nose is also shown.

FIG. 5a shows a top view of an exemplary nasal cushion 3112. The protruding ends 3114 can be seen at either side of the nasal cushion 3112. The nasal gas chamber 3104 and the opening 3103 thereto can also be seen. The shape of the opening 3103 to the nasal gas chamber 3104 may also be similar to that which is shown in FIG. 4a. The recessed portion 3116 that is shaped to receive the tip of the nose is also shown.

FIG. 5b shows a bottom view of the exemplary nasal cushion 3112 sectioned along line 5c-5c of FIG. 5a. This view also shows the nasal gas chamber 3104 and its associated nasal opening 3103.

FIG. 5c shows a side perspective view of the exemplary nasal cushion 3112 sectioned along line 5c-5c of FIG. 5a. This view again shows the nasal gas chamber 3104 and the opening 3103 thereto. The recessed portion 3116 is also indicated. Of particular note in this view is the profile of the nasal cushion 3112 along the section line 5c-5c. As contrasted with the profile of the nasal cushion 3112 in FIG. 4c, it can be seen in this view that the nasal cushion is sloped downwardly as it approaches the distal side 3104.1 opening 3103 to the nasal gas chamber 3104 from the recessed portion 3116. It can also be seen that this example of the nasal cushion 3112 lacks the dip in the anterior region near the recessed portion 3116 that can be seen in the example shown in FIGS. 4b and 4c. In other words, this example shows that the nasal cushion 3112 may be more circular/rounder, relative to the example shown in FIG. 4c in the region from the recessed portion 3116 to the distal side 3104.1 of the opening 3103 to the nasal gas chamber 3104. This view also shows the outline of a nose in dashed lines to indicate how the nose of the patient may be located relative to the nasal cushion 3112.

FIG. 6a shows a top view of an exemplary nasal cushion 3112. The protruding ends 3114 can be seen at either side of the nasal cushion 3112. The nasal gas chamber 3104 and the opening 3103 thereto can also be seen. The shape of the opening 3103 to the nasal gas chamber 3104 may also be similar to that which is shown in FIG. 4a. In FIGS. 4a to 4c, the shape is more balloon like and rounder than the example shown in FIGS. 6a to 6c.

FIG. 6b shows a bottom view of the exemplary nasal cushion 3112 sectioned along line 6c-6c of FIG. 6a. This view also shows the nasal gas chamber 3104 and its associated opening 3103. Additionally, it can be seen in this view that the nasal cushion 3112 has straight sidewalls 3121, in contrast with the sidewalls that curve smoothly from the upper surface of the nasal cushions 3112 shown in FIGS. 4a-c and 5a-c. The straight sidewalls 3121 may have a defined top edge and assumed to increase stability and strength of the nasal cushions 3112.

FIG. 6c shows a side perspective view of the exemplary nasal cushion 3112 sectioned along line 6c-6c of FIG. 6a. This view again shows the nasal gas chamber 3104 and the opening 3103 thereto. The recessed portion 3116 is also indicated. Of particular note in this view is the profile of the nasal cushion 3112 along the section line 6c-6c. It can be seen, as in FIG. 5c that this example of the nasal cushion 3112 lacks the dip in the anterior region near the recessed portion that can be seen in the example shown in FIGS. 4b and 4c. The straight sidewalls 3121 of this exemplary nasal cushion 3112 can also be seen in this view. This view also shows the outline of a nose in dashed lines to indicate how the nose of the patient may be located relative to the nasal cushion 3112.

Furthermore, it should also be understood that the exemplary nasal cushions 3112 depicted in FIGS. 4a-4c, 5a-5c, and 6a-6c are shown in substantially undeformed states. FIGS. 4c, 5c, and 6c may indicate a small amount of deformation due to conformation with the shape of the nose shown in dashed lines. Thus, the nasal cushions 3112 may have the concave shape as shown, when not deformed.

It should also be understood that the nasal cushion 3112 may have a cross-section of variable thickness. Thus, the region of the nasal cushion 3112 proximate to the opening 3103 to the nasal gas chamber 3104 may be thinner than the region where the nasal cushion 3112 attaches to the nasal plenum chamber 3202. Advantageously, this may afford more comfort for the patient by providing a thinner and, thus, more compliant region of cushion material at the area where a large amount of contact is made with the patient's nose.

FIGS. 10a-d show further additional nasal cushions 3112 according to further examples of the present technology. These views depict further variations of the possible shape of the opening 3103 to the nasal gas chamber 3104.

FIGS. 11a-c depict various cross-sectional profiles of the nasal cushion 3112 according to examples of the present technology. The region 3112.1 may be proximal to the opening 3103 to the nasal gas chamber 3104 and the region 3112.3 may be proximal to the connection to the nasal plenum chamber 3202. The region 3112.2 may be the most elevated region around the upper periphery of the nasal cushion 3112.

FIG. 11a shows a cross-section of a nasal cushion 3112 taken across line 11a-11a of FIG. 4a. This cross-section shows a smoothly variable thickness for the nasal cushion 3112 from region 3112.1 to region 3112.3. Also, the thickness x may be less than the thickness z.

FIG. 11b shows a cross-section of a nasal cushion 3112 taken across line 11b, c-11b, c of FIG. 13. This cross-section shows that the region 3112.2 may abruptly become thicker than the regions 3112.1 and 3112.3. Also, the thickness x may be less than the thickness z and the thickness y may be greater than x and z.

FIG. 11c shows a cross-section of a nasal cushion 3112 taken across line 11b, c-11b, c of FIG. 13. Region 3112.2 may be stiffened relative to the other regions 3112.1 and 3112.3. This cross-section shows that the region 3112.2 may abruptly become thicker than the regions 3112.1 and 3112.3. Also, the thickness z may be less than the thickness x and the thickness y may be greater than x and z.

FIG. 13 shows a top view of another exemplary nasal cushion 3112 according to the present technology. The opening 3103 to the nasal gas chamber 3104 and the protruding end 3114 are indicated to allow for understanding of the orientation of the nasal cushion 3112. Regions of various thicknesses are hatched differently to better indicate where the stiffness and/or thickness of the nasal cushion 3112 may vary. Region 3113 may be the thinnest to allow for ready conformation to the tip of the nose. Region 3113, according to an example of the present technology, may have a thickness of about 0.35 mm Region 3115 may be thicker to provide more support for the nasal cushion 3112. Region 3115, according to an example of the present technology, may have a thickness of about 0.5 mm Region 3117 may be thicker than the other regions to provide maximum support, resistance to deformation, and ensure an effective seal at the ala of the patient. Region 3117, according to an example of the present technology, may have a thickness of about 1 mm 5.3.2 Decoupling Structure The decoupling structure 3106 shown in FIG. 3c may provide a connection between the nasal cushion 3112 and the oral cushion 3110. The decoupling structure 3106 may also define a pneumatic connection between the oral gas chamber 3102 and the nasal gas chamber 3104. Thus, during therapy when the patient is provided with breathable gas at positive pressure the gas may enter the patient interface via the port 3600 and flow directly into the oral gas chamber 3102 defined at least in part by the plenum chamber 3200, the faceplate 3204, the oral cushion 3110, and the decoupling structure 3106. The gas may then flow to the mouth of the patient. The breathable gas may also be provided to the nose of the patient via the nasal gas chamber opening 3103 and through the nasal gas chamber 3104 that is defined at least partly by the nasal cushion 3112, the nasal plenum chamber 3202 and the decoupling structure 3106. To reach the nasal gas chamber 3104, the gas must flow from the oral gas chamber 3102 and through the pneumatic pathway defined by the decoupling structure 3106 and then into the nasal gas chamber 3104. It should be understood, however, that a port may be provided to the top plate 3206 or the nasal cushion 3112 to receive breathable gas. In that case, the flow pattern through the patient interface 3000 may simply be reversed.

As to the decoupling structure 3106 depicted in FIG. 3c, this feature may also allow for the nasal cushion 3112 and the oral cushion 3110 to move independently of one another when donned by the patient. When worn by the patient with a positioning and stabilising structure 3300 (e.g., headgear), as will be described in greater detail below, the nasal cushion 3112 may be urged against the face of the patient, particularly the nose, by forces transferred along the rigidiser arms 3302 to the nasal cushion 3112 via the top plate 3206. Also, the oral cushion 3110 may be urged against the face of the patient, particularly the mouth, by forces transferred to the faceplate 3204 from headgear straps 3306. Because different sets of headgear straps 3306 may urge different portions of the patient interface 3000 (e.g., the nasal cushion 3112 and the oral cushion 3110) against different portions of the patient's face (e.g., the nose and the mouth, respectively) it may be advantageous to allow the nasal cushion 3112 and the oral cushion 3110 to move independently of one another because of the decoupling structure 3106.

The decoupling structure 3106 may be used to connect the oral cushion 3110 and the nasal cushion 3112 to facilitate this independent movement. Allowing independent movement of the cushions 3110, 3112 may allow for better sealing against a wider variety of patient facial shapes and it may also aid in maintaining a seal against the patient's face in spite of movement in different regions of the face, movement of the air circuit 4170 or external forces. Moreover, due to the fact that the patient interface 3000 may seal against two separate regions of the face, the nose and the mouth, two separate openings must be provided to supply the breathable gas to the patient. By allowing the sealing structures (e.g., the oral cushion 3110 and the nasal cushion 3112) to move independently a seal may be maintained around the nose independently of the seal around the mouth to prevent undesired leakage and, therefore, pressure loss through one or both openings.

The decoupling structure 3106 may also form part of a wall of the oral plenum chamber 3200 and the nasal plenum chamber 3202 in an anterior direction. The decoupling structure 3106 may also be resiliently flexible to allow for relative movement and/or length extension between the structures that define the oral gas chamber 3102 and the nasal gas chamber 3104. Thus, the oral plenum chamber 3200 and the nasal plenum chamber 3202 may be extended away from one another or compressed together, while a pneumatic connection is maintained between the oral gas chamber 3102 and the nasal gas chamber 3104. Moreover, the decoupling structure 3106 may also allow these structures (e.g., the oral plenum chamber 3200 and the nasal plenum chamber 3202) to be tilted relative to one another, while a pneumatic connection is maintained between the oral gas chamber 3102 and the nasal gas chamber 3104 and a seal is maintained with the patient's face.

The decoupling structure 3106 may also comprise an upper surface 3106.4, a connecting surface 3106.5, and a lower surface 3106.6. The connecting surface 3106.5 may be relatively stiffer than the upper surface 3106.4 and the lower surface 3106.6. The lower surface 3106.6 may be understood to be a separate surface from the oral cushion 3110. The upper surface 3106.4 may be understood to be a separate surface from the nasal cushion 3112. The greater stiffness of the connecting surface 3106.5 may be produced by reinforcement ribs or other reinforcement structures or by making the connecting surface 3106.5 thicker than the upper surface 3106.4 and the lower surface 3106.6. According to one example, the upper surface 3106.4 and the lower surface 3106.6 may each have a thickness of 0.5 mm and the connecting surface 3106.5 may have a thickness of 1.2 mm According to further examples of the present technology, the specific numerical value of the thicknesses may be varied while maintaining the same ratio of thickness as between the upper surface 3106.4, the connecting surface 3106.5, and the lower surface 3106.6.

According to a further example of the present technology, the relative thicknesses of the upper surface 3106.4, the connecting surface 3106.5, and the lower surface 3106.6 may be chosen to allow for a desired amount of flexibility of the decoupling structure 3106. In examples, the decoupling structure 3106 may be able to flex such that the upper surface 3106.4 and the lower surface 3106.6 are positioned at up to about 45° to about 50° relative to each other.

Also, according to further examples of the present technology, the angle between the upper surface 3106.4 and the connecting surface 3106.5 may be between about 80° and about 140°. According to a still further example of the present technology, the angle between the upper surface 3106.4 and the connecting surface 3106.5 may be about 90°. It should be understood that the angle between the upper surface 3106.4 and the connecting surface 3106.5 may vary across the length of the decoupling structure 3106 due to its curved shape. If the angle between the upper surface 3106.4 and the connecting surface 3106.5 is greater than 90° in a given example, then it may be easier to stretch or separate the nasal structures and the oral structures from one another. If the angle between the upper surface 3106.4 and the connecting surface 3106.5 is less than 90° in a given example, then it may be easier to compress the nasal structures and the oral structures toward one another.

According to further examples of the present technology, the angle between the lower surface 3106.6 and the connecting surface 3106.5 may be between about 80° and about 140°. According to a still further example of the present technology, the angle between the lower surface 3106.6 and the connecting surface 3106.5 may be about 90°. If the angle between the lower surface 3106.6 and the connecting surface 3106.5 is greater than 90° in a given example, then it may be easier to stretch or separate the nasal structures and the oral structures from one another. If the angle between the lower surface 3106.6 and the connecting surface 3106.5 is less than 90° in a given example, then it may be easier to compress the nasal structures and the oral structures toward one another.

Another advantageous feature of this exemplary patient interface 3000 may also be seen in FIG. 3m. This feature is the ability of the nasal cushion 3112 and the oral cushion 3110 to each independently form a seal about respective anatomical features of the patient. As already discussed, the nasal cushion 3112 is intended to seal about the nose of the patient and the oral cushion 3110 is intended to seal about the mouth of the patient. The decoupling structure 3106, shown in FIG. 3c for example, may allow the nasal cushion 3112 and the oral cushion 3110 to move independently and seal independently of one another. By attaching the pair of upper straps 3310 to the nasal cushion 3112 via the top plate 3206, the nasal cushion 3112 may be urged against the nose of the patient 1000 when the patient interface 3000 is donned. Also, the pair of lower straps 3312, by their connection to the faceplate 3204, may urge the oral cushion 3110 around the mouth of the patient.

It should be understood that each respective pair of straps, upper 3310 and lower 3312, represent a separate pair of vectors along which tension forces that are directed to retain respective portions of the patient interface 3000 against the face of the patient. In other words, the upper straps 3310 serve to retain the nasal cushion 3112 against the nose and the lower straps 3312 serve to retain the oral cushion 3110 against the mouth. The decoupling structure 3106 allows for a pneumatic connection between the two cushions 3110, 3112 although these cushions may be moved independently of one another. Thus, a variety of different patient head and face shapes may be accommodated by the patient interface 3000. Also, it should be understood that the ability to form separate seals independently may allow the patient interface 3000 to maintain these seals in spite of movement by the patient.

FIG. 7h shows a side view of the exemplary seal-forming structure 3100 and plenum chamber 3200. This view shows the nasal cushion 3112 attached to the nasal plenum chamber 3202, as well as the protruding end 3114 that is supported by the nasal undercushion support wall 3208 that is proximal to the side portion 3106.3 of the decoupling structure 3106. The oral plenum chamber 3200 is shown with the oral cushion 3110 disposed about its perimeter 3210. Also in this view the decoupling structure 3106 can be seen connecting the oral cushion 3110 to the nasal cushion 3112. This view shows particularly well the hinge-like arrangement the nasal plenum chamber 3202 and the nasal cushion 3112 may take with respect to the oral plenum chamber 3200 and the oral cushion 3110 by virtue of the connection via the decoupling structure 3106 and the connection region 3106.2 (not shown in this view). It should be understood that this hinge-like arrangement may allow the nasal plenum chamber 3202 and nasal cushion 3112 to tilt depending on the forces applied by the face of the patient when the complete patient interface 3000 is placed on the patient. Thus, the oral plenum chamber 3200 and the nasal plenum chamber 3202 may approach one another in the gap 3106.1

By providing a gap 3106.1 between respective anterior portions of the oral plenum chamber 3200 and the nasal plenum chamber 3202, as shown in this view, it may be possible to allow the components of the oral plenum chamber 3200 and the nasal plenum chamber 3202 to move independently of one another with some amount of freedom before coming into contact with one another. It should also be understood that the ability of the nasal cushion 3112 and the oral cushion 3110 to move independently of one another while maintaining an effective seal may be furthered by providing the decoupling structure 3106 with a radially variable thickness or varied stiffness. Thus, the decoupling structure 3106 may be thinnest, or least stiff, at the portion that contacts the upper lip of the patient and its thickness/stiffness may increase radially to the anterior portion of the decoupling structure 3106. By this arrangement an effective seal against the upper lip may be maintained while also providing sufficient support and structure to the cushions 3110, 3112. The decoupling structure 3106 may be thicker at its vertex at the closed end of the gap 3106.1 compared to regions proximal to the open end of the gap 3106.1. This variation may prevent distortion and to improve hinging because the thicker portion of the decoupling structure 3106 at the closed end of the gap 3106.1 may serve as a pivot point.

FIG. 14 shows another example of the present technology in a partially exploded side view. This example may include the oral and nasal cushions 3110, 3112 and the oral and nasal plenum chambers 3200, 3202 connected by the decoupling structure 3106 in similar fashion to other examples disclosed herein. The upper portion or top plate 3206 and the lower portion or faceplate 3204 can be seen disconnected from the nasal plenum chamber 3202 and the oral plenum chamber 3200, respectively. Also, the attachment feature 3252 can be seen connected to the connection feature 3304 of the rigidiser arm 3302, which has been partially cut off for clarity. This view also shows a middle or connection portion 3205 that may connect the top plate 3206 and the faceplate 3204 to form a unitary plate member. The connection portion 3205 may be shaped and dimensioned to substantially follow the shape of the decoupling structure 3106 such that when the unitary member of the top plate 3206, faceplate 3204, and connection portion 3205 are attached to the nasal plenum chamber 3202 and the oral plenum chamber 3200 the connection portion 3205 may be substantially flush with the decoupling structure 3106. To allow the oral and nasal plenum chambers 3200, 3202 to move relative to one another as described elsewhere herein, it may be advantageous to form the connection portion 3205 from silicone or any other suitable material that is soft, flexible, air impermeable, and biocompatible.

In another example of the present technology, a portion of the decoupling structure 3106 proximal to the gap 3106.1 may be eliminated such that only the undercushion support walls 3208 and/or the connection region 3106.2 connect the oral and nasal plenum chambers 3200, 3202 and the oral and nasal cushions 3110, 3112. In such an example, the connection portion 3205 may also perform a sealing function to provide a pneumatically sealed connection between the oral gas chamber 3102 and the nasal gas chamber 3104. In other words, the connection portion 3205 may effectively replace the eliminated portion of the decoupling structure 3106 when the unitary member of the top plate 3206, connection portion 3205, and faceplate 3204 are attached to the oral and nasal plenum chambers 3200, 3202. Again, in this example it may be desirable to form the connection portion 3205 from silicone or any other like material.

5.3.3 Top Plate and Faceplate Connection Features, Rigidiser Arms, and Positioning and Stabilising Structure On a anterior side of the nasal cushion 3112, which would be opposite the face of the patient in use, a rigid top plate 3206 may be attached to a nasal plenum chamber 3202. The top plate 3206 may be made from a rigid material such as EMS-Grivory Grilamid® TR 90. The top plate 3206 may include at least one upper attachment feature 3252. In one example, a pair of upper attachment features 3252 may be disposed at either side of the top plate 3206 to releasably and rotatably connect respective rigidiser arms 3302 of the positioning and stabilising structure 3300. UBE America Inc.'s Ubesta® nylon, Hytrel® from DuPont™, TPE and polypropylene and other flexible polymers and materials are possible materials for the rigidiser arms 3302. Other materials may also be used for the rigidiser arms 3302 that are substantially inextensible, while allowing the rigidiser arms 3302 to flex. The rigidiser arms 3302 may be flexible in a direction parallel to the patient's coronal plane (see FIG. 2e), while not being significantly flexible in other directions. The connection of the rigidiser arms 3302 may be a hinge such that the connection features 3304 of the rigidiser arms may rotate about the attachment features 3252 of the top plate 3206. In one example of the technology, the rigidiser arms 3302 may be rotatable about the hinged upper attachment features 3252 up to about 90°. In examples, the rigidiser arms 3302 may be rotatable about the hinged upper attachment features 3252 over 180°. Rotation may also be provided by a ball and socket connection, living hinge, freed style gimble or overmolded with silicone, TPE or TPU. At respective opposite ends of the rigidiser arms 3302, there may be an opening 3308 to receive respective headgear straps 3306 of the positioning and stabilising structure 3300 to be discussed in greater detail below. Between each end of the rigidiser arm 3302 there may also be a curved portion that is shaped to substantially follow the curvature of the face of the patient.

FIGS. 3s-u show further examples of the patient interface 3000 with the rigidiser arms 3302 exploded to depict an exemplary hinge-like connection between respective attachment features 3252 and connection features 3304. As discussed above, it should be understood that the rigidiser arms 3302 may be rotatable in a plane parallel to the patient's coronal plane and up to about 90° or, in another example, over 180°.

On an opposite side of the oral cushion 3110, a faceplate or lower plate 3204 may be attached to the oral plenum chamber 3200. The means of attachment may include being overmolded, push fit with soft material to hard material, or a cushion clip to rely on the hoop stress of silicone. The faceplate 3204 may include a port 3600 that facilitates connection to a air circuit 4170 (not pictured in this view). Also, the faceplate 3204 may include at least one lower attachment feature 3250 to attach respective headgear straps of the positioning and stabilising structure 3300 to be discussed in greater detail below. The lower attachment features 3250 shown in this example may be female clip receiving structures to receive male clips attached to headgear straps 3306. Alternatively, the configuration may include male structures to receive female clips.

The exemplary patient interface 3000, shown in a front view in FIG. 3b, includes the top plate 3206 connected to the nasal cushion 3112 and having at least one upper attachment feature 3252 at either side. A rigidiser arm 3302 is shown connected to respective upper attachment features 3252 via connection features 3304. Also in this view, the faceplate 3204 can be seen connected to the anterior side of the oral plenum chamber 3200. The port 3600 shown on the faceplate 3204 is circular to pneumatically connect to a air circuit 4170 (e.g., via a tube decoupling structure 3500 discussed further below). Lower attachment features 3252 can also be seen on either side of the faceplate 3204. The decoupling structure 3106 is shown in this view and side portions 3106.3 of the decoupling structure can also be seen.

FIG. 3c shows a rear view of the exemplary patient interface 3000. In this view a pair of the rigidiser arms 3302 can be seen extending from and connected to respective upper attachment features 3252 at respective connection features 3304. An opening 3308 can be seen at each respective opposite end of the rigidiser arms 3302 for connecting to headgear straps 3306 of the positioning and stabilising structure 3300. The location of the decoupling structure 3106 is indicated in this view, along with the connection region 3106.2 of the oral cushion 3110 and the nasal cushion 3112.

FIG. 3d shows a top view of a patient interface 3000 in accordance with an example of the present technology. From this top view, the portion of the nasal cushion 3112 that contacts the nose of the patient can be seen, as well as the opening 3103 into the nasal gas chamber 3104. This top view also shows the connection features 3304 of the rigidiser arms 3302 connected to the upper attachment features 3252 on either side of the top plate 3206, which cannot be seen in this particular view. The oral plenum chamber 3200 can also be seen connected to the faceplate 3204 around the periphery 3210 of the plenum chamber. The lower attachment features 3250 are shown on either side of the faceplate 3204. The port 3600 can also be seen on the faceplate 3204.

FIG. 3e shows a bottom view of the exemplary patient interface 3000 in accordance with the present technology. This view shows the oral plenum chamber 3200 connected about its perimeter 3210 to the faceplate 3204. The faceplate 3204 can be seen with the lower attachment features 3250 extending therefrom. The port 3600 on the faceplate 3204 can also be seen. The oral cushion 3110 and the nasal cushion 3112 are shown in this view, along with the protruding ends 3114 of the nasal cushion 3112. The rigidiser arms 3302 are shown as well, however, the connection of the rigidiser arms 3302 to the top plate 3206 is not visible in FIG. 3e.

FIG. 3f shows a side view of the exemplary patient interface 3000 according to the present technology. A rigidiser arm 3302 can be seen extending from the connection feature 3304, which is attached to the upper attachment feature 3252 of the top plate 3206. Also, FIG. 3f depicts the plenum chamber 3200 connected at its perimeter 3210 to the faceplate 3204. On the faceplate 3204, the lower attachment feature 3250 can be seen, as well as the connection port 3600. The nasal cushion 3112 and the oral cushion 3110 can also be seen. This view also depicts the location of the decoupling structure 3106 and one of its side portions 3106.3. The gap 3106.1 between the nasal plenum chamber 3202 and the oral plenum chamber 3200 that allows these components to flex or move toward one another while staying connected is also shown. The gap 3106.1 may be understood to be the distance between the oral plenum chamber 3200 and the nasal plenum chamber 3202 and, as such, the gap 3106.1 may define the distance that these structures are allowed to more toward one another. The gap 3106.1 may extend laterally between the oral plenum chamber 3200 and the nasal plenum chamber 3202 and the gap 3106.1 may face in an anterior direction.

FIG. 3m shows a further front perspective view of an exemplary patient interface 3000. This view depicts similar features to those shown in FIG. 3g and also shows the patient interface 3000 donned on a patient 1000. Headgear straps 3306 of the positioning and stabilising structure 3300 are shown releasably securing the patient interface 3000 to the patient 1000. The headgear straps 3306 are shown with at least one upper strap 3310 connected to a corresponding rigidiser arm 3302 at its corresponding opening 3308. In the depicted example, each upper strap 3310 loops through the corresponding opening 3308, which in this example is an opening in the rigidiser arm 3302. This example also shows at least one lower strap 3312 connected to the lower attachment feature 3250 by looping through a portion of a clip 3314 that is releasably attached to the corresponding lower attachment feature 3250.

FIG. 3n depicts another front view of an exemplary patient interface 3000 retained on a patient 1000. The patient interface 3000 in this view can be seen retained against the face of the patient 1000 by upper straps 3310 and lower straps 3312. The upper straps 3310 are attached to the rigidiser arms 3302 and the lower straps 3312 are attached to the lower attachment features 3250 by clips 3314. Again, it can be seen in this example that the nasal cushion 3112 seals against the nose of the patient 1000 and the oral cushion 3110 seals against the mouth of the patient 1000. The decoupling structure 3106 is shown in this view and side portions 3106.3 of the decoupling structure 3106 can also be seen.

FIG. 3o depicts another side view of the patient interface 3000. In this view the patient interface 3000 is retained against the face of the patient 1000 by the headgear straps 3306. The upper strap 3310 is connected to the rigidiser arm 3302 to urge the nasal cushion 3112 against the nose and the lower strap 3312 is connected to the faceplate 3204 to urge the oral cushion 3110 against the mouth of the patient 1000. In this view the lower strap 3312 can be seen extending below the ear of the patient 1000 and the upper strap 3310 can be seen extending above the ear and below the eye of the patient. As discussed above, the rigidiser arms 3302 may be made of a relatively stiff material such as nylon. As such, the rigidiser arms 3302 may cause irritation to the face of the patient if they rub against and/or directly contact the face of the patient 1000. Thus, FIG. 3o also depicts a sheath 3316 that may surround the rigidiser arm 3302 to cushion the rigidiser arm against the face of the patient 1000. This view also depicts the location of the decoupling structure 3106. The rigidiser arms 3302 may incorporate or be created with face pads 3305 instead of sheaths being added.

FIG. 3p shows another top view of an exemplary patient interface 3000. In this top view the patient interface 3000 can be seen retained against the face of the patient 1000 by the headgear straps 3306. The upper straps 3310 can be seen connected to respective openings 3308 of the rigidiser arms 3302 and the lower straps 3312 can be seen connected to the lower attachment features 3250 by the clips 3314.

In an example, the seal-forming structure 3100 of the patient interface 3000 of the present technology is held in sealing position in use by the positioning and stabilising structure 3300.

In one form of the present technology, the rigidiser arms 3302 discussed above may be comprised as a component of the positioning and stabilising structure 3300. Alternatively, the rigidiser arms 3302 may be comprised as a component of the patient interface 3000.

The positioning and stabilising structure 3300 may comprise headgear straps 3306. The headgear may include at least upper side straps 3310, lower side straps 3312, and a rear portion. Also, the headgear straps 3306 may comprise a one-piece composite of soft, flexible material. One layer of the headgear, e.g., an outer layer that does not contact the skin of the patient when donned, may connect to tabs of material fixed to respective ends of the upper and lower side straps 3310, 3312. This connection may include a hook-and-loop connection and the outer layer may comprise the loop material. This connection may allow the side straps 3310, 3312 to loop through attachment features of the patient interface 3000 to releasably and/or adjustably retain the patient interface to the patient's head via the headgear straps 3306. Other connections may include a ladder lock or sliders that are not hook-and-loop.

By including the rigidiser arms 3302 on the patient interface 3000 and attaching them to the nasal plenum chamber 3202 by the top plate 3206, it may be possible to advantageously locate the upper straps 3310 of the positioning and stabilising structure 3300. To effectively seal the nose of the patient, as described above, it may be desirable to urge the nasal cushion 3112 in a generally upward direction against the underside of the nose. The rigidiser arms 3302 may allow for the proper direction of the tension force vectors generated by the upper straps 3310 of the positioning and stabilising structure 3300 while decoupling these straps 3310 from the nasal plenum chamber 3202 such that the straps 3310 do not pass across the eyes of the patient. In other words, sufficiently stiff rigidiser arms 3302 will allow the upper straps 3310 of the positioning and stabilising structure 3300 to effectively pull the nasal cushion 3112 against the nose of the patient while locating the straps 3310 away from the patient's face so that the patient may be more comfortable, wear glasses, see more easily, etc.

FIGS. 15a-e depict various top plate 3206 and rigidiser arm 3302 connections to the seal-forming structure 3100 according to examples of the present technology.

FIG. 15a shows the seal-forming structure 3100 in stippling. The rigidiser arms 3302 and the top plate 3206 are one piece according to the depicted example. It can be seen that the attachment features 3252 and the connection features 3304 are not shown. Thus, the connection between the top plate 3206 and the rigidiser arms 3302 may be flexible to allow the rigidiser arms 3302 to deflect due to tension from a positioning and stabilising structure 3300. Additionally, according to this example, the top plate 3206 is permanently connected to the seal-forming structure 3100 in this example.

It should be understood that the top plate 3206 may be joined to the nasal plenum chamber 3202 and/or the faceplate 3204 may be joined to the oral plenum chamber 3200 by a permanent connection. A permanent connection may be facilitated by molding to form a mechanical interlock or the components may be joined by a chemical bond. A permanent connection may be understood to mean a connection where disconnecting the components is irreversible such that the components cannot be returned to their connected state. Disconnection of such a permanent connection may, for example, entail tearing, damaging, or breaking one or more of the components such that it cannot reconnected in an operative fashion.

Alternatively, the top plate 3206 may be joined to the nasal plenum chamber 3202 and/or the faceplate 3204 may be joined to the oral plenum chamber 3200 by a non-permanent connection. A non-permanent connection may comprise a connection where the components can be detached from one another and reattached in a manner that is reversible. In other words, the separation of the components does not necessitate, for example, tearing, damaging, or breaking one or more of the components such that it cannot reconnected in an operative fashion. In a non-permanent connection, when detached components are reattached, the device is returned to an operable state.

FIG. 15b shows a similar example to FIG. 15a. In this example the top plate 3206 may be connectable to the seal-forming structure 3100 by a hard to soft connection at a soft connection region 3130. In other words, the top plate 3206 and the rigidiser arms 3302 are removable.

FIG. 15c shows another variation of the example shown in FIG. 15a. In FIG. 15c, this example includes the attachment features 3252 on the top plate 3206 and the connection features 3304 on the rigidiser arms 3302. Thus, the top plate 3206 is permanently fixed to the seal-forming structure 3100 but the rigidiser arms 3302 may be rotatable and may be removed from the top plate 3206.

FIG. 15d shows an example similar to FIG. 15b. In this example there is a hard to hard connection of the top plate 3206 to a hard connection region 3132.

FIG. 15e shows an example that includes the hard to hard connection of the top plate 3206 to the hard connection region 3132. This example also includes the attachment features 3252 on the top plate 3206 and the connection features 3304 on the rigidiser arms 3302. Thus, the top plate 3206 is removable from the seal-forming structure 3100 but the rigidiser arms 3302 may be rotatable and may be removed or disconnected from the top plate 3206.

Another example of the present technology may include lower attachment features 3250 that are magnetic and provided to a living hinge, such as examples described in PCT Application No. PCT/AU2014/000021. The living hinge allows for movement of the lower attachment features 3250 in one plane (e.g., a plane parallel to the patient's transverse plane) and the direction of movement may be about an axis. Such an arrangement may provide for more control of the attachment of the positioning and stabilising structure 3300 to the lower attachment features 3250 and may provide for more stability for the seal of the oral cushion 3110 against the patient's face.

FIGS. 17a to 17f and 19a to 19h show the components of a rigidiser arm assembly 3301 according to another example of the present technology. The rigidiser arm assembly 3301 may be detachable from the top plate 3206. The connection features 3304 of these examples of the rigidiser arm assembly 3301 may comprise holes shaped to conform to respective ones of the upper attachment features 3252.

The rigidiser arm assembly 3301 may comprise two components. The rigidiser arms 3302 and a top plate cover 3303 may be formed in one piece, with the connection features 3304 and the openings 3308 being molded thereon as well. Nylon or Hytrel® may be used to form the rigidiser arms 3302 and the top plate cover 3303. A pad 3305 may be overmolded onto each rigidiser arm 3302 as well. The pads 3305 may be formed from a thermoplastic elastomer. The pads 3305 may cushion the patient's face (e.g., the cheeks) against the rigidiser arms 3302 and prevent marking of the patient's skin when the patient interface 3000 is worn for several hours (e.g., during therapy).

The rigidiser arms 3302 may also be formed with an ellipsoidal curvature, as can be seen in FIG. 19d, for example. Also, the rigidiser arms 3302 may be structured to be flexible only in a direction parallel to the patient's coronal plane (see FIG. 2e), e.g., inwardly and outwardly relative to the patient's face. In other words, the rigidiser arms 3302 may be flexible in substantially a single plane that is parallel to the patient's transverse plane. This may allow the rigidiser arms 3302 to accommodate various patient face widths. Moreover, the rigidiser arms 3302 may be resistant to stretching along their respective longitudinal axes. The rigidiser arms 3302 may also be resistant to twisting about their respective longitudinal axes. Additionally, the rigidiser arms 3302 may also be resistant to bending upwardly or downwardly, e.g., in the superior or inferior direction, relative to the patient's face. The rigidiser arms' 3302 resistance to deformation in these directions may be beneficial for stability of the patient interface 3000 when it is worn by the patient.

According to examples of the present technology, it may be advantageous to ensure that the rigidiser arm assembly 3301 is secured to the top plate 3206 so as to minimize relative movement between the top plate 3206 and the rigidiser arm assembly 3301 when engaged with one another. To ensure that relative movement between the top plate 3206 and the rigidiser arm assembly 3301 is adequately controlled, these components may be structured to engage one another at at least three points. The connection features 3304 may provide two of the points of contact and another structure positioned on the rigidiser arm assembly 3301 between the connection features 3304 may provide a third point of contact.

FIGS. 19d and 19e also show that the rigidiser arm assembly 3301 may include a rib 3307. When the rigidiser arm assembly 3301 is attached to the top plate 3206, the rib 3307 may help to reduce relative movement between the nasal cushion 3112 and the top plate 3206 when engaged with the rigidiser arm assembly 3301. The rib 3307 may have a cross-sectional profile that is triangular in shape to guide the rigidiser arm assembly 3301 into engagement with the top plate 3206. The rib 3307 may also help to reduce flexing and/or twisting between the rigidiser arm assembly 3301 and the top plate 3206 when they are engaged. Thus, the rib 3307 and the connection features 3304 may provide the three points of contact on the rigidiser arm assembly that engage with the top plate 3206.

According to further examples of the present technology, structures other than the rib 3307 may be provided for a third point of contact, in addition to the connection features. For example, the top plate 3206 and the rigidiser arm assembly 3301 may engage at a third point of contact with a rod inserted into a hole.

FIGS. 19f to 19h show another example of the rigidiser arm assembly 3301.

According to this example, a claw 3309 may provided on the posterior side of the rigidiser arm assembly 3301 near where the top plate cover 3303 meets each of the rigidiser arms 3302. The claw 3309 may engage with corresponding ones of the side supports 3207 to secure the rigidiser arm assembly 3301 to the nasal cushion 3112.

FIGS. 29a to 29f show views of another example of the present technology. These views show features that are similar to those shown in FIGS. 17a to 17f. However, the decoupling structure 3500 is not depicted in FIGS. 29a to 29f. It should be understood though that a decoupling structure 3500 as described elsewhere herein may be attached at the connection port 3600.

5.3.3.1 The Top Plate and the Faceplate

As to the faceplate 3204 and the top plate 3206 described above, it may be advantageous to choose a material that is relatively more rigid than the nasal cushion 3112, for example, which may be formed from a flexible material such as silicone. Choosing a relatively rigid material may provide for an effective anchor point for the positioning and stabilising structure 3300 (e.g., the rigidiser arms 3302) so that the positioning and stabilising structure 3300 may attach to the seal-forming structure 3100 at fixed positions. Were the positioning and stabilising structure 3300 to be connected directly to the seal-forming structure 3100, which may be made of a relatively flexible material such as silicone, this arrangement may cause undesirable deformation of the oral and nasal cushions 3110, 3112 when donned by the patient and tension is applied by the positioning and stabilising structure 3300. Tension may be particularly applied in the anterior/posterior directions. Examples of the positioning and stabilising structure 3300 may be made from Breathe-O-Prene™, Soft Edge™, and/or elastic cloth.

Also, by forming the faceplate 3204 and the top plate 3206 from relatively a rigid material, these components may be shaped to have approximately the same curvature as the face of the patient, which may in turn ensure a better seal by properly supporting the seal-forming structure 3100. This may also ensure an effective seal against the airways of the patient when the positioning and stabilising structure 3300 generates a tension force vector V substantially parallel to the Frankfort horizontal as indicated in FIG. 3o.

Forming the faceplate 3204 and the top plate 3206 from a relatively rigid material may also be beneficial in that such a relatively rigid material may prevent the outer portions of the seal-forming structure 3100 from deforming to the point that the periphery folds inward to the face. This arrangement may also help to ensure that sealing pressure is evenly applied over the face of the patient by the seal-forming structure 3100. The headgear strap 3306 of the positioning and stabilising structure 3300 may generate tension force vectors to seal the seal-forming structure 3100 against the patient's face, however, the faceplate 3204 and the top plate 3206 may help to spread these sealing forces out over the oral cushion 3110 and the nasal cushion 3112. By spreading these sealing forces over a broader area, pressure and/or deformation may not be localized to particular regions of the oral cushion 3110 and the nasal cushion 3112, for example near where the headgear straps 3306 are connected.

Additionally, by forming the top plate 3206 from a relatively rigid material this may prevent undesirable vertical flexing of the rigidiser arms 3302 when the patient interface 3000 is donned, but still allow pivoting of the rigidiser arms 3302 in a plane parallel to the patient's coronal plane. It should be understood that a small amount of vertical flexing may be tolerable.

Also, by making the faceplate 3204 from a relatively rigid material it may be easier for the patient to attach the lower straps 3312 of the positioning and stabilising structure 3100. This is so because the lower attachment features 3250 may be held in a relatively fixed position when the patient interface 3000 is donned by the patient.

Furthermore, disassembly and assembly of the patient interface 3000 and positioning and stabilising structure 3300 (e.g., for cleaning purposes) may be easier for the patient if the positioning and stabilising structure 3300 is not directly connected to the seal-forming structure 3100.

By providing separate attachment points for the upper straps 3310 and the lower straps 3312 through the top plate 3206 and the faceplate 3204, respectively, it may be possible to better control the sealing of the nasal cushion 3112 against the nose. For example, decoupling the nasal cushion 3112 may allow the upper straps 3310 to provide targeted pressure upward against the underside of the nose and/or inward against the face. It may also be possible to control the height of the nasal cushion 3112 relative to the nose as well as its lateral position (e.g., left vs. right). Additionally, it may be possible to control the rotation of the nasal cushion 3112 relative to the nose and about an axis parallel to a longitudinal axis of the top plate 3206. These features may provide these benefits which may not be possible when all of the straps of a positioning and stabilising structure 3300 are connected to one common front plate. Thus, the examples disclosed herein may provide for a more effective and stable seal around the nose of the patient. It should also be understood that by virtue of the connection of the nasal plenum chamber 3202 to the oral plenum chamber 3200 by the decoupling structure 3106, the relative height of the oral cushion 3110 may also be controlled by the upper straps 3310 of the positioning and stabilising structure 3300.

In examples of the technology various headgear configurations may be used with the exemplary patient interfaces 3000 described herein. One example of the technology may utilize headgear similar to that disclosed in US Patent Application Publication 2012/0138061. A further variation may include upper straps 3310 that are shorter than those disclosed in the aforementioned publication by virtue of their connection to the rigidiser arms 3302.

In further examples of the technology, the positioning and stabilising structure 3300 may include the features disclosed in PCT Application No. PCT/AU2013/000830 or in US Patent Application Publication No. 2014/0026890. The positioning and stabilising structure 3300 disclosed in that reference may be used as the upper straps 3310. The lower straps 3312 may be neoprene CommonLine headgear straps.

According to a further example of the present technology, one size of the top plate 3206 and the faceplate 3204 may be used for a variety of sizes of seal-forming structure 3100 and plenum chamber 3200. This may be advantageous to reduce the number of parts needed to be produced to manufacture patient interfaces 3000 to accommodate various patient head/face sizes. Thus, only the seal-forming structure 3100 and the plenum chamber 3200 may need to be molded in different sizes according to this example of the technology.

FIGS. 18a to 18f, 21a to 21e, 22a to 22e, and 28a to 28e show examples of the top plate 3206 and the faceplate 3204 according to further examples of the present technology. FIGS. 18a to 18f show the top plate 3206 and the faceplate 3204 attached to the nasal plenum chamber 3202 and the oral plenum chamber 3200, respectively. According to an example of the present technology, the top plate 3206 and the faceplate 3204 may be formed from a material that is relatively rigid as compared to silicone. The top plate 3206 and the faceplate 3204 may be joined to the nasal plenum chamber 3202 and the oral plenum chamber 3200, respectively, by overmolding the nasal plenum chamber 3202 and the oral plenum chamber 3200 to the top plate 3206 and the faceplate 3204. The nasal plenum chamber 3202, the nasal cushion 3112, the oral plenum chamber 3200, the oral cushion 3110, and the decoupling structure 3106 may be molded as one piece from silicone.

FIGS. 18a, 18b, 18c, and 18f also shows a top plate buffer 3214 and a faceplate buffer 3215. The top plate buffer 3214 may be formed in one piece with the nasal plenum chamber 3202 and may be formed from silicone. When the nasal plenum chamber 3202 is overmolded onto the top plate 3206 the silicone may pass through a hole 3217 and into or through core-outs 3216 of the top plate 3206 to form the top plate buffer 3214, as can be seen in FIGS. 21a to 21e. The hole 3217 and the core-outs 3216 together may provide a smooth flow path for the silicone as it is overmolded onto the top plate 3206. Alternatively, the core-outs 3216 may not be open to provide a passage for the flow of silicone during overmolding, but instead the core-outs 3216 may comprise recessed pockets that can be filled with silicone to form a mechanical interlock and provide cushioning. The top plate buffer 3214 may be pressed against the posterior side of the top plate cover 3303 when the rigidiser arm assembly 3301 is joined to the top plate 3206. The top plate buffer 3214 being made of a material that is relatively softer than the top plate 3206 and the top plate cover 3303, e.g., silicone, may dampen the hard-to-hard connection to reduce or eliminate rattling of these components.

The top plate buffer 3214 being formed in one piece with the nasal plenum chamber 3202 and connecting through the hole 3217 in the top plate 3206 may also provide a retaining function to retain the top plate 3206 in position against the nasal plenum chamber 3202.

The rib 3307 may also work in conjunction with the top plate buffer 3214 to provide dampening and/or retention of the engagement between the top plate 3206 and the rigidiser arm assembly 3301. The engagement of the rib 3307 with the top plate buffer 3214 and the top plate 3206 may provide the dampening and/or retention and the relative dimensions of these components may be selected to ensure the desired level of dampening and/or retention.

The faceplate buffer 3215 may extend from the periphery of the oral plenum chamber 3200 in an anterior direction. The faceplate buffer 3215 may be formed in one piece with the oral plenum chamber 3200. The faceplate buffer 3215 may be formed from silicone. The faceplate buffer 3215 may also dampen the hard-to-hard connection between the faceplate 3204 and the frame 3251 to reduce or eliminate rattling that may result from the connection.

FIGS. 21a to 21e show the top plate 3206 in isolation and FIGS. 22a to 22e show the faceplate 3204 in isolation.

The upper attachment features 3252 of the top plate 3206 may connect the rigidiser arm assembly 3301 at the connection features 3304, as shown in FIGS. 17a to 17f. The upper attachment features 3252 of these examples may comprise rigid pockets and/or undercuts that engage with respective connection features 3304 to attach the rigidiser arm assembly 3301.

The faceplate 3204 may also include a cutout 3213 on each side to connect a frame 3251 to the faceplate. Each cutout 3213 may extend laterally from the faceplate 3204. The cutouts 3213 may facilitate a hard-to-hard connection (e.g., between two relatively rigid components) between the faceplate 3204 and the frame 3251. The hard-to-hard connection may take the form of a snap-fit and may produce an audible click when the frame 3251 is attached to the faceplate 3204. Also, the connection port 3600 can be seen formed in the faceplate 3204. In FIGS. 17a to 17f, the frame 3251 can be seen attached around the faceplate 3204.

FIGS. 28a to 28e show another example of the top plate 3206 similar to the views shown in FIGS. 21a to 21e. However, the example shown in FIGS. 28a to 28e shows that a recess 3219 may be provided to each core-out 3216 on a posterior side thereof. The recess 3219 may provide more depth for the flow of silicone during the molding of the seal-forming structure 3100 and plenum chamber 3200 to the top plate 3206. The recess 3219 may be hemispherical and, as such, may also provide for more surface area for the attachment of silicone to the top plate 3206, which according to an example of the present technology, may be a self-adhesive liquid silicone rubber (LSR).

FIGS. 27a to 27f show another example of the present technology. In these views the seal-forming structure 3100 is shown with the faceplate 3204 and the top plate 3204. The example shown in these views is similar to the example shown in FIGS. 18a to 18f in that the seal-forming structure 3100 may be formed from silicone and may be overmolded to the top plate 3206 and the faceplate 3204 to join these components. FIGS. 27a to 27f depict an alternative example in that the top plate 3206 may be nearly completely embedded in the seal-forming structure 3100. In other words, the seal-forming structure 3100, when overmolded to the top plate 3206, may completely surround the top plate 3206 such that a minimal amount of the top plate 3206 is exposed. Additionally, an extension 3218 may be formed to extend from the top plate 3206 and may be formed in one-piece with the seal-forming structure 3100. The extension 3218 may serve cushioning and/or dampening functions similar to the top plate buffer 3214 when the rigidiser arm assembly 3301 is joined to the top plate 3206. Also, the extension 3218 may be formed with a barb shape and thus may serve a retaining function.

In a further alternative example, the extension 3218 may be formed in one piece with the top plate 3206. In this example, the barb shape of the extension 3218 may serve the retaining function but due to being made from the same, relatively rigid material of the top plate 3206 it may not serve the cushioning and/or dampening functions. As such, the overmolded silicone of the seal-forming structure 3100 that substantially surrounds the top plate 3206 may serve the cushioning and/or dampening functions.

FIGS. 20*a* to 20*s*, 23*a* to 23*f*, 24*a* to 24*f*, and 25*a* to 25*f* show several views of the frame 3251 with clips 3314 and lower attachment features 3250, in addition to view of their respective subcomponents.

The frame 3251 may also include a catch 3253 on each side to engage with respective ones of the cutouts 3213 to facilitate attachment to the faceplate 3204. The engagement of the catches 3253 with the cutouts 3213 may generate a hoop stress in the frame 3251 that holds the frame onto the faceplate 3204. The lower attachment features 3250 may also be formed on the frame 3251. As shown in FIG. 20*f*, for example, the lower attachment features 3250 may each include a mating surface 3254 to which each of the clips 3314 is joined. FIG. 20*g* shows that each mating surface 3254 may be on a mating portion 3255 of the lower attachment features 3250. Each lower attachment feature 3250 may include a wing portion 3257 to join the frame 3251 to each of the mating portions 3255.

The wing portions 3257 may be joined to the frame 3251 by overmolding the wing portions 3257 onto frame extensions 3259 of the frame such that a mechanical interlock is formed. The frame extensions 3259 may then extend into respective recesses 3258 of the wing portions 3257. The mating portions 3255 may also be joined to the wing portions 3257 by simultaneous overmolding such that a mechanical interlock is also formed between the wing portions 3257 and the mating portions 3255. Thus, mating portion extensions 3256 may also extend into the recesses 3258 of the wing portions 3257.

The wing portions 3257 may be formed from thermoplastic elastomer. The wing portions 3257 may also be flexible such that the lower attachment features 3250 function as living hinges. In other words, the lower attachment features 3250 may be able to move in an anterior/posterior direction due to their flexibility so that the tension of the straps 3306 causes them to flex and retain the patient interface 3000 on the patient when donned. The mating portions 3255 may also be formed from a thermoplastic elastomer.

The clip 3314 may include a bar 3315 around which the lower strap 3312 is looped to attach the clip 3314 to the lower strap 3312.

To join the clips 3314 to the lower attachment features 3250 a magnetic connection may be provided. A clip magnet 3260 may be provided to each of the clips 3314 in a clip pocket 3317 and a mating portion magnet 3261 may be provided to each of the mating portions 3255 of the lower attachment features 3250 within a mating portion pocket 3262. The poles of each clip magnet 3260 and each mating portion magnet 3261 may be aligned such that a magnetic attraction is generated between these magnets to draw and retain the clips 3314 to the lower attachment features 3250. Further examples of these attachment arrangements are disclosed in PCT Application No. PCT/AU2014/000021, which is incorporated herein by reference in its entirety.

The mating portions 3255 of these examples may also include a guide surface 3263 and a protrusion 3264 to position the clip 3314 as it is attached. Also, each of the clips 3314 may include a receiving surface 3319 to engage with a respective guide surface 3263 and a notch 3318 to engage with a respective protrusion 3264. When the clips 3314 are attached to respective mating portions 3255 of the lower attachment features 3250, the engagement of the notch 3318 and the protrusion 3264 may prevent rotation of the clip 3314 relative to the mating portion 3255 of the lower attachment feature 3250. This may help ensure that the direction of the tension force vectors of the lower straps 3312 become and remain properly aligned when the patient interface 3000 is donned by the patient.

The guide surface 3263 may have a curved profile. The guide surface 3263 may also be shaped to form an overhang. The receiving surface 3319 may be shaped to correspond to the shape of the guide surface 3263. The shape of the guide surface 3263 may also have a guiding and/or retaining function. The curved profile and slope of the guide surface 3263 may allow the receiving surface 3319 to slide along the guide surface 3263 and into position such that the protrusion 3264 engages with the notch 3318. This may be advantageous because it may be difficult for the patient to align the clips 3314 with the lower attachment features 3250 when the patient interface 3000 is being donned. Also, the patient may be in a darkened environment, may have limited tactile ability, and/or may have limited vision to align the clips 3314 with the lower attachment features 3250. Thus, structuring the guide surface 3263 such that it guides the receiving surface 3319 and, therefore, the clip 3314 into place may be helpful to ensure a proper and secure fit of the patient interface 3000.

FIG. 20*n* shows a rear view of frame 3251 and lower attachment features 3250. According to this example, each of the lower attachment features 3250 may comprise a flex point which is depicted as a reduced thickness section 3266 in this view. The lower attachment features 3250, when subjected to tension by the lower side straps 3312 of the positioning and stabilizing structure 3300, may be deformed and flex in a posterior direction at the flex point. The lower attachment features may comprise thermoplastic elastomer.

FIGS. 20*q* to 20*s* show further examples of the present technology with a top view of the frame 3251 and the lower attachment features 3250. FIG. 20*q* shows a notch 3265 at the flex point on an anterior side of each of the lower attachment features 3250. The notch 3265 shown in FIG. 20*q* may allow the lower attachment feature 3250 to flex through the notch 3265 in an anterior direction. FIG. 20*r* shows a notch 3265 at the flex point on a posterior side of each of the lower attachment features 3250. The notch 3265 shown in FIG. 20*r* may allow the lower attachment feature 3250 to flex through the notch 3265 in a posterior direction. It should be understood that according to a further example of the present technology a notch 3265 may be provided on the posterior and anterior side of each lower attachment feature 3250.

FIG. 20*s* shows another top view of the frame 3251 and lower attachment features 3250 according to an example of the present technology. According to this example, the flex point may comprise a reduced thickness section 3266 that reduces the thickness of the lower attachment features 3250 from the posterior and anterior sides to allow the lower attachment features to flex in both directions.

FIGS. 20*o* and 20*p* show exploded views depicting features similar to FIGS. 20*g* and 20*h*. However, FIGS. 20*o* and 20*p* also depict mating portion magnet receivers 3267. Each of the mating portion magnet receivers 3267 may be structured to receive a corresponding mating portion magnet 3261. FIGS. 23*g* to 23*m* also depict the mating portion magnet receivers 3267.

FIGS. 20*p* and 25*g* to 25*l* also show that the clips 3314 may include a clip magnet receiver 3321 and a clip magnet cover 3320 to secure the clip magnet 3260 within the clip 3314. The clip magnet cover 3320 may secure the clip magnet 3260 in the clip magnet receiver 3321 with a snap-fit.

5.3.4 Vent, Tube Decoupling Structure(s), Connection Port, and Anti-Asphyxia Valve In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes. More than 80 holes is also envisaged.

In an example, the vent 3400 is located in the plenum chamber 3200. Alternatively, the vent 3400 is located in a tube decoupling structure 3500, e.g. a swivel 3510.

In another example of the present technology the vent 3400 may be located on the top plate 3206 and/or the faceplate 3204. In such an example, the tube decoupling structure 3500 may not include a vent.

The vent 3400 may be laser cut or made from a mesh material or a linear array. The vent 3400 may also be made from a material or textile of interlacing plastic fibers. The material of the interlacing plastic fibers is a thermoplastic polymer including polycarbonate, nylon, polyethylene and preferably polypropylene. Specifically, the textile may be SEFAR material Tetex Mono 05-1010-K 080 woven polypropylene material. The textile is typically provided in the form of a roll or ribbon. The weave of the textile is preferably a satin weave. However, other weaves are envisaged including plain weave, plain reverse dutch weave and twill weave. The voids or holes defined by the weave of fibers through the textile do not necessarily have a uniform dimension since there is some variation between the positioning, spacing and compression of the fibers in the weave of the textile. The voids are preferably not straight through holes but rather define a tortuous air flow path between adjacent fibers through the thickness of the textile. A tortuous air flow path significantly diffuses the air flow and thereby reduces noise. If the voids are straight through holes, then the fibers of the textile may be arranged in the form of a mesh grid.

In one example, the airflow rate of the vent portion of the textile is first measured by an airflow meter. A determination is made on whether there is a difference between the measured airflow rate and a desired airflow rate. If the airflow rate through the vent portion exceeds a predetermined range, the amount of porosity of the vent portion is selectively reduced. The desired predetermined range is about 42 to about 59 litres per minute at 20 cm $H_2O$ pressure, preferably, about 47 to about 53 litres per minute at 20 cm $H_2O$ pressure. For example, the airflow rate through the SEFAR material Tetex Mono 05-1010-K 080 woven polypropylene material may be about 37 to about 64 litres at 20 cm $H_2O$ pressure, preferably, about 42 to about 58 litres at 20 cm $H_2O$ pressure. The variance over the length of the SEFAR textile may be sinusoidal over the length of the textile ribbon. Different areas of the SEFAR textile when first received from a textile manufacturer exhibit different air flow rates. After the porosity has been reduced, the airflow rate is measured again for verification to confirm it is now within the predetermined range. The average diameter of the opening of the voids is preferably less than 0.1 mm, and preferably provide a total open area of approximately 1% to 10% of the superficial area of the vent. For example, the total open area may be 22 mm2 where the superficial area of the vent is 240 mm2.

If the desired air flow rate exists in the textile, optionally, the holes in a peripheral edge region of a desired vent portion are occluded. The peripheral edge region of the vent portion is overmolded to the top plate 3206 and/or the faceplate 3204. Since the holes that existed at the peripheral edge region have been occluded, the airflow rate of the vent portion should not differ after overmolding.

In some examples, the airflow rate may be measured after the vent portion is cut from the textile, and also the vents may be measured after being overmolded to the top plate 3206 and/or the faceplate 3204. This enables the airflow rate to be known and determined to be within the desired predetermined range after each step. This may prevent wastage so that the part may be discarded as soon as it is known that it is not within the desired predetermined range.

The porosity of the vent portion can be reduced by several ways, including: heat staking, plastic deformation by compression, ultrasonic welding, applying a sealant (e.g. hot melt adhesive) and applying a thin film. Preferably, heat staking by a staking punch is used to reduce porosity due to increased precision, greater certainty of occlusion of holes in the textile, manufacturing speed, good visual appeal after heat staking, and no additional material is required. Some material shrinkage occurs when heating a thermoplastic which is accounted for by having excess material surrounding the specific physical dimension for the shape of the vent. The porosity of the vent portion is reduced by partially occluding or by fully occluding holes in the vent portion.

Any area or region of the vent portion may be selected to reduce porosity. Preferably, the porosity of a continuous peripheral edge region of the vent portion is reduced. This provides good visual appeal because this is adjacent to or at the location where the vent portion is overmolded to the top plate 3206 and/or the faceplate 3204. Any visual differences between the continuous peripheral edge region and the rest of the vent portion may be less noticeable to the human eye at this location since it may appear to be a defined edge of the top plate 3206 and/or the faceplate 3204 for receiving the vent 3400. Alternatively, the area for porosity reduction may be in the form of a character/letter or logo in a central region of the vent portion to enhance visual impact and improve brand awareness.

Sound caused by exhaled carbon dioxide passing through the vent 3400 is minimised because of greater air diffusion as it passes through the textile, in particular, for nasal pillows when a patient exhales out of their nose and the carbon dioxide flows out through the vent. Diffusion of the exhaled carbon dioxide avoids direct or focused airflow to a bed partner or the patient depending on vent orientation and sleeping position.

The vent of the patient interface is easy to clean. A mild cleaning solution or soapy water can be used for cleaning the vent. Hot water can also be used to flow through the vent for cleaning. The vent can be hand washed and rinsed without disassembly from the top plate 3206 and/or the faceplate 3204 because it may be permanently connected, for example, overmolded, to the top plate 3206 and/or the faceplate 3204. Less detachable parts for the patient interface avoids the possibility of losing individual parts and also reduces cleaning time by not having to detach and re-attach each part from each other. Since the vent is formed with plastic fibers, durability of the vent is maintained even after repeated cleaning in contrast to a vent made from another less durable material, for example, a cloth textile.

The vent is quiet. Sound energy generated by exhaled carbon dioxide is spread evenly. Vibrations caused by the exhaled carbon dioxide coming in contact with the top plate 3206 and/or the faceplate 3204 may produce vibrations in the top plate 3206 and/or the faceplate 3204. Such vibrations may be dampened by the vent.

In one form the patient interface 3000 includes at least one tube decoupling structure 3500, for example a swivel or a ball and socket. The tube decoupling structure 3500 may also include an elbow feature. The tube decoupling structure 3500 may be divided between the hose and mouth.

A connection port 3600 may allow for connection to the air circuit 4170. The air circuit 4170 may include a short tube connected to a longer tube. Examples of the tubes may include the tube features disclosed in PCT Application No. PCT/AU2013/000830. A rotatable adapter may also be included to connect the short tube and long tube.

In one form, the patient interface 3000 includes an anti-asphyxia valve 3800.

FIG. 3g shows another front perspective view of an exemplary patient interface 3000 according to the present technology. This view depicts features similar to those shown in FIG. 3a, however, this view also includes features to connect the patient interface 3000 to a PAP device 4000. These additionally depicted features include at least one vent 3400 disposed radially about the port 3600. In the example depicted, the vent 3400 comprises a plurality of vent holes around the port 3600. The features of the vent 3400 will be discussed in greater detail below. Also shown in this view is a tube decoupling structure 3500 to connect the air circuit 4170 to the port 3600 on the faceplate 3204 of the patient interface 3000. The tube decoupling structure 3500 may be an elbow and it may include a swivel 3510 to allow the tube decoupling structure 3500 and the air circuit 4170 to rotate relative to the patient interface 3000 about the port 3600. The tube decoupling structure 3500 in this view also includes an anti-asphyxiation valve 3800 that will be described in greater detail below. Also, FIG. 3g shows that the air circuit 4170 may include a cuff 4172 to attach the air circuit to the decoupling structure 3500.

FIG. 3h depicts features of the exemplary patient interface 3000 in a rear view, similar to FIG. 3c. FIG. 3h, however, also shows that the patient interface 3000 may include a vent 3400 in the form of a plurality of vent holes disposed radially about the port 3600. The cuff 4172 and the air circuit 4170 can also be seen. The location of the decoupling structure 3106 is indicated in this view, along with the connection region 3106.2 of the oral cushion 3110 and the nasal cushion 3112.

FIG. 3i shows a front view of an exemplary patient interface 3000, similar to FIG. 3b. Also shown in FIG. 3i, is the tube decoupling structure 3500 attached to the port 3600 on the faceplate 3204 of the patient interface 3000. This view also shows the vent 3400 in the form of a plurality of vent holes disposed radially about the port 3600. The anti-asphyxiation valve 3800 can also be seen on the tube decoupling structure 3500. The cuff 4172 and the air circuit 4170 can also be seen connected to the tube decoupling structure 3500. The decoupling structure 3106 is shown in this view and side portions 3106.3 of the decoupling structure 3106 can also be seen.

FIG. 3j shows a top view of an exemplary patient interface 3000 with features similar to those shown in FIG. 3d. FIG. 3d additionally depicts the vent 3400 in the form of a plurality of vent holes disposed around the port 3600. Extending from the port 3600 is the tube decoupling structure 3500 with the anti-asphyxia valve 3800 disposed thereon.

FIG. 3k shows a bottom view of an exemplary patient interface 3000. This view is similar to FIG. 3e and thus depicts similar features. Additionally, this view depicts the vent 3400 comprising a plurality of vent holes disposed radially about the port 3600. The tube decoupling structure 3500 is shown extending from the port 3600. The cuff 4172 and air circuit 4170 can be seen as well.

FIG. 3l shows a side view of an exemplary patient interface 3000 that is similar to the view shown in FIG. 3f. Accordingly, FIG. 3l depicts features similar to those shown in FIG. 3f. However, FIG. 3l also shows the vent 3400 including a plurality of vent holes disposed radially about the port 3600. The tube decoupling structure 3500 is shown connected to the port 3600 at one end and connected to the air circuit 4170 via the cuff 4172 at the other end. This view also depicts the location of the decoupling structure 3106 and one of its side portions 3106.3. The gap 3106.1 between the nasal plenum chamber 3202 and the oral plenum chamber 3200 that allows these components to flex or move toward one another is also shown.

According to the examples shown in FIGS. 17a to 17f and FIGS. 26a to 26d, the decoupling structure 3500 may be joined to the faceplate 3204 and the connection port 3600. In these examples, the vent 3400 may be formed on the tube decoupling structure 3500. In these examples, the tube decoupling structure 3500 may comprise an elbow that is rotatable at the connection with the connection port 3600. The decoupling structure 3500 may also include a swivel 3510 to connect to a air circuit 4170. The decoupling structure 3500 may include a baffle 3520 to separate the flow path of pressurized gas from the PAP device 4000 from the flow path of exhaled gas (e.g., $CO_2$) from the patient that exits through the vent 3400. By separating these flow paths, the baffle 3520 may improve washout of exhaled gas (e.g., $CO_2$). The tube decoupling structure 3500 may also include a quick release mechanism 3530 that allows the patient to easily attach and detach the tube decoupling structure 3500 to and from the connection port 3600 on the faceplate 3204. The quick release mechanism 3530 may also be structured to provide a snap-fit connection between the connection port 3600 and the tube decoupling structure 3500 and engagement may result in an audible click that ensures the patient that the connection has been made. The tube decoupling structure 3500 may also include an anti-asphyxiation valve 3800.

5.4 Glossary

In certain forms of the present technology, one or more of the following definitions may apply. In other forms of the present technology, alternative definitions may apply.

5.4.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.4.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

5.4.3 Anatomy of the Face

Ala: The external outer wall or "wing" of each nostril (plural: alae)

Alar angle: The angle defined between the ala, from an inferior view.

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the major alar cartilage.

Lip, lower (labrale inferius): A point where the boundary of the vermilion border of the lower lip and the skin is intersected by the median sagittal plane.

Lip, upper (labrale superius): The point on the upper lip lying in the median sagittal plane on a line drawn across the boundary of the vermilion border and skin.

Major alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture. Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.4.4 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.4.5 Anatomy of the Respiratory System

Diaphragm: A sheet of muscle that extends across the bottom of the rib cage.

The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx), the oropharynx (mesopharynx), and the laryngopharynx (hypopharynx).

5.4.6 Materials

Silicone or Silicone Elastomer: A synthetic rubber. In this specification, a reference to silicone is a reference to liquid silicone rubber (LSR) or a compression molded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.4.7 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow or air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: The functional dead space refers to at least one region within a breathing circuit where a patient's exhalate may collect such that the normal flow of gas within the breathing circuit cannot effectively flush the exhalate from the breathing circuit.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurized above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air circuit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.4.8 Terms Used in Relation to Patient Interface

Curvature (of a surface): A region of a surface having a saddle shape, which curves up in one direction and curves down in a different direction, will be taken to have a negative curvature. A region of a surface having a dome shape, which curves the same way in two principle directions, will be taken to have a positive curvature. A flat surface will be taken to have zero curvature.

Floppy: A quality of a material, structure or composite that is the combination of features of:
  Readily conforming to finger pressure.
  Unable to retain its shape when caused to support its own weight.
  Not rigid.
  Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.5 Other Remarks

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

It must be noted that as used herein and in the appended claims, the singular forms "a", "an", and "the" include their plural equivalents, unless the context clearly dictates otherwise.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE NUMERAL LIST

| | |
|---|---|
| patient | 1000 |
| bed partner | 1100 |
| patient interface | 3000 |
| seal-forming structure | 3100 |
| nasal opening | 3101 |
| oral gas chamber | 3102 |
| oral opening | 3103 |
| nasal gas chamber | 3104 |
| distal major side | 3104.1 |
| minor side | 3104.2 |
| proximal major side | 3104.3 |
| nare port | 3105 |
| decoupling structure | 3106 |
| gap | 3106.1 |
| connection region | 3106.2 |
| side portion | 3106.3 |
| upper surface | 3106.4 |
| connecting surface | 3106.5 |
| lower surface | 3106.6 |
| oral cushion | 3110 |
| nasal cushion | 3112 |
| region | 3112.1 |
| region | 3112.2 |
| region | 3112.3 |
| region | 3113 |
| protruding end | 3114 |
| region | 3115 |
| recessed portion | 3116 |
| region | 3117 |
| peak | 3118 |
| nasal sling | 3119 |
| oral undercushion | 3120 |
| straight sidewalls | 3121 |
| tapered region | 3122 |
| thickened nasal cushion section | 3124 |
| soft connection region | 3130 |
| hard connection region | 3132 |
| oral plenum chamber | 3200 |
| nasal plenum chamber | 3202 |
| faceplate | 3204 |
| connection portion | 3205 |
| top plate | 3206 |
| side support | 3207 |
| nasal undercushion support wall | 3208 |
| pocket | 3208.1 |
| notch | 3209 |
| perimeter | 3210 |
| oral plenum chamber section | 3212 |
| cutout | 3213 |
| top plate buffer | 3214 |
| faceplate buffer | 3215 |
| recess | 3216 |

-continued

| | |
|---|---|
| hole | 3217 |
| extension | 3218 |
| depression | 3219 |
| lower attachment feature | 3250 |
| frame | 3251 |
| upper attachment feature | 3252 |
| catch | 3253 |
| mating surface | 3254 |
| mating portion | 3255 |
| mating portion extension | 3256 |
| wing portion | 3257 |
| recess | 3258 |
| frame extension | 3259 |
| clip magnet | 3260 |
| mating portion magnet | 3261 |
| mating portion pocket | 3262 |
| guide surface | 3263 |
| protrusion | 3264 |
| notch | 3265 |
| reduced thickness section | 3266 |
| mating portion magnet receiver | 3267 |
| positioning and stabilising structure | 3300 |
| rigidiser arm assembly | 3301 |
| rigidiser arm | 3302 |
| top plate cover | 3303 |
| connection feature | 3304 |
| pad | 3305 |
| headgear straps | 3306 |
| rib | 3307 |
| opening | 3308 |
| claw | 3309 |
| upper strap | 3310 |
| lower strap | 3312 |
| clip | 3314 |
| bar | 3315 |
| sheath | 3316 |
| clip pocket | 3317 |
| notch | 3318 |
| receiving surface | 3319 |
| clip magnet cover | 3320 |
| clip magnet receiver | 3321 |
| vent | 3400 |
| tube decoupling structure | 3500 |
| swivel | 3510 |
| baffle | 3520 |
| quick release mechanism | 3530 |
| connection port | 3600 |
| anti-asphyxiation valve | 3800 |
| pap device | 4000 |
| air circuit | 4170 |
| cuff | 4172 |
| humidifier | 5000 |

The invention claimed is:

1. A patient interface to provide breathable gas to a patient, comprising:
a cushion assembly, comprising:
a nasal cushion having a concave shape between a first lateral side and a second lateral side to receive and seal against an inferior periphery of the patient's nose, the nasal cushion including a nasal opening configured to direct breathable gas to the patient's nares in use;
an oral cushion configured to contact and seal against the patient's face surrounding the patient's mouth, the oral cushion including an oral opening configured to direct breathable gas to the patient's mouth in use; and
a plenum chamber including a nasal portion and an oral portion, and the plenum chamber, the nasal cushion, and the oral cushion at least partly forming a gas chamber;
an anti-asphyxiation valve;
a positioning and stabilizing structure including a pair of upper side straps, a pair of lower side straps, and a rear portion, the pair of upper side straps and the pair of lower side straps extending from the rear portion; and
a unitary plate member removably connected to the cushion assembly, the unitary plate member including a connection port configured to be connected to an air delivery tube, the connection port being configured to receive breathable gas from the air delivery tube and direct breathable gas into the cushion assembly for breathing by the patient during use, the unitary plate member including an upper portion and a lower portion, and the upper portion of the unitary plate member contacting the nasal portion of the plenum chamber to support the nasal cushion against the patient's face in use,
wherein the nasal portion of the plenum chamber includes an anterior side and lateral sides that extend posteriorly from the anterior side, the anterior side and the lateral sides including a depressed region, and
wherein the upper portion of the unitary plate member is shaped and dimensioned to complement a lower surface of the depressed region along the anterior side and lateral sides of the nasal portion of the plenum chamber when the unitary plate member is removably connected to the cushion assembly.

2. The patient interface of claim 1, wherein the nasal cushion includes a recessed portion configured to receive the tip of the patient's nose in use,
wherein the nasal cushion includes a pair of peaks, each of the peaks being positioned laterally outward of the recessed portion and configured to extend in a superior direction relative to the patient in use, and
wherein the recessed portion is recessed below the peaks.

3. The patient interface of claim 1, wherein the oral portion of the plenum chamber further comprises a vent configured to allow for washout of exhaled carbon dioxide, the vent having a plurality of holes.

4. The patient interface of claim 1, wherein the nasal cushion further comprises a pair of protruding ends, each of the protruding ends being positioned on a corresponding lateral side of the nasal cushion and configured to contact and seal against the patient's face between the respective ala and the respective nasolabial sulcus of the patient.

5. The patient interface of claim 1, wherein the nasal opening increases in lateral width from an anterior edge to a posterior edge relative to the patient in use.

6. The patient interface of claim 1, wherein the nasal cushion increases in thickness in a direction that is laterally outward from the nasal opening.

7. The patient interface of claim 1, wherein a lower portion of the nasal cushion is concave to seal against the upper lip of the patient in use.

8. The patient interface of claim 1, wherein the positioning and stabilizing structure includes a pair of clips,
wherein the lower portion of the unitary plate member includes a pair of lower attachment features, each of the lower side straps being removably connected to a corresponding one of the clips, each of the lower attachment features comprising a clip receptacle, and each of the clips being removably connected to a corresponding one of the lower attachment features, and
wherein each of the lower side straps includes hook material and loop material to removably connect to a corresponding one of the clips.

9. The patient interface of claim 1, wherein the upper portion of the unitary plate member includes a pair of lateral portions that extend farther in a superior direction relative to the patient in use than a medial portion positioned between the lateral portions, and
   wherein the lateral portions and the medial portion are shaped and dimensioned to be substantially flush with the lower surface of the depressed region when the unitary plate member is removably connected to the cushion assembly.

10. The patient interface of claim 1, further comprising a rigidiser arm assembly removably connected to the upper portion of the unitary plate member,
    wherein the rigidiser arm assembly is formed in one piece and extends across the upper portion of the unitary plate member,
    wherein each of the upper side straps is removably connected to the rigidiser arm assembly,
    wherein the unitary plate member is constructed from a single piece of material, and
    wherein the unitary plate member is relatively more rigid than the nasal cushion and the oral cushion.

11. The patient interface of claim 1, wherein the nasal opening is a single opening configured to direct breathable gas to both of the patient's nares in use.

12. The patient interface of claim 1, wherein the nasal cushion comprises:
    a first region positioned proximal to the opening on each lateral side of the opening, the first region being configured to contact the patient's nose;
    a second region positioned adjacent to and laterally outward of the first region, the second region being thicker than the first region; and
    a third region positioned adjacent to and laterally outward of the second region, the third region having a different thickness relative to the second region.

13. The patient interface of claim 12, wherein the nasal cushion has curved shape from the first region, through the second region, and to third region, an apex of the curved shape being located in the second region.

14. The patient interface of claim 13, wherein the third region is thicker than the second region,
    wherein the third region is thinner than the second region and thicker than the first region, or
    wherein the third region is thinner than the first region and the second region.

15. The patient interface of claim 1, wherein:
    the nasal cushion includes a recessed portion configured to receive the tip of the patient's nose in use,
    the nasal cushion includes a pair of peaks, each of the peaks being positioned laterally outward of the recessed portion and configured to extend in a superior direction relative to the patient in use,
    the recessed portion is recessed below the peaks,
    the nasal opening increases in lateral width from an anterior edge to a posterior edge relative to the patient in use,
    a lower portion of the nasal cushion is concave to seal against the upper lip of the patient in use,
    the positioning and stabilizing structure includes a pair of clips,
    the lower portion of the unitary plate member includes a pair of lower attachment features, each of the lower side straps being removably connected to a corresponding one of the clips, each of the lower attachment features comprising a clip receptacle, and each of the clips being removably connected to a corresponding one of the lower attachment features,
    each of the lower side straps includes hook material and loop material to removably connect to a corresponding one of the clips,
    the upper portion of the unitary plate member includes a pair of lateral portions that extend farther in a superior direction relative to the patient in use than a medial portion positioned between the lateral portions,
    the lateral portions and the medial portion are shaped and dimensioned to be substantially flush with the lower surface of the depressed region when the unitary plate member is removably connected to the cushion assembly, and
    the nasal opening is a single opening configured to direct breathable gas to both of the patient's nares in use.

16. A patient interface to provide breathable gas to a patient, comprising:
    a cushion assembly, comprising:
       a nasal plenum chamber portion including a nasal cushion having a concave shape between a first lateral side and a second lateral side to receive and seal against an inferior periphery of the patient's nose, the nasal cushion including a nasal opening configured to direct breathable gas to the patient's nares in use; and
       an oral plenum chamber portion including an oral cushion configured to contact and seal against the patient's face surrounding the patient's mouth, the oral cushion including an oral opening configured to direct breathable gas to the patient's mouth in use,
    an anti-asphyxiation valve;
    a positioning and stabilizing structure including upper straps, lower straps, and a rear portion, the upper straps and the lower straps extending from the rear portion; and
    a faceplate having a connection port configured to be connected to an air delivery tube, the connection port being configured to receive breathable gas from the air delivery tube and direct breathable gas into the cushion assembly for breathing by the patient during use;
    a top plate; and
    a connection portion that joins the top plate and the faceplate to form a unitary structure that is removably connected to the cushion assembly, wherein the top plate contacts the nasal plenum chamber portion to support the nasal cushion against the patient's face in use,
    wherein the nasal portion of the plenum chamber includes an anterior side and lateral sides that extend in a posterior direction relative to the patient from the anterior side, the nasal portion of the plenum chamber including a depressed region that extends across the anterior side and the lateral sides, and
    wherein the top plate is shaped and dimensioned to complement a lower surface of the depressed region across the anterior side and lateral sides of the nasal plenum chamber portion when the unitary structure is removably connected to the cushion assembly.

17. The patient interface of claim 16, wherein the nasal cushion includes a recessed portion configured to receive the tip of the patient's nose in use,
    wherein the nasal cushion includes a pair of peaks, each of the peaks being positioned laterally outward of the recessed portion and configured to extend in a superior direction relative to the patient in use, and
    wherein the recessed portion is recessed below the peaks.

18. The patient interface of claim 16, wherein the oral plenum chamber portion further comprises a vent configured to allow for washout of exhaled carbon dioxide, the vent having a plurality of holes.

19. The patient interface of claim 16, wherein the nasal cushion further comprises a pair of protruding ends, each of the protruding ends being positioned on a corresponding lateral side of the nasal cushion and configured to contact and seal against the patient's face between the respective ala and the respective nasolabial sulcus of the patient.

20. The patient interface of claim 16, wherein the nasal opening increases in lateral width from an anterior edge to a posterior edge relative to the patient in use.

21. The patient interface of claim 16, wherein the nasal cushion increases in thickness in a direction that is laterally outward from the nasal opening.

22. The patient interface of claim 16, wherein a lower portion of the nasal cushion is concave to seal against the upper lip of the patient in use.

23. The patient interface of claim 16, wherein the positioning and stabilizing structure includes clips,
wherein the faceplate includes lower attachment features, each of the lower straps being removably connected to a corresponding one of the clips, each of the lower attachment features comprising a clip receptacle, and each of the clips being removably connected to a corresponding one of the lower attachment features, and
wherein the lower straps include hook material and loop material to removably connect to a corresponding one of the clips.

24. The patient interface of claim 16, wherein the top plate includes a pair of lateral portions that extend farther in a superior direction relative to the patient in use than a medial portion positioned between the lateral portions, and
wherein the lateral portions and the medial portion are shaped and dimensioned to be substantially flush with the lower surface of the depressed region when the unitary structure is removably connected to the cushion assembly.

25. The patient interface of claim 16, further comprising a rigidiser arm assembly removably connected to the top plate of the unitary structure,
wherein the rigidiser arm assembly is formed in one piece and extends across the top plate of the unitary structure,
wherein each of the upper straps is removably connected to the rigidiser arm assembly,
wherein the unitary structure is constructed from a single piece of material, and
wherein the unitary structure is relatively more rigid than the nasal cushion and the oral cushion.

26. The patient interface of claim 16, wherein the nasal opening is a single opening configured to direct breathable gas to both of the patient's nares in use.

27. The patient interface of claim 16, wherein the nasal cushion comprises:
a first region positioned proximal to the opening on each lateral side of the opening, the first region being configured to contact the patient's nose;
a second region positioned adjacent to and laterally outward of the first region, the second region being thicker than the first region; and
a third region positioned adjacent to and laterally outward of the second region, the third region having a different thickness relative to the second region.

28. The patient interface of claim 27, wherein the nasal cushion has curved shape from the first region, through the second region, and to third region, an apex of the curved shape being located in the second region.

29. The patient interface of claim 27, wherein the third region is thicker than the second region,
wherein the third region is thinner than the second region and thicker than the first region, or
wherein the third region is thinner than the first region and the second region.

30. The patient interface of claim 16, wherein:
the nasal cushion includes a recessed portion configured to receive the tip of the patient's nose in use,
the nasal cushion includes a pair of peaks, each of the peaks being positioned laterally outward of the recessed portion and configured to extend in a superior direction relative to the patient in use,
the recessed portion is recessed below the peaks,
the nasal opening increases in lateral width from an anterior edge to a posterior edge relative to the patient in use,
a lower portion of the nasal cushion is concave to seal against the upper lip of the patient in use,
the positioning and stabilizing structure includes a pair of clips,
the lower portion of the unitary structure includes a pair of lower attachment features, each of the lower side straps being removably connected to a corresponding one of the clips, each of the lower attachment features comprising a clip receptacle, and each of the clips being removably connected to a corresponding one of the lower attachment features,
each of the lower side straps includes hook material and loop material to removably connect to a corresponding one of the clips,
the top plate of the unitary structure includes a pair of lateral portions that extend farther in a superior direction relative to the patient in use than a medial portion positioned between the lateral portions,
the lateral portions and the medial portion are shaped and dimensioned to be substantially flush with the lower surface of the depressed region when the unitary structure is removably connected to the cushion assembly, and
the nasal opening is a single opening configured to direct breathable gas to both of the patient's nares in use.

* * * * *